(12) United States Patent
Rice et al.

(10) Patent No.: US 7,338,759 B1
(45) Date of Patent: Mar. 4, 2008

(54) HCV VARIANTS

(75) Inventors: Charles M. Rice, New York, NY (US); Keril J. Blight, St. Louis, MO (US)

(73) Assignee: Washington University, St. Louis, MO (US)

( * ) Notice: Subject to any disclaimer, the term of this patent is extended or adjusted under 35 U.S.C. 154(b) by 641 days.

(21) Appl. No.: 10/276,051

(22) PCT Filed: May 23, 2001

(86) PCT No.: PCT/US01/16822

§ 371 (c)(1), (2), (4) Date: Apr. 1, 2003

(87) PCT Pub. No.: WO01/89364

PCT Pub. Date: Nov. 29, 2001

Related U.S. Application Data

(63) Continuation-in-part of application No. 09/576,989, filed on May 23, 2000, now Pat. No. 7,049,428, which is a continuation-in-part of application No. 09/034,756, filed on Mar. 4, 1998, now Pat. No. 6,392,028, which is a continuation of application No. 08/811,566, filed on Mar. 4, 1997, now Pat. No. 6,127,116.

(60) Provisional application No. 60/039,843, filed on Mar. 4, 1997.

(51) Int. Cl.
C12Q 1/70 (2006.01)
C12Q 1/68 (2006.01)
C12N 15/09 (2006.01)
C12P 21/00 (2006.01)
C12N 7/02 (2006.01)
C12N 5/10 (2006.01)
C07H 21/00 (2006.01)

(52) U.S. Cl. .......... 435/6; 435/69.1; 435/70.1; 435/320.1; 435/235.1; 435/239; 435/5; 536/23.72; 536/24.1

(58) Field of Classification Search .......... 435/5, 435/6, 7.1, 235.1, 236, 237, 239, 325, 363, 435/366, 367, 370, 320.1; 536/23.7, 23.72, 536/24.1
See application file for complete search history.

(56) References Cited

U.S. PATENT DOCUMENTS

| 4,631,211 | A | 12/1986 | Houghten |
|---|---|---|---|
| 5,010,175 | A | 4/1991 | Rutter et al. |
| 5,077,193 | A | 12/1991 | Mishiro et al. |
| 5,106,726 | A | 4/1992 | Wang |
| 5,176,994 | A | 1/1993 | Mishiro et al. |
| 5,218,099 | A | 6/1993 | Reyes et al. |
| 5,298,394 | A | 3/1994 | Arima et al. |
| 5,312,737 | A | 5/1994 | Bolling et al. |
| 5,350,671 | A | 9/1994 | Houghton et al. |
| 5,371,017 | A | 12/1994 | Houghton et al. |
| 5,372,928 | A | 12/1994 | Miyamura et al. |
| 5,378,814 | A | 1/1995 | Houghton et al. |
| 5,389,528 | A | 2/1995 | Houghton et al. |
| 5,427,909 | A | 6/1995 | Okamoto et al. |
| 5,428,145 | A | 6/1995 | Okamoto et al. |
| 5,436,126 | A | 7/1995 | Wang |
| 5,443,965 | A | 8/1995 | Reyes et al. |
| 5,527,669 | A | 6/1996 | Resnick et al. |
| 5,538,865 | A | 7/1996 | Reyes et al. |
| 5,550,016 | A | 8/1996 | Okamoto |
| 5,552,310 | A | 9/1996 | Yoshikura et al. |
| 5,576,302 | A | 11/1996 | Cook et al. |
| 5,580,718 | A | 12/1996 | Resnick et al. |
| 5,585,258 | A | 12/1996 | Houghton et al. |
| 5,597,691 | A | 1/1997 | Houghton et al. |
| 5,610,054 | A | 3/1997 | Draper |
| 5,620,843 | A | 4/1997 | Hellings et al. |
| 5,625,034 | A | 4/1997 | Liao et al. |
| 5,625,043 | A | 4/1997 | Priebe et al. |
| 5,641,654 | A | 6/1997 | Maki et al. |
| 5,645,983 | A | 7/1997 | Liao et al. |
| 5,654,179 | A | 8/1997 | Lin |
| 5,656,731 | A | 8/1997 | Urdea |

(Continued)

FOREIGN PATENT DOCUMENTS

CA 2012311 9/1990

(Continued)

OTHER PUBLICATIONS

Yanagi et al. (Virol. (1998) 244, 161-172.*

(Continued)

Primary Examiner—Zachariah Lucas
(74) Attorney, Agent, or Firm—Thompson Coburn LLP

(57) ABSTRACT

HCV variants are described. The variants include polynucleotides comprising non-naturally occurring HCV sequences and HCV variants that have a transfection efficiency and ability to survive subpassage greater than HCV that have wild-type polyprotein coding regions. Expression vectors comprising the above polynucleotides and HCV variants are also described, as are the provision of cells and host cells comprising the expression vectors. Methods for identifying a cell line that is permissive for infection with HCV are also provided, as are vaccines comprising the above polynucleotides in a pharmaceutically acceptable carrier. Additionally, methods for inducing immunoprotection to HCV in a primate are described, as are methods for testing a compound for inhibiting HCV replication.

3 Claims, 11 Drawing Sheets

U.S. PATENT DOCUMENTS

Figure 1:
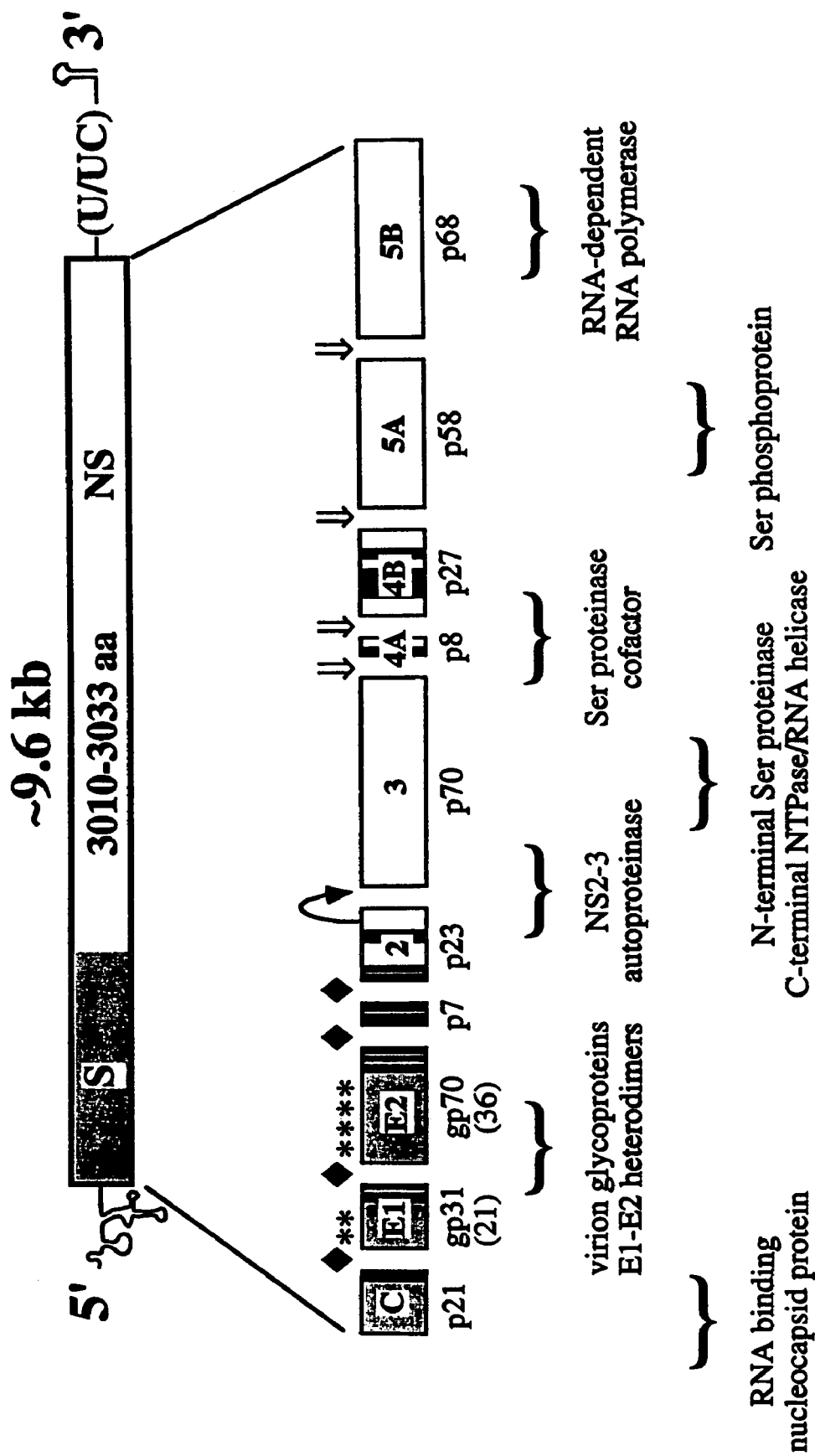

| | | | |
|---|---|---|---|
| 5,667,992 | A | 9/1997 | Casey et al. |
| 5,670,152 | A | 9/1997 | Weiner et al. |
| 5,670,153 | A | 9/1997 | Weiner et al. |
| 5,677,124 | A | 10/1997 | DuBois et al. |
| 5,679,342 | A | 10/1997 | Houghton et al. |
| 5,683,864 | A | 11/1997 | Houghton et al. |
| 5,698,390 | A | 12/1997 | Houghton et al. |
| 5,712,088 | A | 1/1998 | Houghton et al. |
| 5,714,596 | A | 2/1998 | Houghton et al. |
| 5,837,463 | A | 11/1998 | Tanaka et al. |
| 5,874,565 | A | 2/1999 | Rice et al. |
| 6,127,116 | A | 10/2000 | Rice et al. |
| 6,153,421 | A | 11/2000 | Yanagi et al. |
| 6,392,028 | B1 | 5/2002 | Rice et al. |
| 6,630,343 | B1 | 10/2003 | Bartenschlager |

FOREIGN PATENT DOCUMENTS

| | | |
|---|---|---|
| EP | 0 318 216 | 5/1989 |
| EP | 0 388 232 | 9/1990 |
| EP | 0 510 952 | 10/1992 |
| EP | 0 521 318 | 1/1993 |
| EP | 0 645 451 A1 | 3/1995 |
| EP | 1 267 167 | 12/2002 |
| GB | 2212511 | 7/1989 |
| JP | 6105690 | 4/1994 |
| WO | WO 89/04669 | 6/1989 |
| WO | WO 90/11089 | 10/1990 |
| WO | WO 91/02820 | 3/1991 |
| WO | WO 91/15771 | 10/1991 |
| WO | WO 92/08734 | 5/1992 |
| WO | WO 93/00365 | 1/1993 |
| WO | WO 93/03186 | 2/1993 |
| WO | WO 93/19183 | 9/1993 |
| WO | WO 95/20660 | 8/1995 |

OTHER PUBLICATIONS

Pietschmann et al., "Persistent and transient replication of full-length hepatitis C virus genomes in cell culture," Journal of Virology, vol. 76, No. 8, pp. 4008-4021 (Apr. 2002).*
BLAST 2 sequences results: Sequence 1 length 1985 and Sequence 2, AJ242652.1.*
Bowie et al., Deciphering the Message in Protein Sequences: Tolerance to Amino Acid Substutitions, Science, vol. 247 No. 4948, pp. 1306-1310 (Mar. 1990).*
Heller et al., "An in vitro model of hepatitis C viron production," Proceedings of National Academy of Sciences, USA, vol. 102 No. 7, pp. 2579-2583 (Feb. 2005).*
Ikeda et al., "Selectable Subgenomic and Genome-Length Dicistronic RNAs Derived from an Infectious Molecular Clone of the HCV-N Strain Hepatatis C Virus Replicate Effciently in Cultured Huh7 Cells," Journal of Virology, vol. 76 No. 6, pp. 2997-3006 (Mar. 2002).*
Blight et al., Efficient replication of hepatatis C virus genotype 1s RNAs in cell culture, Mar. 2003, pp. 3181-3190, Journal Of Virology.
Friebe and Bartenschlager, Genetic analysis of Sequences in the 3' nontranslated reigon of hepatatis C virus that are important for RNA replication, J Virol, Jun. 2002, pp. 5326-5338.
Guo et al., Effect of alpha interferon on the hepatatis C virus replicon, J Virol, Sep. 2001, pp. 8516-8523.
Ito et al., The 3' untranslated region of hepatatis C virus RNA enhances translation from an internal ribsomal entry site, J Virol, Nov. 1998, pp. 8789-8796.
Murray et al., Persistent replication of hepatitis C virus replicons expressing the beta-lactamase reporter in subpopulations of highly permissive Huh7 cells, J Virol, 2003, pp. 2928-2935.
Yanagi et al., Transcripts from a single full-length cDNA clone of hepatitis C virus are infectious when directly transfected into the liver of a chimpanzee, Proc Natl Acad Sci USA, 1997, pp. 8738-8743.
Yi and Lemon, Adaptive mutations producing efficient replication of genotype 1a hepatitis D virus RNA in normal Huh7 cells, J Virol, Aug. 2004, pp. 7904-7915.
Yi and Lemon, 3' nonstranslated RNA signals required for replication of hepatitis C virus RNA, J Virol, Mar. 2003, pp. 3557-3568.
Verma et al., "Gene Therapy—Promises, Problems and Prospects", Nature, vol. 389, pp. 239-242 (1997).
Eck et al., "Gene-Based Therapy", The Pharmacological Basis of Therapeutics, Goodman and Gilman, Eds., pp. 77-101 (1996).
Orkin et al., "Report and Recommendations of the Panel to Assess the NIH Investment in Research on Gene Therapy", NIH (1995). Online at www.nih.gov/news/panelrep.html.
Houdebine, "Production of Pharmaceutical Proteins From Transgenic Animals", Journal of Biotechnology, vol. 34, pp. 269-287 (1994).
Lanford et al., "Advances in Model Systems for Hepatitis C Virus Research", Virology, vol. 293 No. 1, pp. 1-9 (Feb. 2002).
Zhu et al., "Replication of Hepatitis C Virus Subgenomes in Nonhepatic Epithelial and Mouse Hepatoma Cells", Journal of Virology, vol. 77 No. 17, pp. 9204-9210 (Sep. 2003).
Grobler et al., "Identification of a Key Determinant of Hepatitis C Virus Cell Culture Adaptation in Domain II of NS3 Helicase", The Journal of Biological Chemistry, vol. 278 No. 19, pp. 16741-16746 (May 2003).
Blight et al., "Highly Permissive Cell Lines for Subgenomic and Genomic Hepatits C Virus RNA Replication", Journal of Virology, vol. 76 No. 24, pp. 13001-13014 (Dec. 2002).
Chung et al., "Hepatiitis C virus replication is directly inhibited by IFN-alpha in a full-length binary expression system", Proceedings of the National Academy of Sciences, USA, vol. 98 No. 17, pp. 9847-9852 (Aug. 2001).
Bartenschlager et al., "Replication of the hepatitis C virsus in cell culture", Antiviral Research, vol. 60 No. 2, pp. 91-102 (Oct. 2003).
Patent Cooperation Treaty; International Search Report; Jan. 3, 2005.
Ahlquist et al., *Proc. Natl. Acad. Sci. USA* 81:7066-7070 (1984).
Barton and Flanegan, *J. Virol.* 67:822-831 (1993).
Ball, *J. Virol.* 66:2335-2345 (1992).
Battegay et al., *J. Virol* 69:2462-2470 (1995).
Behrens et al. *Embo. J.* 15:12022 (1996).
Blight and Gowans, *Viral Hepatatis Rev.* 1:143-155 (1995).
Blight et al., "Efficient Initiation of HCV RNA Replication in Cell Culture", *Science*, Dec. 8, 2000, vol. 290, pp. 1972-1974.
Blight et al., *Amer. J. Path.* 143:1568-1573 (1993).
Boyer and Haenni, *J. Gen. Virol.* 198:415-426 (1994).
Boyer et al., *J. Hepatol.* 32(1 Suppl.) 98-112 (2000).
Bredenbeek and Rice, *Semin. Virol.* 3:297-310 (1992).
Bredenbeek et al., *J. Virol.* 67:6439-6446 (1993).
Bresters et al., *J. Med. Virol.* 43:262-8 (1994).
Brown et al., *Bucl. Acids Res.* 20:5041-5045 (1992).
Bukh et al., *Proc. Natl. Acad. Sci. USA* 89:4942-4946 (1992).
Bukh et al., *Sem. Liver Dis.* 15:41-63 (1995).
Butkiewicz et al., *J. Virol.* 74, 4291-4301 (2000).
Carloni, et al., "Suspectibility of human liver cell cultures to hepatitis C virus infection", *Arch Virol* (1993) [Suppl] 8:31-39.
Carrick et al., *J. Virol. Meth.* 39:279-289 (1992).
Cha et al., *J. Clin. Microbiol.* 29:2528-34 (1991).
Chambers et al., *Virology* 177:159-174 (1990).
Chazouilleres et al., *Gastroenterology* 106:994-9 (1994).
Chen et al., *Nucleic Acids Res.* 22:2114-2120 (1994).
Chen et al., *Virology* 188:102-113 (1992).
Choo et al., *Proc. Natl. Acad. Sci. USA* 88:2451-5 (1991).
Choo et al., *Proc. Natl. Acad. Sci. USA* 91:1294-1298 (1994).
Choo et al. *Science* 244:359-362 (1989).
Clark et al., *Exp. Opin. Ther. Patents* 7(9):979-987 (1997).
Davis et al., *Hepatology* 19:1337-41 (1994).
Enomoto et al., *J. Hepatol.* 17:415-416 (1993).
Farci et al., *Science* 288:339-344 (2000).
Feinstone et al., *J. Infect Dis.* 144:588-498 (1981).
Feray et al., *Hepatology* 20:1137-43 (1994).
Filocamo et al., *J. Virol.* 71:1417-1427 (1997).
Fong et al, *Journal of Clinical Investigation* 88:1058-60 (1991).
Francki et al., *Arch Virol.* Suppl2:223 (1991).

Frolov et al., *J. Virol.*, vol. 73, Selection of RNA replicons capable of noncytopathic replication in mammalian cells; pp. 3854-3856; 1999.
Fukushi et al., *Biochem. Biophys. Res. Comm.* 199:425-432 (1994).
Furka et al., *14th Intl. Congress of Biochem.*, vol. 5, Abstract FR:013 (1998).
Furka, *Int. J. Peptide Protein Res.* 37:487-493 (1991).
Gale, et al., "Evidence That Hepatitis C Virus Resistance to Interferon Is Mediated Through Repression of the PKR Protein Kinase by the Nonstructural 5A Protein," *J. Virol* 230, 217-227 (1997), Article No. VY978493.
Ghosh et al., *J. Biol. Chem.* 275:7184-7188 (2000).
Gordon et al., *Am. J. Gastroenterol.* 89:1458-61 (1994).
Grakoui et al., *J. Virol.* 67:2832-2843 (1993a).
Grakoui et al., *Proc. Natl. Acad. Sci. USA* 90:10583-10587 (1993b).
Gunji et al., *Arch. Virol.* 134:293-302 (1994).
Hahm et al., *Virology* 226:318-326 (1996).
Hahn et al. Conserved Elements in the 3' Untranslated Region of Flavivirus RNAs and Potential Cyclization Sequences, *J. of Mol. Bio.* 198:33-41 (1987).
Han et al., *Nuc. Acids Res.* 20:3520 (1992).
Han et al., *Proc. Natl. Acad. Sci. USA* 88:1711-1715 (1991).
He et al. *J. Infect. Dis.* 156:636-640 (1987).
Hijikata et al. *Biochem. Biophys. Res. Comm.* 175:220-228 (1991).
Hijikata et al., *J. Virol.*, 67, 1953-1958 (1993).
Honda et al. *J. Virol.* 73:4941-4951 (1999).
Houghton et al. *Curr. Stud Hematol. Blood Transfus* 61:1-11 (1994).
Houghton, In *"Fields Virology"* (B.N. Fields, D.M. Knipe and P.M. Howley, Eds.), vol. pp. 1035-1058, Raven Press, New York (1996).
Hutchison et al., *Proc. Nat'l. Acad. Sci.* USA 83:710 (1986).
Hwang et al., *Virology* 227:438 (1997).
Inchauspe et al., *Proc. Natl. Acad. Sci. USA* 88:10292-6 (1991).
Ito et al., *J. Gen. Virol.* 77:1043-1054 (1996).
Jang et al., *Enzyme* 44:292-309 (1991).
Jansen et al. Virology, vol. 163, Complete nucleotide sequence of a cell culture-adapted variant of hepatitis A virus: comparison with wild-type virus with restricted capacity for in vitro replication, pp. 299-307, 1988.
Jin and Peterson, *Arch Biochem. Biophys.* 323:47-53 (1995).
Kanai et al., *FEBS Lett.* 376:221-4 (1995).
Kato et al., *Biochem. Biophys. Res. Comm.* 189:119-127 (1992).
Kato et al., *J. Virol.* 67:3923-3930 (1993).
Kim et al., *Biochem. Biophys. Res. Commun.* 215:160-6 (1995).
Kolykhalov et al., *J. Virol.* 68:7525-7533 (1944).
Kolykhalov et al., *J. Virol.* 70:3363-3371 (1996).
Kolykhalov et al., *Science* 277:570 (1997).
Koziel et al., *J. Clin. Invest.* 96:2311-21 (1995).
Krieger et al., *J. Virol.*, vol. 75, Enhancement of Hepatitis C Virus RNA replication by cell culture-adaptive mutations, pp. 4616-4624, 2001.
Kurosaki et al., *Hepatology* 18:1293-1299 (1993).
Lai, *Hepatology* 27:299-302 (1998).
Lanford et al., *Virology* 202:606-14 (1994).
Lemm and Rice, *J. Virol.* 67:1905-1915 (1993).
Lemm et al., *EMBO J.* 13: 2925-2934 (1994).
Lesniewski et al., *J. Med. Virol.* 40:150-156 (1993).
Lewin, When does homology mean something else, *Science* 237:1570 1987.
Lin and Rice, *Proc. Natl. Acad. Sci. USA* 92:7622-7626 (1995).
Lin et al., *J. Virol.* 68: 5063-5073 (1994).
Lin et al., *J Virol.* 68:5063-5037 (1994a).
Lin et al. *J. Virol.* 68:8147-8157 (1994b).
Lin et al., *J. Virol.* 69:4373-4380 (1995).
Lohmann et al. *Science* 285:110-113 (1999).
Lohmann et al., *J. Virol.*, vol. 75, Mutations in Hepatitis C Virus RNAs conferring cell culture adaptation, pp. 1437-1449, 2001.
Lu and Wimmer, *Proc. Natl. Acad. Sci. USA* 93: 1412-1417 (1996).
Lundkvist et al., *J. of Virol.*, vol. 71, Cell culture adaption of puumala hantavirus changes the infectivity for its natural reservoir, Clethrionomys glareolus, and leads to accumlation of mutants with altered genomic RNA S Segment, pp. 9515-9523, 1997.
Macejak et al., *Hepatology* 31:769-776 (2000).
Mandl et al., *Biotechniques* 10:486 1991.
Martell et al., *J. Virol.* 66:3225-3229 (1992).
Martell et al., *J. Virol.* 68: 3425-3436 (1994).
Matsumoto et al., *J. Virol.* 71:1301-1309 (1997).
Mizushima et al., *J. Virol.* 68:6215-6222 (1994).
Mizutani et al., *J. Virol*, 70: 7219-7223 (1996).
Mizutani et al., *Biochem. Biophys. Res. Comm.* 227:822-826 (1996a).
Mizutani et al., *J. Virol.* 70:7219-23 (1996).
Molla et al., *Nature* 356: 255-257 (1992).
Nakajima et al. *J. Virol.* 70:3325-3329 (1996).
Ogata et al., *Proc. Natl. Acad. Sci. USA* 88:3392-3396 (1991).
Okamoto et al., *J. Gen. Virol.* 72:2697-2704 (1991).
Okamoto et al., *J. Gen. Virol.* 75:629-635 (1994).
Okamoto et al., *Virology* 190:894-899 (1992).
Pattnaik et al., *Cell* 69:1011-1020 (1992).
Pileri et al., *Science* 282:938-941 (1998).
Purcell, *Hepatology* 26:11S-14S (1997).
Ray et al., *J. Virol.* 70:4438-4443 (1996a).
Ray et al., *Virol.* 226:176-182 (1996b).
Ray et al., *Virus Res.* 37:209-220 (1995).
Reeck et al., "Homology" in proteins and nucleic acids: A terminology muddle and a way out of it, *Cell* 50:667 1987.
Reed et al., *J. Virol.* 69:4127-4136 (1995).
Rice et al., *J. Virol.* 61: 3908-3819 (1987).
Rice et al., *New Biol.* 1:285-296 (1989).
Rice, *In "Fields Virology"* (B.N. Fields, D.M. Knipe and P.M. Howley, Eds.), vol. pp. 931-960, Raven Press, New York (1996).
Sakamoto et al., *J. Gen. Virol.* 75:1761-1768 (1994).
Sakamuro et al., *J. Virol.* 69:3893-6 (1995).
Selby et al., Expression, identification and subcellular localization of the proteins encoded by the hepatitis C viral genome, J. Gen. Virol. 74:1103-1113 1993.
Selby et al., *Virology* 204:114-122 (1994).
Shih et al., *J. Virol.* 67:5823-5832 (1993).
Shih et al., *J. Virol.* 69:1160-1171 (1995).
Shimizu and Yoshikura, *J. Virol.* 68:8406-8408 (1994).
Shimizu et al., *J. Virol.* 68:1494-1500 (1994).
Shimizu et al., *Proc. Natl. Acad. Sci. USA* 87:6441-6444 (1990).
Shimizu et al., *Proc. Natl. Acad. Sci. USA* 89:5477-5481 (1992).
Shimizu et al., *Proc. Natl. Acad. Sci. USA* 90:6037-6041 (1993).
Shimotohno et al., *J. Hepatol.* 22:87-92 (1995) (Suppl. 1).
Shimotohno, *Hepatol.* 21:887-8 (1995).
Simmonds et al., *Hepatology* 19:1321-1324 (1994).
Simmonds et al., *J. Gen. Virol.* 75:1053-1061 (1994).
Simmonds, *Hepatology* 21:570-83 (1995).
Sullenger et al., *Cell* 63:601-608 (1990).
Suzich et al., *J. Virol.* 67:6152-6158 (1993).
Tagawa, *J. Gastroenterol. And Hepatol.*, 10:523-527 (1995).
Tanaka et al., *Biochem. Biophys. Res. Comm.* 215:744-749 (1996).
Tanaka et al., *J. Virol.* 70:3307-3315 (1996).
Tanji et al., *J. Virol.* 69:3980-3986 (1995).
Thomssen et al., *Med. Microbiol. Immmunol. 181*:293-300 (1992).
Tokita et al., *J. Gen. Virol.* 75:931-936 (1994).
Tokita et al., *J. Gen. Virol.* 77:293-303 (1996).
Trowbridge et al., *Arch Virol.* 143:501-511 (1998).
Tsukiyama-Kohara et al., *J. Virol.* 66:1476-1473 (1992).
Umlauft et al., *J. Clin. Microbiol.* 34:2552-2558 (1996).
Wang et al., *J. Virol.* 67:3338-3344 (1993).
Weiner et al., *Proc. Natl. Acad. Sci. USA* 89:3468-3472 (1992).
Weiner et al., *Virology* 180:842-848 (1991).
Wright et al., *Hepatology* 20:773-9 (1994).
Yamada et al., *Virology* 223:255-261 (1996).
Yanagi et al., *Virology* 244:161-172 (1999).
Yanagi et al., *Virology* 262:250-263 (1999).
Yoo et al., *J. Virol.* 69:32-38 (1995).
Yoo et al., *Virology* 191:889-899 (1992).

* cited by examiner

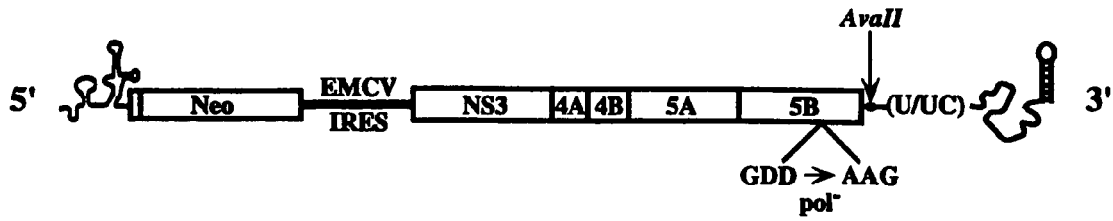

- DNase digest RNA transcripts
- Electroporate RNA into Huh7 cells
- G418-resistant colonies were generated at low frequency
- 28 colonies were picked & 90% of these could be passaged
- No colonies observed for the replicon RNA containing an inactive RDRP

| Clone | Copy number/cell | Cytoplasmic NS3 | Growth Rate |
|---|---|---|---|
| I | >1000 | Yes | Fast |
| II | ~1000-5000 | Yes | Fast |
| IV | ND | Yes | Fast |
| V | 500 | ND | Moderate |
| VI | ~1000 | Yes | Fast |
| VII | >800 | Yes | Fast |
| Clone E | <400 | No | Very slow |

Figure 4

| aa 1163 | | | | | | | | | | | | | | | | | | 1182 | | 1229 |
|---|---|---|---|---|---|---|---|---|---|---|---|---|---|---|---|---|---|---|---|---|
| Arg CGT | Arg AGG | Leu CTG | Ala GCC | Arg AGG | Gly GGA | Ser TCT | Pro CCC | Pro CCC | Ser TCC | Leu TTG | Ala GCC | Ser AGC | Ser TCA | Ser TCA | Ala GCT | Ser AGC | Gln CAG | Leu CTG | Ser TCT | Asp GAC |
| I | ... | ... | ... | ... | ... | ... | ... | ... | ... | ... | ... | ... | ... | ... | ... | ... | ... | ... | ... Tyr ⟋⟋ Δ47aa | ... |
| II | Gly GGG | ... | ... | ... | ... | ... | ... | ... | ... | ... | ... | ... | ... | ... | ... | ... | ... | ... | ⟋⟋ | ... |
| III | ... | ... | ... | ... | ... | ... | Pro CCC | ... | ... | ... | ... | ... | ... | ... | ... | ... | ... | ... | ⟋⟋ | ... |
| IV | ... | ... | ... | ... | ... | ... | Cys TGC | ... | ... | ... | ... | ... | ... | ... | ... | ... | ... | ... | ⟋⟋ | ... |
| V | ... | ... | ... | ... | ... | ... | ... | ... | Ser TCC | ... | ... | ... | ... | ... | ... | ... | ... | ... | ⟋⟋ | ... |
| VI/VII | ... | ... | ... | ... | ... | ... | ... | ... | ... | ... | ... | ... | ... | ... | Ile ATC | ... | ... | ... | ⟋⟋ | ... |

Figure 7

HCV VARIANTS

CROSS-REFERENCE TO RELATED APPLICATIONS

This application is the national stage application of PCT Patent Application No. PCT/US2001/016822, filed May 23, 2001, which is a continuation-in-part of U.S. patent application Ser. No. 09/576,989, filed May 23, 2000, now U.S. Pat. No. 7,049,428, which is a continuation-in-part of U.S. patent application Ser. No. 09/034,756, filed Mar. 4, 1998, now U.S. Pat. No. 6,392,028, which is a continuation of U.S. patent application Ser. No. 08/811,566, filed Mar. 4, 1997, now U.S. Pat. No. 6,127,116, and which claims priority to U.S. Provisional Application No. 60/039,843, filed Mar. 4, 1997.

REFERENCE TO GOVERNMENT GRANT

This invention was made with government support under Public Health Service Grants CA 57973 and AI 40034. The government has certain rights in this invention.

BACKGROUND OF THE INVENTION

(1) Field of the Invention

The invention relates to materials and methodologies relating to the production and use of hepatitis C virus (HCV) variants. More specifically, HCV variants are provided that are useful for diagnostic, therapeutic, vaccines and other uses.

(2) Description of the Related Art

Brief General Overview of Hepatitis C Virus

After the development of diagnostic tests for hepatitis A virus and hepatitis B virus, an additional agent, which could be experimentally transmitted to chimpanzees [Alter et al., *Lancet* 1, 459-463 (1978); Hollinger et al., *Intervirology* 10, 60-68 (1978); Tabor et al., *Lancet* 1, 463-466 (1978)], became recognized as the major cause of transfusion-acquired hepatitis. cDNA clones corresponding to the causative non-A non-B (NANB) hepatitis agent, called hepatitis C virus (HCV), were reported in 1989 [Choo et al., *Science* 244, 359-362 (1989)]. This breakthrough has led to rapid advances in diagnostics, and in our understanding of the epidemiology, pathogenesis and molecular virology of HCV (For review, see Houghton et al., *Curr Stud Hematol Blood Transfus* 61, 1-11 (1994); Houghton (1996), pp. 1035-1058 in FIELDS VIROLOGY, Fields et al., Eds., Raven Press, Philadelphia; Major et al., *Hepatology* 25, 1527-1538 (1997); Reed and Rice, pp. 1-37 in HEPATITIS C VIRUS, Reesink, Ed., Karger, Basel; Hagedorn and Rice (1999), THE HEPATITIS C VIRUSES, Springer, Berlin). Evidence of HCV infection is found throughout the world, and the prevalence of HCV-specific antibodies ranges from 0.4-2% in most countries to more than 14% in Egypt [Hibbs et al., *J. Inf. Dis.* 168, 789-790 (1993)]. Besides transmission via blood or blood products, or less frequently by sexual and congenital routes, sporadic cases, not associated with known risk factors, occur and account for more than 40% of HCV cases [Alter et al., *J. Am. Med. Assoc.* 264, 2231-2235 (1990); Mast and Alter, *Semin. Virol.* 4, 273-283 (1993)]. Infections are usually chronic [Alter et al., *N. Eng. J. Med.* 327, 1899-1905 (1992)], and clinical outcomes range from an inapparent carrier state to acute hepatitis, chronic active hepatitis, and cirrhosis which is strongly associated with the development of hepatocellular carcinoma.

Although interferon (IFN)-α has been shown to be useful for the treatment of a minority of patients with chronic HCV infections [Davis et al., *N. Engl. J. Med.* 321, 1501-1506 (1989); DiBisceglie et al., *New Engl. J. Med.* 321, 1506-1510 (1989)] and subunit vaccines show some promise in the chimpanzee model [Choo et al., *Proc. Natl. Acad. Sci. USA* 91, 1294-1298 (1994)], future efforts are needed to develop more effective therapies and vaccines (See, e.g., Tsambiras et al., 1999, Hepatitis C: Hope on the Horizon, Hepatitis C Symposium of $37^{th}$ Annual Meeting of the Infectious Diseases Society of America, reviewed at http://www.medscape.com/medscape/cno/1999/IDSA/Story.cfm-?story_id=913). The considerable diversity observed among different HCV isolates [for review, see Bukh et al., *Sem. Liver Dis.* 15, 41-63 (1995); Fanning et al., 2000, *Medscape Gastroenterology* 2:mgi6558.fann], the emergence of genetic variants in chronically infected individuals [Enomoto et al., *J. Hepatol.* 17, 415-416 (1993); Hijikata et al., *Biochem. Biophys. Res. Comm.* 175, 220-228 (1991); Kato et al., *Biochem. Biophys. Res. Comm.* 189, 119-127 (1992); Kato et al., *J. Virol.* 67, 3923-3930 (1993); Kurosaki et al., *Hepatology* 18, 1293-1299 (1993); Lesniewski et al., *J. Med. Virol.* 40, 150-156 (1993); Ogata et al., *Proc. Natl. Acad. Sci. USA* 88, 3392-3396 (1991); Weiner et al., *Virology* 180, 842-848 (1991); Weiner et al., *Proc. Natl. Acad. Sci. USA* 89, 3468-3472 (1992)], and the lack of protective immunity elicited after HCV infection [Farci et al., *Science* 258, 135-140 (1992); Prince et al., *J. Infect. Dis.* 165, 438-443 (1992)] present major challenges towards these goals.

Molecular Biology of HCV

Classification. Based on its genome structure and virion properties, HCV has been classified as a separate genus in the flavivirus family, which includes two other genera: the flaviviruses (e.g., yellow fever (YF) virus) and the animal pestiviruses (e.g., bovine viral diarrhea virus (BVDV) and classical swine fever virus (CSFV)) [Francki et al., *Arch. Virol. Suppl.* 2, 223 (1991)]. All members of this family have enveloped virions that contain a positive-strand RNA genome encoding all known virus-specific proteins via translation of a single long open reading frame (ORF).

Structure and physical properties of the virion. Studies on the structure and physical properties of the HCV virion have been hampered by the lack of a cell culture system able to support efficient virus replication and the typically low titers of infectious virus present in serum. The size of infectious virus, based on filtration experiments, is between 30-80 nm [Bradley et al., *Gastroenterology* 88, 773-779 (1985); He et al., *J. Infect. Dis.* 156, 636-640 (1987); Yuasa et al., *J. Gen. Virol.* 72, 2021-2024 (1991)]. Initial measurements of the buoyant density of infectious material in sucrose yielded a range of values, with the majority present in a low density pool of <1.1 g/ml [Bradley et al., *J. Med. Virol.* 34, 206-208 (1991)]. Subsequent studies have used RT/PCR to detect HCV-specific RNA as an indirect measure of potentially infectious virus present in sera from chronically infected humans or experimentally infected chimpanzees. From these studies, it has become increasingly clear that considerable heterogeneity exists between different clinical samples, and that many factors can affect the behavior of particles containing HCV RNA [Hijikata et al., *J. Virol.* 67, 1953-1958 (1993); Thomssen et al., *Med. Microbiol. Immunol.* 181, 293-300 (1992)]. Such factors include association with immunoglobulins [Hijikata et al., (1993) supra] or low density lipoprotein [Thomssen et al., 1992, supra; Thomssen et al., *Med. Microbiol. Immunol.* 182, 329-334 (1993)]. In highly infectious acute phase chimpanzee serum, HCV-specific RNA is usually detected in fractions of low buoyant density (1.03-1.1 g/ml) [Carrick et al., *J. Virol. Meth.* 39, 279-289 (1992); Hijikata et al., (1993) supra]. In other samples, the presence of HCV antibodies and formation of immune complexes correlate with particles of higher density and lower infectivity [Hijikata et al., (1993) supra]. Treatment of particles with chloroform, which destroys infectivity [Bradley et al., *J. Infect. Dis.* 148, 254-265 (1983); Feinstone et al., *Infect. Immun.* 41, 816-821 (1983)], or with nonionic detergents, produced RNA containing particles of higher density (1.17-1.25 g/ml) believed to represent HCV nucleocapsids [Hijikata et al., (1993) supra; Kanto et al., *Hepatology* 19, 296-302 (1994); Miyamoto et al., *J. Gen Virol.* 73, 715-718 (1992)].

There have been reports of negative-sense HCV-specific RNAs in sera and plasma [see Fong et al., *Journal of Clinical Investigation* 88:1058-60 (1991)]. However, it seems unlikely that such RNAs are essential components of infectious particles since some sera with high infectivity can have low or undetectable levels of negative-strand RNA [Shimizu et al., *Proc. Natl. Acad. Sci. USA* 90: 6037-6041 (1993)].

The virion protein composition has not been rigorously determined, but HCV structural proteins include a basic C protein and two membrane glycoproteins, E1 and E2.

HCV replication. Early events in HCV replication are poorly understood. A hepatocyte receptor may be CD81, which binds the E2 envelope glycoprotein (Peleri et al., 1998, *Science* 282:938-41). The association of some HCV particles with beta-lipoprotein and immunoglobulins raises the possibility that these host molecules may modulate virus uptake and tissue tropism.

Studies examining HCV replication have been largely restricted to human patients or experimentally inoculated chimpanzees. In the chimpanzee model, HCV RNA is detected in the serum as early as three days post-inoculation and persists through the peak of serum alanine aminotransferase (ALT) levels (an indicator of liver damage) [Shimizu et al., *Proc. Natl. Acad. Sci. USA* 87: 6441-644 (1990)]. The onset of viremia is followed by the appearance of indirect hallmarks of HCV infection of the liver. These include the appearance of a cytoplasmic antigen [Shimizu et al., (1990) supra] and ultrastructural changes in hepatocytes such as the formation of microtubular aggregates for which HCV previously was referred to as the chloroform-sensitive "tubule forming agent" or "TFA" [reviewed by Bradley, *Prog. Med. Virol.* 37: 101-135 (1990)]. As shown by the appearance of viral antigens [Blight et al., *Amer. J. Path.* 143: 1568-1573 (1993); Hiramatsu et al., *Hepatology* 16: 306-311 (1992); Krawczynski et al., *Gastroenterology* 103: 622-629 (1992); Yamada et al., *Digest. Dis. Sci.* 38: 882-887 (1993)] and the detection of positive and negative sense RNAs [Fong et al., (1991) supra; Gunji et al., *Arch. Virol.* 134: 293-302 (1994); Haruna et al., *J. Hepatol.* 18: 96-100 (1993); Lamas et al., *J. Hepatol.* 16: 219-223 (1992); Nouri Aria et al., *J. Clin. Inves.* 91: 2226-34 (1993); Sherker et al., *J. Med. Virol.* 39: 91-96 (1993); Takehara et al., *Hepatology* 15: 387-390 (1992); Tanaka et al., *Liver* 13: 203-208 (1993)], hepatocytes appear to be a major site of HCV replication, particularly during acute infection [Negro et al., *Proc. Natl. Acad. Sci. USA* 89: 2247-2251 (1992)]. In later stages of HCV infection the appearance of HCV-specific antibodies, the persistence or resolution of viremia, and the severity of liver disease, vary greatly both in the chimpanzee model and in human patients (Fanning et al., supra). Although some liver damage may occur as a direct consequence of HCV infection and cytopathogenicity, the emerging consensus is that host immune responses, in particular virus-specific cytotoxic T lymphocytes, may play a more dominant role in mediating cellular damage.

It has been speculated that HCV may also replicate in extra-hepatic reservoir(s). In some cases, RT/PCR or in situ hybridization has shown an association of HCV RNA with peripheral blood mononuclear cells including T-cells, B-cells, and monocytes [reviewed in Blight and Gowans, *Viral Hepatitis Rev.* 1: 143-155 (1995)]. Such tissue tropism could be relevant to the establishment of chronic infections and might also play a role in the association between HCV infection and certain immunological abnormalities such as mixed cryoglobulinemia [reviewed by Ferri et al., *Eur. J. Clin. Invest.* 23: 399-405 (1993)], glomerulonephritis, and rare non-Hodgkin's B-lymphomas [Ferri et al., (1993) supra; Kagawa et al., *Lancet* 341: 316-317 (1993)]. However, the detection of circulating negative strand RNA in serum, the difficulty in obtaining truly strand-specific RT/PCR [Gunji et al., (1994) supra], and the low numbers of apparently infected cells have made it difficult to obtain unambiguous evidence for replication in these tissues in vivo.

Genome structure. Full-length or nearly full-length genome sequences of numerous HCV isolates have been reported [see, e.g., Lin et al., *J. Virol.* 68: 5063-5073 (1994a); Okamoto et al., *J. Gen. Virol.* 75: 629-635 (1994); Sakamoto et al., *J. Gen. Virol.* 75: 1761-1768 (1994); Trowbridge et al., *Arch Virol.* 143:501-511 (1998); Chamberlain et al., *J. Gen. Virol.* 78:1341-1347 (1997); and citations within Davis, *Am. J. Med.* 27:21S-26S]. HCV genome RNAs are ~9.6 kilobases (kb) in length (FIG. 1) and consist of a 5' nontranslated region (5' NTR), a polyprotein coding region consisting of a single long open reading frame (ORF), and a 3' NTR. The 5' NTR is 341-344 bases long and highly conserved. The length of the long ORF varies slightly among isolates, encoding polyproteins of about 3010 to about 3033 amino acids.

The 3' NTR can be divided into three domains. The first (most 5') domain shows considerable diversity both in composition and length (28-42 bases). Recent work by Yanagi et al. [Proc. Natl. Acad. Sci. USA 96:2291-2295 (1999)] demonstrate that this region is not necessary for virus replication. The second domain consists of a variable length polypyrimidine region of poly(A) (in at least HCV-1, type 1a [Han et al., *Proc. Natl. Acad. Sci. USA* 88:1711-1715 (1991)]) or poly(U-UC) (see Chen et al., *Virology* 188:102-113 (1992); Okamoto et al., *J. Gen. Virol.* 72:2697-2704 (1991); Tokita et al., *J. Gen. Virol.* 66:1476-83 (1994)]. The third domain, at the extreme 3' end of the genome, is a highly conserved, novel RNA element of about 98 nucleotides, which is necessary for efficient initiation of viral RNA replication [see, e.g., U.S. Pat. No. 5,874,565 and U.S. patent application Ser. No. 08/811,566 (Now U.S. Pat. No. 6,127,116); Kolykhalov et al., *J. Virol.* 70: 3363-3371 (1996); Tanaka et al., *Biochem. Biophys. Res. Comm.* 215: 744-749 (1996); Tanaka et al., *J. Virol.* 70:3307-12 (1996); Yamada et al., *Virology* 223:255-261 (1996); Cheng et al. *J. Virol.* 73:7044-7049]. This domain and the polypyrimidine regions appear to be critical for infectivity in vivo [Yanagi et al., *Proc. Natl. Acad. Sci. USA* 96:2291-2295 (1999)].

Translation and proteolytic processing. The highly conserved 5' NTR sequence contains multiple short AUG-initiated ORFs and shows significant homology with the 5' NTR region of pestiviruses [Bukh et al., *Proc. Natl. Acad.*

Sci. USA 89: 4942-4946 (1992); Han et al., (1991) supra]. A series of stem-loop structures that interact with host factors are present. These structures interact with host factors to initiate polyprotein synthesis through an internal ribosome entry site (IRES) allowing efficient translation initiation at the first AUG of the long ORF [Honda et al., *J. Virol* 73:4941-4951 (1999); Tang et al., *J. Virol.* 73:2359-2364 (1999); Psaridi et al., *FEBS Lett.* 453:49-53 (1999)]. Some of the predicted features of the HCV and pestivirus IRES elements are similar to one another [Brown et al., (1992) supra]. The ability of this element to function as an IRES suggests that HCV genome RNAs may lack a 5' cap structure.

The organization and processing of the HCV polyprotein (FIG. 1) appears to be most similar to that of the pestiviruses. At least 10 polypeptides have been identified and the order of these cleavage products in the polyprotein is NH2-C-E1-E2-p7-NS2-NS3-NS4A-NS4B-NS5A-NS5B-COOH. As shown in FIG. 1, proteolytic processing is mediated by host signal peptidase and two HCV-encoded proteinases, the NS2-3 autoproteinase and the NS3-4A serine proteinase [see Rice, In "Fields Virology" (B. N. Fields, D. M. Knipe and P. M. Howley, Eds.), Vol. pp. 931-960. Raven Press, New York (1996); Shimotohno et al., *J. Hepatol.* 22: 87-92 (1995) for reviews]. C is a basic protein that serves as the viral core or capsid protein; E1 and E2 are virion envelope glycoproteins; p7 is a hydrophobic protein of unknown function that is inefficiently cleaved from the E2 glycoprotein [Lin et al., (1994a) supra; Mizushima et al., *J. Virol.* 68: 6215-6222 (1994); Selby et al., *Virology* 204: 114-122 (1994)]. NS2-NS5B are nonstructural (NS) proteins which function in viral RNA replication complexes. Their functions have been identified as follows: NS2 is a metalloprotease; NS3 is a protease/helicase that contains motifs characteristic of RNA helicases and that has been shown to possess an RNA-stimulated NTPase activity [Suzich et al., *J. Virol.* 67, 6152-6158 (1993)]; NS4A is a co-factor for NS3; NS4B is of unknown function; NS5A interacts with cellular factors to transcriptionally modulate cellular genes and promote cell growth [Ghosh et al., *J. Biol. Chem.* 275:7184-7188] and provide IFNα resistance; and NS5B is a replicase that contains the GDD motif characteristic of the RNA-dependent RNA polymerases of other positive-strand RNA viruses.

Virion assembly and release. This process has not been examined directly, but the lack of complex glycans, the ER localization of expressed HCV glycoproteins [Dubuisson et al., *J. Virol.* 68: 6147-6160 (1994); Ralston et al., *J. Virol.* 67: 6753-6761 (1993)] and the absence of these proteins on the cell surface [Dubuisson et al., (1994) supra; Spaete al., *Virology* 188: 819-830 (1992)] suggest that initial virion morphogenesis may occur by budding into intracellular vesicles. Thus far, efficient particle formation and release has not been observed in transient expression assays, suggesting that essential viral or host factors are absent or blocked. HCV virion formation and release may be inefficient, since a substantial fraction of the virus remains cell-associated, as found for the pestiviruses. Extracellular HCV particles partially purified from human plasma contain complex N-inked glycans, although these carbohydrate moieties were not shown to be specifically associated with E1 or E2 [Sato et al., *Virology* 196: 354-357 (1993)]. Complex glycans associated with glycoproteins on released virions would suggest transit through the trans-Golgi and movement of virions through the host secretory pathway. If this is correct, intracellular sequestration of HCV glycoproteins and virion formation might then play a role in the establishment of chronic infections by minimizing immune surveillance and preventing lysis of virus-infected cells via antibody and complement.

Genetic variability. As for all positive-strand RNA viruses, the RNA-dependent RNA polymerase of HCV (NS5B) is believed to lack a 3'-5' exonuclease proofreading activity for removal of misincorporated bases. Replication is therefore error-prone, leading to a "quasi-species" virus population consisting of a large number of variants [Martell et al., *J. Virol.* 66: 3225-3229 (1992); Martell et al., *J. Virol.* 68: 3425-3436 (1994)]. This variability is apparent at multiple levels. First, in a chronically infected individual, changes in the virus population occur over time [Ogata et al., (1991) supra; Okamoto et al., *Virology* 190: 894-899 (1992)]; and these changes may have important consequences for disease. A particularly interesting example is the N-terminal 30 residue segment of the E2 glycoprotein, which exhibits a much higher degree of variability than the rest of the polyprotein [for examples, see Higashi et al., *Virology* 197, 659-668. 1993; Hijikata et al., (1991) supra; Weiner et al., (1991) supra]. There is accumulating evidence that this hypervariable region, called hypervariable region 1 (HVR1), perhaps analogous to the V3 domain of HIV-1 gp120, may be under immune selection by circulating HCV-specific antibodies [Kato et al., (1993) supra; Taniguchi et al., *Virology* 195: 297-301 (1993); Weiner et al., (1992) supra. In this model, antibodies directed against this portion of E2 may contribute to virus neutralization and thus drive the selection of variants with substitutions that permit escape from neutralization. This plasticity suggests that a specific amino acid sequence in the E2 hypervariable region is not essential for other functions of the protein such as virion attachment, penetration, or assembly. Genetic evolution of HVR1 within the first 4 months of infection has been correlated with the ability of a particular strain of the virus to cause chronic infection [Farci et al., *Science* 288:339-344 (2000)].

Genetic variability may also contribute to the spectrum of different responses observed after IFN-α treatment of chronically infected patients. Diminished serum ALT levels and improved liver histology, which usually correlates with a decrease in the level of circulating HCV RNA, is seen in ~40% of those treated [Greiser-Wilke et al., *J. Gen. Virol.* 72: 2015-2019 (1991)]. After treatment, approximately 70% of the responders relapse. In some cases, after a transient loss of circulating viral RNA, renewed viremia is observed during or after the course of treatment. While this might suggest the existence or generation of IFN-resistant HCV genotypes or variants, further work is needed to determine the relative contributions of virus genotype and host-specific differences in immune response.

Sequence comparisons of different HCV isolates around the world have also revealed enormous genetic diversity [reviewed in Bukh et al., (1995) supra]. Because of the lack of biologically relevant serological assays such as cross-neutralization tests, HCV types (designated by numbers), subtypes (designated by letters), and isolates are currently grouped on the basis of nucleotide or amino acid sequence similarity. Worldwide, HCV has been classified into six major genotypes and more than 50 subtypes [Purcell, *Hepatology* 26:11S-14S (1997)]. Those of greatest importance in the U.S. are genotype 1, subtypes 1a and 1b (see below and Bukh et al., (1995) supra for a discussion of genotype prevalence and distribution). Amino acid sequence similarity between the most divergent genotypes can be a little as ~50%, depending upon the protein being compared. This diversity has important biological implications, particularly for diagnosis, vaccine design, and therapy.

HCV RNA replication. By analogy with other flaviviruses, replication of the positive-sense HCV virion RNA is thought to occur via a minus-strand intermediate. This strategy can be described briefly as follows: (i) uncoating of the incoming virus particle releases the genomic plus-strand, which is translated to produce a single long polyprotein that is probably processed co- and post-translationally to produce individual structural and nonstructural proteins; (ii) the nonstructural proteins form a replication complex that utilizes the virion RNA as template for the synthesis of minus strands; (iii) these minus strands in turn serve as templates for synthesis of plus strands, which can be used for additional translation of viral protein, minus strand synthesis, or packaging into progeny virions. Very few details about HCV replication process are available, due to the lack of a good experimental system for virus propagation. Detailed analyses of authentic HCV replication and other steps in the viral life cycle would be greatly facilitated by the development of an efficient system for HCV replication in cell culture.

Many attempts have been made to infect cultured cells with serum collected from HCV-infected individuals, and low levels of replication have been reported in a number of cell types infected by this method, including B-cell [Bertolini et al., *Res. Virol.* 144:281-285 (1993); Nakajima et al., *I Virol.* 70:9925-9 (1996); Valli et al., *Res. Virol.* 146:285-288 (1995)]. T-cell (Kato et al., *Biochem. Biophys. Res. Commun.* 206:863-9 (1996); Mizutani et al., *Biochem. Biophys. Res. Comm.* 227:822-826; Mizutani et al., *J. Virol.* 70:7219-7223 (1996); Nakajima et al., (1996) supra; Shimizu and Yoshikura, *J Virol,* 68: 8406-8408 (1994); Shimizu et al., *Proc. Natl. Acad. Sci. USA,* 89: 5477-5481 (1992), Shimizu et al., *Proc. Natl. Acad. Sci. USA,* 90: *J. Gastroenterol. and Hepatol.,* 10: 523-527 (1995)] cell lines, as well as peripheral blood monocular cells (PBMCs) [Cribier et al., *J. Gen. Virol.,* 76: 2485-2491 (1995)], and primary cultures of human fetal hepatocytes [Carloni et al., *Arch. Virol. Suppl.* 8: 31-39 (1993); Cribier et al., (1995) supra; Iacovacci et al., *Res. Virol.,* 144:275-279 (1993)] or hepatocytes from adult chimpanzees [Lanford et al., *Virology* 202:606-14 (1994)]. HCV replication has also been detected in primary hepatocytes derived from a human HCV patient that were infected with the virus in vivo prior to cultivation [Ito et al., *J. Gen. Virol.* 77:1043-1054 (1996)] and in the human hepatoma cell line Huh7 following transfection with RNA transcribed in vitro from an HCV-1 cDNA clone [Yoo et al., *J. Virol.,* 69: 32-38 (1995)]. The reported observation of replication in cells transfected with RNA derived from the HCV-1 clone was puzzling, since this clone lacks the required terminal 3 'NTR sequence downstream of the homopolymer tract (see below), and because a number of unusual observations were reported (see the background section of U.S. patent application Ser. No. 08/811,566 (Now U.S. Pat. No. 6,127,116)). The most well-characterized cell-culture systems for HCV replication utilize a B-cell line (Daudi) or T-cell lines persistently infected with retroviruses (HPB-Ma or MT-2) [Kato et al., (1995) supra; Mizutani et al., *Biochem Biophys Res. Comm.,* 227:822-826 (1996a); Mizutani et al., (1996) supra; Nakajima et al., (1996) supra; Shimizu and Yoshikura, (1994) supra]; Shimizu, Proc. Natl. Acad. Sci. USA, 90:6037-6041 (1993)]. HPBMa is infected with an amphotropic murine leukemia virus pseudotype of murine sarcoma virus, while MT-2 is infected with human T-cell lymphotropic virus type I (HTLV-I). Clones (HPBMa10-2 and MT-2C) that support HCV replication more efficiently than the uncloned population have been isolated for the two T-cell lines HPBMa and MT-2 [Mizutani et al. *J. Virol.* (1996) supra; Shimizu et al., (1993) supra]. However, the maximum levels of RNA replication obtained in these lines or in the Daudi lines after degradation of the input RNA is still only about $5 \times 10^4$ RNA molecules per $10^6$ cells [Mizutani et al., (1996) supra; Mizutani et al., (1996) supra] or $10^4$ RNA molecules per ml of culture medium [Nakajima et al., (1996) supra]. Although the level of replication is low, long-term infections of up to 198 days in one system [Mizutani et al., *Biochem. Biophys. Res. Comm.* 227: 822-826 (1996a)] and more than a year in another system [Nakajima et al., (1996) supra] have been documented, and infectious virus production has been demonstrated by serial cell-free or cell-mediated passage of the virus to naive cells.

However, efficient replication of an HCV clone comprising the essential conserved terminal 3 'NTR sequence had not been observed until the work described in co-pending application Ser. No. 08/811,566, now U.S. Pat. No. 6,127, 116, also reported in Kolykhalov et al., *Science* 2 77:570 (1997), which describes an infectious clone of an isolate of the H strain (type 1a). HCV clones of other subtypes are now known. See, e.g., Yanagi et al., *Virology* 262:250-263 (1999) and Yanagi et al., *Virology* 244:161-172 (1998). While RNA transcripts of these clones are able to infect chimpanzees, cell cultures with these clones only support replication of the virus poorly if at all.

As described in U.S. patent application Ser. No. 08/811, 566 (Now U.S. Pat. No. 6,127,116) (see, e.g., FIG. 2 therein) many variations of a functional clone are possible. These include full length or partial sequences where a foreign gene is inserted. The foreign gene can include, e.g., a reporter gene such as β-galactosidase or luciferase, or a gene encoding a selectable marker such as neo, DHFR, or tk. In a specific example disclosed therein, the neo gene is operably linked to an internal ribosome entry site (IRES), in order for infected cells to be selected by neomycin or G418 resistance. In this way, presence of replicating HCV RNA in essentially all surviving cells is assured. Additionally, the HCV polyprotein coding region of these clones can be deficient in some or all of the structural genes C, E1 and E2. Thus, replicons can be created without the production of virions. By combining the structural gene-deficient construct with a selectable marker such as neo, an efficiently replicating replicon system can be created that can be used to study HCV replication and for other purposes.

Examples of the replicons disclosed in U.S. patent application Ser. No. 08/811,566 (Now U.S. Pat. No. 6,127,116) is provided in Lohmann et al., *Science* 285:110-113 (1999). In that work, DNA clones of HCV replicons of genotype 1, subtype 1b were constructed. Features of those replicons that are not wild-type HCV features are: a polyprotein coding region lacking the genes encoding the HCV structural proteins; an EMCV IRES immediately 5' to the polyprotein region; and a neo gene immediately 3' to the 5' NTR (and the HCV IRES), where the 5' end of the HCV C protein gene is fused to the 5' end of the neo gene. When Huh-7 cells were transfected with RNA transcripts of these clones, 6 to >60 G418-resistant colonies arose per experiment. Although the number of cells treated was not specified, about $10^6$-$10^7$ cells are normally treated in experiments of this type. Therefore, it is believed that the transfection efficiency, as measured by G418-resistant colonies/total treated, was less than 0.01% in those studies.

Controls in the Lohmann et al. work included in-frame deletions of the active site of the NS5B polymerase. Although care was taken to remove template DNA from the control transcripts, several G418-resistant control colonies arose. Still, the number of G418-resistant control colonies that arose was much less than the colonies arising from the cells transfected with the replicons containing the wild-type NS5B.

When the G418-resistant colonies were subpassaged, most could not be maintained. Out of more than 303 G418-resistant colonies from non-control replicon treatments, 9 (<3%) could be subpassaged to establish stable cell lines. Replicons established in infected cell lines were sequenced. Although each replicon had a number of amino acid substitutions, the substitutions were scattered throughout the polyprotein coding region. Therefore, there were no mutations that were consistently in one area of the polyprotein coding region, and it was concluded that the establishment of the nine cell lines was not due to adaptive mutations in those replicons. This contention was experimentally tested by transfection/reconstitution experiments that did not provide evidence for adaptive changes.

Despite the advances described above, more efficient HCV-infected cell systems are needed for the production of concentrated virus stocks, structural analysis of virion components, evaluation of putative antiviral therapies including vaccines and antiviral compounds, and improved analyses of intracellular viral processes, including RNA replication. Thus, there is a need for various types of HCV clones that can be used for any of the above purposes. There is also a need to characterize HCV with respect to regions of the genome that might contribute to more efficient in vitro or in vivo replication and virion production.

SUMMARY OF THE INVENTION

Thus, a primary object of the present invention has been to provide DNA encoding non-naturally occurring HCV that is capable of replication.

A related object of the invention is to provide genomic RNA from the above DNA. Still another object of the invention is to provide attenuated HCV DNA or genomic RNA suitable for vaccine development, which can invade a cell and replicate but cannot propagate infectious virus.

Another object of the invention is to provide in vitro and in vivo models of HCV infection and RNA replication for testing anti-HCV (or antiviral) drugs, for evaluating drug resistance, and for testing attenuated HCV viral vaccines.

An additional object of the invention is to provide replicating HCV replicons. These replicons do not encode structural proteins but may encode a foreign protein such as a reporter gene or a selectable marker.

Still another object of the invention is to provide adaptive replicons, with increased ability to establish replication in continuous or primary cell lines.

Briefly, therefore, the inventors have succeeded in discovering methods of creating replicating HCV variants, including variants with adaptive mutations in HCV that improve their ability to establish RNA replication in culture to create continuous cell lines. These HCV variants and the cell lines that harbor them are useful for studying replication and other HCV characteristics. The cell lines are also useful for developing vaccines and for testing compounds for antiviral properties.

Thus, in some embodiments, the present invention is directed to a polynucleotide comprising a non-naturally occurring HCV sequence that is capable of productive replication in a host cell, or is capable of being transcribed into a non-naturally occurring HCV sequence that is capable of productive replication in a host cell. The HCV sequence comprises, from 5' to 3' on the positive-sense nucleic acid, a functional 5' non-translated region (5' NTR); one or more protein coding regions, including at least one polyprotein coding region that is capable of replicating HCV RNA; and a functional HCV 3' non-translated region (3' NR). In preferred embodiments of these polynucleotides, the 5' NTR is an HCV 5' NTR, the polynucleotide comprises at least one IRES selected from the group consisting of a viral IRES, a cellular IRES, and an artificial IRES, and the polyprotein coding region is an HCV polyprotein coding region.

In certain aspects of these embodiments, the above polynucleotides further comprise an adaptive mutation. The adaptive mutation can be such that the polynucleotide has a transfection efficiency into mammalian cells of greater than 0.01%; more preferably greater than 0.1%; even more preferably, greater than 1%; still more preferably greater than 5%, may be about 6%. The adaptive mutations can be such that the polynucleotide is capable of replication in a non-hepatic cell, for example HeLa cells. The adaptive mutations can also cause the polynucleotide to have attenuated virulence, wherein the HCV is impaired in its ability to cause disease, establish chronic infections, trigger autoimmune responses, and transform cells.

In some embodiments of the above described adaptive mutants, the polyprotein region comprises an NS5A gene that is not a wild-type NS5A gene. Preferably, the NS5A gene comprises a mutation. The mutation is preferably within 50 nucleotides of an ISDR or includes the ISDR; more preferably the mutati9 on is within 20 nt of the ISDR, or includes the ISDR. Examples of these adaptive mutations are those that encode an amino acid sequence change selected from the group consisting of Ser (1179) to Ile, Arg (1164) to Gly, Ala(1174) to Ser, Ser(1172) to Cys, and Ser(1172) to Pro of SEQ ID NO:3. Other adaptive mutations include a deletion of at least a portion of the ISDR, and may comprise the entire ISDR. In a particular embodiment, the adaptive mutation comprises a deletion of nucleotides 5345 to 5485 of SEQ ID NO:6.

In some embodiments of the invention polynucleotides, the HCV polyprotein coding region encodes all HCV structural and nonstructural proteins. In other embodiments, the polyprotein coding region is incapable of making infectious HCV particles, making the HCV variant a replicon. Preferably the inability to make HCV particles is due to a deletion in the structural protein coding region. Some embodiments of these replicons further comprise a foreign gene operably linked to a first IRES and the HCV polyprotein coding region operably linked to a second IRES. Preferably, the replicon comprises a genotype 1 HCV sequence, most preferably subtype 1b. Preferred foreign genes in these replicons are selectable markers or reporter genes. In other preferred replicon embodiments, the first IRES is an HCV IRES, the foreign gene is a neo gene, and the second IRES is a EMCV IRES. Examples of the above replicons include SEQ ID NO:5, SEQ ID NO:6, SEQ ID NO:22 and SEQ ID NO:25. The above replicons also preferably comprise an adaptive mutation, including any of the adaptive phenotypes previously described, including increased transfection efficiency, replication in a non-hepatic cell including HeLa cells, and attenuated virulence, and further comprising any of the adaptive mutations previously described, such as the various NS5A mutations and deletions previously described.

The polynucleotides of the present invention can be in the form of RNA or DNA. Preferred embodiments of the polynucleotides are SEQ ID NOs:5-13 and 22-25, the complements thereof, and the RNA equivalents of the sequences or their complements. In certain embodiments, the polynucleotides are capable of productive infection in a chimpanzee upon intrahepatic injection.

The present invention is also directed to expression vectors comprising DNA forms of any of the above polynucleotides, operably associated with a promoter. Additionally, the invention is directed to cells comprising the above expression vectors as well as host cells comprising any of the polynucleotides described above. The host cells are preferably mammalian cells, more preferably human cells. The host cells are preferably hepatocytes, T-cells, B-cells, or foreskin fibroblasts; most preferably hepatocytes. Certain adaptive mutants can also replicate in HeLa cells. The host cells can be within a non-human mammal capable of supporting transfection and replication of the HCV RNA, and infection when the HCV RNA encodes a virus particle. A preferred non-human mammal is a chimpanzee.

In additional embodiments, the present invention is directed to methods for identifying a cell line that is permissive for RNA replication with HCV. The method includes the steps of contacting a cell in tissue culture with an infectious amount of the above-described polynucleotides, and detecting replication of HCV variants in cells of the cell line.

The present invention is also directed to a method for producing a cell line comprising replicating HCV. The method includes the steps of (a) transcribing the above-described expression vector to synthesize HCV RNA; (b) transfecting a cell with the HCV RNA; and (c) culturing the cell.

Additionally, the present invention is directed to a vaccine. The vaccine includes any of the above-described polynucleotides, in a pharmaceutically acceptable carrier. In related embodiments, the present invention is directed to a method of inducing immunoprotection to HCV in a primate. The method includes administering the vaccine to the primate.

In further embodiments, the present invention is directed to a method of testing a compound for inhibiting HCV replication. The method includes the steps of (a) treating the above described host cells with the compound; and (b) evaluating the treated host cell for reduced replication, wherein reduced HCV replication indicates the ability of the compound to inhibit replication.

In additional embodiments, the present invention is directed to a method of testing a compound for inhibiting HCV infection. The method comprises treating a host cell with the compound before, during or after infecting the host cell with any of the invention polynucleotides.

In still other embodiments, the present invention is directed to an HCV variant that has (a) transfection efficiency greater than 0.01%, as determined by replication-dependent neomycin resistance, or (b) greater ability of initial colonies of cells transfected with the variant to survive subpassage than wild-type HCV genotype 1, subtype 1b. The HCV variant also has, from 5' to 3' on the positive-sense nucleic acid, a functional HCV 5' non-translated region (5'NTR) comprising an extreme 5'-terminal conserved sequence; an HCV polyprotein coding region; and a functional HCV 3' non-translated region (3'NTR) comprising a variable region, a polypyrimidine region, and an extreme 3'-terminal conserved sequence. In preferred embodiments, the transfection efficiency is greater than 0.1%; in more preferred embodiments greater than 1%; in still more preferred embodiments, greater than 5%. In the most preferred embodiments, the transfection efficiency is about 6%.

The variants can have any of the characteristics of the polynucleotides described above. However, preferred variants comprise the NS5A mutation or deletion described for the polynucleotides above.

Among the several advantages achieved by the present invention are the provision of polynucleotides comprising non-naturally occurring HCV sequences; the provision of HCV variants that have a transfection efficiency and ability to survive subpassage greater than HCV forms that have wild-type polyprotein coding regions; the provision of expression vectors comprising the above polynucleotides and HCV variants; the provision of cells and host cells comprising the above expression vectors, the provision of methods for identifying a cell line that is permissive for RNA replication with HCV; the provision of vaccines comprising the above polynucleotides in a pharmaceutically acceptable carrier; the provision of methods for inducing immunoprotection to HCV in a primate; and the provision of methods for testing a compound for inhibiting HCV replication.

BRIEF DESCRIPTION OF THE DRAWINGS

FIG. 1. HCV genome structure, polyprotein processing, and protein features. At the top is depicted the viral genome with the structural and nonstructural protein coding regions, and the 5' and 3' NTRs, and the putative 3' secondary structure. Boxes below the genome indicate proteins generated by the proteolytic processing cascade. Putative structural proteins are indicated by shaded boxes and the nonstructural proteins by open boxes. Contiguous stretches of uncharged amino acids are shown by black bars. Asterisks denote proteins with N-inked glycans but do not necessarily indicate the position or number of sites utilized. Cleavage sites shown are for host signalase (♦), the NS2-3 proteinase (curved arrow), an the NS34A serine protease (⇓).

FIG. 2. Strategies for expression of heterologous RNAs and proteins using HCV vectors. At the top is a diagram of the positive-polarity RNA virus HCV, which expresses mature viral proteins by translation of a single long ORF and proteolytic processing. The regions of the polyprotein encoding the structural proteins (STRUCTURAL) and the nonstructural proteins (REPLICASE) are indicated as lightly-shaded and open boxes, respectively. Below are shown a number of proposed replication-competent "replicon" expression constructs. The first four constructs (A-D) lack structural genes and would therefore require a helper system to enable packaging into infectious virions. Constructs E-G would not require helper functions for replication or packaging. Darkly shaded boxes indicate heterologous or foreign gene sequences (FG). Translation initiation (aug) and termination signals (trm) are indicated by open triangles and solid diamonds, respectively Internal ribosomes entry sites (IRES) are shown as boxes with vertical stripes. Constructs A and H illustrate the expression of a heterologous product as an in-frame fusion with the HCV polyprotein. Such protein fusion junctions can be engineered such that processing is mediated either by host or viral proteinases (indicated by the arrow).

FIG. 3. Structure of HCVrep1bBartMan. Two versions of this infectious replicon were constructed as described in Example 1. The first, HCVrep1bBartMan/AvaII, has a AvaII restriction site in the variable domain of the 3' NTR that is not present in the 3' NR of wild-type HCV subtype 1b. The second variant, HCVrep1bBartMan/Δ2U's, has 32, rather than the wild-type 34, U's in the longest stretch of contiguous U's in the polypyrimidine domain of the 3' NTR. The "GDD→AGG" designation shows the inactivating mutation in the non-replicating replicons that were used as polymerase-minus controls in Example 1.

FIG. 4. Generation of G418-resistant cell clones. At the top is a diagram of the HCVrep1bBartMan replicons as described in FIG. 3. The middle text summarizes the steps used to isolate the adaptive mutants, which are further described in Example 1. The bottom chart summarizes several characteristics of some of the replicons isolated as described in the Example.

Figure 5A:
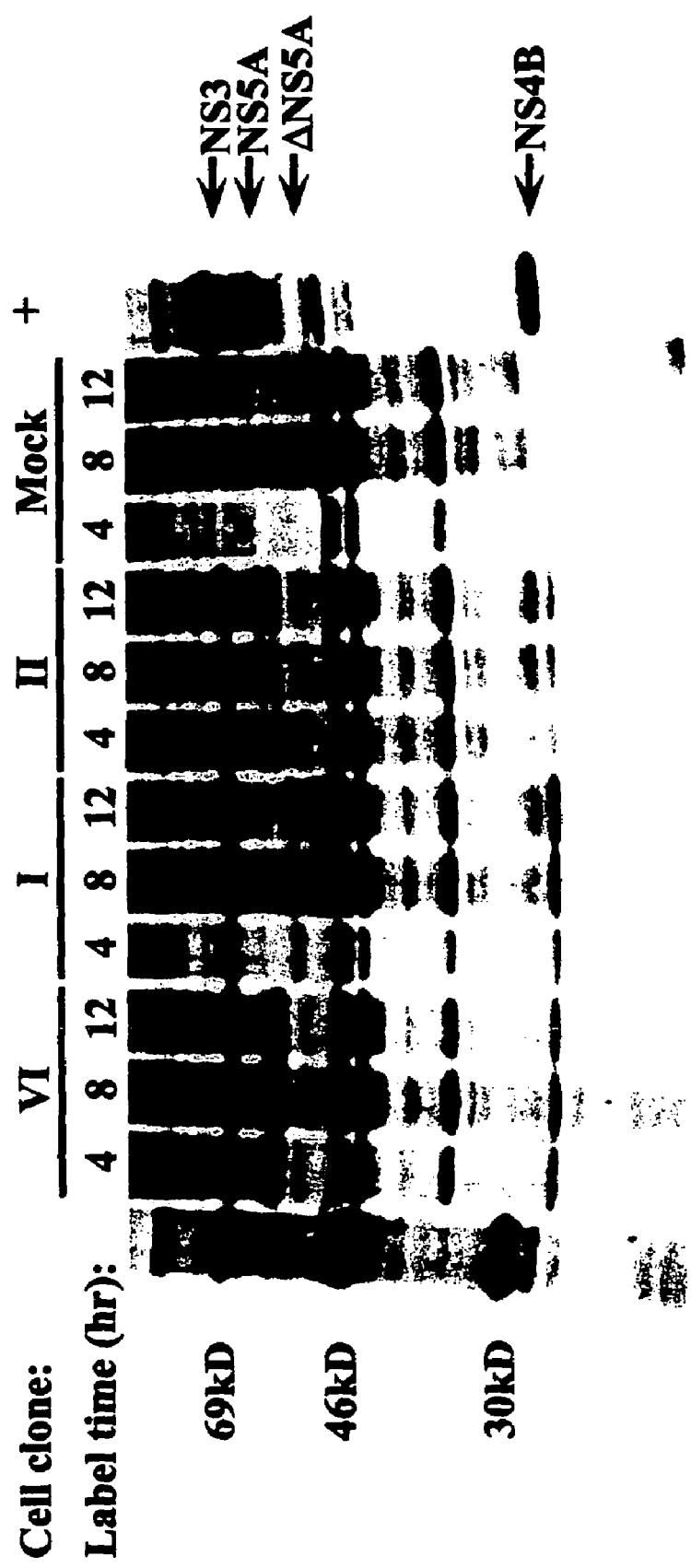
Figure 5B:
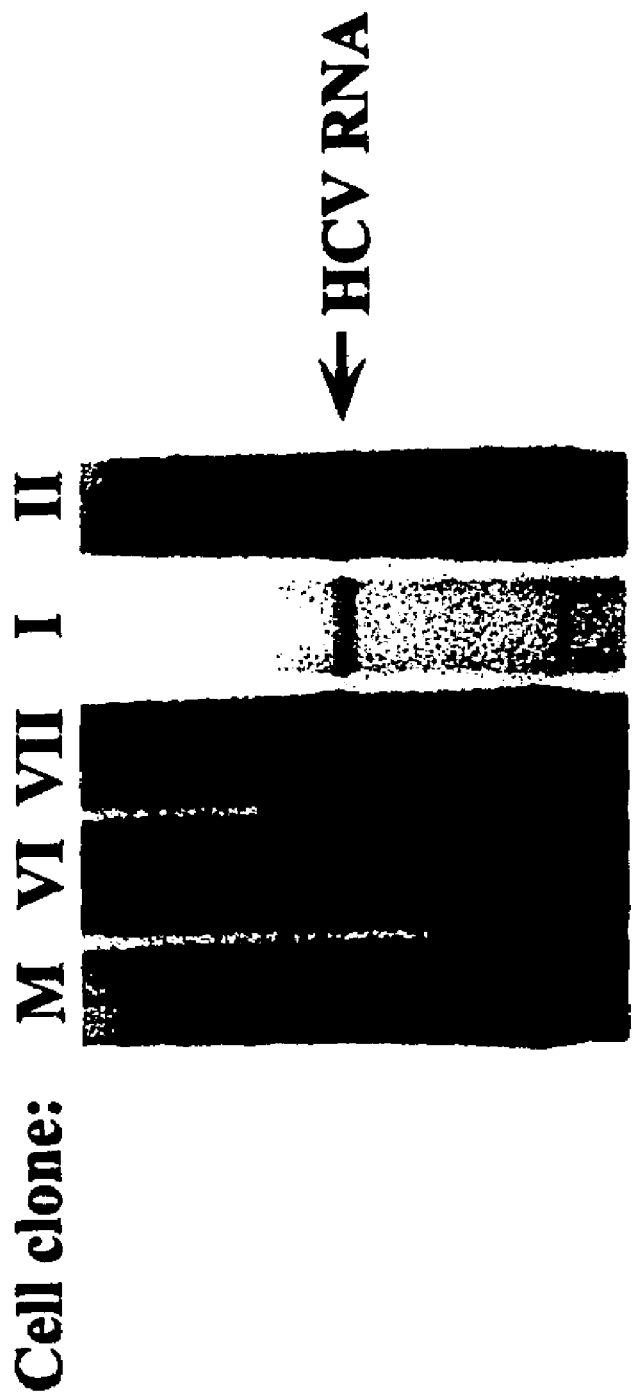

FIG. 5. Synthesis of HCV-specific RNA and proteins. FIG. 5A illustrates actinomycin D-resistant RNA replication of four adaptive replicons as further described in the Example. FIG. 5B illustrates the immunoprecipitation of $^{35}$S-labeled HCV-specific proteins of three adaptive replicons as further described in Example 1.

Figure 6:
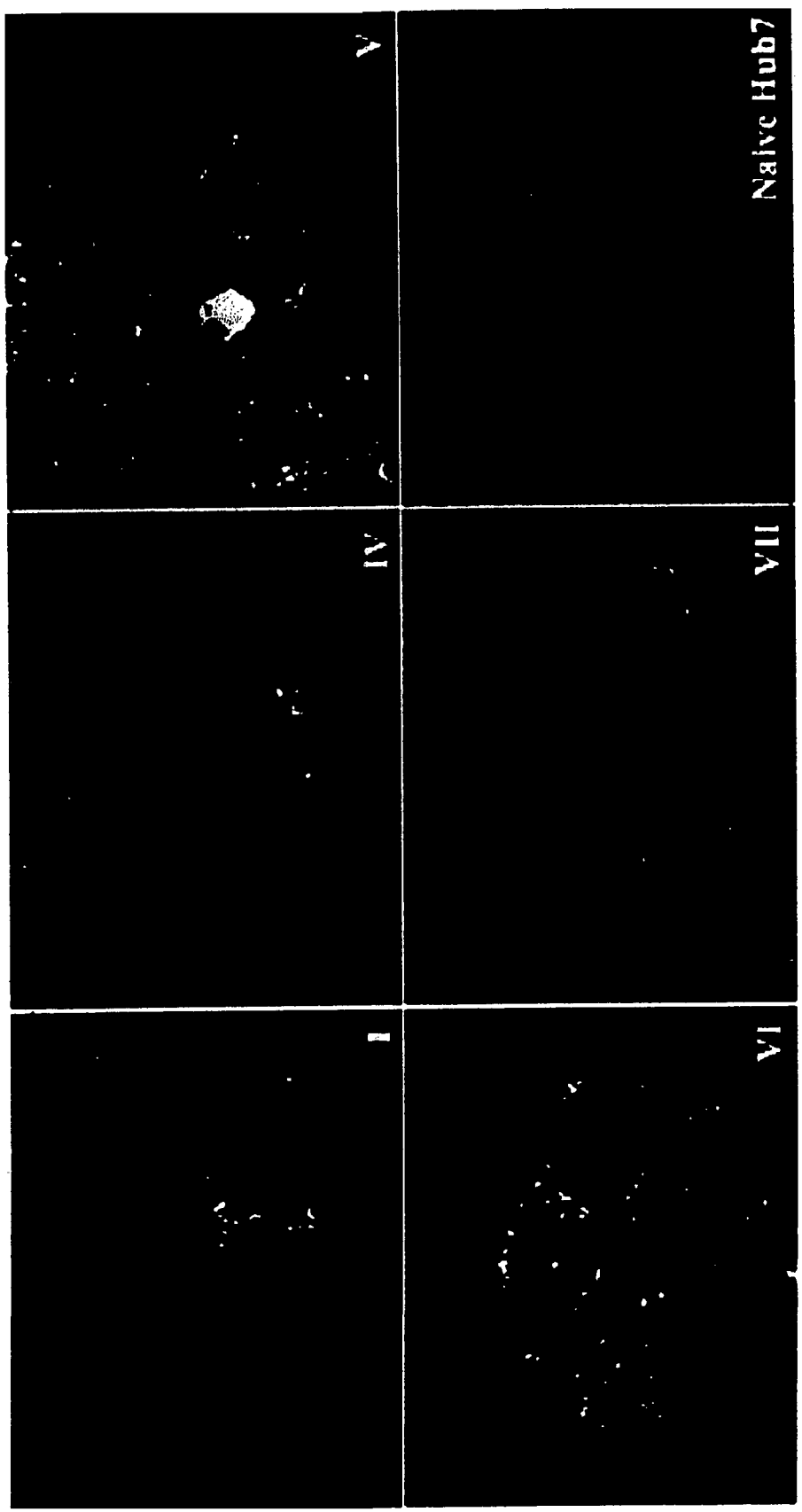

FIG. 6. Detection of NS3 in G418-resistant cell clones. Monolayers of cells transfected with various replicons as indicated were immunostained with an anti-NS3 antibody. Patterns of staining were similar to cells stained from an infected liver.

FIG. 7. Nucleotides and amino acid changes in the NS5A coding region of HCV. Nucleotide and amino acid changes in a portion of the NS5A coding region of seven adaptive clones are indicated. In the Figure, the unmodified sequence of amino acid residues 1163-1182 are shown as found in SEQ ID NO: 3, with the corresponding coding sequence shown as nucleotides 5287-5346 of SEQ ID NO: 5.

Figure 8:
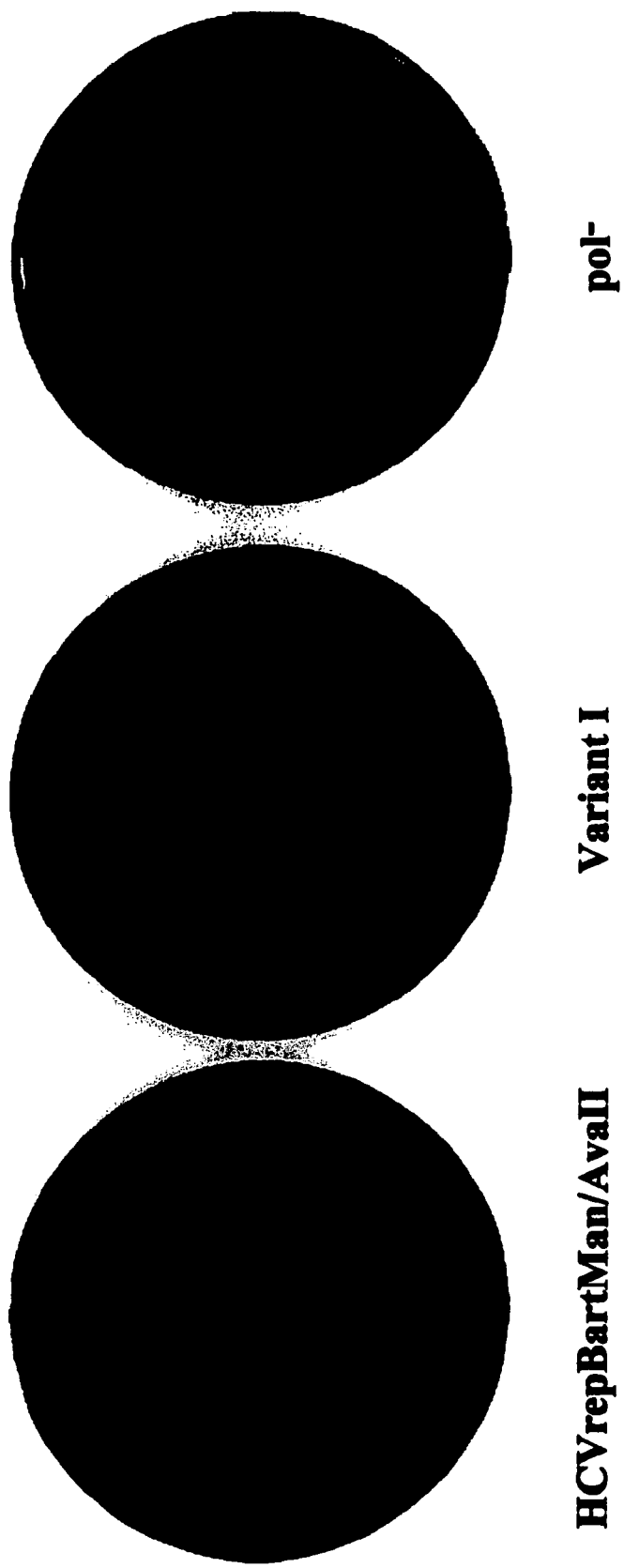

FIG. 8. G418-resistant colonies generated after electroporation of replicon RNAs into Huh 7 cells. The ability of an adaptive replicon (Replicon I) to establish colonies after transfection into Huh7 cells middle) is compared to the original replicon HCVrepBartMan/AvaII (left) and the same adaptive replicon, but with an inactivating mutation in the polymerase gene (right).

Figure 9:
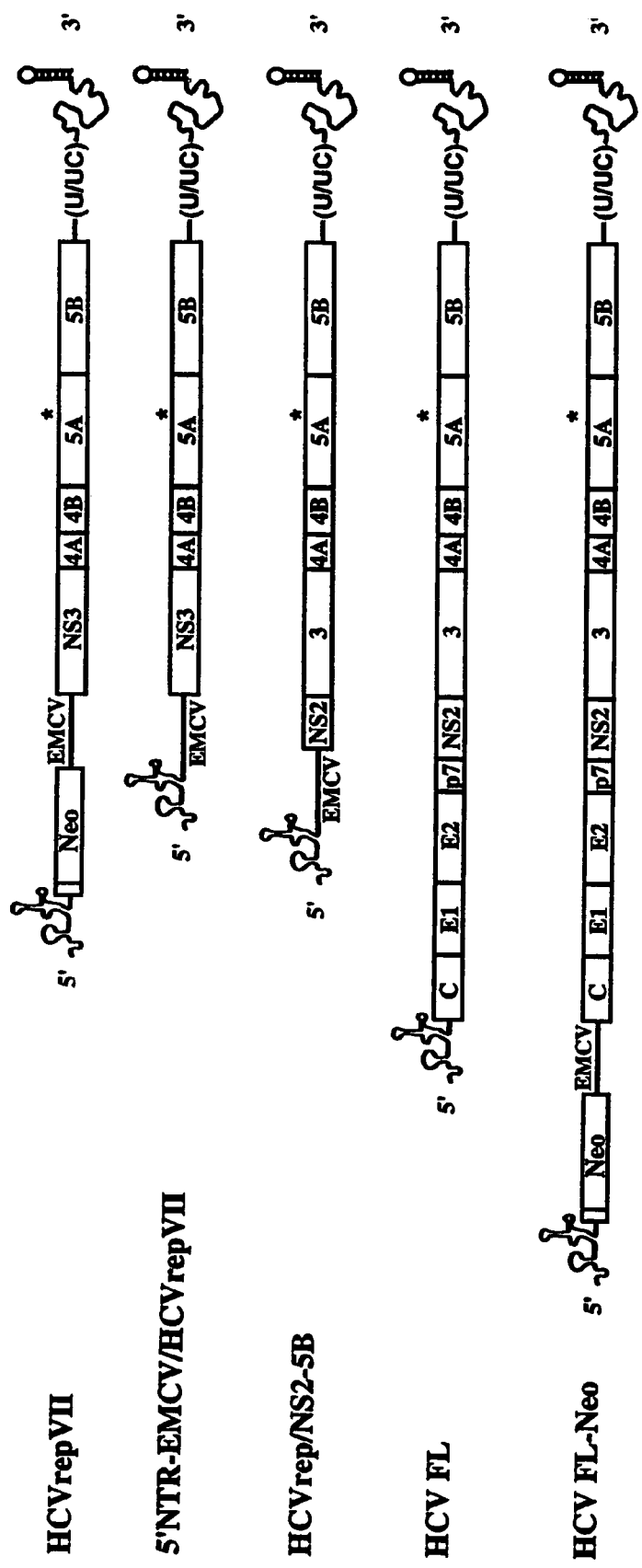

FIG. 9. Structures of HCV replicons and full-length HCV RNAs. The adaptive replicon 5'NTR-EMCV has the 5'NTR fused directly to the EMCV IRES upstream of NS3. Another adaptive replicon, HCVrep/NS2-5B has the non-structural protein, NS2, upstream of NS3. A full-length HCV cDNA clone, HCV FL, was assembled. Also, a bicistronic derivative, HCV FL-neo, was assembled where the 5'NTR is fused to the neomycin phosphotransferase gene and the EMCV IRES is upstream of the HCV open reading frame. In both full-length clones, the open reading frame comprises the structural and non-structural regions, from capsid to NS5B. In addition, all of the replicons and full-length HCV RNAs comprise the mutation coding for Ser to Ile substitution at position 1179 of SEQ ID NO:3, in NS5A.

Figure 10:
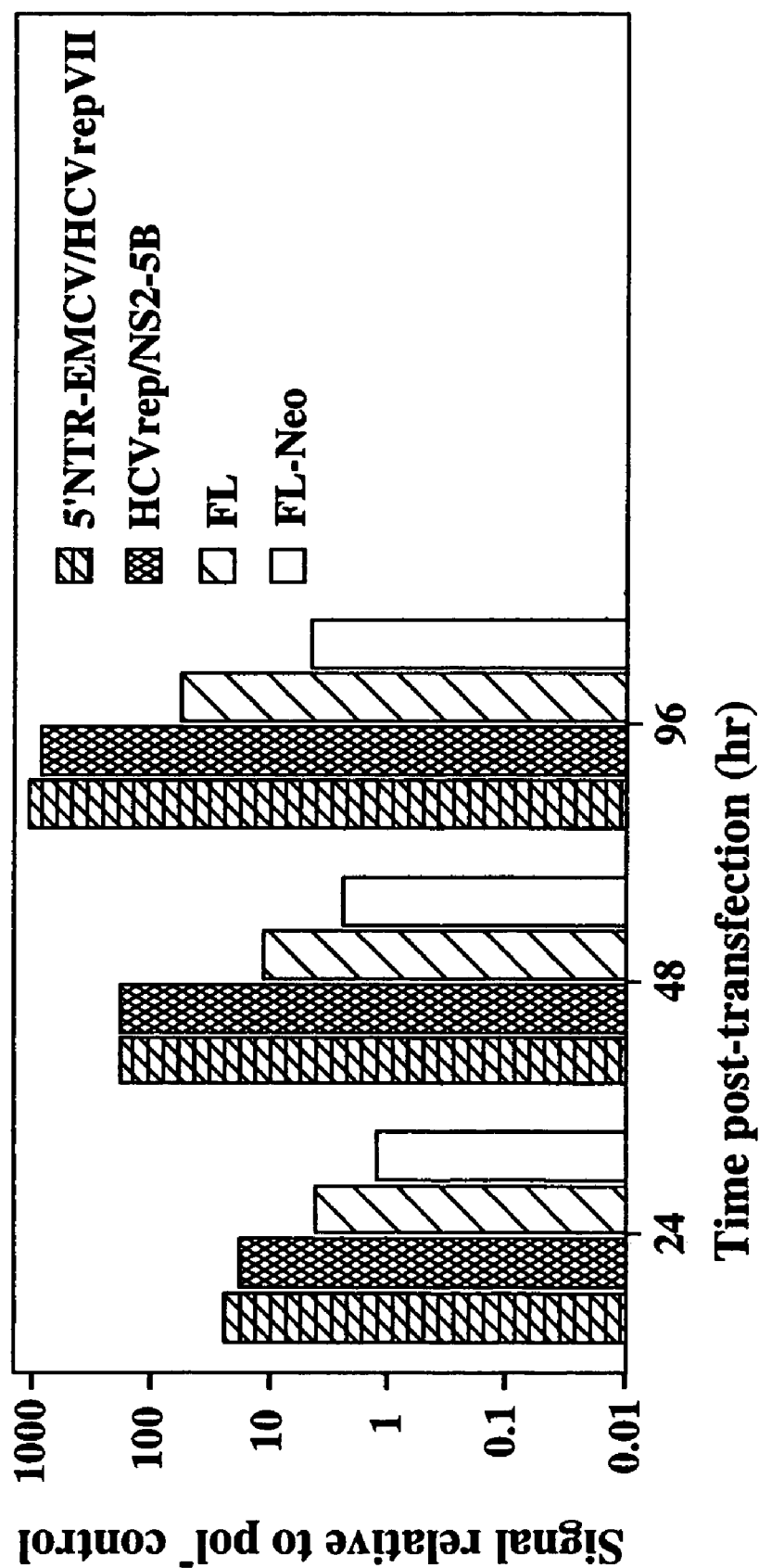

FIG. 10. RNA replication of replicons and full-length HCV RNAs. The HCV replicons and full-length HCV RNAs shown in FIG. 9 are replication competent.

DETAILED DESCRIPTION OF THE INVENTION

Definitions

Various terms are used herein, which have the following definitions:

As used herein, "HCV polyprotein coding region" means the portion of a hepatitis C virus that codes for the polyprotein open reading frame (ORF). This ORF may encode proteins that are the same or different than wild-type HCV proteins. The ORF may also encode only some of the functional proteins encoded by a wild-type polyprotein coding region. The proteins encoded therein may also be from different isolates of HCV, and non-HCV proteins may also be encoded therein.

The phrase "pharmaceutically acceptable" refers to molecular entities and compositions that are physiologically tolerable and do not typically produce an allergic or similar untoward reaction, such as gastric upset, dizziness and the like, when administered to a human. Preferably, as used herein, the term "pharmaceutically acceptable" means approved by a regulatory agency of the Federal or a state government or listed in the U.S. Pharmacopoeia or other generally recognized pharmacopoeia for use in animals, and more particularly in humans. The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E. W. Martin.

The phrase "therapeutically effective amount" is used herein to mean an amount sufficient to reduce by at least about 15 percent, preferably by at least 50 percent, more preferably by at least 90 percent, and most preferably prevent, a clinically significant deficit in the activity, function and response of the host. Alternatively, a therapeutically effective amount is sufficient to cause an improvement in a clinically significant condition in the host.

The term "adjuvant" refers to a compound or mixture that enhances the immune response to an antigen. An adjuvant can serve as a tissue depot that slowly releases the antigen and also as a lymphoid system activator that non-specifically enhances the immune response (Hood et al., *Immunology, Second Ed.*, 1984, Benjamin/Cummings: Menlo Park, Calif., p. 384). Often, a primary challenge with an antigen alone, in the absence of an adjuvant, will fail to elicit a humoral or cellular immune response. Adjuvants include, but are not limited to, complete Freund's adjuvant, incomplete Freund's adjuvant, saponin, mineral gels such as aluminum hydroxide, surface active substances such as lysolecithin, pluronic polyols, polyanions, peptides, oil or hydrocarbon emulsions, keyhole limpet hemocyanins, dinitrophenol, and potentially useful human adjuvants such as BCG (bacille Calmette-Guerin) and *Corynebacterium parvum*. Preferably, the adjuvant is pharmaceutically acceptable.

In a specific embodiment, the term "about" or "approximately" means within 20%, preferably within 10%, and more preferably within 5% of a given value or range.

The term "virus infection" as used herein, refers to the usual way that wild-type virus particles become established in host cells. This generally includes binding to the host cell, uptake, delivery to the cytosol or nucleus, and initiation of replication.

The term "transfection" as used herein, refers to the infection of a cell with a polynucleotide. The polynucleotide can be DNA or RNA. A preferred method of transfecting a cell with an HCV polynucleotide is with replication competent RNA. Delivery to permissive cells can be facilitated by electroporation, charged liposomes, high salt, DE dextran, etc. Replication competent RNAs can also be launched in cells after transfection of DNA such as plasmids or DNA viruses that have been appropriately engineered to provide transcription initiation and termination signals. The transfected RNAs can represent full-length genome RNAs capable of initating a complete replication cycle (including production of progeny virus), or they may be defective lacking one or more RNA elements or proteins essential for virion production but not RNA replication. The latter RNAs, which are lacking in the ability to produce a virion, will be referred to generally herein as "replication competent RNAs", "RNA replicons" or "replicons".

As used herein, the term "subpassage" connotes the transfer of a colony from one vessel of media to another vessel of media. Examples of vessels of media include dishes, bottles or test tubes with solid or liquid growth media. Unless otherwise indicated, "subpassage" means the transfer of a colony of HCV-transfected cells from a vessel of media where the newly transfected cells were plated to a vessel of media where the colony is isolated.

The term "authentic" is used herein to refer to an HCV polynucleotide, whether a DNA or RNA, that provides for replication and production of functional HCV proteins, or components thereof. The authentic HCV polynucleotides of the present invention are capable of replication and may be infectious, e.g., in a chimpanzee model or in tissue culture, to form viral particles (i.e., "virions"). An authentic HCV polynucleotide of the present invention may also be a "replicon", such that it is incapable of producing the full complement of structural proteins to make a replication competent infectious virion. However, such replicons are capable of RNA replication. Thus, the authentic HCV polynucleotides exemplified in the present application contains all of the virus-encoded information, whether in RNA elements or encoded proteins, necessary for initiation of an HCV RNA replication cycle. The authentic HCV polynucleotides of the invention include modifications described herein, e.g., by site-directed mutagenesis or by culture adaptation, producing a defective or attenuated derivative, or an adaptive variant. Alternatively, sequences from other genotypes or isolates can be substituted for the homologous sequence of the specific embodiments described herein. For example, an authentic HCV nucleic acid of the invention may comprise the adaptive mutations disclosed herein, e.g., on a recipient plasmid, engineered into the polyprotein coding region of a functional clone from another isolate or genotype (either a consensus region or one obtained by very high fidelity cloning). In addition, the HCV polynucleotide of the present invention can include a foreign gene, such as a gene encoding a selectable marker or a reporter protein.

General Description

The practice of the present invention will employ, unless otherwise indicated, conventional techniques of cell culture, molecular biology, microbiology, recombinant DNA, and immunology, which are within the skill of the art. Such techniques are explained fully in the literature. See, e.g., Ausubel et al. (ed.) (1993) "Current protocols in molecular biology. Green Publishing Associates, New York; Ausubel et al. (1995), "Short Protocols in Molecular Biology", John Wiley and Sons; Joseph Sambrook et al. (1989), "Molecular Cloning, A Laboratory Manual", second ed., Cold Spring Harbor Laboratory Press; the series, METHODS IN ENZYMOLOGY (Academic Press, Inc.); *Animal Cell Culture* [R. I. Freshney, ed. (1986)]; Lau, ed. (1999), HEPATITIS C PROTOCOLS, Humana Press, New York; and *Immobilized Cells And Enzymes* [IRL Press, (1986)]; all of which are incorporated by reference.

The present invention is directed to variants of hepatitis C virus (HCV) and methods for producing the variants. As used herein, an HCV variant is a non-naturally occurring HCV sequence that is capable of productive replication in a host cell. The genetic sequence of these variants may comprise insertions, deletions, or base mutations from wild type HCV sequences. As further discussed infra, the variants may be produced by genetic engineering, by methods known to the skilled artisan (see, e.g., U.S. patent application Ser. No. 08/811,566 (Now U.S. Pat. No. 6,127,116); Lohmann et al., *Science* 285:110-113(1999)). Alternatively, as further discussed infra, the variants may also be produced by culture selection methods, or a combination of culture selection and genetic engineering.

The variants are in the form of DNA or RNA and can be incorporated into any useful form of those compounds, for example in extrachromosomal DNA that replicates in a microorganism such as *E. coli* or yeast. Included among these are plasmids, phage, BACs, YACs, etc. RNA and virions comprising the variant are also envisioned as within the scope of the invention. The variants of the present invention can also be in the form of cassettes for insertion into a DNA cloning vector. The HCV RNAs are envisioned to be complementary to any HCV DNA disclosed herein. An infectious HCV RNA is a positive strand RNA created from the negative strand template of the HCV DNA clone of the invention.

The variants of the present invention are not narrowly limited to any particular virus subtype. Thus, any particular component of the variant, or the entire variant, may be from any HCV subtype. Preferred subtypes are 1a and 1b, due to the widespread occurrence, as well as the large amount of knowledge available for those two subtypes. However, the use of any other genotype or subtype, as would be considered within the skill of the art, is envisioned as within the scope of the invention. These subtypes include, but are not limited to, any subtypes within genotypes HCV-1, HCV-2, HCV-3, HCV-4, HCV-5, and HCV-6. Moreover, since HCV lacks proofreading activity, the virus itself readily mutates, forming mutant "quasi-species" of HCV that are also contemplated as useful for the present invention. Such mutations are easily identified by sequencing isolates from a subject, as detailed herein or in U.S. patent application Ser. No. 08/811,566 (Now U.S. Pat. No. 6,127,116). It would be expected that the methods and compositions disclosed herein are useful for any known subtype or quasi-species, or any subtype or quasi-species not now known but that is discovered in the future.

The HCV variants of the invention include a 5'-NTR conserved sequence, which generally comprises the 5'-terminal sequence GCCAGCC, and which may have additional bases upstream of this conserved sequence without affecting functional activity of the HCV nucleic acid. In a preferred embodiment, the 5'-GCCAGCC includes from 0 to about 10 additional upstream bases; more preferably it includes from 0 to about 5 upstream bases; more preferably still it includes 0, one, or two upstream bases. In specific embodiments, the extreme 5'-terminal sequence may be GCCAGCC; GGCCAGCC; UGCCAGCC; AGCCAGCC; AAGCCAGCC; GAGCCAGCC; GUGCCAGCC; or GCGCCAGCC, wherein the sequence GCCAGCC is the 5'-terminus of SEQ ID NO:1. However, the scope of the HCV variants of the invention encompasses any functional HCV 5' NTR, whether now known or later discovered.

The HCV variants of the invention also include a 3' NTR that comprises a poly-pyrimidine region as is known in wild-type HCV. These polypyrimidine regions are known to comprise, on the positive-strand HCV RNA, a poly(U)/poly (UC) tract or a poly(A) tract. However, the polypyrimidine region of the present invention may also include other polypyrimidine tracts that are not now known but are later found to be functional in infectious HCV. As is known in the art, the polypyrimidine tract may be of variable length: both short (about 75 bases) and long (133 bases) are effective, although an HCV clone containing a long poly(J/UC) tract is found to be highly infectious. Longer tracts may be found in naturally occurring HCV isolates. Thus, an authentic HCV nucleic acid of the invention may have a variable length polypyrimidine tract.

The 3' NTR also comprises, at its extreme 3' end, the highly conserved RNA element of about 98 nucleotides known in the art, and as described in, e.g., U.S. Pat. No. 5,874,565, U.S. patent application Ser. No. 08/811,566 (Now U.S. Pat. No. 6,127,116), and U.S. Pat. No. 5,837,463. In a specific aspect, the 3'-NTR extreme terminus is RNA homologous to a DNA having the sequence 5'-TGGTG-GCTCCATCTTAGCCCTAGTCACGGCTAGCTGTGAA-AGGTCCGTGAGCCGCATGACTGCAGAGAGTGCTG-ATACTGGCCTCTCTGCTGATCATGT-3' (SEQ ID NO:2). However, the scope of the invention is meant to encompass HCV variants with any HCV 3' NTR that allows virus replication; whether the sequence is now known or later discovered. Included are 3' NTRs that do not comprise a variable region.

The HCV variants of the present invention also include a polyprotein coding region sufficient to allow replication of the HCV RNA. Thus, the polyprotein coding region may be deficient in functional genes encoding the full complement of the HCV structural genes C, E1 and E2. In addition, the polyprotein coding region may comprise deletions, insertions, or mutations that do not occur in wild-type HCV strains. Further, the polyprotein coding region may be chimeric, such that some of the genes encoded therein are from analogous regions of another virus, as discussed infra.

The HCV variants encompassed by the present invention include variants that do not produce virus particles. These variants, which may be termed "replicons", lack the ability to produce a fully functional complement of the structural proteins C, E1 and E2. The inability to produce the functional structural protein component of the HCV virus may be conferred by deletion of the genes encoding one, two, or all three of these proteins. Alternatively, a deletion of a small portion of the coding sequence of one of the structural proteins, or a mutation in a critical region of the coding sequence, or an insertion into the coding sequence could lead to an HCV that cannot produce virions. In the latter case, the insertion can be any sequence that disrupts the ability of the structural protein from becoming part of a virion, and can include functional sequences, such as those that encode a reporter gene (such as β-galactosidase) or those that confers selectability to the cell harboring the replicon (such as neo). The above manipulations are entirely within the skill of the art. See, e.g., Lohmann et al., supra and Example 1. As discussed infra, such variants are useful for studying replication of the HCV virus, among other things.

The variants of the present invention can also comprise an alteration in the coding sequence of the polyprotein coding region that does not affect the production of functional virions or replicons. These alterations can be such that the amino acid sequence of the mature protein is not changed from the wild-type sequence, due to the degeneracy of the genetic code. Such alterations can be useful, e.g., when they introduce or remove a restriction site, such that the size of HCV fragments produced by digestion with a restriction enzyme is altered. This provides a distinguishing characteristic of that variant, which can be used, e.g., to identify a particular infectious isolate in a multiple infection animal model, or to provide convenient sites for subsequent engineering. Any technique for mutagenesis known in the art can be used, including but not limited to in vitro site-directed mutagenesis [Hutchinson, C., et al., 1978, J. Biol. Chem. 253:6551; Zoller and Smith, 1984, DNA 3:479-488; Oliphant et al., 1986, Gene 44:177; Hutchinson et al., 1986, Proc. Natl. Acad. Sci. U.S.A. 83:710], use of TAB® linkers (Pharmacia), etc. PCR techniques are preferred for site directed mutagenesis [see Higuchi, 1989, "Using PCR to Engineer DNA", in *PCR Technology: Principles and Applications for DNA Amplification*, H. Erlich, ed., Stockton Press, Chapter 6, pp. 61-70].

Alterations in the polyprotein coding sequence can also introduce conservative amino acid substitutions in the HCV-encoded proteins. Conservative amino acid substitutions refer to the interchangeability of residues having similar side chains. Conservatively substituted amino acids can be grouped according to the chemical properties of their side chains. For example, one grouping of amino acids includes those amino acids have neutral and hydrophobic side chains (A, V, L, I, P, W, F, and M); another grouping is those amino acids having neutral and polar side chains (G, S, T, Y, C, N, and Q); another grouping is those amino acids having basic side chains (K, R, and H); another grouping is those amino acids having acidic side chains (D and E); another grouping is those amino acids having aliphatic side chains (G, A, V, L, and I); another grouping is those amino acids having aliphatic-hydroxyl side chains (S and T); another grouping is those amino acids having amine-containing side chains (N, Q, K, R, and H); another grouping is those amino acids having aromatic side chains (F, Y, and W); and another grouping is those amino acids having sulfur-containing side chains (C and M). Preferred conservative amino acid substitutions are: R-K; E-D, Y-F, L-M; V-I, and Q-H. Conservative amino acid substitutions, when conferred on the structural proteins, can alter antigenic epitopes, and thus the immune reactivity of the virus. Those substitutions could also alter the function of the non-structural proteins, such that the virus reproduces at a different rate or is altered in its ability to replicate in cell culture or in an organism. See, e.g., Example 1, where replicon IV is adaptive to cell culture conditions due to the conservative amino acid substitution Ser→Cys in the NS5A protein.

Alterations in the polyprotein coding region could also introduce nonconservative amino acid substitutions in one or more of the proteins encoded therein. Nonconservative substitutions would be expected to alter protein function more drastically than conservative substitutions, and would thus be more likely than conservative substitutions to alter phenotypic characteristics of the virus such as replication rate, adaptation to cell culture or in vivo culture, and displayed antigenic determinants. Examples are several adaptive mutations in the NS5A coding region described in the, infra.

In some embodiments of the invention, the polyprotein coding region has a consensus sequence derived from more than one HCV isolate. For example, an authentic HCV nucleic acid of the invention may comprise a 5' and 3' sequence from any one subtype of the virus and a polyprotein region from any other subtype. Alternatively, only one of the proteins encoded in the polyprotein might be from another viral subtype. In this way, the effect of a particular protein in conferring characteristics of a particular strain (e.g., reduced virulence, increased replication rate etc.) can be studied.

Chimeras with other viruses, such as with bovine viral diarrhea virus, or another flavivirus, are also envisioned.

See, e.g., PCT/US99/08850, incorporated herein by reference. In these embodiments, components of the functional clones can be used to construct chimeric viruses for assay of HCV gene functions and inhibitors thereof [Filocamo et al., *J. Virol.* 71: 1417-1427 (1997); Hahm et al., *Virology* 226: 318-326 (1996); Lu and Wimmer, *Proc Natl Acad Sci USA* 93: 1412-7 (1996)]. In one such extension of the invention, functional HCV elements such as the 5' IRES, proteases, RNA helicase, polymerase, or 3' NTR are used to create chimeric derivatives of BVDV whose productive replication is dependent on one or more of these HCV elements. Such BVDV/HCV chimeras can then be used to screen for and evaluate antiviral strategies against these functional components.

Chimeras where a gene encoding a structural or nonstructural protein from a closely related virus such as GB virus B replaces the corresponding HCV gene would also be expected to be functional. See, e.g., Butkiewicz et al., 2000, *J. Virol.* 74, 4291-4301.

Other alterations in the polyprotein coding region contemplated by the present invention include deletions or insertions in the sequence. Such alterations may also alter replication rate, adaptation to various growth conditions, or antigenic determinants. A preferred example of a useful deletion includes the 47 amino acid deletion and replacement of Ser 1182 to Asp 1229 of SEQ ID NO:3 with Tyr, which is an adaptive mutation in the NS5A that provides greater transfection efficiency than HCVs with wild-type NS5A. See Example 1.

Insertions into the polyprotein coding region can be of any length and into any area of the region, provided the modified HCV is still able to replicate. Preferably, the insertion is engineered in frame with the rest of the polyprotein coding region, to allow correct translation of the polyprotein region downstream from the insertion.

Insertions into the polyprotein coding region could introduce a gene encoding a heterologous protein. The choice of heterologous protein is not narrowly limited and can include a protein that is therapeutic to the infected host or cell, or a protein that is harvested and purified for another purpose. Particularly useful heterologous genes include those used for detection of the variant (i.e., reporter genes), or for selection of cells having the variant. Nonlimiting examples of reporter genes useful in the present invention include β-galactosidase, β-glucuronidase, firefly or bacterial luciferase, green fluorescent protein (GFP) and humanized derivatives thereof, cell surface markers, and secreted markers. Such products are either assayed directly or may activate the expression or activity of additional reporters. Nonlimiting examples of selectable markers for mammalian cells include, but are not limited to, the genes encoding dihydrofolate reductase (DHFR; methotrexate resistance), thymidine kinase (tk; methotrexate resistance), puromycin acetyl transferase (pac; puromycin resistance), neomycin resistance (neo; resistance to neomycin or G418), mycophenolic acid resistance (gpt), hygromycin resistance, blasticidin resistance, and resistance to zeocin. Other selectable markers can be used in different hosts such as yeast (ura3, his3, leu2, trp1).

The present invention also encompasses HCV variants that have alterations in the noncoding regions of the virus. For example, the foreign gene discussed above can also be inserted into a noncoding region of the virus, provided the region with the insert continues to be sufficiently functional to allow replication. To provide for translation of a foreign gene inserted into a noncoding region, the foreign gene must be operatively linked to translational start signals, preferably an internal ribosome entry site (IRES) derived from cellular or viral mRNAs [Jang et al., *Enzyme* 44: 292-309 (1991); Macejak and Sarnow, *Nature* 353: 90-94 1991); Molla et al., *Nature* 356: 255-257 (1992)]. In essence, this strategy creates a second cistron in the variant, separate from the polyprotein coding region cistron. A preferred IRES is the encephalomyocarditis virus (EMCV) IRES.

The foreign gene can also be inserted into the 3' NTR or the 5' NTR. In the 3' NTR, the foreign gene/IRES cassette is preferably inserted into the most 5', variable domain. However, insertions are also envisioned for other regions of the 3' NTR, such as at the junction of the variable region and the polypyrimidine region, or within the polypyrimidine region. In the 5' NTR, the foreign gene is preferably inserted into the area just adjacent (3' to) the internal HCV IRES. In these variants, the foreign gene is engineered to be operably linked to the HCV IRES. Where this is the case, it is preferred that the second IRES (e.g., an EMCV IRES) is engineered just 5' to the polyprotein coding region, to be operably linked to that region. See Example and Lohmann et al., supra.

Some of the above strategies for functional expression of heterologous genes have been previously described. See Bredenbeek and Rice, (1992) supra for review; see, also FIG. 2, which is also FIG. 2 of U.S. patent application Ser. No. 08/811,566 (Now U.S. Pat. No. 6,127,116).

Additionally, noncoding region alterations such as mutations, deletions or insertions that do not encode a foreign protein are within the scope of the invention. For example, mutations, deletions of insertions in the variable or polypyrimidine regions of the 3' NTR, including deletions of the entire variable region, or in the 5' NTR region, that create or destroy restriction sites or make the variant otherwise identifiable can be used advantageously to create a "tagged" variant. See, e.g., Example, where a mutation in the variable region of the 3' NTR created an easily identifiable AvaII restriction site, and where a deletion in the polypyrimidine region created another identifiable variant.

The polyprotein coding sequence can comprise mutants with desirable functional adaptations such as adaptive or attenuated variants. These improved variants can be superior in any desired characteristic. Nonlimiting examples of characteristics that can be improved by the present methods include more rapid or more accurate replication in vivo or in culture, improved transfection efficiency, improved ability to establish subpassaged cell lines, ability to infect a host or a host cell line, virulence, and attenuation of disease symptoms.

Such HCV variants may be adaptive, e.g., by selection for propagation in animals or in vitro. See, e.g., Example. Alternatively, the variants can be engineered by design to comprise the functional adaptation. See, e.g., Example, where a deletion was designed that had increased transfection efficiency and ability to be subpassaged to create a stable cell line, supporting persistent HCV replication.

Non-functional HCV clones, e.g., that are incapable of genuine replication, that fail to produce HCV proteins, that do not produce HCV RNA as detected by Northern analysis, or that fail to infect susceptible animals or cell lines in vitro, can be corrected using components of the variants of the present invention. By comparing a variant of an authentic HCV nucleic acid sequence of the invention, with the sequence of the non-functional HCV clone, defects in the non-functional clone can be identified and corrected, and the corrected, replicating variant could have characteristics like the variant, such as an adaptive mutation, etc. All of the methods for modifying nucleic acid sequences available to one of skill in the art to effect modifications in the non-functional HCV genome, including but not limited to site-directed mutagenesis, substitution of the functional sequence from an authentic HCV variant for the homologous sequence in the non-functional clone, etc.

Adaptation of HCV for more improved cell culture characteristics. Replication and transfection efficiency and stability of virions and replicons that have wild-type polyprotein replication in cell culture is inefficient. That is, cells transfected with, e.g., RNA transcripts of clones of these strains replicate slowly in culture and the transfected cells are difficult to maintain. Additionally, transfection efficiency is poor. That is, very few cells that are transfected with the RNA replicon are able to support HCV replication. See, e.g., Example 1 and Lohmann et al., supra, where less than 0.01% of Huh-7 cells transfected with RNA transcripts of replicons that have a wild-type (genotype 1, subtype 1b) nonstructural polyprotein coding region grew into colonies on the petri dish where the transfectants were plated. Furthermore, a low percentage of colonies that arose from the original plating (<3%) could be subpassaged onto another dish of media to form an isolated stable cell line supporting HCV replication.

"Transfection efficiency" is defined by determining the percent of cells having replicating HCV RNA that continue to translate proteins encoded by the transfected nucleic acids. The easiest way to measure this is by determining the percentage of cells that exhibit a characteristic conferred by the HCV RNA. See, e.g., Example 1, where replicons comprising a neo gene conferred G418 resistance to the transfected cells, and where the cells were G418 resistant after dividing and forming colonies on the dish where the transfected cells were plated. In that example, G418 resistance would not persist sufficiently for colonies to form unless the HCV RNA was able to replicate and partition into the dividing cells while continuing to replicate and translate the neo gene to confer G418 resistance. Transfection efficiency is thus replication dependent, in that the transfected HCV must replicate, transcribe, and translate the measured characteristic (here, G418 resistance). In the context of the neo selectable marker, this method of determining transfection efficiency is termed "replication-dependent neomycin resistance". This is the preferred way of measuring transfection efficiency because it only measures transcription from HCV that established itself sufficiently to replicate and partition into dividing cells to form a colony.

Another disadvantageous cell culture characteristic of HCV nucleic acid that has wild-type nonstructural polyprotein genes is that only a low percentage of colonies that form after transfection and selection are able to continue to be maintained upon subpassage as continuous cell lines harboring replicating RNA. This was <3% in Lohmann et al., as discussed supra.

Disadvantageous characteristics of HCV having wild-type nonstructural polyprotein genes can be reduced by utilizing certain adaptive mutations and deletions in the NS5A coding region or elsewhere as disclosed herein. Preferred mutations comprise alterations in the encoded amino acid sequence in a region of the NS5A that is just 5' to the coding region of the "interferon sensitivity-determining region" (ISDR). Specifically, various mutations within about 50 nucleotides 5' to the ISDR, more preferably within about 20 nucleotides of the ISDR, where the encoded amino acid sequence is altered, have the effect of adapting an HCV to have higher transfection efficiency and increased ability to withstand subpassage to establish a cell line harboring persistent HCV replication. Specific mutations having this effect include Ser to Ile at amino acid 1179 of SEQ ID NO:3 (subtype 1b nonstructural polyprotein region), conferred, for example, by the mutation g to t at position 5336 of SEQ ID NO:6, embodied in SEQ ID NO:8 (nucleotide[nt]) and SEQ ID NO:16 (amino acid[aa]); Arg to Gly at amino acid 1164 of SEQ ID NO:3, conferred, for example, by the mutation from a to g at position 5289 of SEQ ID NO:6, embodied in SEQ ID NO:9 (nt) and SEQ ID NO:17 (aa); Ala to Ser at amino acid 1174 of SEQ ID NO:3, conferred, for example, by the mutation from g to t at position 5320 of SEQ ID NO:6, embodied in SEQ ID NO:10 (nt) and the NS5A amino acid sequence of SEQ ID NO:19; Ser to Cys at amino acid 1172 of SEQ ID NO:3, conferred, for example, by the mutation c to g at position 5315 of SEQ ID NO:6, embodied in the NS5A gene SEQ ID NO:11 and the NS5A amino acid sequence of SEQ ID NO:20; and Ser to Pro at amino acid 1172 of SEQ ID NO:3, conferred, for example by the mutation t to c at position 5314 of SEQ ID NO:6, embodied in the NS5A gene SEQ ID NO:12 and the NS5A amino acid SEQ ID NO:21. The adaptive effect of these mutations is surprising since this region of HCV is normally conserved among HCV isolates. Additionally, deletions within the ISDR, including deletions of the entire ISDR and various flanking sequences, cause this adaptive effect. Among these deletions is the substitution of the ISDR and flanking sequence comprising amino acids 1182 to 1229 of SEQ ID NO:3 with a tyrosine, conferred, for example, by the deletion of nt 5345-5485 of SEQ ID NO:6, and embodied in SEQ ID NO:7 (nt) and the NS5A amino acid SEQ ID NO:14.

HCV variants comprising mutations adaptive to cell culture may also be attenuated, that is impaired in its ability to cause disease, establish chronic infections, trigger autoimmune responses, and transform cells.

The present invention also discloses methods for selecting for adaptive HCV variants. These methods comprise the use of an HCV virion or preferably a replicon, which further comprises a dominant selectable marker such as a neo gene. Cells are transfected with these variants. The transfectants are plated into selection media, such as G418 when the neo gene is utilized in the variant. Colonies that arise to exhibit resistance to the selectable marker are subpassaged into fresh selection media. HCV in colonies that withstand subpassage to establish a cell line harboring HCV replication can be isolated and used to transfect additional cells. Any of these colonies that show increased transfection efficiency or other desirable characteristics, such as the ability to withstand subpassage, are adaptive variants, where the adaptive nature of the variant is conferred by at least one mutation or deletion. Selected areas of the HCV in these adaptive variants are sequenced. Preferably, at least the NS5A is sequenced. More preferably, the entire polyprotein coding region is sequenced. Any mutations in these variants can be further evaluated to determine the adaptive nature of the mutations. That evaluation preferably involves recreating the mutation in an otherwise wild-type coding region and determining if the recreated HCV mutant exhibits the adaptive phenotype of the original mutant.

Adaptive mutations could also be manifested, but are not restricted to: (i) altering the tropism of HCV RNA replication; (ii) altering viral products responsible for deleterious effects on host cells; (iii) increasing or decreasing HCV RNA replication efficiency; (iv) increasing or decreasing HCV RNA packaging efficiency and/or assembly and release of HCV particles; (v) altering cell tropism at the level of receptor binding and entry. Thus, the engineered dominant selectable marker, whose expression is dependent upon productive HCV RNA replication, can be used to select for adaptive mutations in either the HCV replication machinery or the transfected host cell, or both. In addition, dominant selectable markers can be used to select for mutations in the HCV replication machinery that allow higher levels of RNA replication or particle formation. In one example, engineered HCV derivatives expressing a mutant form of DHFR can be used to confer resistance to methotrexate (MTX). As a dominant selectable marker, mutant DHFR is inefficient since nearly stoichiometric amounts are required for MTX resistance. By successively increasing concentrations of MIX in the medium, increased quantities of DHFR will be required for continued survival of cells harboring the replicating HCV RNA. This selection scheme, or similar ones based on this concept, can result in the selection of mutations in the HCV RNA replication machinery allowing higher levels of HCV RNA replication and RNA accumulation. Similar selections can be applied for mutations allowing production of higher yields of HCV particles in cell culture or for mutant HCV particles with altered cell tropism. Such selection schemes involve harvesting HCV particles from culture supernatants or after cell disruption and selecting for MTX-resistant transducing particles by reinfection of naive cells.

Methods similar to the above can be used to establish adaptive variants with variations in characteristics such as the increased or decreased ability to cause infection, the ability to cause infection in a host that wild-type strains are unable to infect, or cells of such a host.

The invention also provides host cell lines transfected with any of the HCV DNA (or HCV RNA) as set forth above. Examples of host cells include, but are by no means limited to, the group consisting of a bacterial cell, a yeast cell, an insect cell, and a mammalian cell. Preferably, the host cell is capable of providing for expression of functional HCV RNA replicase, virions or virus particle proteins.

In a related aspect, as briefly described above, the invention provides a vector for gene therapy or a gene vaccine (also termed herein a genetic vaccine), in which a heterologous protein is inserted into the HCV nucleic acid under conditions that permit expression of the heterologous protein. These vaccines can be either DNA or RNA. In particular, the invention provides an infectious hepatitis C virus (HCV) DNA vector comprising from 5' to 3' on the positive-sense DNA, a promoter; an HCV 5'-non-translated region (NTR) containing the extreme 5'-terminal sequence GCCAGCC; an HCV polyprotein coding region comprising a coding region for a heterologous gene; and a 3' non-translated region (NTR). Preferably, the promoter is selected from the group consisting of bacteriophage T3, T7, and SP6.

In the embodiments of the invention where the functional HCV nucleic acid is DNA, it may further comprise a promoter operatively associated with the 5' NTR. For example, but not by way of limitation, the promoter may be selected from the group consisting of bacteriophage T7, T3, and SP6. However, any suitable promoter for transcription of HCV genomic RNA corresponding to the HCV DNA can be used, depending on the specific transcription system employed. For example, for nuclear transcription (e.g., in an animal transgenic for HCV), an endogenous or viral promoter, such as CMV, may be used. Additionally, these promoter-driven HCV DNAs can be incorporated into an extrachromosomally replicating DNA such as a plasmid or a phage.

Various uses of the invention variants are envisioned herein. Uses relevant to therapy and vaccine development include: (i) the generation of defined HCV virus stocks to develop in vitro and in vivo assays for virus neutralization, attachment, penetration and entry; (ii) structure/function studies on HCV proteins and RNA elements and identification of new antiviral targets; (iii) a systematic survey of cell culture systems and conditions to identify those that support wild-type and variant HCV RNA replication and particle release; (iv) production of adaptive HCV variants capable of more efficient replication in cell culture; (v) production of HCV variants with altered tissue or species tropism; (vi) establishment of alternative animal models for inhibitor evaluation including those supporting HCV variant replication; (vii) development of cell-free HCV replication assays; (viii) production of immunogenic HCV particles for vaccination; (ix) engineering of attenuated HCV derivatives as possible vaccine candidates; (x) engineering of attenuated or defective HCV derivatives for expression of heterologous gene products for gene therapy and vaccine applications; (xi) utilization of the HCV glycoproteins for targeted delivery of therapeutic agents to the liver or other cell types with appropriate receptors.

The invention further provides a method for infecting an animal with HCV variants, where the method comprises administering an infectious dose of HCV variant RNA prepared by transcription of infectious HCV variant DNA. The invention extends to a non-human animal infected with HCV variants or transfected with HCV variant RNA or DNA. Similarly, the invention provides a method for propagating infectious HCV variants in vitro comprising culturing a cell line contacted with an infectious amount of HCV variant RNA prepared by transcription of the infectious HCV DNA, as well as an in vitro cell line infected with HCV variants. In a specific embodiment, the cell line is a hepatocyte cell line transfected or infected with an HCV variant in which an IRES-antibiotic resistance cassette has been engineered to provide for selection. The variant may also comprise the adaptive mutations described above.

In accordance with the gene therapy (genetic vaccine) embodiment of the invention, also provided is a method for transducing an animal capable of HCV RNA replication with a heterologous gene, comprising administering an amount of an HCV variant RNA prepared by transcription of the HCV variant DNA vector.

In another embodiment, the invention provides a method for producing HCV particle proteins comprising culturing a host expression cell line transfected with an HCV variant of the invention under conditions that permit expression of HCV particle proteins; and isolating HCV particle proteins from the cell culture. In a specific embodiment, such an expression cell line may be a cell selected from the group consisting of a bacterial cell, a yeast cell, an insect cell, and a mammalian cell.

The invention further provides an HCV virion comprising an HCV variant RNA genome. Such virions can be used in an HCV vaccine, preferably after attenuation, e.g., by heat or chemical treatment, or through selection of attenuated variants by the methods described above.

The in vivo and in vitro HCV variants of the invention permits controlled screening for anti-HCV agents (i.e., drugs for treatment of HCV), as well as for evaluation of drug resistance. An in vivo method for screening for agents capable of modulating HCV replication may comprise administering a candidate agent to an animal containing an HCV variant, and testing for an increase or decrease in a level of HCV variant infection, replication or activity compared to a level of HCV variant infection, replication or activity in the animal prior to administration of the candidate agent; wherein a decrease in the level of HCV variant infection, replication or activity compared to the level of HCV variant infection, replication or activity in the animal prior to administration of the candidate agent is indicative of the ability of the agent to inhibit HCV variant infection, replication or activity. Testing for the level of HCV variant infection or replication can involve measuring the viral titer (e.g., RNA levels) in a serum or tissue sample from the animal; testing for the level of HCV variant activity can involve measuring liver enzymes. Alternatively, an in vitro method for screening for agents capable of modulating HCV replication can comprise contacting a cell line supporting a replicating HCV variant with a candidate agent; and thereafter testing for an increase or decrease in a level of HCV variant replication or activity compared to a level of HCV variant replication or activity in a control cell line or in the cell line prior to administration of the candidate agent, wherein a decrease in the level of HCV variant replication or activity compared to the level of HCV variant replication or activity in a control cell line or in the cell line prior to administration of the candidate agent is indicative of the ability of the agent to inhibit HCV variant replication or activity. In a specific embodiment, testing for the level of HCV variant replication in vitro may involve measuring the HCV titer, (e.g., RNA levels) in the cell culture; testing for the level of HCV activity in vitro may involve measuring HCV replication.

In addition to the specific HCV variant DNA clones and related HCV variant RNAs, the invention is directed to a method for preparing an HCV variant DNA clone that is capable of replication in a host or host cell line, comprising joining from 5' to 3' on the positive-sense DNA a promoter; an HCV 5' non-translated region (NTR) an HCV polyprotein coding region; and a 3' non-translated region (NTR), where at least one of these regions is not a naturally occurring region. Preferably, the promoter is selected from the group consisting of bacteriophage T7, T3, and SP6. In a specific embodiment, the extreme 5'-terminal sequence is homologous to SEQ ID NO:1, e.g., the 5'-terminal sequence may be selected from the group consisting of GCCAGCC; GGCCAGCC; UGCCAGCC; AGCCAGCC; AAGCCAGCC; GAGCCAGCC; GUGCCAGCC; and GCGCCAGCC, wherein the sequence GCCAGCC is the 5'-terminus of SEQ ID NO:1.

The 3'-NTR poly-U for use in the method of preparing an HCV variant DNA clone may include a long poly-U region. Similarly, the 3'-NTR extreme terminus may be RNA homologous to a DNA having the sequence 5'-TGGTG-GCTCCATCTTAGCCCTAGTCACGGCTAGCTGTGAA-AGGTCCGTGAGCCGCATGACTGCAGAGAGTGCTG-ATACTGGCCTCTCTGCTGATCATGT-3' (SEQ ID NO:2); in a specific embodiment, the 3'-NTR extreme terminus has the foregoing sequence.

Components of functional HCV variant DNA clones. Components of the functional HCV variant DNA described in this invention can be used to develop cell-free, cell culture, and animal-based screening assays for known or newly identified HCV antiviral targets as described infra. For each selected target, it is preferred that the HCV variant used has the wild-type form of the target. Examples of known or suspected targets and assays include [see Houghton, In "Fields Virology" (B. N. Fields, D. M. Knipe and P. M. Howley, Eds.), Vol. pp. 1035-1058. Raven Press, New York (1996); Rice, (1996) supra; Rice et al., Antiviral Therapy 1, Suppl. 4, 11-17 (1997); Shimotohno, Hepatology 21:887-8 (1995) for reviews], but are not limited to, the following:

The highly conserved 5' NTR, which contains elements essential for translation of the incoming HCV genome RNA, is one target. It is also likely that this sequence, or its complement, contains RNA elements important for RNA replication and/or packaging. Potential therapeutic strategies include: antisense oligonucleotides (supra); trans-acting ribozymes (supra); RNA decoys; small molecule compounds interfering with the function of this element (these could act by binding to the RNA element itself or to cognate viral or cellular factors required for activity).

Another target is the HCV C (capsid or core) protein, which is highly conserved and is associated with the following functions: RNA binding and specific encapsidation of HCV genome RNA; transcriptional modulation of cellular [Ray et al., Virus Res. 37: 209-220 (1995)] and other viral [Shih et al., J. Virol. 69: 1160-1171 (1995); Shih et al., J. Virol. 67: 5823-5832 (1993)] genes; binding of cellular helicase [You et al., J. Virol. 73:2841-2853 (1999)]; cellular transformation [Ray et al., J. Virol. 70: 4438-4443 (1996a); Ray et al., J. Biol. Chem. 272:10983-10986(1997)]; prevention of apoptosis [Ray et al., Virol. 226: 176-182 (1996b)]; modulation of host immune response through binding to members of the TNF receptor superfamily [Matsumoto et al., J. Virol. 71: 1301-1309 (1997)].

The E1, E2, and perhaps the E2-p7 glycoproteins that form the components of the virion envelope are targets for potentially neutralizing antibodies. Key steps where intervention can be targeted include: signal peptidase mediated cleavage of these precursors from the polyprotein (Lin et al., (1994a) supra]; ER assembly of the E1E2 glycoprotein complex and association of these proteins with cellular chaperones and folding machinery [Dubuisson et al., (1994) supra; Dubuisson and Rice, J. Virol. 70: 778-786 (1996)]; assembly of virus particles including interactions between the nucleocapsid and virion envelope; transport and release of virus particles; the association of virus particles with host components such as VLDL [Hijikata et al., (1993) supra; Thomssen et al., (1992) supra; Thomssen et al., Med. Microbiol. Immunol. 182: 329-334 (1993)] which may play a role in evasion of immune surveillance or in binding and entry of cells expressing the LDL receptor; conserved and variable determinants in the virion which are targets for neutralization by antibodies or which bind to antibodies and facilitate immune-enhanced infection of cells via interaction with cognate Fc receptors; conserved and variable determinants in the virion important for receptor binding and entry; virion determinants participating in entry, fusion with cellular membranes, and uncoating the incoming viral nucleocapsid.

The NS2-3 autoprotease, which is required for cleavage at the ⅔ site is a further target.

The NS3 serine protease and NS4A cofactor which form a complex and mediate four cleavages in the HCV polyprotein [see Rice, (1997) supra for review) is yet another suitable target. Targets include the serine protease activity itself; the tetrahedral $Zn^{2+}$ coordination site in the C-terminal domain of the serine protease; the NS3-NS4A cofactor interaction; the membrane association of NS4A; stabilization of NS3 by NS4A; transforming potential of the NS3 protease region [Sakamuro et al., J Virol 69: 3893-6 (1995)].

The NS3 RNA-stimulated NTPase [Suzich et al., (1993) supra], RNA helicase [Jin and Peterson, Arch Biochem Biophys 323: 47-53 (1995); Kim et al., Biochem. Biophys. Res. Commun. 215: 160-6 (1995)], and RNA binding [Kanai et al., FEBS Lett 376: 2214 (1995)] activities; the NS4A protein as a component of the RNA replication complex is another potential target.

The NS5A protein, another replication component, represents another target. This protein is phosphorylated predominantly on serine residues [Tanji et al., J. Virol. 69:

3980-3986 (1995)]. Transcription modulating, cell growth promoting, and apoptosis inhibiting activities of NS5A [Ghosh et al., *J. Biol. Chem.* 275:7184-7188 (2000)] can be targeted. Other characteristics of NS5A that could be targets for therapy include the kinase responsible for NS5A phosphorylation and its interaction with NS5A, and the interaction with NS5A and other components of the HCV replication complex.

The NS5B RNA-dependent RNA polymerase, which is the enzyme responsible for the actual synthesis of HCV positive and negative-strand RNAs, is another target. Specific aspects of its activity include the polymerase activity itself [Behrens et al., *EMBO J.* 15: 12-22 (1996)1; interactions of NS5B with other replicase components, including the HCV RNAs; steps involved in the initiation of negative- and positive-strand RNA synthesis; phosphorylation of NS5B [Hwang et al., *Virology* 227:438 (1997)].

Other targets include structural or nonstructural protein functions important for HCV RNA replication and/or modulation of host cell function. Possible hydrophobic protein components capable of forming channels important for viral entry, egress or modulation of host cell gene expression may be targeted.

The 3' NTR, especially the highly conserved elements (poly (U/UC) tract; 98-base terminal sequence) can be targeted. Therapeutic approaches parallel those described for the 5' NTR, except that this portion of the genome is likely to play a key role in the initiation of negative-strand synthesis. It may also be involved in other aspects of HCV RNA replication, including translation, RNA stability, or packaging.

The functional HCV variants of the present invention may encode all of the viral proteins and RNA elements required for RNA packaging. These elements can be targeted for development of antiviral compounds. Electrophoretic mobility shift, UV cross-linking, filter binding, and three-hybrid [SenGupta et al., *Proc. Natl. Acad. Sci. USA* 93: 8496-8501 (1996)] assays can be used to define the protein and RNA elements important for HCV RNA packaging and to establish assays to screen for inhibitors of this process. Such inhibitors might include small molecules or RNA decoys produced by selection in vitro [Gold et al., (1995) supra].

Complex libraries of the variants of the present invention can be prepared using PCR shuffling, or by incorporating randomized sequences, such as are generated in "peptide display" libraries. Using the "phage method" [Scott and Smith, 1990, *Science* 249:386-390 (1990); Cwirla, et al., *Proc. Natl. Acad. Sci. USA.,* 87:6378-6382 (1990); Devlin et al., *Science,* 249:404-406 (1990)], very large libraries can be constructed ($10^6$-$10^8$ chemical entities). Clones from such libraries can be used to generate other variants or chimeras, e.g., using various HCV subtypes. Such variants can be generated by methods known in the art, without undue experimentation.

A clone that includes a primer and run-off sequence can be used directly for production of functional HCV variant RNA. A large number of vector-host systems known in the art may be used. Examples of vectors include, but are not limited to, *E. coli*, bacteriophages such as lambda derivatives, or plasmids such as pBR322 derivatives or pUC plasmid derivatives, e.g., pGEX vectors, pmal-c, pFLAG, pTET, etc. As is well known, the insertion into a cloning vector can, for example, be accomplished by ligating the DNA fragment into a cloning vector that has complementary cohesive termini. However, if the complementary restriction sites used to fragment the DNA are not present in the cloning vector, the ends of the DNA molecules may be enzymatically modified. Alternatively, any site desired could be produced by ligating nucleotide sequences (linkers) onto the DNA termini; these ligated linkers may comprise specific chemically synthesized oligonucleotides encoding restriction endonuclease recognition sequences. Recombinant molecules can be introduced into host cells via transformation, transfection, infection, electroporation, etc., so that many copies of the gene sequence are generated.

Expression of HCV RNA and Polypeptides

The HCV variant DNA, which codes for HCV variant RNA and HCV proteins, particularly HCV RNA replicase or virion proteins, can be inserted into an appropriate expression vector, i.e., a vector which contains the necessary elements for the transcription and translation of the inserted protein-coding sequence. Such elements are termed herein a "promoter." Thus, the HCV variant DNA of the invention is operationally (or operably) associated with a promoter in an expression vector of the invention. An expression vector also preferably includes a replication origin. The necessary transcriptional and translational signals can be provided on a recombinant expression vector. In a preferred embodiment for in vitro synthesis of functional RNAs, the T7, T3, or SP6 promoter is used.

Potential host-vector systems include but are not limited to mammalian cell systems infected with virus recombinant (e.g., vaccinia virus, adenovirus, Sindbis virus, Semliki Forest virus, etc.); insect cell systems infected with recombinant viruses (e.g., baculovirus); microorganisms such as yeast containing yeast vectors; plant cells; or bacteria transformed with bacteriophage, DNA, plasmid DNA, or cosmid DNA. The expression elements of vectors vary in their strengths and specificities. Depending on the host-vector system utilized, any one of a number of suitable transcription and translation elements may be used.

The cell into which the recombinant vector comprising the HCV variant DNA clone has been introduced is cultured in an appropriate cell culture medium under conditions that provide for expression of HCV RNA or such HCV proteins by the cell. Any of the methods previously described for the insertion of DNA fragments into a cloning vector may be used to construct expression vectors containing a gene consisting of appropriate transcriptional/translational control signals and the protein coding sequences. These methods may include in vitro recombinant DNA and synthetic techniques and in vivo recombination (genetic recombination).

Expression of HCV variant RNA or protein may be controlled by any promoter/enhancer element known in the art, but these regulatory elements must be functional in the host selected for expression. Promoters which may be used to control expression include, but are not limited to, the SV40 early promoter region (Benoist and Chambon, 1981, Nature 290:304-310), the promoter contained in the 3' long terminal repeat of Rous sarcoma virus (Yamamoto, et al., 1980, Cell 22:787-797), the herpes thymidine kinase promoter (Wagner et al., 1981, Proc. Natl. Acad. Sci. U.S.A. 78:1441-1445), the regulatory sequences of the metallothionein gene (Brinster et al., 1982, Nature 296:39-42); prokaryotic expression vectors such as the β-lactamase promoter (Villa-Kamaroff, et al., 1978, Proc. Natl. Acad. Sci. U.S.A. 75:3727-3731), or the tac promoter (DeBoer, et al., 1983, Proc. Natl. Acad. Sci. U.S.A. 80:21-25); promoter elements from yeast or other fungi such as the Gal 4 promoter, the ADC (alcohol dehydrogenase) promoter, PGK (phosphoglycerol kinase) promoter, alkaline phosphatase promoter; and the animal transcriptional control regions, which exhibit tissue specificity and have been utilized in transgenic animals: elastase I gene control region which is active in pancreatic acinar cells (Swift et al., 1984, Cell 38:639-646; Ornitz et al., 1986, Cold Spring Harbor Symp. Quant. Biol. 50:399-409; MacDonald, 1987, Hepatology 7:425-515); insulin gene control region which is active in pancreatic beta cells (Hanahan, 1985, Nature 315:115-122), immunoglobulin gene control region which is active in lymphoid cells (Grosschedl et al., 1984, Cell 38:647-658; Adames et al., 1985, Nature 318:533-538; Alexander et al., 1987, Mol. Cell. Biol. 7:1436-1444), mouse mammary tumor virus control region which is active in testicular, breast, lymphoid and mast cells (Leder et al., 1986, Cell 45:485-495), albumin gene control region which is active in liver (Pinkert et al., 1987, Genes and Devel. 1:268-276), alpha-fetoprotein gene control region which is active in liver (Krumlauf et al., 1985, Mol. Cell. Biol. 5:1639-1648; Hammer et al., 1987, Science 235:53-58), alpha 1-antitrypsin gene control region which is active in the liver (Kelsey et al., 1987, Genes and Devel. 1:161-171), beta-globin gene control region which is active in myeloid cells (Mogram et al., 1985, Nature 315:338-340; Kollias et al., 1986, Cell 46:89-94), myelin basic protein gene control region which is active in oligodendrocyte cells in the brain (Readhead et al., 1987, Cell 48:703-712), myosin light chain-2 gene control region which is active in skeletal muscle (Sani, 1985, Nature 314:283-286), and gonadotropic releasing hormone gene control region which is active in the hypothalamus (Mason et al., 1986, Science 234:1372-1378).

A wide variety of host/expression vector combinations may be employed in expressing the DNA sequences of this invention. Useful expression vectors, for example, may consist of segments of chromosomal, non-chromosomal and synthetic DNA sequences. Suitable vectors include derivatives of SV40 and known bacterial plasmids, e.g., *E. coli* plasmids col E1, pCR1, pBR322, pMal-C2, pET, pGEX [Smith et al., 1988, Gene 67:3140], pMB9 and their derivatives, plasmids such as RP4; phage DNAS, e.g., the numerous derivatives of phage λ e.g., NM989, and other phage DNA, e.g., M13 and filamentous single stranded phage DNA; yeast plasmids such as the 2μ plasmid or derivatives thereof; vectors useful in eukaryotic cells, such as vectors useful in insect or mammalian cells; vectors derived from combinations of plasmids and phage DNAs, such as plasmids that have been modified to employ phage DNA or other expression control sequences; and the like known in the art.

In addition to the preferred sequencing analysis, expression vectors containing an HCV variant DNA clone of the invention can be identified by four general approaches: (a) PCR amplification of the desired plasmid DNA or specific mRNA, (b) nucleic acid hybridization, (c) presence or absence of selection marker gene functions, (d) analysis with appropriate restriction endonucleases and (e) expression of inserted sequences. In the first approach, the nucleic acids can be amplified by PCR to provide for detection of the amplified product. In the second approach, the presence of nucleic acids in an expression vector can be detected by nucleic acid hybridization using probes comprising sequences that are homologous to the HCV variant DNA. In the third approach, the recombinant vector/host system can be identified and selected based upon the presence or absence of certain "selection marker" gene functions (e.g., β-galactosidase activity, thymidine kinase activity, resistance to antibiotics, transformation phenotype, occlusion body formation in baculovirus, etc.) caused by the insertion of foreign genes in the vector. In the fourth approach, recombinant expression vectors are identified by digestion with appropriate restriction enzymes. In the fifth approach, recombinant expression vectors can be identified by assaying for the activity, biochemical, or immunological characteristics of the gene product expressed by the recombinant, e.g., HCV RNA, HCV virions, or HCV viral proteins.

For example, in a baculovirus expression systems, both non-fusion-transfer vectors, such as but not limited to pVL941 (BamHI cloning site; Summers), pVL1393 (BamHI, SmaI, XbaI, EcoR1, NotI, XmaIII, BglII, and PstI cloning site; Invitrogen), pVL1392 (BglII, PstI, NotI, XmaIII, EcoRI, XbaI, SmaI, and BamHI cloning site; Summers and Invitrogen), and pBlueBacIII (BamHI, BglII, PstI, NcoI, and HindIII cloning site, with blue/white recombinant screening possible; Invitrogen), and fusion transfer vectors, such as but not limited to pAc700 (BamHI and KpnI cloning site, in which the BamHI recognition site begins with the initiation codon; Summers), pAc701 and pAc702 (same as pAc700, with different reading frames), pAc360 (BamHI cloning site 36 base pairs downstream of a polyhedrin initiation codon; Invitrogen(195)), and pBlueBacHisA, B, C (three different reading frames, with BamHI, BglII, PstI, NcoI, and HindIII cloning site, an N-terminal peptide for ProBond purification, and blue/white recombinant screening of plaques; Invitrogen) can be used.

Examples of mammalian expression vectors contemplated for use in the invention include vectors with inducible promoters, such as the dihydrofolate reductase (DHFR) promoter, e.g., any expression vector with a DHFR expression vector, or a DHFR/methotrexate co-amplification vector, such as pED (PstI, SalI, SbaI, SmaI, and EcoRI cloning site, with the vector expressing both the cloned gene and DHFR); [see Kaufman, *Current Protocols in Molecular Biology*, 16.12 (1991)]. Alternatively, a glutamine synthetase/methionine sulfoximine co-amplification vector, such as pEE14 (HindIII, XbaI, SmaI, SbaI, EcoRI, and BclI cloning site, in which the vector expresses glutamine synthase and the cloned gene; Celltech). In another embodiment, a vector that directs episomal expression under control of Epstein Barr Virus (EBV) can be used, such as pREP4 (BamHI, SfiI, XhoI, NotI, NheI, HindIII, NheI, PvuII, and KpnI cloning site, constitutive RSV-LTR promoter, hygromycin selectable marker; Invitrogen), pCEP4 (BamHI, SfiI, XhoI, NotI, NheI, HindIII, NheI, PvuII, and KpnI cloning site, constitutive hCMV immediate early gene, hygromycin selectable marker; Invitrogen), pMEP4 (KpnI, PvuI, NheI, HindIII, NotI, XhoI, SfiI, BamHI cloning site, inducible methallothionein IIa gene promoter, hygromycin selectable marker: Invitrogen), pREP8 (BamHI, XhoI, NotI, HindIII, NheI, and KpnI cloning site, RSV-LTR promoter, histidinol selectable marker; Invitrogen), pREP9 (KpnI, NheI, HindIII, NotI, XhoI, SfiI, and BamHI cloning site, RSV-LTR promoter, G418 selectable marker; Invitrogen), and pEBVHis (RSV-LTR promoter, hygromycin selectable marker, N-terminal peptide purifiable via ProBond resin and cleaved by enterokinase; Invitrogen). Regulatable mammalian expression vectors, can be used, such as Tet and rTet [Gossen and Bujard, *Proc. Natl. Acad. Sci. USA* 89:5547-51 (1992); Gossen et al., *Science* 268:1766-1769 (1995)]. Selectable mammalian expression vectors for use in the invention include pRc/CMV (HindIII, BstXI, NotI, SbaI, and ApaI cloning site, G418 selection; Invitrogen), pRc/RSV (HindIII, SpeI, BstXI, NotI, XbaI cloning site, G418 selection; Invitrogen), and others. Vaccinia virus mammalian expression vectors [see, Kaufman (1991) supra] for use according to the invention include but are not limited to pSC11 (SmaI cloning site, TK- and β-gal selection), pMJ601 (SalI, SmaI AflI, NarI, BspMII, BamHI, ApaI, NheI, SacII, KpnI, and HindIII cloning site; TK- and β-gal selection), and pTKgptF1S (EcoRI, PstI, SalI, AccI, HindII, SbaI, BamHI, and Hpa cloning site, TK or XPRT selection).

Examples of yeast expression systems include the non-fusion pYES2 vector (XbaI, SphI, ShoI, NotI, GstXI, EcoRI, BstXI, BamHI, SacI, KpnI, and HindIII cloning sit; Invitrogen) or the fusion pYESHisA, B, C (XbaI, SphI, ShoI, NotI, BstXI, EcoRI, BamHI, SacI, KpnI, and HindII cloning site, N-terminal peptide purified with ProBond resin and cleaved with enterokinase; Invitrogen), to mention just two, can be employed according to the invention.

In addition, a host cell strain may be chosen that modulates the expression of the inserted sequences, or modifies and processes the gene product in the specific fashion desired. Different host cells have characteristic and specific mechanisms for the translational and post-translational processing and modification (e.g., glycosylation, cleavage [e.g., of signal sequence]) of proteins. Expression in yeast can produce a glycosylated product. Expression in eukaryotic cells can increase the likelihood of "native" glycosylation and folding of an HCV protein. Moreover, expression in mammalian cells can provide a tool for reconstituting, or constituting, native HCV virions or virus particle proteins.

A variety of transfection methods, useful for other RNA virus studies, can be utilized herein without undue experimentation. Examples include microinjection, cell fusion, calcium-phosphate cationic liposomes such as lipofectin [Rice et al., New Biol. 1:285-296 (1989); see "HCV-based Gene Expression Vectors", infra], DE-dextran [Rice et al., J. Virol. 61: 3809-3819 (1987)], and electroporation [Bredenbeek et al., J. Virol. 67: 6439-6446 (1993); Liljeström et al., J. Virol. 65: 4107-4113 (1991)]. Scrape loading [Kumar et al., Biochem. Mol. Biol. Int. 32: 1059-1066 (1994)] and ballistic methods [Burkholder et al., J. Immunol. Meth. 165: 149-156 (1993)] may also be considered for cell types refractory to transfection by these other methods. A DNA vector transporter may be considered [see, e.g., Wu et al., 1992, J. Biol. Chem. 267:963-967; Wu and Wu, 1988, J. Biol. Chem. 263:14621-14624; Hartmut et al., Canadian Patent Application No. 2,012,311, filed Mar. 15, 1990].

In Vitro Transfection with HCV Variants

Identification of cell lines supporting HCV replication. An important aspect of the invention is a method it provides for developing new and more effective anti-HCV therapy by conferring the ability to evaluate the efficacy of different therapeutic strategies using an authentic and standardized in vitro HCV variant replication system. Such assays are invaluable before moving on to trials using rare and valuable experimental animals, such as the chimpanzee, or HCV-infected human patients. The adaptive variants of the invention are particularly useful for this work because their growth in culture and their ability to withstand subpassage is superior to wild-type strains. Also, the replicons disclosed herein are useful because replication can be evaluated without the confounding effects of the structural proteins.

The HCV variant infectious clone technology can also be used to establish in vitro and in vivo systems for analysis of HCV replication and packaging. These include, but are not restricted to, (i) identification or selection of permissive cell types (for RNA replication, virion assembly and release); (ii) investigation of cell culture parameters (e.g., varying culture conditions, cell activation, etc.) or selection of adaptive mutations that increase the efficiency of HCV replication in cell cultures; and (iii) definition of conditions for efficient production of infectious HCV variant particles (either released into the culture supernatant or obtained after cell disruption). These and other readily apparent extensions of the invention have broad utility for HCV therapeutic, vaccine, and diagnostic development.

General approaches for identifying permissive cell types are outlined below. Optimal methods for RNA transfection (see also, supra) vary with cell type and are determined using RNA reporter constructs. These include, for example, the bicistronic replicons disclosed supra and in the Examples, and bicistronic virus [Wang et al., J. Virol. 67: 3338-44 (1993)] with the structure 5'-CAT-HCV IRES-LUC-3'. These HCV variants are used both to optimize transfection conditions (using, e.g., by measuring β-galactosidase or CAT [chloramphenicol acetyltransferase] activity to determine transfection efficiency) and to determine if the cell type is permissive for HCV IRES-mediated translation (e.g., by measuring LUC; luciferase activity). For actual HCV RNA transfection experiments, cotransfection with a 5' capped luciferase reporter RNA [Wang et al., (1993) supra] provides an internal standard for productive transfection and translation. Examples of cell types potentially permissive for HCV replication include, but are not restricted to, primary human cells (e.g., hepatocytes, T-cells, B-cells, foreskin fibroblasts) as well as continuous human cell lines (e.g., HepG2, Huh7, HUT78, HPB-Ma, MT-2, MT-2C, and other HTLV-1 and HTLV-II infected T-cell lines, Namalawa, Daudi, EBV-transformed LCLs). In addition, cell lines of other species, especially those which are readily transfected with RNA and permissive for replication of flaviviruses or pestiviruses (e.g., SW-13, Vero, BHK-21, COS, PK-15, MBCK, etc.), can be tested. Cells are transfected using a method as described supra.

For replication assays, RNA transcripts are prepared using the HCV variant and the corresponding non-functional, e.g., ΔGDD (see Examples) derivative as a negative control, for persistence of HCV RNA and antigen in the absence of productive replication. Template DNA (which complicates later analyses) is removed by repeated cycles of DNaseI treatment and acid phenol extraction followed by purification by either gel electrophoresis or gel filtration, to preferably achieve less than one molecule of amplifiable DNA per $10^9$ molecules of transcript RNA. DNA-free RNA transcripts are mixed with LUC reporter RNA and used to transfect cell cultures using optimal conditions determined above. After recovery of the cells, RNaseA is added to the media to digest excess input RNA and the cultures incubated for various periods of time. An early timepoint (~1 day post-transfection) will be harvested and analyzed for LUC activity (to verify productive transfection) and positive-strand RNA levels in the cells and supernatant (as a baseline). Samples are collected periodically for 2-3 weeks and assayed for positive-strand RNA levels by QC-RT/PCR [see Kolykhalov et al., (1996) supra]. Cell types showing a clear and reproducible difference between the intact infectious transcript and the non-functional derivative, e.g., ΔGDD deletion, control can be subjected to more thorough analyses to verify authentic replication. Such assays include measurement of negative-sense HCV RNA accumulation by QC-RT/PCR [Gunji et al., (1994) supra; Lanford et al., Virology 202: 606-14 (1994)], Northern-blot hybridization, or metabolic labeling [Yoo et al., (1995) supra] and single cell methods, such as in situ hybridization [ISH; Gowans et al, In "Nucleic Acid Probes" (R. H. Symons, Eds.), Vol. pp. 139-158. CRC Press, Boca Raton. (1989)], in situ PCR [followed by ISH to detect only HCV-specific amplification products; Haase et al., *Proc. Natl. Acad. Sci. USA* 87: 4971-4975 (1990)], and immunohistochemistry.

HCV particles for studying virus-receptor interactions. In combination with the identification of cell lines that are permissive for HCV replication, defined HCV variant stocks can be used to evaluate the interaction of the HCV with cellular receptors. Assays can be set up which measure binding of the virus to susceptible cells or productive infection, and then used to screen for inhibitors of these processes.

Identification of cell lines for characterization of HCV receptors. Cell lines permissive for HCV RNA replication, as assayed by RNA transfection, can be screened for their ability to be infected by the virus using the HCV variants of the present invention. Cell lines permissive for RNA replication but which cannot be infected by the homologous virus may lack one or more host receptors required for HCV binding and entry. Such cells provide valuable tools for (i) functional identification and molecular cloning of HCV receptors and co-receptors; (ii) characterization of virus-receptor interactions; and (iii) developing assays to screen for compounds or biologics (e.g., antibodies, SELEX RNAs cartel and Szostak, In "RNA-protein interactions" (K. Nagai and I. W. Mattaj, Eds.), Vol. pp. 82-102. IRL Press, Oxford (1995); Gold et al., *Annu. Rev. Biochem.* 64: 763-797 (1995)], etc.) that inhibit these interactions. Once defined in this manner, these HCV receptors serve not only as therapeutic targets but may also be expressed in transgenic animals rendering them susceptible to HCV infection [Koike et al., *Dev Biol Stand* 78: 101-7 (1993); Ren and Racaniello, *J Virol* 66: 296-304 (1992)]. Such transgenic animal models supporting HCV replication and spread have important applications for evaluating anti-HCV drugs.

The ability to manipulate the HCV glycoprotein structure may also be used to create HCV variants with altered receptor specificity. In one example, HCV glycoproteins can be modified to express a heterologous binding domain for a known cell surface receptor. The approach should allow the engineering of HCV derivatives with altered tropism and perhaps extend infection to non-chimeric small animal models.

Alternative approaches for identifying permissive cell lines. As previously discussed, and as exemplified in the Examples, functional HCV variants can be engineered that comprise selectable markers for HCV replication. For instance, genes encoding dominant selectable markers can be expressed as part of the HCV polyprotein, or as separate cistrons located in permissive regions of the HCV RNA genome.

Animal Models for HCV Infection and Replication

In addition to chimpanzees, the present invention permits development of alternative animal models for studying HCV replication and evaluating novel therapeutics. Using clones of the authentic HCV variants described in this invention as starting material, multiple approaches can be envisioned for establishing alternative animal models for HCV replication. In one manifestation, the variants could be used to inoculate immunodeficient mice harboring human tissues capable of supporting HCV replication. An example of this art is the SCID:Hu mouse, where mice with a severe combined immunodeficiency are engrafted with various human (or chimpanzee) tissues, which could include, but are not limited to, fetal liver, adult liver, spleen, or peripheral blood mononuclear cells. Besides SCID mice, normal irradiated mice can serve as recipients for engraftment of human or chimpanzee tissues. These chimeric animals would then be substrates for HCV replication after either ex vivo or in vivo infection with defined virus-containing inocula.

In another manifestation, adaptive mutations allowing HCV replication in alternative species may produce variants that are permissive for replication in these animals. For instance, adaptation of HCV for replication and spread in either continuous rodent cell lines or primary tissues (such as hepatocytes) could enable the virus to replicate in small rodent models. Alternatively, complex libraries of HCV variants created by DNA shuffling [Stemmer, *Proc. Natl. Acad. Sci. USA* 91:10747 (1994)] or other methods known in the art can be created and used for inoculation of potentially susceptible animals. Such animals could be either immunocompetent or immunodeficient, as described above.

The functional activity of HCV variants can be evaluated transgenically. In this respect, a transgenic mouse model can be used [see, e.g., Wilmut et al., *Experientia* 47:905 (1991)]. The HCV RNA or DNA clone can be used to prepare transgenic vectors, including viral vectors, plasmid or cosmid clones (or phage clones). Cosmids may be introduced into transgenic mice using published procedures [Jaenisch, *Science,* 240:1468-1474 (1988)]. In the preparation of transgenic mice, embryonic stem cells are obtained from blastocyst embryos [Joyner, *In Gene Targeting: A Practical Approach. The Practical Approach Series*, Rickwood, D., and Hames, B. D., Eds., IRL Press: Oxford (1993)] and transfected with HCV variant DNA or RNA. Transfected cells are injected into early embryos, e.g., mouse embryos, as described [Hammer et al., *Nature* 315: 680 (1985); Joyner, supra]. Various techniques for preparation of transgenic animals have been described [U.S. Pat. No. 5,530,177, issued Jun. 25, 1996; U.S. Pat. No. 5,898, 604, issued Dec. 31, 1996]. Of particular interest are transgenic animal models in which the phenotypic or pathogenic effects of a transgene are studied. For example, the effects of a rat phosphoenolpyruvate carboxykinase-bovine growth hormone fusion gene has been studied in pigs [Wieghart et al., *J. Reprod. Fert., Suppl.* 41:89-96 (1996)]. Transgenic mice that express of a gene encoding a human amyloid precursor protein associated with Alzheimer's disease are used to study this disease and other disorders [International Patent Publication WO 96/06927, published Mar. 7, 1996; Quon et al., *Nature* 352:239 (1991)]. Transgenic mice have also been created for the hepatitis delta agent [Polo et al., *J. Virol.* 69:5203 (1995)] and for hepatitis B virus [Chisari, *Curr. Top. Microbiol. Immunol.* 206:149 (1996)], and replication occurs in these engineered animals.

Thus, the functional HCV variants described here, or parts thereof, can be used to create transgenic models relevant to HCV replication and pathogenesis. In one example, transgenic animals harboring the entire genome of an HCV variant can be created. Appropriate constructs for transgenic expression of the entire HCV variant genome in a transgenic mouse of the invention could include a nuclear promoter engineered to produce transcripts with the appropriate 5' terminus, the full-length HCV variant cDNA sequence, a cis-cleaving delta ribozyme [Ball, *J. Virol.* 66: 2335-2345 (1992); Pattnaik et al., *Cell* 69: 1011-1020 (1992)] to produce an authentic 3' terminus, followed possibly by signals that promote proper nuclear processing and transport to the cytoplasm (where HCV RNA replication occurs). Besides the entire HCV variant genome, animals can be engineered to express individual or various combinations of HCV proteins and RNA elements. For example, animals engineered to express an HCV gene product or reporter gene under the control of the HCV IRES can be used to evaluate therapies directed against this specific RNA target. Similar animal models can be envisioned for most known HCV targets.

Such alternative animal models are useful for (i) studying the effects of different antiviral agents on replication of HCV variants, including replicons, in a whole animal system; (ii) examining potential direct cytotoxic effects of HCV gene products on hepatocytes and other cell types, defining the underlying mechanisms involved, and identifying and testing strategies for therapeutic intervention; and (iii) studying immune-mediated mechanisms of cell and tissue damage relevant to HCV pathogenesis and identifying and testing strategies for interfering with these processes.

Selection and Analysis of Drug-Resistant Variants

Cell lines and animal models supporting HCV replication can be used to examine the emergence of HCV variants with resistance to existing and novel therapeutics. Like all RNA viruses, the HCV replicase is presumed to lack proofreading activity and RNA replication is therefore error prone, giving rise to a high level of variation [Bukh et al., (1995) supra]. The variability manifests itself in the infected patient over time and in the considerable diversity observed between different isolates. The emergence of drug-resistant variants is likely to be an important consideration in the design and evaluation of HCV mono and combination therapies. HCV replication systems of the invention can be used to study the emergence of variants under various therapeutic formulations. These might include monotherapy or various combination therapies (e.g., IFN-α, ribavirin, and new antiviral compounds). Resistant mutants can then be used to define the molecular and structural basis of resistance and to evaluate new therapeutic formulations, or in screening assays for effective anti-HCV drugs (infra).

Screening for Anti-HCV Agents

HCV-permissive cell lines or animal models (preferably rodent models) comprising adaptive HCV variants can be used to screen for novel inhibitors or to evaluate candidate anti-HCV therapies. Such therapies include, but would not be limited to, (i) antisense oligonucleotides or ribozymes targeted to conserved HCV RNA targets; (ii) injectable compounds capable of inhibiting HCV replication; and (iii) orally bioavailable compounds capable of inhibiting HCV replication. Targets for such formulations include, but are not restricted to, (i) conserved HCV RNA elements important for RNA replication and RNA packaging; (ii) HCV-encoded enzymes; (iii) protein-protein and protein-RNA interactions important for HCV RNA replication, virus assembly, virus release, viral receptor binding, viral entry, and initiation of viral RNA replication; (iv) virus-host interactions modulating the ability of HCV to establish chronic infections; (v) virus-host interactions modulating the severity of liver damage, including factors affecting apoptosis and hepatotoxicity; (vi) virus-host interactions leading to the development of more severe clinical outcomes including cirrhosis and hepatocellular carcinoma; and (vii) virus-host interactions resulting in other, less frequent, HCV-associated human diseases.

Evaluation of antisense and ribozyme therapies. The present invention extends to the preparation of antisense nucleotides and ribozymes that may be tested for the ability to interfere with HCV replication. This approach utilizes antisense nucleic acid and ribozymes to block translation of a specific mRNA, either by masking that mRNA with an antisense nucleic acid or cleaving it with a ribozyme.

Antisense nucleic acids are DNA or RNA molecules that are complementary to at least a portion of a specific mRNA molecule. Reviews of antisense technology include: Baertschi, *Mol. Cell. Endocrinol.* 101:R15-R24 (1994); Crooke et al., *Annu. Rev. Pharmacol. Toxicol.* 36:107-129 (1996); Alama et al., *Pharmacol. Res.* 36:171-178; and Boyer et al., *J. Hepatol.* 32(1 Suppl):98-112(2000). The last review discusses antisense technology as it applies to HCV.

In the cell, they hybridize to that mRNA, forming a double stranded DNA:RNA or RNA:RNA molecule. The cell does not translate an mRNA in this double-stranded form. Therefore, antisense nucleic acids interfere with the expression of mRNA into protein. Oligomers of about fifteen nucleotides and molecules that hybridize to the AUG initiation codon will be particularly efficient, since they are easy to synthesize and are likely to pose fewer problems than larger molecules when introducing them into organ cells. Antisense methods have been used to inhibit the expression of many genes in vitro. Preferably synthetic antisense nucleotides contain phosphoester analogs, such as phosphorothiolates, or thioesters, rather than natural phophoester bonds. Such phosphoester bond analogs are more resistant to degradation, increasing the stability, and therefore the efficacy, of the antisense nucleic acids.

In the genetic antisense approach, expression of the wild-type allele is suppressed because of expression of antisense RNA. This technique has been used to inhibit K synthesis in tissue culture and to produce phenotypes of the Kruppel mutation in *Drosophila*, and the *Shiverer* mutation in mice [Izant et al., *Cell*, 36:1007-1015 (1984); Green et al., *Annu. Rev. Biochem.*, 55:569-597 (1986); Katsuki et al., *Science*, 241:593-595 (1988)]. An important advantage of this approach is that only a small portion of the gene need be expressed for effective inhibition of expression of the entire cognate mRNA. The antisense transgene will be placed under control of its own promoter or another promoter expressed in the correct cell type, and placed upstream of the SV40 polyA site.

Ribozymes are RNA molecules possessing the ability to specifically cleave other single stranded RNA molecules in a manner somewhat analogous to DNA restriction endonucleases. Ribozymes were discovered from the observation that certain mRNAs have the ability to excise their own introns. By modifying the nucleotide sequence of these RNAs, researchers have been able to engineer molecules that recognize specific nucleotide sequences in an RNA molecule and cleave it. Recent reviews include Shippy et al., *Mol. Biotechnol.* 12:117-129 (1999); Schmidt, *Mol. Cells.* 9:459-463 (1999); Phylactou et al., *Meth. Enzymol.* 313: 485-506 (2000); Oketani et al., *J. Hepatol* 31:628-634 (1999); Macejak et al., *Hepatology* 31:769-776 (2000). The last two references disclose the use of ribozymes for inhibiting HCV. Because they are sequence-specific, only mRNAs with particular sequences are inactivated.

Investigators have identified two types of ribozymes, *Tetrahymena*-type and "hammerhead"-type. *Tetrahymena*-type ribozymes recognize four-base sequences, while "hammerhead"-type recognize eleven- to eighteen-base sequences. The longer the recognition sequence, the more likely it is to occur exclusively in the target mRNA species. Therefore, hammerhead-type ribozymes are preferable to *Tetrahymena*-type ribozymes for inactivating a specific mRNA species, and eighteen base recognition sequences are preferable to shorter recognition sequences.

Screening compound libraries for anti-HCV activity. Various natural product or synthetic libraries can be screened for anti-HCV activity in the in vitro or in vivo models comprising HCV variants as provided by the invention. One approach to preparation of a combinatorial library uses primarily chemical methods, of which the Geysen method [Geysen et al., *Molecular Immunology* 23:709-715 (1986); Geysen et al. *J. Immunologic Method* 102:259-274 (1987)] and the method of Fodor et al. [*Science* 251:767-773 (1991)] are examples. Furka et al. [14*th International Congress of Biochemistry, Volume* 5, Abstract FR:013 (1988); Furka, *Int. J. Peptide Protein Res.* 37:487-493 (1991)], Houghton [U.S. Pat. No. 4,631,211, issued December 1986] and Rutter et al. [U.S. Pat. No. 5,010,175, issued Apr. 23, 1991] describe methods to produce a mixture of peptides that can be tested for anti-HCV activity.

In another aspect, synthetic libraries [Needels et al., *Proc. Natl. Acad. Sci. USA* 90:10700-4 (1993); Ohlmeyer et al., *Proc. Natl. Acad. Sci. USA* 90:10922-10926 (1993); Lam et al., International Patent Publication No. WO 92/00252; Kocis et al., International Patent Publication No. WO 9428028], and the like can be used to screen for anti-HCV compounds according to the present invention. The references describe adaption of the library screening techniques in biological assays.

Defined/engineered HCV variant virus particles for neutralization assays. The variants described herein can be used to produce defined stocks of HCV particles for infectivity and neutralization assays. Homogeneous stocks can be produced in the chimpanzee model, in cell culture systems, or using various heterologous expression systems (e.g., baculovirus, yeast, mammalian cells; see supra). These stocks can be used in cell culture or in vivo assays to define molecules or gene therapy approaches capable of neutralizing HCV particle production or infectivity. Examples of such molecules include, but are not restricted to, polyclonal antibodies, monoclonal antibodies, artificial antibodies with engineered/optimized specificity, single-chain antibodies (see the section on antibodies, infra), nucleic acids or derivatized nucleic acids selected for specific binding and neutralization, small orally bioavailable compounds, etc. Such neutralizing agents, targeted to conserved viral or cellular targets, can be either genotype or isolate-specific or broadly cross-reactive. They could be used either prophylactically or for passive immunotherapy to reduce viral load and perhaps increase the chances of more effective treatment in combination with other antiviral agents (e.g., IFN-α, ribavirin, etc.). Directed manipulation of HCV infectious clones can also be used to produce HCV stocks with defined changes in the glycoprotein hypervariable regions or in other epitopes to study mechanisms of antibody neutralization, CTL recognition, immune escape and immune enhancement. These studies will lead to identification of other virus-specific functions for anti-viral therapy.

Dissection of HCV Replication

Other HCV replication assays. This invention allows directed molecular genetic dissection of HCV replication. Such analyses are expected to (i) validate antiviral targets which are currently being pursued; and (ii) uncover unexpected new aspects of HCV replication amenable to therapeutic intervention. Targets for immediate validation through mutagenesis studies include the following: the 5' NTR, the HCV polyprotein and cleavage products, and the 3' NTR. As described above, analyses using the HCV variants and permissive cell cultures can be used to compare parental and mutant replication phenotypes after transfection of cell cultures with infectious RNA. Even though RT-PCR allows sensitive detection of viral RNA accumulation, mutations which decrease the efficiency of RNA replication may be difficult to analyze, unless conditional mutations are recovered. As a complement to first cycle analyses, trans-complementation assays can be used to facilitate analysis of HCV mutant phenotypes and inhibitor screening. Chimeric variants comprising portions of heterologous systems (vaccinia, Sindbis, or non-viral) can be used to drive expression of the HCV RNA replicase proteins and/or packaging machinery [see Lemm and Rice, *J. Virol.* 67: 1905-1915 (1993a); Lemm and Rice, *J. Virol.* 67: 1916-1926 (1993b); Lemm et al., *EMBO J.* 13: 2925-2934 (1994); Li et al., *J. Virol.* 65: 6714-6723 (1991)]. If these elements are capable of functioning in trans, then co-expression of RNAs with appropriate cis-elements should result in RNA replication/packaging. Such systems therefore mimic steps in authentic RNA replication and virion assembly, but uncouple production of viral components from HCV replication. If HCV replication is somehow self-limiting, heterologous systems may drive significantly higher levels of RNA replication or particle production, facilitating analysis of mutant phenotypes and antiviral screening. A third approach is to devise cell-free systems for HCV template-dependent RNA replication. A coupled translation/replication and assembly system has been described for poliovirus in HeLa cells [Barton and Flanegan, *J. Virol.* 67: 822-831 (1993); Molla et al., *Science* 254: 1647-1651 (1991)], and a template-dependent in vitro assay for initiation of negative-strand synthesis has been established for Sindbis virus. Similar in vitro systems using HCV variants are invaluable for studying many aspects of HCV replication as well as for inhibitor screening and evaluation. An example of each of these strategies follows.

Trans-complementation of HCV RNA replication and/or packaging using viral or non-viral expression systems. Heterologous systems can be used to drive HCV replication. For example, the vaccinia/T7 cytoplasmic expression system has been extremely useful for trans-complementation of RNA virus replicase and packaging functions [see Ball, (1992) supra; Lemm and Rice, (1993a) supra; Lemm and Rice, (1993b) supra; Lemm et al., (1994) supra; Pattnaik et al., (1992) supra; Pattnaik et al., *Virology* 206: 760-4 (1995); Porter et al., *J. Virol.* 69: 1548-1555 (1995)]. In brief, a vaccinia recombinant (vTF7-3) is used to express T7 RNA polymerase (T7RNApol) in the cell type of interest. Target cDNAs, positioned downstream from the T7 promoter, are delivered either as vaccinia recombinants or by plasmid transfection. This system leads to high level RNA and protein expression. A variation of this approach, which obviates the need for vaccinia (which could interfere with HCV RNA replication or virion formation), is the pT7T7 system where the T7 promoter drives expression of T7RNApol [Chen et al., *Nucleic Acids Res.* 22: 2114-2120. (1994)]. pT7T7 is mixed with T7RNApol (the protein) and co-transfected with the T7-driven target plasmid of interest. Added T7RNApol initiates transcription, leading to it own production and high level expression of the target gene. Using either approach, RNA transcripts of variants with precise 5' and 3' termini can be produced using the T7 transcription start site (5') and the cis-cleaving HCV ribozyme (Rz) (3') [Ball, (1992) supra; Pattnaik et al., (1992) supra].

These or similar expression systems can be used to establish assays for HCV RNA replication and particle formation using HCV variants, and for evaluation of compounds which might inhibit these processes. T7-driven protein expression constructs and full-length HCV variants incorporating the HCV ribozyme following the 3' NTR can also be used. A typical experimental plan to validate the assay as described for pT7T7, although essentially similar assays can be envisioned using vTF7-3 or cell lines expressing the T7 RNA polymerase. HCV-permissive cells are co-transfected with pT7T7+T7RNApol+p90/HCVFLlong pU Rz (or a negative control, such as ΔGDD). At different times post-transfection, accumulation of HCV proteins and RNAs, driven by the pT7T7 system, are followed by Western and Northern blotting, respectively. To assay for HCV-specific replicase function, actinomycin D is added to block DNA-dependent T7 transcription [Lemm and Rice, (1993a), supra] and actinomycin D-resistant RNA synthesis is monitored by metabolic labeling. Radioactivity will be incorporated into full-length HCV RNAs for p90/HCVFL long pU/Rz, but not for p90/HCVFLΔGDD/Rz. Using HCV variants of the invention, this assay system, or elaborated derivatives, can be used to screen for inhibitors and to study their effects on HCV RNA replication.

Cell-free systems for assaying HCV replication and inhibitors thereof. Cell-free assays for studying HCV RNA replication and inhibitor screening can also be established using the variants described in this invention. Either virion or transcribed RNAs are used as substrate RNA. For HCV, full-length HCV variant RNAs transcribed in vitro can be used to program such in vitro systems and replication assayed essentially as described for poliovirus [see Barton et al., (1995) supra]. In case hepatocyte-specific or other factors are required for HCV variant RNA replication, the system can be supplemented with hepatocyte or other cell extracts, or alternatively, a comparable system can be established using cell lines which have been shown to be permissive for replication of the HCV variants.

One concern about this approach is that proper cell-free synthesis and processing of the HCV polyprotein must occur. Sufficient quantities of properly processed replicase components may be difficult to produce. To circumvent this problem, the T7 expression system can be used to express high levels of HCV replicase components in appropriate cells [see Lemm et al., (1997) supra]. P15 membrane fractions from these cells (with added buffer, $Mg^{2+}$, an ATP regenerating system, and NTPs) should be able to initiate and synthesize full-length negative-strand RNAs upon addition of HCV-specific template RNAs.

Establishment of either or both of the above assays allows rapid and precise analysis of the effects of HCV mutations, host factors, involved in replication and inhibitors of the various steps in HCV RNA replication. These systems will also establish the requirements for helper systems for preparing replication-deficient HCV vectors.

Vaccination and Protective Immunity

There are still many unknown parameters that impact on development of effective HCV vaccines. It is clear in both man and the chimpanzee that some individuals can clear the infection. Also, 10-20% of those treated with IFN or about twice this percentage treated with IFN and ribavirin show a sustained response as evidenced by lack of circulating HCV RNA. Other studies have shown a lack of protective immunity, as evidenced by successful reinfection with both homologous virus as well as with more distantly related HCV types [Farci et al., (1992) supra; Prince et al., (1992) supra]. Nonetheless, chimpanzees immunized with subunit vaccines consisting of E1E2 oligomers and vaccinia recombinants expressing these proteins are partially protected against low dose challenges [Choo et al., Proc. Natl. Acad. Sci. USA 91:1294 (1994)]. The HCV variant technology described in this invention has utility not only for basic studies aimed at understanding the nature of protective immune responses against HCV, but also for novel vaccine production methods.

Active immunity against HCV can be induced by immunization (vaccination) with an immunogenic amount of an attenuated or inactivated HCV variant virion, or HCV virus particle proteins, preferably with an immunologically effective adjuvant. An "immunologically effective adjuvant" is a material that enhances the immune response.

Selection of an adjuvant depends on the subject to be vaccinated. Preferably, a pharmaceutically acceptable adjuvant is used. For example, a vaccine for a human should avoid oil or hydrocarbon emulsion adjuvants, including complete and incomplete Freund's adjuvant. One example of an adjuvant suitable for use with humans is alum (alumina gel). A vaccine for an animal, however, may contain adjuvants not appropriate for use with humans.

An alternative to a traditional vaccine comprising an antigen and an adjuvant involves the direct in vivo introduction of DNA or RNA encoding the antigen into tissues of a subject for expression of the antigen by the cells of the subjects tissue. Such vaccines are termed herein genetic vaccines, DNA vaccines, genetic vaccination, or nucleic acid-based vaccines. Methods of transfection as described above, such as DNA vectors or vector transporters, can be used for DNA vaccines.

DNA vaccines are described, e.g., in International Patent Publication WO 95/20660 and International Patent Publication WO 93/19183, the disclosures of which are hereby incorporated by reference in their entireties. The ability of directly injected DNA that encodes a viral protein or genome to elicit a protective immune response has been demonstrated in numerous experimental systems [Conry et al., Cancer Res., 54:1164-1168 (1994); Cox et al., Virol, 67:5664-5667 (1993); Davis et al., Hum. Mole. Genet., 2:1847-1851 (1993); Sedegah et al., Proc. Natl. Acad. Sci., 91:9866-9870 (1994); Montgomery et al., DNA Cell Bio., 12:777-783 (1993); Ulmer et al., Science, 259:1745-1749 (1993); Wang et al., Proc. Natl. Acad. Sci., 90:4156-4160 (1993); Xiang et al., Virology, 199:132-140 (1994)]. Studies to assess this strategy in neutralization of influenza virus have used both envelope and internal viral proteins to induce the production of antibodies, but in particular have focused on the viral hemagglutinin protein (HA) [Fynan et al., DNA Cell. Biol., 12:785-789 (1993A); Fynan et al., Proc. Natl. Acad. Sci., 90:11478-11482 (1993B); Robinson et al., Vaccine, 11:957, (1993); Webster et al., Vaccine, 12:1495-1498 (1994)].

Vaccination through directly injecting DNA or RNA that encodes a protein to elicit a protective immune response produces both cell-mediated and humoral responses. This is analogous to results obtained with live viruses [Raz et al., Proc. Natl. Acad. Sci., 91:9519-9523 (1994); Ulmer, 1993, supra; Wang, 1993, supra; Xiang, 1994, supra]. Studies with ferrets indicate that DNA vaccines against conserved internal viral proteins of influenza, together with surface glycoproteins, are more effective against antigenic variants of influenza virus than are either inactivated or subvirion vaccines [Donnelly et al., Nat. Medicine, 6:583-587 (1995)]. Indeed, reproducible immune responses to DNA encoding nucleoprotein have been reported in mice that last essentially for the lifetime of the animal [Yankauckas et al., DNA Cell Biol., 12: 771-776 (1993)].

A vaccine of the invention can be administered via any parenteral route, including but not limited to intramuscular, intraperitoneal, intravenous, intraarterial (e.g. Ripatic artery) and the like. Preferably, since the desired result of vaccination is to elucidate an immune response to HCV, administration directly, or by targeting or choice of a viral vector, indirectly, to lymphoid tissues, e.g., lymph nodes or spleen. Since immune cells are continually replicating, they are ideal target for retroviral vector-based nucleic acid vaccines, since retroviruses require replicating cells.

Passive immunity can be conferred to an animal subject suspected of suffering an infection with HCV by administering antiserum, neutralizing polyclonal antibodies, or a neutralizing monoclonal antibody against HCV to the patient. Although passive immunity does not confer long-term protection, it can be a valuable tool for the treatment of an acute infection of a subject who has not been vaccinated. Preferably, the antibodies administered for passive immune therapy are autologous antibodies. For example, if the subject is a human, preferably the antibodies are of human origin or have been "humanized," in order to minimize the possibility of an immune response against the antibodies. In addition, genes encoding neutralizing antibodies can be introduced in vectors for expression in vivo, e.g., in hepatocytes.

Antibodies for passive immune therapy. Preferably, HCV variant virions or virus particle proteins prepared as described above are used as an immunogen to generate antibodies that recognize HCV. The variants utilized should have wild-type coat Such antibodies include but are not limited to polyclonal, monoclonal, chimeric, single chain, Fab fragments, and an Fab expression library. Various procedures known in the art may be used for the production of polyclonal antibodies to HCV. For the production of antibody, various host animals can be immunized by injection with the HCV virions or polypeptide, e.g., as describe infra, including but not limited to rabbits, mice, rats, sheep, goats, etc. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *Corynebacterium parvum*.

For preparation of monoclonal antibodies directed toward HCV as described above, any technique that provides for the production of antibody molecules by continuous cell lines in culture may be used. These include but are not limited to the hybridoma technique originally developed by Kohler and Milstein [*Nature* 256:495-497 (1975)], as well as the trioma technique, the human B-cell hybridoma technique [Kozbor et al., *Immunology Today* 4:72 1983); Cote et al., *Proc. Natl. Acad. Sci. U.S.A.* 80:2026-2030 (1983)], and the EBV-hybridoma technique to produce human monoclonal antibodies [Cole et al., in *Monoclonal Antibodies and Cancer Therapy*, Alan R. Liss, Inc., pp. 77-96 (1985)]. In an additional embodiment of the invention, monoclonal antibodies can be produced in germ-free animals [International Patent Publication No. WO 89/12690, published 28 Dec. 1989]. In fact, according to the invention, techniques developed for the production of "chimeric antibodies" [Morrison et al., *J. Bacteriol.* 159:870 (1984); Neuberger et al., *Nature* 312:604-608 (1984); Takeda et al., *Nature* 314:452-454 (1985)] by splicing the genes from a mouse antibody molecule specific for HCV together with genes from a human antibody molecule of appropriate biological activity can be used; such antibodies are within the scope of this invention. Such human or humanized chimeric antibodies are preferred for use in therapy of human diseases or disorders (described infra), since the human or humanized antibodies are much less likely than xenogenic antibodies to induce an immune response, in particular an allergic response, themselves.

According to the invention, techniques described for the production of single chain antibodies [U.S. Pat. Nos. 5,476,786 and 5,132,405 to Huston; U.S. Pat. No. 4,946,778] can be adapted to produce HCV-specific single chain antibodies. An additional embodiment of the invention utilizes the techniques described for the construction of Fab expression libraries [Huse et al., *Science* 246:1275-1281 (1989)] to allow rapid and easy identification of monoclonal Fab fragments with the desired specificity.

Antibody fragments containing the idiotype of the antibody molecule can be generated by known techniques. For example, such fragments include but are not limited to: the $F(ab')_2$ fragment which can be produced by pepsin digestion of the antibody molecule; the Fab' fragments which can be generated by reducing the disulfide bridges of the $F(ab')_2$ fragment, and the Fab fragments which can be generated by treating the antibody molecule with papain and a reducing agent.

HCV particles for subunit vaccination. The functional HCV variants of the present invention can be used to produce HCV-like particles for vaccination. Proper glycosylation, folding, and assembly of HCV particles may be important for producing appropriately antigenic and protective subunit vaccines. Several methods can be used for particle production. They include engineering of stable cell lines for inducible or constitutive expression of HCV-like particles (using bacterial, yeast or mammalian cells), or the use of higher level eukaryotic heterologous expression systems such as recombinant baculoviruses, vaccinia viruses [Moss, *Proc. Natl. Acad. Sci. U.S.A.* 93: 11341-11348 (1996)], or alphaviruses [Frolov et al., (1996) supra]. HCV particles for immunization may be purified from either the media or disrupted cells, depending upon their localization. Such purified HCV particles or mixtures of particles representing a spectrum of HCV genotypes, can be injected with our without various adjuvants to enhance immunogenicity.

Infectious non-replicating HCV particles. In another manifestation, particles of HCV variants capable of receptor binding, entry, and translation of genome RNA can be produced. Heterologous expression approaches for production of such particles include, but are not restricted to, *E. coli*, yeast, or mammalian cell lines, appropriate host cells infected or harboring recombinant baculoviruses, recombinant vaccinia viruses, recombinant alphaviruses or RNA replicons, or recombinant adenoviruses, engineered to express appropriate HCV RNAs and proteins. In one example, two recombinant baculoviruses are engineered. One baculovirus expresses the HCV structural proteins (e.g. C-E1-E2-p7) required for assembly of HCV particles. A second recombinant expresses the entire HCV genome RNA, with precise 5' and 3' ends, except that a deletion, such as ΔGDD or GDD→AAG (see example 1), is included to inactivate the HCV NS5B RDRP. Other mutations abolishing productive HCV replication could also be utilized instead or in combination. Cotransfection of appropriate host cells (Sf9, Sf21, etc.) with both recombinants will produce high levels of HCV structural proteins and genome RNA for packaging into HCV-like particles. Such particles can be produced at high levels, purified, and used for vaccination. Once introduced into the vaccinee, such particles will exhibit normal receptor binding and infection of HCV-susceptible cells. Entry will occur and the genome RNA will be translated to produce all of the normal HCV antigens, except that further replication of the genome will be completely blocked given the inactivated NS5B polymerase. Such particles are expected to elicit effective CTL responses against structural and nonstructural HCV protein antigens. This vaccination strategy alone or preferably in conjunction with the subunit strategy described above can be used to elicit high levels of both neutralizing antibodies and CTL responses to help clear the virus. A variety of different HCV genome RNA sequences can be utilized to ensure broadly cross-reactive and protective immune responses. In addition, modification of the HCV particles, either through genetic engineering, or by derivatization in vitro, could be used to target infection to cells most effective at eliciting protective and long lasting immune responses.

Live-attenuated HCV derivatives. The ability to manipulate the HCV genome RNA sequence and thereby produce mutants with altered pathogenicity provides a means of constructing live-attenuated HCV variants appropriate for vaccination. Such vaccine candidates express protective antigens but would be impaired in their ability to cause disease, establish chronic infections, trigger autoimmune responses, and transform cells.

Additionally, viruses propagated in cell culture frequently acquire mutations in their RNA genomes that display attenuated phenotypes in vivo, while still retaining their immunogenicity. Attenuated virus strains would be impaired in their ability to cause disease and establish chronic infections. Production of HCV variants adapted for tissue culture may represent potential candidates for live-attenuated vaccines. An attractive possibility is the production of HCV derivatives containing the deletion in NS5A described in this application as clone I (see Example 1). Such a variant is less likely to revert to wild type in the host.

HCV Variant-Based Gene Expression Vectors

Figure 2:
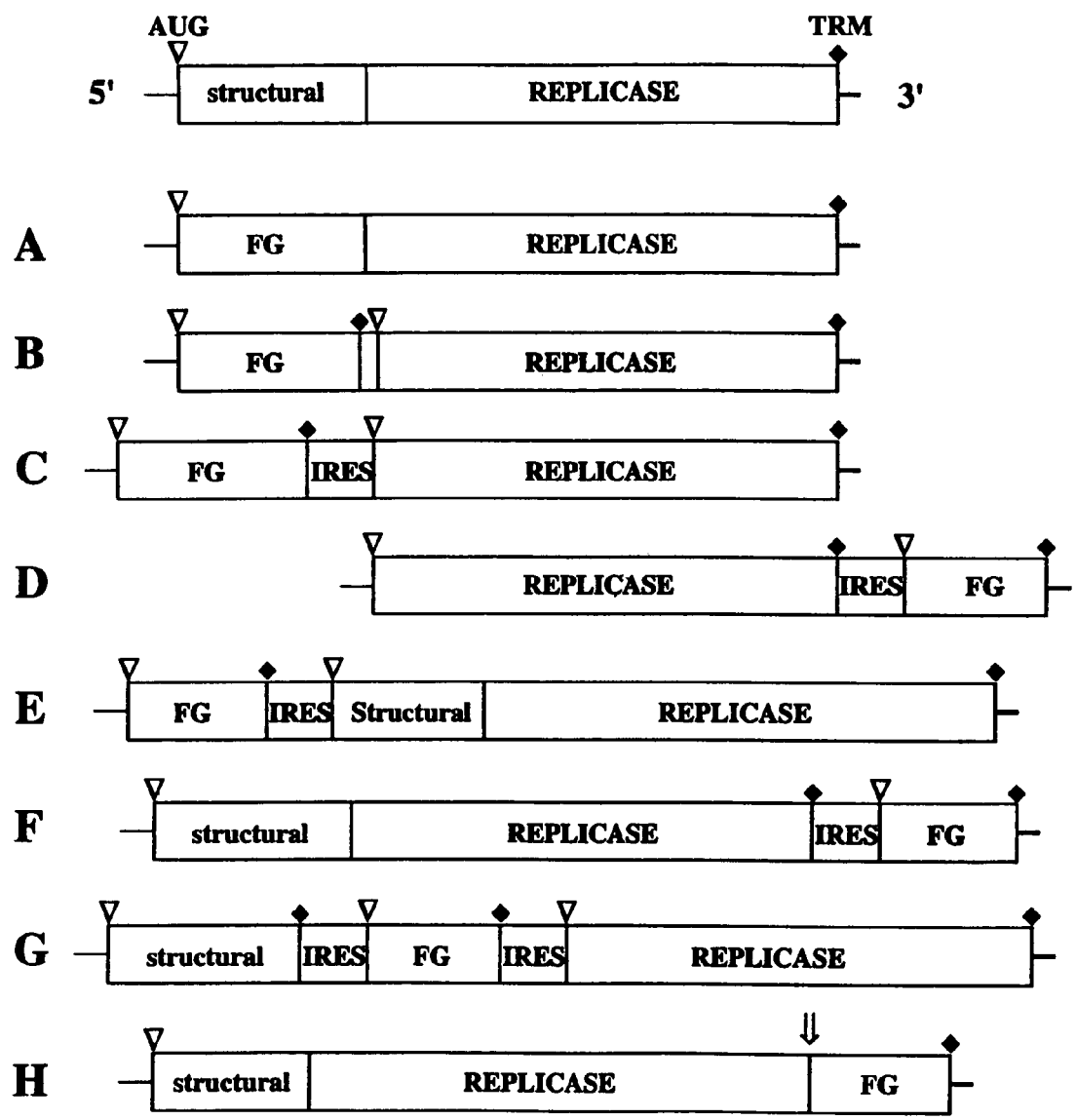

Some of the same properties of HCV leading to chronic liver infection of humans may also be of great utility for designing vectors for gene expression in cell culture systems, genetic vaccination, and gene therapy. The HCV variants described herein can be engineered to produce chimeric RNAs designed for the expression of heterologous gene products (RNAs and proteins). Strategies have been described above and elsewhere [Bredenbeek and Rice, (1992) supra; Frolov et al., (1996) supra] and include, but are not limited to (i) in-frame fusion of the heterologous coding sequences with the HCV polyprotein; (ii) creation of additional cistrons in the HCV genome RNA; and (iii) inclusion of IRES elements to create multicistronic self-replicating HCV vector RNAs capable of expressing one or more heterologous genes (FIG. 2). Functional HCV RNA backbones utilized for such vectors include, but are not limited to, (i) live-attenuated derivatives capable of replication and spread; (ii) RNA replication competent "dead end" derivatives lacking one or more viral components (e.g. the structural proteins) required for viral spread; (iii) mutant derivatives capable of high and low levels of HCV-specific RNA synthesis and accumulation; (iv) mutant derivatives adapted for replication in different human cell types; (v) engineered or selected mutant derivatives capable of prolonged noncytopathic replication in human cells. Vectors competent for RNA replication but not packaging or spread can be introduced either as naked RNA, DNA, or packaged into virus-like particles. Such virus-like particles can be produced as described above and composed of either unmodified or altered HCV virion components designed for targeted transfection of the hepatocytes or other human cell types. Alternatively, HCV RNA vectors can be encapsidated and delivered using heterologous viral packaging machineries or encapsulated into liposomes modified for efficient gene delivery. These packaging strategies, and modifications thereof, can be utilized to efficiently target HCV vector RNAs to specific cell types. Using methods detailed above, similar HCV-derived vector systems, competent for replication and expression in other species, can also be derived.

Various methods, e.g., as set forth supra in connection with transfection of cells and DNA vaccines, can be used to introduce an HCV vector of the invention. Of primary interest is direct injection of functional HCV RNA or virions, e.g., in the liver. Targeted gene delivery is described in International Patent Publication WO 95/28494, published October 1995. Alternatively, the vector can be introduced in vivo by lipofection. For the past decade, there has been increasing use of liposomes for encapsulation and transfection of nucleic acids in vitro. Synthetic cationic lipids designed to limit the difficulties and dangers encountered with liposome mediated transfection can be used to prepare liposomes for in vivo transfection of a gene encoding a marker [Felgner, et. al., *Proc. Natl. Acad. Sci. U.S.A.* 84:7413-7417 (1987); see Mackey, et al., *Proc. Natl. Acad. Sci. U.S.A.* 85:8027-8031 (1988); Ulmer et al., *Science* 259:1745-1748 (1993)]. The use of cationic lipids may promote encapsulation of negatively charged nucleic acids, and also promote fusion with negatively charged cell membranes [Felgner and Ringold, *Science* 337:387-388 (1989)]. The use of lipofection to introduce exogenous genes into the specific organs in vivo has certain practical advantages. Molecular targeting of liposomes to specific cells represents one area of benefit. It is clear that directing transfection to particular cell types would be particularly advantageous in a tissue with cellular heterogeneity, such as pancreas, liver, kidney, and the brain. Lipids may be chemically coupled to other molecules for the purpose of targeting [see Mackey, et. al., supra]. Targeted peptides, e.g., hormones or neurotransmitters, and proteins such as antibodies, or non-peptide molecules could be coupled to liposomes chemically. Receptor-mediated DNA delivery approaches can also be used [Curiel et al., *Hum. Gene Ther.* 3:147-154 (1992); Wu and Wu, *J. Biol. Chem.* 262:4429-4432 (1987)].

Examples of applications for gene therapy include, but are not limited to, (i) expression of enzymes or other molecules to correct inherited or acquired metabolic defects; (ii) expression of molecules to promote wound healing; (iii) expression of immunomodulatory molecules to promote immune-mediated regression or elimination of human cancers; (iv) targeted expression of toxic molecules or enzymes capable of activating cytotoxic drugs in tumors; (v) targeted expression of anti-viral or anti-microbial agents in pathogen-infected cells. Various therapeutic heterologous genes can be inserted in a gene therapy vector of the invention, such as but not limited to adenosine deaminase (ADA) to treat severe combined immunodeficiency (SCID); marker genes or lymphokine genes into tumor infiltrating (TIL) T cells [Kasis et al., *Proc. Natl. Acad. Sci. U.S.A.* 87:473 (1990); Culver et al., ibid. 88:3155 (1991)]; genes for clotting factors such as Factor VIII and Factor IX for treating hemophilia [Dwarki et al. *Proc. Natl. Acad. Sci. USA,* 92:1023-1027 (19950); Thompson, *Thromb. and Haemostatis,* 66:119-122 (1991)]; and various other well known therapeutic genes such as, but not limited to, β-globin, dystrophin, insulin, erythropoietin, growth hormone, glucocerebrosidase, β-glucuronidase, α-antitrypsin, phenylalanine hydroxylase, tyrosine hydroxylase, ornithine transcarbamylase, apolipoproteins, and the like. In general, see U.S. Pat. No. 5,399,346 to Anderson et al.

Examples of applications for genetic vaccination (for protection from pathogens other than HCV) include, but are not limited to, expression of protective antigens from bacterial (e.g., uropathogenic *E. coli, Streptoccoci, Staphlococci, Nisseria*), parasitic (e.g., *Plasmodium, Leishmania, Toxoplama*), fungal (e.g., *Candida, Histoplasma*), and viral (e.g., HIV, HSV, CMV, influenza) human pathogens. Immunogenicity of protective antigens expressed using HCV-derived RNA expression vectors can be enhanced using adjuvants, including co-expression of immunomodulatory molecules, such as cytokines (e.g., IL-2, GM-CSF) to facilitate development of desired Th1 versus Th2 responses. Such adjuvants can be either incorporated and co-expressed by HCV vectors themselves or administered in combination with these vectors using other methods.

Diagnostic Methods for Infectious HCV

Diagnostic cell lines. The invention described herein can also be used to derive cell lines for sensitive diagnosis of infectious HCV in patient samples. In concept, functional HCV components are used to test and create susceptible cell lines (as identified above) in which easily assayed reporter systems are selectively activated upon HCV infection. Examples include, but are not restricted to, (i) defective HCV RNAs lacking replicase components that are incorporated as transgenes and whose replication is upregulated or induced upon HCV infection; and (ii) sensitive heterologous amplifiable reporter systems activated by HCV infection. In the first manifestation, RNA signals required for HCV RNA amplification flank a convenient or a selectable marker (see above). Expression of such chimeric RNAs is driven by an appropriate nuclear promoter and elements required for proper nuclear processing and transport to the cytoplasm. Upon infection of the engineered cell line with HCV, cytoplasmic replication and amplification of the transgene is induced, triggering higher levels of reporter expression, as an indicator of productive HCV infection.

In the second example, cell lines are designed for more tightly regulated but highly inducible reporter gene amplification and expression upon HCV infection. Although this amplified system is described in the context of specific components, other equivalent components can be used. In one such system, an engineered alphavirus replicon transgene is created which lacks the alphavirus nsP4 polymerase, an enzyme absolutely required for alphavirus RNA amplification and normally produced by cleavage from the nonstructural polyprotein. Additional features of this defective alphavirus replicon include a subgenomic RNA promoter, driving expression of a luciferase or GFP reporter gene. This promoter element is quiescent in the absence of productive cytoplasmic alphavirus replication. The cell line contains a second transgene for expression of gene fusion consisting of the HCV NS4A protein and the alphavirus nsP4 RDRP. This fused gene is expressed and targeted to the cytoplasmic membrane compartment, but this form of nsP4 would be inactive as a functional component of the alphavirus replication complex because a discrete nsP4 protein, with a precise N terminus is required for nsP4 activity [Lemm et al., *EMBO J.* 13:2925 (1994)]. An optional third transgene expresses a defective alphavirus RNA with cis signals for replication, transcription of subgenomic RNA encoding a ubiquitin-nsP4 fusion, and an alphavirus packaging signal. Upon infection of such a cell line by HCV, the HCV NS3 proteinase is produced, mediating trans cleavage of the NS4A-nsP4 fusion protein, activating the nsP4 polymerase. This active polymerase, which functions in trans and is effective in minute amounts, then forms a functional alphavirus replication complex leading to amplification of the defective alphavirus replicon as well as the defective alphavirus RNA encoding ubiquitin-nsP4. Ubiquitin-nsP4, expressed from its subgenomic RNA, is cleaved efficiently by cellular ubiquitin carboxyterminal hydrolase to product additional nsP4, in case this enzyme is limiting. Once activated, this system would produce extremely high levels of the reporter protein. The time scale of such an HCV infectivity assay is expected to be from hours (for sufficient reporter gene expression).

Antibody diagnostics. In addition to the cell lines described here, HCV variant virus particles (virions) or components thereof, produced by the transfected or infected cell lines, or isolated from an inflected animal, may be used as antigens to detect anti-HCV antibodies in patient blood or blood products. Because the HCV variant virus particles are derived from an authentic HCV genome, particular components such as the coat proteins are likely to have immunogenic properties that more closely resemble or are identical to natural HCV virus than if those components were produced outside of a replicating HCV. Examples of such immunogenic properties include the display of wild-type HCV immunogenic epitopes, and modulation of transcription of genes encoding cellular immune-modulating cytokines. These reagents can be used to establish that a patient is infected with HCV by detecting seroconversion, i.e., generation of a population of HCV-specific antibodies.

Alternatively, antibodies generated to the HCV variant products prepared as described herein can be used to detect the presence of HCV in biological samples from a subject.

Preferred embodiments of the invention are described in the following example. Other embodiments within the scope of the claims herein will be apparent to one skilled in the art from consideration of the specification or practice of the invention as disclosed herein. It is intended that the specification, together with the examples, be considered exemplary only, with the scope and spirit of the invention being indicated by the claims which follow the examples.

EXAMPLE 1

This example describes the production and evaluation of replicons comprising a neo selectable marker and a polyprotein coding region encoding subtype 1b nonstructural proteins.

Materials and Methods

Cell lines. The Huh7 cell lines were generously provided by Robert Lanford (Southwest Foundation for Biomedical Research, San Antonio, U.S.A.) and Ralf Bartenschlager (Johannes Gutenberg University Mainz, Mainz, Germany) and maintained in Dulbecco's modified minimal essential media (DMEM; Gibco-BRL) supplemented with 10% fetal calf serum (FCS), and nonessential amino acids.

Assembly of a selectable subtype 1b replicon. An HCV subtype 1b replicon was constructed which is similar to the replicon described in Lohmann et al., *Science* 285:110-113 (1999). For that construction, a step-wise PCR-based assay utilizing KlenTaqLA DNA polymerase (Wayne Barnes, Washington University) was developed. cDNAs spanning 600-750 bases in length were assembled from 10-12 gel-purified oligonucleotides (60-80 nucleotides in length) with unique complementary overlaps of 16 nucleotides. Four or six oligonucleotides representing the 5' portion of the region to be assembled were annealed and extended in a standard PCR. The remaining six oligonucleotides for the synthesis of the 3' half of the intended cDNA were mixed in a parallel PCR reaction. After 12 cycles of PCR, the extended double-stranded DNA products were combined and subjected to an additional 12 cycles. The product of this reaction resolved as a smear on agarose gels which was excised and the DNA isolated from the agarose. One-fifth of the purified double-stranded DNA product was amplified by PCR using an outer primer pair containing unique restriction enzyme sites to facilitate directional cloning into the pGEM3Zf(+) plasmid vector (Promega). PCR products were purified, digested with appropriate restriction enzymes, and ligated into similarly cleaved pGEM3Zf(+). Multiple recombinant clones were sequenced and the correct clones identified. The overlapping cDNA fragments were assembled into the contiguous replicon sequence. In parallel, a replicon carrying the lethal mutation in the NS5B active site (Gly-Asp-Asp [GDD] to Ala-Ala-Gly [AGG]; pol-) was constructed.

RNA transcription and transfection. RNA transcripts were synthesized in a 100 μl reaction mixture containing 40 mM Tris-HCl (pH 7.9), 10 mM NaCl, 12 mM $MgCl_2$, 2mM spermidine, 3 mM each ATP, CTP, GTP and UTP, 10 mM dithiothreitol, 100 U RNasin (Promega) and 100 U T7 RNA polymerase (Epicentre), and 2 μg Sca I-linearized DNA. The DNA template was rigorously removed by serial digestions with 30 U DNase I (Boehringer). Ten μg of the DNase-digested RNA transcripts were electroporated into $6 \times 10^6$ Huh7 cells using a model T820 squareporator (BTX), and plated on 150 mm dishes. For selection of replicon-containing cells, medium was changed to complete medium containing geneticin (G418; 1 mg/ml; Gibco-BRL) at 24 hr post-transfection and thereafter the media was changed every 3-4 days.

RNA analysis. Approximately $5 \times 10^5$ cells were preincubated for 1 h in DMEM lacking phosphate supplemented with 5% dialyzed FCS, $1/20^{th}$ the normal concentration of phosphate and actinomycin D (4 μg/ml; Sigma). [$^{32}$P]orthophosphate (200 μCi/ml; ICN) was added and the incubation continued for an additional 12 h. Total cellular RNA was extracted with TRIZOL, precipitated, and resuspended in $H_2O$ (Gibco-BRL). Radiolabeled RNA was analyzed by denaturing agarose gel electrophoresis and visualized by autoradiography.

Protein analysis. For immunoprecipitation, cell monolayers were incubated for either 4, 8 or 12 h in methionine- and cysteine-deficient MEM containing $1/40^{th}$ the normal concentration of methionine, 5% dialyzed FCS and Express $^{35}S^{35}S$ protein labeling mix (100 μCi/ml; NEN). Cells were lysed in 100 mM $NaPO_4$ pH 7.0 containing 1% sodium dodecyl sulfate (SDS) and protease inhibitors, and cellular DNA sheared by repeated passage through a 27.5 gauge needle. Viral proteins were immunoprecipitated essentially as described previously (Grakoui et al., 1993), using patient serum, JHF, recognizing NS3, NS4B and NS5A or rabbit anti-NS5B and Pansorbin cells (Calbiochem). Immunoprecipitates were separated on 10% SDS-PAGE and visualized by autoradiography.

Immunostaining. Cells cultured in 8 well chamber slides (Falcon) were fixed in acetone for 10 min at 4° C. and allowed to air dry. Rehydrated monolayers were incubated at 37° C. with an antibody directed against NS3, followed by incubation with a species-specific fluorescein-conjugated secondary antibody (Pierce), and mounted in 90% glycerol saline containing 50 mM Tris-HCl (pH 8.8).

Reverse transcription (R1)-PCR RNA was isolated from cells using TRIZOL (Gibco-BRL), precipitated and resuspended in $H_2O$. Levels of HCV RNA were quantitated using competitive RT-PCR assays designed to amplify the 5' and 3' NTR sequences of HCV (Kolykhalov et al., 1996). For RT-PCR designed to amplify long cDNA fragments, about 1000 molecules of HCV RNA was mixed with the HCV-specific primer, and the primer extended at 43.5° C. for 1 h using Superscript II reverse transcriptase (Gibco-BRL). cDNAs were then amplified with KlenTaqLA DNA polymerase using 35 cycles of 95° C. for 30 s, 55-60° C. for 30 s, and 68° C. for 4 min. PCR products were recovered from preparative low melting-point agarose electrophoresis by phenol extraction, and ~40 ng of purified PCR product directly sequenced.

Results

Figure 3:
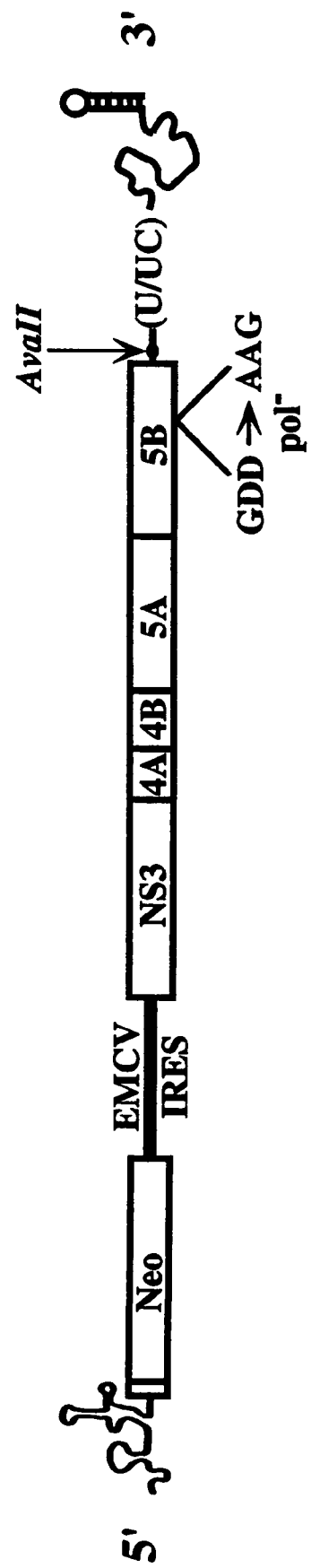

Establishment of G418-resistant colonies. Replicons similar to that described in Lohmann et al., supra, but derived from the H77 infectious clone, failed to confer resistance to G418 in five different hepatoma cell lines. Sequences of subtype 1b were also used to assemble the replicon $I_{377}$/NS3-3' (EMBL accession number AJ242652). Replicon RNAs were composed of the HCV internal ribosome entry site (IRES) driving neomycin phosphotransferase gene (Neo) expression and the IRES from encephalomyocarditis virus (EMCV), directing translation of HCV proteins NS3 to NS5B, followed by the 3' NTR) (FIG. 3). Two derivatives were constructed which either lacked 2 U nucleotides in the poly (U/UC) tract or carried an AvaII restriction enzyme site in the variable region of the 3' NTR, designated HCVrep1bBartMan/Δ2U's and HCVrep1bBartMan/AvaII, respectively. Prior to transfection, translation and correct polyprotein processing was confirmed for each cDNA sequence using the vaccinia-T7 RNA polymerase expression system (data not shown).

DNase-treated replicon RNAs were electroporated into Huh7 cells and after 2-3 weeks in culture G418-resistant colonies were clearly visible. Both replicon derivatives were able to confer G418 resistance, and on average, only 1 in $10^6$ cells became G418 resistant. In contrast, colonies were never observed for Huh7 cells electroporated in parallel with the replicon RNAs containing an inactive NS5B polymerase.

Verification of autonomous replication. Twenty-two independent colonies were isolated, 5 colonies corresponded to Huh7 cells transfected with RNA transcribed from HCVrep1bBartMan/Δ2U's and the remaining 17 colonies were derived from HCVrep1bBartMan/AvaII RNA. A number of assays were performed to verify that G418 resistance was mediated by autonomously replicating HCV.

Identification of mutations in HCV replicons. The low frequency of G418-resistant colonies may be attributed to either a cell factor(s) requirement for replication or adaptive changes within the replicon sequence necessary for the establishment of HCV replication. To address the latter possibility, the entire replicon sequence was amplified from cDNA reverse transcribed from RNA isolated from five independent G418-resistant cell clones. Upon direct sequencing of the purified PCR population, multiple mutations were identified. The striking observation was that each cell clone carried a single nucleotide change within NS5A resulting in a coding change (FIG. 7). In one instance, a deletion of 47 amino acids (I; FIG. 7), encompassing the interferon sensitivity determining region (ISDR), was found. Sequence analysis of NS5A from another 8 G418-resistant cell clones revealed similar point mutations, although 2 clones, which have low levels of HCV replication and slow growth rates (e.g., clone E in FIG. 4), were found to contain wild type NS5A. In addition to the identified NS5A mutations, nucleotide substitutions were also noted in NS3 and NS4B; Clone II (SEQ ID NO:9) contains substitutions at nt 3550 (NS3) and nt 4573 (NS4B) (Lys (584) to Glu, and Ser(925) to Gly of SEQ ID NO:3, embodied in SEQ ID NO:17), whereas nt 2060 (NS3) was mutated in Clone VI (FIG. 7, corresponding to Gln (87) to Arg of SEQ ID NO:3, embodied in SEQ ID NO:15).

Reconstruction of mutant replicons. To determine if the nucleotide changes and the deletion identified in NS5A were adaptive, each mutation, except mutation II, was independently engineered back into the HCVrep1bBartMan/AvaII backbone. RNA transcribed from each reconstructed replicon was electroporated into naive Huh7 cells, and the number of G418-resistant colonies compared to that obtained for the HCVrep1bBartMan/AvaII replicon containing wild type NS5A. The 47 amino acid deletion, as well as the point mutations, were capable of increasing the frequency of G418-resistant colonies to at least 1% of the initial electroporated cell population (FIG. 8), indicating these mutations targeting NS5A are adaptive allowing efficient HCV replication in Huh7 cells. In addition, G418-resistant colonies were observed after transfection of HeLa cells, a human epithelial cell line, with replicon RNA of clone I. Therefore, at least one of the mutations that was adaptive in Huh7 cells also allows the establishment of HCV replication in a non-hepatic cell line.

EXAMPLE 2

This example describes the production of cell lines permissive for HCV replication; a replicon comprising the NS2 coding region; and full-length HCV cDNA clones comprising the Ser to Ile substitution at position 1179 of SEQ ID NO: 3.

Generation of cell lines. As shown in the previous example, G418-resistant cell clones harboring persistently replicating HCV RNAs were isolated. Two of these G418-resistant cell clones were treated extensively with the antiviral, interferon-α, to obtain 2 cell lines void of HCV RNA. These are referred to as interferon-treated cell lines I and II.

HCVrep1bBartMan/AvaII, HCV adaptive replicon I or HCV adaptive replicon VII were transfected into the interferon-treated cell lines, I and II. This resulted in a greater G418 transduction efficiency than that observed for the parental Huh-7 cells (see Table 1). Early post-transfection HCV RNA amplification was greatest for the IFN-treated cell line. These results indicate that the cell lines, interferon-treated cell lines I and II, are more permissive for HCV replication than is the parental Huh-7 cell line.

Such cell lines are not only valuable for genetic study of HCV, but also for examining the cellular environments more permissive for HCV replication. For example, microarray technology will allow us to look globally at differences in gene expression profiles between the different cell lines.

Construction of replicons. A replicon was constructed wherein the 5'NTR of HCV was fused to the IRES of EMCV upstream of NS3, thus creating a replicon lacking the neomycin phosphotransferase gene. This replicon, 5'NTR-EMCV/HCVrepVII (SEQ ID NO:25), replicates to high levels in Huh7 cells, as shown in FIG. 10. Another replicon, HCVrep/NS2-5B (SEQ ID NO:22) was made wherein the non-structural protein, NS2, is upstream of NS3. As shown in FIG. 10, this replicon is also replication-competent in Huh7 cells. This latter replicon can be used advantageously, for example, in testing compounds for inhibiting HCV replication. The addition of the NS2 coding region provides an additional target for such antiviral compounds, as well as providing an additional protein for genetic study.

Full-length HCV RNAs. Two full-length HCV cDNA clones were assembled. The first, HCV FL (SEQ ID NO:24), contains the mutation that encodes a Ser to Ile substitution in NS5A, as shown at position 1179 of SEQ ID NO:3 (see FIG. 9). The second, HCV FL-Neo (SEQ ID NO:23), also encodes the Ser to Ile mutation, and in addition, comprises the neomycin phosphotransferase gene immediately 3' of the 5' NTR and the EMCV IRES immediately 5' to the HCV open reading frame (see FIG. 9). Both of these full-length clones replicate in the interferon-treated cell line I, as shown in FIG. 10. This result indicates that HCV replication is not dependent on the EMCV IRES driving the non-structural proteins of HCV, because the non-structural proteins of the HCV FL clone are driven by the HCV IRES in the full-length clone HCV FL.

In addition, a G418 resistant cell line comprising the HCV FL-Neo clone has been generated from the interferon-treated cell line I described above. This cell line supports high levels of persistently replicating HCV FL-Neo RNA.

All references cited in this specification are hereby incorporated by reference. The discussion of the references herein is intended merely to summarize the assertions made by the authors and no admission is made that any reference constitutes prior art. Applicants reserve the right to challenge the accuracy and pertinence of the cited references.

In view of the above, it will be seen that the several advantages of the invention are achieved and other advantages attained.

As various changes could be made in the above methods and compositions without departing from the scope of the invention, it is intended that all matter contained in the above description and shown in the accompanying drawings and appendix shall be interpreted as illustrative and not in a limiting sense.

APPENDIX

| SEQ ID NOs |
| --- |
| SEQ ID NO: 1: 5' portion of an HCV 5' NTR |
| GGCGACACTC CACCATAGAT C |
| SEQ ID NO: 2: 3' portion of a 3' NTR from a wild-type HCV subtype 1a |
| TGGTGGCTCCATCTTAGCCCTAGTCACGGCTAGCTGTGAAAGGT CCGTGAGCCGCATGACTGCAGAGAGTGCTGATACTGGCCTCTCT GCTGATCATGT |
| SEQ ID NO: 3: Amino acid sequence of the polyprotein region of HCVrep1bBartMan |
| MAPITAYSQQTRGLLGCIITSLTGRDRNQVEGEVQVVSTATQSFLAT CVNGVCWTVYHGAGSKTLAGPKGPITQMYTNVDQDLVGWQAPPG ARSLTPCTCGSSDLYLVTRHADVIPVRRRGDSRGSLLSPRPVSYLKG SSGGPLLCPSGHAVGIFRAAVCTRGVAKAVDFVPVESMETTMRSPV FTDNSSPPAVPQTFQVAHLHAPTGSGKSTKVPAAYAAQGYKVLVL NPSVAATLGFGAYMSKAHGIDPNIRTGVRTITTGAPITYSTYGKFLA DGGCSGGAYDIIICDECHSTDSTTILGIGTVLDQAETAGARLVVLAT ATPPGSVTVPHPNIEEVALSSTGEIPFYGKAIPIETIKGGRHLIFCHSK KKCDELAAKLSGLGLNAVAYYRGLDVSVIPTSGDVIVVATDALMT GFTGDFDSVIDCNTCVTQTVDFSLDPTFTIETTTVPQDAVSRSQRRG RTGRGRMGIYRFVTPGERPSGMFDSSVLCECYDAGCAWYELTPAE TSVRLRAYLNTPGLPVCQDHLEFWESVFTGLTHIDAHFLSQTKQAG DNFPYLVAYQATVCARAQAPPPSWDQMWKCLIRLKPTLHGPTPLL |

-continued

| SEQ ID NOs |
|---|
| YRLGAVQNEVTTTHPITKYIMACMSADLEVVTSTWVLVGGVLAAL AAYCLTTGSVVIVGRIILSGKPAIIPDREVLYREFDEMEECASHLPYI EQGMQLAEQFKQKAIGLLQTATKQAEAAAPVVESKWRTLEAFWA KHMWNFISGIQYLAGLSTLPGNPAIASLMAFTASITSPLTTQHTLLFN ILGGWVAAQLAPPSAASAFVGAGIAGAAVGSIGLGKVLVDILAGYG AGVAGALVAFKVMSGEMPSTEDLVNLLPAILSPGALVVGVVCAAI LRRHVGPGEGAVQWMNRLIAFASRGNHVSPTHYVPESDAAARVTQ ILSSLTITQLLKRLHQWINEDCSTPCSGSWLRDVWDWICTVLTDFKT WLQSKLLPRLPGVPFFSCQRGYKGVWRGDGIMQTTCPCGAQITGH VKNGSMRIVGPRTCSNTWHGTFPINAYTTGPCTPSPAPNYSRALWR VAAEEYVEVTRVGDFHYVTGMTTDNVKCPCQVPAPEFFTEVDGVR LHRYAPACKPLLREEVTFLVGLNQYLVGSQLPCEPEPDVAVLTSML TDPSHITAETAKRRLARGSPPSLASSSASQLSAPSLKATCTTRHDSPD ADLIEANLLWRQEMGGNITRVESENKVVILDSFEPLQAEEDEREVS VPAEILRRSRKFPRAMPIWARPDYNPPLLESWKDPDYVPPVVHGCP LPPAKAPPIPPPRRKRTVVLSESTVSSALAELATKTFGSSESSAVDSG TATASPDQPSDDGDAGSDVESYSSMPPLEGEPGDPDLSDGSWSTVS EEASEDVVCCSMSYTWTGALITPCAAEETKLPINALSNSLLRHHNL VYATTSRSASLRQKKVTFDRLQVLDDHYRDVLKEMKAKASTVKA KLLSVEEACKLTPPHSARSKFGYGAKDVRNLSSKAVNHIRSVWKD LLEDTETPIDTTIMAKNEVFCVQPEKGGRKPARLIVFPDLGVRVCEK MALYDVVSTLPQAVMGSSYGFQYSPGQRVEFLVNAWKAKKCPMG FAYDTRCFDSTVTENDIRVEESIYQCCDLAPEARQAIRSLTERLYIGG PLTNSKGQNCGYRRCRASGVLTTSCGNTLTCYLKAAAACRAAKLQ DCTMLVCGDDLVVICESAGTQEDEASLRAFTEAMTRYSAPPGDPPK PEYDLELITSCSSNVSVAHDASGKRVYYLTRDPTTPLARAAWETAR HTPVNSWLGNIIMYAPTLWARMILMTHFFSILLAQEQLEKALDCQI YGACYSIEPLDLPQIIQRLHGLSAFSLHSYSPGEINRVASCLRKLGVP PLRVWRHRARSVRARLLSQGGRAATCGKYLFNWAVRTKLKLTPIP AASQLDLSSWFVAGYSGGDIYHSLSRARPRWFMWCLLLLSVGVGI YLLPNR |
| SEQ ID NO: 4: Amino acid sequence of the NS5A protein of HCVrep1bBartMan |
| SGSWLRDVWDWICTVLTDFKTWLQSKLLPRLPGVPFFSCQRGYKG VWRGDGIMQTTCPCGAQITGHVKNGSMRIVGPRTCSNTWHGTFPI NAYTTGPCTPSPAPNYSRALWRVAAEEYVEVTRVGDFHYVTGMTT DNVKCPCQVPAPEFFTEVDGVRLHRYAPACKPLLREEVTFLVGLNQ YLVGSQLPCEPEPDVAVLTSMLTDPSHITAETAKRRLARGSPPSLA SSSASQLSAPSLKATCTTRHDSPDADLIEANLLWRQEMGGNITRVES ENKVVILDSFEPLQAEEDEREVSVPAEILRRSRKFPRAMPIWARPDY NPPLLESWKDPDYVPPVVHGCPLPPAKAPPIPPPRRKRTVVLSESTV SSALAELATKTFGSSESSAVDSGTATASPDQPSDDGDAGSDVESYSS MPPLEGEPGDPDLSDGSWSTVSEEASEDVVCC |
| SEQ ID NO: 5: Nucleotide sequence of DNA clone of HCVrep1bBartMan/Δ2U's |
| GCCAGCCCCCGATTGGGGGCGACACTCCACCATAGATCACTCCC CTGTGAGGAACTACTGTCTTCACGCAGAAAGCGTCTAGCCATGG CGTTAGTATGAGTGTCGTGCAGCCTCCAGGACCCCCCCTCCCGG GAGAGCCATAGTGGTCTGCGGAACCGGTGAGTACACCGGAATTG CCAGGACGACCGGGTCCTTTCTTGGATCAACCCGCTCAATGCCT GGAGATTTGGGCGTGCCCCCGCGAGACTGCTAGCCGAGTAGTGT TGGGTCGCGAAAGGCCTTGTGGTACTGCCTGATAGGGTGCTTGC GAGTGCCCCGGGAGGTCTCGTAGACCGTGCACCATGAGCACGAA TCCTAAACCTCAAAGAAAAACCAAAGGGCGCGCCATGATTGAA CAAGATGGATTGCACGCAGGTTCTCCGGCCGCTTGGGTGGAGA GGCTATTCGGCTATGACTGGGCACAACAGACAATCGGCTGCTCT GATGCCGCCGTGTTCCGGCTGTCAGCGCAGGGGCGCCCGGTTCT TTTTGTCAAGACCGACCTGTCCGGTGCCCTGAATGAACTGCAGG ACGAGGCAGCGCGGCTATCGTGGCTGGCCACGACGGGCGTTCCT TGCGCAGCTGTGCTCGACGTTGTCACTGAAGCGGGAAGGGACTG GCTGCTATTGGGCGAAGTGCCGGGGCAGGATCTCCTGTCATCTC ACCTTGCTCCTGCCGAGAAAGTATCCATCATGGCTGATGCAATG CGGCGGCTGCATACGCTTGATCCGGCTACCTGCCCATTCGACCA CCAAGCGAAACATCGCATCGAGCGAGCACGTACTCGGATGGAA GCCGGTCTTGTCGATCAGGATGATCTGGACGAAGAGCATCAGGG GCTCGCGCCAGCCGAACTGTTCGCCAGGCTCAAGGCGCGCATGC CCGACGGCGAGGATCTCGTCGTGACCCATGGCGATGCCTGCTTG CCGAATATCATGGTGGAAAATGGCCGCTTTTCTGGATTCATCGA CTGTGGCCGGCTGGGTGTGGCGGACGGCTATCAGGACATAGCGT TGGCTACCCGTGATATTGCTGAAGAGCTTGGCGGCGAATGGGCT GACCGCTTCCTCGTGCTTTACGGTATCGCCGCTCCCGATTCGCAG CGCATCGCCTTCTATCGCCTTCTTGACGAGTTCTTCTGAGTTTAA ACAGACCACAACGGTTTCCCTCTAGCGGGATCAATTCCGCCCCT CTCCCTCCCCCCCCCCTAACGTTACTGGCCGAAGCCGCTTGGAAT AAGGCCGGTGTGCGTTTGTCTATATGTTATTTTCCACCATATTGC |

-continued

| SEQ ID NOs |
|---|
| CGTCTTTTGGCAATGTGAGGGCCCGGAAACCTGGCCCTGTCTTCT TGACGAGCATTCCTAGGGGTCTTTCCCCTCTCGCCAAAGGAATG CAAGGTCTGTTGAATGTCGTGAAGGAAGCAGTTCCTCTGGAAGC TTCTTGAAGACAAACAACGTCTGTAGCGACCCTTTGCAGGCAGC GGAACCCCCCACCTGGCGACAGGTGCCTCTGCGGCCAAAAGCCA CGTGTATAAGATACACCTGCAAAGGCGGCACAACCCCAGTGCCA CGTTGTGAGTTGGATAGTTGTGGAAAGAGTCAAATGGCTCTCCT CAAGCGTATTCAACAAGGGGCTGAAGGATGCCCAGAAGGTACC CCATTGTATGGGATCTGATCTGGGGCCTCGGTGCACATGCTTTAC ATGTGTTTAGTCGAGGTTAAAAAACGTCTAGGCCCCCCGAACCA CGGGGACGTGGTTTTCCTTTGAAAAACACGATAATACCATGGCG CCTATTACGGCCTACTCCCAACAGACGCGAGGCCTACTTGGCTG CATCATCACTAGCCTCACAGGCCGGGACAGGAACCAGGTCGAG GGGGAGGTCCAAGTGGTCTCCACCGCAACACAATCTTTCCTGGC GACCTGCGTCAATGGCGTGTGTTGGACTGTCTATCATGGTGCCG GCTCAAAGACCCTTGCCGGCCCAAAGGGCCCAATCACCCAAATG TACACCAATGTGGACCAGGACCTCGTCGGCTGGCAAGCGCCCCC CGGGGCGCGTTCCTTGACACCATGCACCTGCGGCAGCTCGGACC TTTACTTGGTCACGAGGCATGCCGATGTCATTCCGGTGCGCCGG CGGGGCGACAGCAGGGGGAGCCTACTCTCCCCCAGGCCCGTCTC CTACTTGAAGGGCTCTTCGGGCGGTCCACTGCTCTGCCCCTCGGG GCACGCTGTGGGCATCTTTCGGGCTGCCGTGTGCACCCGAGGGG TTGCGAAGGCGGTGGACTTTGTACCCGTCGAGTCTATGGAAACC ACTATGCGGTCCCCGGTCTTCACGGACAACTCGTCCCCTCCGGCC GTACCGCAGACATTCCAGGTGGCCCATCTACACGCCCCTACTGG TAGCGGCAAGAGCACTAAGGTGCCGGCTGCGTATGCAGCCCAA GGGTATAAGGTGCTTGTCCTGAACCCGTCCGTCGCCGCCACCCT AGGTTTCGGGGCGTATATGTCTAAGGCACATGGTATCGACCCTA ACATCAGAACCGGGGTAAGGACCATCACCACGGGTGCCCCCATC ACGTACTCCACCTATGGCAAGTTTCTTGCCGACGGTGGTTGCTCT GGGGGCGCCTATGACATCATAATATGTGATGAGTGCCACTCAAC TGACTCGACCACTATCCTGGGCATCGGCACAGTCCTGGACCAAG CGGAGACGGCTGGAGCGCGACTCGTCGTGCTCGCCACCGCTACG CCTCCGGGATCGGTCACCGTGCCACATCCAAACATCGAGGAGGT GGCTCTGTCCAGCACTGGAGAAATCCCCTTTTATGGCAAAGCCA TCCCCATCGAGACCATCAAGGGGGGGAGGCACCTCATTTTCTGC CATTCCAAGAAGAAATGTGATGAGCTCGCCGCGAAGCTGTCCGG CCTCGGACTCAATGCTGTAGCATATTACCGGGGCCTTGATGTATC CGTCATACCAACTAGCGGAGACGTCATTGTCGTAGCAACGGACG CTCTAATGACGGGCTTTACCGGCGATTTCGACTCAGTGATCGACT GCAATACATGTGTCACCCAGACAGTCGACTTCAGCCTGGACCCG ACCTTCACCATTGAGACGACGACCGTGCCACAAGACGCGGTGTC ACGCTCGCAGCGGCGAGGCAGGACTGGTAGGGGCAGGATGGGC ATTTACAGGTTTGTGACTCCAGGAGAACGGCCCTCGGGCATGTT CGATTCCTCGGTTCTGTGCGAGTGCTATGACGCGGGCTGTGCTTG GTACGAGCTCACGCCCGCCGAGACCTCAGTTAGGTTGCGGGCTT ACCTAAACACACCAGGGTTGCCCGTCTGCCAGGACCATCTGGAG TTCTGGGAGAGCGTCTTTACAGGCCTCACCCACATAGACGCCCA TTTCTTGTCCCAGACTAAGCAGGCAGGAGACAACTTCCCCTACC TGGTAGCATACCAGGCTACGGTGTGCGCCAGGGCTCAGGCTCCA CCTCCATCGTGGGACCAAATGTGGAAGTGTCTCATACGGCTAAA GCCTACGCTGCACGGGCCAACGCCCCTGCTGTATAGGCTGGGAG CCGTTCAAAACGAGGTTACTACCACACACCCCATAACCAAATAC ATCATGGCATGCATGTCGGCTGACCTGGAGGTCGTCACGAGCAC CTGGGTGCTGGTAGGCGGAGTCCTAGCAGCTCTGGCCGCGTATT GCCTGACAACAGGCAGCGTGGTCATTGTGGGCAGGATCATCTTG TCCGGAAAGCCGGCCATCATTCCCGACAGGGAAGTCCTTTACCG GGAGTTCGATGAGATGGAAGAGTGCGCCTCACACCTCCCTTACA TCGAACAGGGAATGCAGCTCGCCGAACAATTCAAACAGAAGGC AATCGGGTTGCTGCAAACAGCCACCAAGCAAGCGGAGGCTGCT GCTCCCGTGGTGGAATCCAAGTGGCGGACCCTCGAAGCCTTCTG GGCGAAGCATATGTGGAATTTCATCAGCGGGATACAATATTTAG CAGGCTTGTCCACTCTGCCTGGCAACCCCGCGATAGCATCACTG ATGGCATTCACAGCCTCTATCACCAGCCCGCTCACCACCCAACA TACCCTCCTGTTTAACATCCTGGGGGGATGGGTGGCCGCCCAAC TTGCTCCTCCCAGCGCTGCTTCTGCTTTCGTAGGCGCCGGCATCG CTGGAGCGGCTGTTGGCAGCATAGGCCTTGGGAAGGTGCTTGTG GATATTTTGGCAGGTTATGGAGCAGGGGTGGCAGGCGCGCTCGT GGCCTTTAAGGTCATGAGCGGCGAGATGCCCTCCACCGAGGACC TGGTTAACCTACTCCCTGCTATCCTCTCCCCTGGCGCCCTAGTCG TCGGGGTCGTGTGCGCAGCGATACTGCGTCGGCACGTGGGCCCA GGGGAGGGGGCTGTGCAGTGGATGAACCGGCTGATAGCGTTCG CTTCGCGGGGTAACCACGTCTCCCCCACGCACTATGTGCCTGAG AGCGACGCTGCAGCACGTGTCACTCAGATCCTCTCTAGTCTTACC ATCACTCAGCTGCTGAAGAGGCTTCACCAGTGGATCAACGAGGA CTGCTCCACGCCATGCTCCGGCTCGTGGCTAAGAGATGTTTGGG ATTGGATATGCACGGTGTTGACTGATTTCAAGACCTGGCTCCAG |

| SEQ ID NOs |
|---|
| TCCAAGCTCCTGCCGCGATTGCCGGGAGTCCCCTTCTTCTCATGT
CAACGTGGGTACAAGGGAGTCTGGCGGGGCGACGGCATCATGC
AAACCACCTGCCCATGTGGAGCACAGATCACCGGACATGTGAAA
AACGGTTCCATGAGGATCGTGGGGCCTAGGACCTGTAGTAACAC
GTGGCATGGAACATTCCCCATTAACGCGTACACCACGGGCCCCT
GCACGCCCTCCCCGGCGCCAAATTATTCTAGGGCGCTGTGGCGG
GTGGCTGCTGAGGAGTACGTGGAGGTTACGCGGGTGGGGGATTT
CCACTACGTGACGGGCATGACCACTGACAACGTAAAGTGCCCGT
GTCAGGTTCCGGCCCCCGAATTCTTCACAGAAGTGGATGGGGTG
CGGTTGCACAGGTACGCTCCAGCGTGCAAACCCCTCCTACGGGA
GGAGGTCACATTCCTGGTCGGGCTCAATCAATACCTGGTTGGGT
CACAGCTCCCATGCGAGCCCGAACCGGACGTAGCAGTGCTCAC
TTCCATGCTCACCGACCCCTCCCACATTACGGCGGAGACGGCTA
AGCGTAGGCTGGCCAGGGGATCTCCCCCCTCCTTGGCCAGCTCA
TCAGCTAGCCAGCTGTCTGCGCCTTCCTTGAAGGCAACATGCAC
TACCCGTCATGACTCCCCGGACGCTGACCTCATCGAGGCCAACC
TCCTGTGGCGGCAGGAGATGGGCGGGAACATCACCCGCGTGGA
GTCAGAAAATAAGGTAGTAATTTTGGACTCTTCGAGCCGCTCCA
AGCGGAGGAGGATGAGAGGGAAGTATCCGTTCCGGCGGAGATC
CTGCGGAGGTCCAGGAAATTCCCTCGAGCGATGCCCATATGGG
CACGCCCGGATTACAACCCTCCACTGTTAGAGTCCTGGAAGGAC
CCGGACTACGTCCCTCCAGTGGTACACGGGTGTCCATTGCCGCC
TGCCAAGGCCCCTCCGATACCACCTCCACGGAGGAAGAGGACG
GTTGTCCTGTCAGAATCTACCGTGTCTTCTGCCTTGGCGGAGCT
CGCCACAAAGACCTTCGGCAGCTCCGAATCGTCGGCCGTCGACA
GCGGCACGGCAACGGCCTCTCCTGACCAGCCCTCCGACGACGGC
GACGCGGGATCCGACGTTGAGTCGTACTCCTCCATGCCCCCCTT
GAGGGGGAGCCGGGGGATCCCGATCTCAGCGACGGGTCTTGGTC
TACCGTAAGCGAGGAGGCTAGTGAGGACGTCGTCTGCTGCTCGA
TGTCCTACACATGGACAGGCGCCCTGATCACGCCATGCGCTGCG
GAGGAAACCAAGCTGCCCATCAATGCACTGAGCAACTCTTTGCT
CCGTCACCACAACTTGGTCTATGCTACAACATCTCGCAGCGCAA
GCCTGCGGCAGAAGAAGGTCACCTTTGACAGACTGCAGGTCCTG
GACGACCACTACCGGGACGTGCTCAAGGAGATGAAGGCGAAGG
CGTCCACAGTTAAGGCTAAACTTCTATCCGTGGAGGAAGCCTGT
AAGCTGACGCCCCCACATTCGGCCAGATCTAAATTTGGCTATGG
GGCAAAGGACGTCCGGAACCTATCCAGCAAGGCCGTTAACCAC
ATCCGCTCCGTGTGGAAGGACTTGCTGGAAGACACTGAGACACC
AATTGACACCACCATCATGGCAAAAAATGAGGTTTTCTGCGTCC
AACCAGAGAAGGGGGGCCGCAAGCCAGCTCGCCTTATCGTATTC
CCAGATTTGGGGGTTCGTGTGTGCGAGAAAATGGCCCTTTACGA
TGTGGTCTCCACCCTCCCTCAGGCCGTGATGGGCTCTTCATACGG
ATTCCAATACTCTCCTGGACAGCGGGCTCGAGTTCCTGAGGTGCC
CCTGGAAAGCGAAGAAATGCCCTATGGGCTTCGCATATGACACC
CGCTGTTTTGACTCAACGGTCACTGAGAATGACATCCGTGTTGA
GGAGTCAATCTACCAATGTTGTGACTTGGCCCCCGAAGCCAGAC
AGGCCATAAGGTCGCTCACAGAGCGGCTTTACATCGGGGGCCCC
CTGACTAATTCTAAAGGGCAGAACTGCGGCTATCGCCGGTGCCG
CGCGAGCGGTGTACTGACGACCAGCTGCGGTAATACCCTCACAT
GTTACTTGAAGGCCGCTGCGGCCTGTCGAGCTGCGAAGCTCCAG
GACTGCACGATGCTCGTATGCGGAGACGACCTTGTCGTTATCTG
TGAAAGCGCGGGGACCCAAGAGGACGAGGCGAGCCTACGGGCC
TTCACGGAGGCTATGACTAGATACTCTGCCCCCCCTGGGGACCC
GCCCAAACCAGAATACGACTTGGAGTTGATAACATCATGCTCCT
CCAATGTGTCAGTCGCGCACGATGCATCTGGCAAAAGGGTGTAC
TATCTCACCCGTGACCCCACCACCCCCCTTGCGCGGGCTGCGTG
GGAGACAGCTAGACACACTCCAGTCAATTCCTGGCTAGGCAACA
TCATCATGTATGCGCCCACCTTGTGGGCAAGGATGATCCTGATG
ACTCATTTCTTCTCCATCCTTCTAGCTCAGGAACAACTTGAAAAA
GCCCTAGATTGTCAGATCTACGGGGCCTGTTACTCCATTGAGCC
ACTTGACCTACCTCAGATCATTCAACGACTCCATGGCCTTAGCGC
ATTTTCACTCCATAGTTACTCTCCAGGTGAGATCAATAGGGTGGC
TTCATGCCTCAGGAAACTTGGGGTACCGCCCTTGCGAGTCTGGA
GACATCGGGCCAGAAGTGTCCGCGCTAGGCTACTGTCCCAGGGG
GGGAGGGCTGCCACTTGTGGCAAGTACCTCTTCAACTGGGCAGT
AAGGACCAAGCTCAAACTCACTCCAATCCCGGCTGCGTCCCAGT
TGGATTTATCCAGCTGGTTCGTTGCTGGTTACAGCGGGGGAGAC
ATATATCACAGCCTGTCTCGTGCCCGACCCCGCTGGTTCATGTGG
TGCCTACTCCTACTTTCTGTAGGGGTAGGCATCATCTACTCCCC
AACCGATGAACGGGGAGCTAAACACTCCAGGCCAATAGGCCAT
CCTGTTTTTTCCCTTTTTTTTTTCTTTTTTTTTTTTTTTTTTTTT
TTTTTTTTTCTCCTTTTTTTTCCTCTTTTTTCCTTTTCTTTCCTTT
GGTGGCTCCATCTTAGCCCTAGTCACGGCTAGCTGTGAAAGGTC
CGTGAGCCGCTTGACTGCAGAGAGTGCTGATACTGGCCTCTCTG
CAGATCAAGT |

SEQ ID NO: 6: Nucleotide sequence of DNA clone of HCVrep1bBartMan/AvaII, where the nucleotide change creating the AvaII site is in lower case and highlighted in bold

GCCAGCCCCCGATTGGGGGCGACACTCCACCATAGATCACTCCC
CTGTGAGGAACTACTGTCTTCACGCAGAAAGCGTCTAGCCATGG
CGTTAGTATGAGTGTCGTGCAGCCTCCAGGACCCCCCCTCCCGG
GAGAGCCATAGTGGTCTGCGGAACCGGTGAGTACACCGGAATTG
CCAGGACGACCGGGTCCTTTCTTGGATCAACCCGCTCAATGCCT
GGAGATTTGGGCGTGCCCCCGCGAGACTGCTAGCCGAGTAGTGT
TGGGTCGCGAAAGGCCTTGTGGTACTGCCTGATAGGGTGCTTGC
GAGTGCCCCGGGAGGTCTCGTAGACCGTGCACCATGAGCACGAA
TCCTAAACCTCAAAGAAAAACCAAAGGGCGCGCCATGATTGAA
CAAGATGGATTGCACGCAGGTTCTCCGGCCGCTTGGGTGGAGAG
GCTATTCGGCTATGACTGGGCACAACAGACAATCGGCTGCTCTG
ATGCCGCCGTGTTCCGGCTGTCAGCGCAGGGGCGCCCGGTTCTT
TTTGTCAAGACCGACCTGTCCGGTGCCCTGAATGAACTGCAGGA
CGAGGCAGCGCGGCTATCGTGGCTGGCCACGACGGGCGTTCCTT
GCGCAGCTGTGCTCGACGTTGTCACTGAAGCGGGAAGGGACTGG
CTGCTATTGGGCGAAGTGCCGGGGCAGGATCTCCTGTCATCTCA
CCTTGCTCCTGCCGAGAAAGTATCCATCATGGCTGATGCAATGC
GGCGGCTGCATACGCTTGATCCGGCTACCTGCCCATTCGACCAC
CAAGCGAAACATCGCATCGAGCGAGCACGTACTCGGATGGAAG
CCGGTCTTGTCGATCAGGATGATCTGGACGAAGAGCATCAGGGG
CTCGCGCCAGCCGAACTGTTCGCCAGGCTCAAGGCGCGCATGCC
CGACGGCGAGGATCTCGTCGTGACCCATGGCGATGCCTGCTTG
CCGAATATCATGGTGGAAAATGGCCGCTTTTCTGGATTCATCGA
CTGTGGCCGGCTGGGTGTGGCGGACCGCTATCAGGACATAGCGT
TGGCTACCCGTGATATTGCTGAAGAGCTTGGCGGCGAATGGGCT
GACCGCTTCCTCGTGCTTTACGGTATCGCCGCTCCCGATTCGCAG
CGCATCGCCTTCTATCGCCTTCTTGACGAGTTCTTCTGAGTTTAA
ACAGACCACAACGGTTTCCCTCTAGCGGGATCAATTCCGCCCCT
CTCCCTCCCCCCCCCCTAACGTTACTGGCCGAAGCCGCTTGGAAT
AAGGCCGGTGTGCGTTTGTCTATATGTTATTTTCCACCATATTGC
CGTCTTTTGGCAATGTGAGGGCCCGGAAACCTGGCCCTGTCTTCT
TGACGAGCATTCCTAGGGGTCTTTCCCCTCTCGCCAAAGGAATG
CAAGGTCTGTTGAATGTCGTGAAGGAAGCAGTTCCTCTGGAAGC
TTCTTGAAGACAAACAACGTCTGTAGCGACCCTTTGCAGGCAGC
GGAACCCCCCACCTGGCGACAGGTGCCTCTGCGGCCAAAAGCCA
CGTGTATAAGATACACCTGCAAAGGCGGCACAACCCCAGTGCCA
CGTTGTGAGTTGGATAGTTGTGGAAAGAGTCAAATGGCTCTCCT
CAAGCGTATTCAACAAGGGGCTGAAGGATGCCCAGAAGGTACC
CCATTGTATGGGATCTGATCTGGGGCCTCGGTGCACATGCTTTAC
ATGTGTTTAGTCGAGGTTAAAAAACGTCTAGGCCCCCCGAACCA
CGGGGACGTGGTTTTCCTTTGAAAAACACGATCCTACCATGGCG
CCTATTACGGCCTACTCCCAACAGACGCGAGGCCTACTTGGCTG
CATCATCACTAGCCTCACAGGCCGGGACAGGAACCAGGTCGAG
GGGGAGGTCCAAGTGGTCTCCACCGCAACACAATCTTTCCTGGC
GACCTGCGTCAATGGCGTGTGTTGGACTGTCTATCATGGTGCCG
GCTCAAAGACCCTTGCCGGCCCAAAGGGCCCAATCACCCAAATG
TACACCAATGTGGACCAGGACCTCGTCGGCTGGCAAGCGCCCCC
CGGGGCGCGTTCCTTGACACCATGCACCTGCGGCAGCTCGGACC
TTTACTTGGTCACGAGGCATGCCGATGTCATTCCGGTGCGCCGG
CGGGGCGACAGCAGGGGGAGCCTACTCTCCCCCAGGCCCGTCTC
CTACTTGAAGGGCTCTTCGGGCGGTCCACTGCTCTGCCCCTCGGG
GCACGCTGTGGGCATCTTTCGGGCTGCCGTGTGCACCCGAGGGG
TTGCGAAGGCGGTGGACTTTGTACCCGTCGAGTCTATGGAAACC
ACTATGCGGTCCCCGGTCTTCACGGACAACTCGTCCCCTCCGGCC
GTACCGCAGACATTCCAGGTGGCCCATCTACACGCCCCTACTGG
TAGCGGCAAGAGCACTAAGGTGCCGGCTGCGTATGCAGCCCAA
GGGTATAAGGTGCTTGTCCTGAACCCGTCCGTCGCCGCCACCCT
AGGTTTCGGGGCGTATATGTCTAAGGCACATGGTATCGACCCTA
ACATCAGAACCGGGGTAAGGACCATCACCACGGGTGCCCCCATC
ACGTACTCCACCTATGGCAAGTTTCTTGCCGACGGTGGTTGCTCT
GGGGGCGCCTATGACATCATAATATGTGATGAGTGCCACTCAAC
TGACTCGACCACTATCCTGGGCATCGGCACAGTCCTGGACCAAG
CGGAGACGGCTGGAGCGCGACTCGTCGTGCTCGCCACCGCTACG
CCTCCGGGATCGGTCACCGTGCCACATCCAAACATCGAGGAGGT
GGCTCTGTCCAGCACTGGAGAAATCCCCTTTTATGGCAAAGCCA
TCCCCATCGAGACCATCAAGGGGGGGAGGCACCTCATTTTCTGC
CATTCCAAGAAGAAATGTGATGAGCTCGCCGCGAAGCTGTCCGG
CCTCGGACTCAATGCTGTAGCATATTACCGGGGCCTTGATGTATC
CGTCATACCAACTAGCGGAGACGTCATTGTCGTAGCAACGGACG
CTCTAATGACGGGCTTTACCGGCGATTTCGACTCAGTGATCGACT
GCAATACATGTGTCACCCAGACAGTCGACTTCAGCCTGGACCCG
ACCTTCACCATTGAGACGACGACCGTGCCACAAGACGCGGTGTC

| SEQ ID NOs |
|---|
| ACGCTCGCAGCGGCGAGGCAGGACTGGTAGGGGCAGGATGGGC
ATTTACAGGTTTGTGACTCCAGGAGAACGGCCCTCGGGCATGTT
CGATTCCTCGGTTCTGTGCGAGTGCTATGACGCGGGCTGTGCTTG
GTACGAGCTCACGCCCGCCGAGACCTCAGTTAGGTTGCGGGCTT
ACCTAAACACACCAGGGTTGCCCGTCTGCCAGGACCATCTGGAG
TTCTGGGAGAGCGTCTTTACAGGCCTCACCCACATAGACGCCCA
TTTCTTGTCCCAGACTAAGCAGGCAGGAGACAACTTCCCCTACC
TGGTAGCATACCAGGCTACGGTGTGCGCCAGGGCTCAGGCTCCA
CCTCCATCGTGGGACCAAATGTGGAAGTGTCTCATACGGCTAAA
GCCTACGCTGCACGGGCCAACGCCCCTGCTGTATAGGCTGGGAG
CCGTTCAAAACGAGGTTACTACCACACACCCCATAACCAAATAC
ATCATGGCATGCATGTCGGCTGACCTGGAGGTCGTCACGAGCAC
CTGGGTGCTGGTAGGCGGAGTCCTAGCAGCTCTGGCCGCGTATT
GCCTGACAACAGGCAGCGTGGTCATTGTGGGCAGGATCATCTTG
TCCGGAAAGCCGGCCATCATTCCCGACAGGGAAGTCCTTTACCG
GGAGTTCGATGAGATGGAAGAGTGCGCCTCACACCTCCCTTACA
TCGAACAGGGAATGCAGCTCGCCGAACAATTCAAACAGAAGGC
AATCGGGTTGCTGCAAACAGCCACCAAGCAAGCGGAGGCTGCT
GCTCCCGTGGTGGAATCCAAGTGGCGGACCCTCGAAGCCTTCTG
GGCGAAGCATATGTGGAATTTCATCAGCGGGATACAATATTTAG
CAGGCTTGTCCACTCTGCCTGGCAACCCCGCGATAGCATCACTG
ATGGCATTCACAGCCTCTATCACCAGCCCGCTCACCACCCAACA
TACCCTCCTGTTTAACATCCTGGGGGGATGGGTGGCCGCCCAAC
TTGCTCCTCCCAGCGCTGCTTCTGCTTTCGTAGGCGCCGGCATCG
CTGGAGCGGCTGTTGGCAGCATAGGCCTTGGGAAGGTGCTTGTG
GATATTTTGGCAGGTTATGGAGCAGGGGTGGCAGGCGCGCTCGT
GGCCTTTAAGGTCATGAGCGGCGAGATGCCCTCCACCGAGGACC
TGGTTAACCTACTCCCTGCTATCCTCTCCCCTGGCGCCCTAGTCG
TCGGGGTCGTGTGCGCAGCGATACTGCGTCGGCACGTGGGCCCA
GGGGAGGGGGCTGTGCAGTGGATGAACCGGCTGATAGCGTTCG
CTTCGCGGGGTAACCACGTCTCCCCCACGCACTATGTGCCTGAG
AGCGACGCTGCAGCACGTGTCACTCAGATCCTCTCTAGTCTTACC
ATCACTCAGCTGCTGAAGAGGCTTCACCAGTGGATCAACGAGGA
CTGCTCCACGCCATGCTCCGGCTCGTGGCTAAGAGATGTTTGGG
ATTGGATATGCACGGTGTTGACTGATTTCAAGACCTGGCTCCAG
TCCAAGCTCCTGCCGCGATTGCCGGGAGTCCCCTTCTTCTCATGT
CAACGTGGGTACAAGGGAGTCTGGCGGGGCGACGGCATCATGC
AAACCACCTGCCCATGTGGAGCACAGATCACCGGACATGTGAAA
AACGGTTCCATGAGGATCGTGGGGCCTAGGACCTGTAGTAACAC
GTGGCATGGAACATTCCCCATTAACGCGTACACCACGGGCCCT
GCACGCCCTCCCCGGCGCCAAATTATTCTAGGG

| SEQ ID NOs |
|---|
| ACATGTGTTTAGTCGAGGTTAAAAAACGTCTAGGCCCCCCGAAC
CACGGGGACGTGGTTTTCCTTTGAAAAACACGATAATACCATGG
CGCCTATTACGGCCTACTCCCAACAGACGCGAGGCCTACTTGGC
TGCATCATCACTAGCCTCACAGGCCGGGACAGGAACCAGGTCGA
GGGGGAGGTCCAAGTGGTCTCCACCGCAACACAATCTTTCCTGG
CGACCTGCGTCAATGGCGTGTGTTGGACTGTCTATCATGGTGCC
GGCTCAAAGACCCTTGCCGGCCCAAAGGGCCCAATCACCCAAAT
GTACACCAATGTGGACCAGGACCTCGTCGGCTGGCAAGCGCCCC
CCGGGGCGCGTTCCTTGACACCATGCACCTGCGGCAGCTCGGAC
CTTTACTTGGTCACGAGGCATGCCGATGTCATTCCGGTGCGCCG
GCGGGGCGACAGCAGGGGGAGCCTACTCTCCCCCAGGCCCGTCT
CCTACTTGAAGGGCTCTTCGGGCGGTCCACTGCTCTGCCCCTCG
GGGCACGCTGTGGGCATCTTTCGGGCTGCCGTGTGCACCCGAGG
GGTTGCGAAGGCGGTGGACTTTGTACCCGTCGAGTCTATGGAAA
CCACTATGCGGTCCCCGGTCTTCACGGACAACTCGTCCCCTCCG
GCCGTACCGCAGACATTCCAGGTGGCCCATCTACACGCCCTAC
TGGTAGCGGCAAGAGCACTAAGGTGCCGGCTGCGTATGCAGCCC
AAGGGTATAAGGTGCTTGTCCTGAACCCGTCGTCGCCGCCACC
CTAGGTTTCGGGGCGTATATGTCTAAGGCACATGGTATCGACCC
TAACATCAGAACCGGGGTAAGGACCATCACCACGGGTGCCCCA
TCACGTACTCCACCTATGGCAAGTTTCTTGCCGACGGTGGTTGC
TCTGGGGGCGCCTATGACATCATAATATGTGATGAGTGCCACTC
AACTGACTCGACCACTATCCTGGGCATCGGCACAGTCCTGGACC
AAGCGGAGACGGCTGGAGCGCGACTCGTCGTGCTCGCCACCGCT
ACGCCTCCGGGATCGGTCACCGTGCCACATCCAAACATCGAGGA
GGTGGCTCTGTCCAGCACTGGAGAAATCCCCTTTTATGGCAAAG
CCATCCCCATCGAGACCATCAAGGGGGGGAGGCACCTCATTTTC
TGCCATTCCAAGAAGAAATGTGATGAGCTCGCCGCGAAGCTGTC
CGGCCTCGGACTCATGCTGTAGCATATTACCGGGGCCTTGATGT
ATCCGTCATACCAACTAGCGGAGACGTCATTGTCGTAGCAACGG
ACGCTCTAATGACGGGCCTTTACCGGCGATTTCGACTCAGTGATC
GACTGCAATACATGTGTCACCCAGACAGTCGACTTCAGCCTGGA
CCCGACCTTCACCATTGAGACGACGACCGTGCCACAAGACGCGG
TGTCACGCTCGCAGCGGCGAGGCAGGACTGGTAGGGGCAGGATG
GGCATTTACAGGTTTGTGACTCCAGGAGAACGGCCCTCGGGCAT
GTTCGATTCCTCGGTTCTGTGCGAGTGCTATGACGCGGGCTGTG
CTTGGTACGAGCTCACGCCCGCCGAGACCTCAGTTAGGTTGCGG
GCTTACCTAAACACACCAGGGTTGCCCGTCTGCCAGGACCATCT
GGAGTTCTGGGAGAGCGTCTTTACAGGCCTCACCCACATAGACG
CCCATTTCTTGTCCCAGACTAAGCAGGCAGGAGACAACTTCCCC
TACCTGGTAGCATACCAGGCTACGGTGTGCGCCAGGGCTCAGGC
TCCACCTCCATCGTGGGACCAAATGTGGAAGTGTCTCATACGGC
TAAAGCCTACGCTGCACGGGCCAACGCCCCTGCTGTATAGGCTG
GGAGCCGTTCAAAACGAGGTTACTACCACACACCCCATAACCAA
ATACATCATGGCATGCATGTCGGCTGACCTGGAGGTCGTCACGA
GCACCTGGGTGCTGGTAGGCGGAGTCCTAGCAGCTCTGGCCGCG
TATTGCCTGACAACAGGCAGCGTGGTCATTGTGGGCAGGATCAT
CTTGTCCGGAAAGCCGGCCATCATTCCCGACAGGGAAGTCCTTT
ACCGGGAGTTCGATGAGATGGAAGAGTGCGCCTCACACCTCCCT
TACATCGAACAGGGAATGCAGCTCGCCGAACAATTCAAACAGAA
GGCAATCGGGTTGCTGCAAACAGCCACCAAGCAAGCGGAGGCTG
CTGCTCCCGTGGTGGAATCCAAGTGGCGGACCCTCGAAGCCTTC
TGGGCGAAGCATATGTGGAATTTCATCAGCGGGATACAATATTT
AGCAGGCTTGTCCACTCTGCCTGGCAACCCCGCGATAGCATCAC
TGATGGCATTCACAGCCTCTATCACCAGCCCGCTCACCACCCAA
CATACCCTCCTGTTTAACATCCTGGGGGGATGGGTGGCCGCCCA
ACTTGCTCCTCCCAGCGCTGCTTCTGCTTTCGTAGGCGCCGGCA
TCGCTGGAGCGGCTGTTGGCAGCATAGGCCTTGGGAAGGTGCTT
GTGGATATTTTGGCAGGTTATGGAGCAGGGGTGGCAGGCGCGCT
CGTGGCCTTTAAGGTCATGAGCGGCGAGATGCCCTCCACCGAGG
ACCTGGTTAACCTACTCCCTGCTATCCTCTCCCCTGGCGCCCTA
GTCGTCGGGGTCGTGTGCGCAGCGATACTGCGTCGGCACGTGGG
CCCAGGGGAGGGGGCTGTGCAGTGGATGAACCGGCTGATAGCGT
TCGCTTCGCGGGGTAACCACGTCTCCCCCACGCACTATGTGCT
GAGAGCGACGCTGCAGCACGTGTCACTCAGATCTCTCTAGTCT
TACCATCACTCAGCTGCTGAAGAGGCTTCACCAGTGGATCAACG
AGGACTGCTCCACGCCATGCTCCGGCTCGTGGCTAAGAGATGTT
TGGGATTGGATATGCACGGTGTTGACTGATTTCAAGACCTGGT
CCAGTCCAAGCTCCTGCCGCGATTGCCGGGAGTCCCCTTCTTCT
CATGTCAACGTGGGTACAAGGGAGTCTGGCGGGGCGACGGCATC
ATGCAAACCACCTGCCCATGTGGAGCACAGATCACCGGACATGT
GAAAAACGGTTCCATGAGGATCGTGGGGCCTAGGACCTGTAGTA
ACACGTGGCATGGAACATTCCCCATTAACGCGTACACCACGGGC
CCCTGCACGCCCTCCCCGGCGCCAAATTATTCTAGGGCGCTGTG
GCGGGTGGCTGCTGAGGAGTACGTGGAGGTTACGCGGGTGGGGG
ATTTCCACTACGTGACGGGCATGACCACTGACAACGTAAAGTGC
CCGTGTCAGGTTCCGGCCCCCGAATTCTTCACAGAAGTGGATGG |
| GGTGCGGTTGCACAGGTACGCTCCAGCGTGCAAACCCCTCCTAC
GGGAGGAGGTCACATTCCTGGTCGGGCTCAATCAATACCTGGTT
GGGTCACAGCTCCCATGCGAGCCCGAACCGGACGTAGCAGTGCT
CACTTCCATGCTCACCGACCCCTCCCACATTACGGCGGAGACGG
CTAAGCGTAGGCTGGCCAGGGGATCTCCCCCCTCCTTGGCCAGC
TCATCAGCTAGCCAGCTGtacTCTTTCGAGCCGCTCCAAGCGGAG
GAGGATGAGAGGGAAGTATCCGTTCCGGCGGAGATCCTGCGGAG
GTCCAGGAAATTCCCTCGAGCGATGCCCATATGGGCACGCCCGG
ATTACAACCCTCCACTGTTAGAGTCCTGGAAGGACCCGGACTAC
GTCCCTCCAGTGGTACACGGGTGTCCATTGCCGCCTGCCAAGGC
CCCTCCGATACCACCTCCACGGAGGAAGAGGACGGTTGTCCTGT
CAGAATCTACCGTGTCTTCTGCCTTGGCGGAGCTCGCCACAAAG
ACCTTCGGCAGCTCCGAATCGTCGGCCGTCGACAGCGGCACGGC
AACGGCCTCTCCTGACCAGCCCTCCGACGACGGCGACGCGGGAT
CCGACGTTGAGTCGTACTCCTCCATGCCCCCCCTTGAGGGGGAG
CCGGGGGATCCCGATCTCAGCGACGGGTCTTGGTCTACCGTAAG
CGAGGAGGCTAGTGAGGACGTCGTCTGCTGCTCGATGTCCTACA
CATGGACAGGCGCCCTGATCACGCCATGCGCTGCGGAGGAAACC
AAGCTGCCCATCAATGCACTGAGCAACTCTTTGCTCCGTCACCA
CAACTTGGTCTATGCTACAACATCTCGCAGCGCAAGCCTGCGGC
AGAAGAAGGTCACCTTTGACAGACTGCAGGTCCTGGACGACCAC
TACCGGGACGTGCTCAAGGAGATGAAGGCGAAGGCGTCCACAGT
TAAGGCTAAACTTCTATCCGTGGAGGAAGCCTGTAAGCTGACGC
CCCCACATTCGGCCAGATCTAAATTTGGCTATGGGCAAAGGAC
GTCCGGAACCTATCCAGCAAGGCCGTTACCACATCCGCTCCGTG
TGGAAGGACTTGCTGGAAGACACTGAGACACCAATTGACACCAC
CATCATGGCAAAAAATGAGGTTTTCTGCGTCCAACCAGAGAAGG
GGGGCCGCAAGCCAGCTCGCCTTATCGTATTCCCAGATTTGGGG
GTTCGTGTGTGCGAGAAAATGGCCCTTTACGATGTGGTCTCCAC
CCTCCCTCAGGCCGTGATGGGCTCTTCATACGGATTCCAATACT
CTCCTGGACAGCCGGTCGAGTTCCTGGTGAATGCCTGGAAAGCG
AAGAAATGCCCTATGGGCTTCGCATATGACACCCGCTGTTTTGA
CTCAACGGTCACTGAGAATGACATCCGTGTTGAGGAGTCAATCT
ACCAATGTTGTGACTTGGCCCCCGAAGCCAGACAGGCCATAAGG
TCGCTCACAGAGCCGGCTTTACATCGGGGGCCCCCTGACTAATTC
TAAAGGGCAGAACTGCGGCTATCGCCGGTGCCGCGCGAGCGGTG
TACTGACGACCAGCTGCGGTAATACCCTCACATGTTACTTGAAG
GCCGCTGCGGCCTGTCGAGCTGCGAAGCTCCAGGACTGCACGAT
GCTCGTATGCGGAGACGACCTTGTCGTTATCTGTGAAAGCGCGG
GGACCCAAGAGGACGAGGCGAGCCTACGGGCCTTCACGGAGGCT
ATGACTAGATACTCTGCCCCCCCTGGGGACCCGCCCAAACCAGA
ATACGACTTGGAGTTGATAACATCATGCTCCTCCAATGTGTCAG
TCGCGCACGATGCATCTGCCAAAAGGGTGTACTATCTCACCCGT
GACCCCACCACCCCCCTTGCGCGGGCTGCGTGGGAGACAGCTAG
ACACACTCCAGTCAATTCCTGGCTAGGCAACATCATCATGTATG
CGCCCACCTTGTGGGCAAGGATGATCCTGATGACTCATTTCTTC
TCCATCCTTCTAGCTCAGGAACAACTTGAAAAAGCCCTAGATTG
TCAGATCTACGGGGCCTGTTACTCCATTGAGCCACTTGACCTAC
CTCAGATCATTCAACGACTCCATGGCCTAGCGCATTTTCACTC
CATAGTTACTCTCCAGGTGAGATCAATAGGGTGGCTTCATGCCT
CAGGAAACTTGGGGTACCGCCCTTGCGAGTCTGGAGACATCGGG
CCAGAAGTGTCCGCGCTAGGCTACTGTCCCAGGGGGGGAGGGCT
GCCACTTGTGGCAAGTACCTCTTCAACTGGGCAGTAAGGACCAA
GCTCAAACTCACTCCAATCCCGGCTGCGTCCCAGTTGGATTTAT
CCAGCTGGTTCGTTGCTGGTTACAGCGGGGGAGACATATATCAC
AGCCTGTCTCGTGCCCGACCCCGCTGGTTCATGTGGTGCCTACT
CCTACTTTCTGTAGGGGTAGGCATCTATCTACTCCCCAACCGAT
GAACGGGGACCTAAACACTCCAGGCCAATAGGCCATCCTGTTTT
TTTCCCTTTTTTTTTTCTTTTTTTTTTTTTTTTTTTTTTTTTTT
TTTTTTTTCTCCTTTTTTTTCCTCTTTTTTTCCTTTTCTTTCC
TTTGGTGGCTCCATCTTAGCCCTAGTCACGGCTAGCTGTGAAAG
GTCCGTGAGCCGCTTGACTGCAGAGAGTGCTGATACTGGCCTCT
CTGCAGATCAAGT |

SEQ ID NO: 8: Nucleotide sequence of DNA clone of HCV adaptive replicon VI, where nucleotide changes are in lower case and high CTATTCGGCTATGACTGGGCACAACAGACAATCGGCTGCTCTGA
TGCCGCCGTGTTCCGGCTGTCAGCGCAGGGGCGCCCGGTTCTTT
TTGTCAAGACCGACCTGTCCGGTGCCCTGAATGAACTGCAGGAC
GAGGCAGCGCGGCTATCGTGGCTGGCCACGACGGGCGTTCCTTG
CGCAGCTGTGCTCGACGTTGTCACTGAAGCGGGAAGGGACTGGC
TGCTATTGGGCGAAGTGCCGGGGCAGGATCTCCTGTCATCTCAC
CTTGCTCCTGCCGAGAAAGTATCCATCATGGCTGATGCAATGCG
GCGGCTGCATACGCTTGATCCGGCTACCTGCCCATTCGACCACC
AAGCGAAACATCGCATCGAGCGAGCACGTACTCGGATGGAAGCC
GGTCTTGTCGATCAGGATGATCTGGACGAAGAGCATCAGGGGCT
CGCGCCAGCCGAACTGTTCGCCAGGCTCAAGGCGCGCATGCCCG
ACGGCGAGGATCGTCGTGACCCATGGCGATGCCTGCTTGCCG
AATATCATGGTGGAAAATGGCCGCTTTTCTGGATTCATCGACTG
TGGCCGGCTGGGTGTGGCGGACCGCTATCAGGACATAGCGTTGG
CTACCCGTGATATTGCTGAAGAGCTTGGCGGCGAATGGGCTGAC
CGCTTCCTCGTGCTTTACGGTATCGCCGCTCCCGATTCGCAGCG
CATCGCCTTCTATCGCCTTCTTGACGAGTTCTTCTGAGTTTAAA
CAGACCACAACGGTTTCCCTCTAGCGGGATCAATTCCGCCCCTC
TCCCTCCCCCCCCCCTAACGTTACTGGCCGAAGCCGCTTGGAAT
AAGGCCGGTGTGCGTTTGTCTATATGTTATTTTCCACCATATTG
CCGTCTTTTGGCAATGTGAGGGCCCGGAAACCTGGCCCTGTCTT
CTTGACGAGCATTCCTAGGGGTCTTTCCCCTCTCGCCAAAGGAA
TGCAAGGTCTGTTGAATGTCGTGAAGGAAGCAGTTCCTCTGGAA
GCTTCTTGAAGACAAACAACGTCTGTAGCGACCCTTTGCAGGCA
GCGGAACCCCCACCTGGCGACAGGTGCCTCTGCGGCCAAAAGC
CACGTGTATAAGATACACCTGCAAAGGCGGCACAACCCCAGTGC
CACGTTGTGAGTTGGATAGTTGTGGAAAGAGTCAAATGCTCTC
CTCAAGCGTATTCAACAAGGGGCTGAAGGATGCCCAGAAGGTAC
CCCATTGTATGGGATCTGATCTGGGGCCTCGGTGCACATGCTTT
ACATGTGTTAGTCGAGGTTAAAAAACGTCTAGGCCCCCCGAAC
CACGGGGACGTGGTTTTCCTTTGAAAAACACGATAATACCATGG
CGCCTATTACGGCCTACTCCCAACAGACGCGAGGCCTACTTGGC
TGCATCATCACTAGCCTCACAGGCCGGGACAGGAACCAGGTCGA
GGGGGAGGTCCAAGTGGTCTCCACCGCAACACAATCTTTCCTGG
CGACCTGCGTCAATGGCGTGTGTTGGACTGTCTATCATGGTGCC
GGCTCAAAGACCCTTGCGGCCCAAAGGGCCCAATCACCCAAAT
GTACACCAATGTGGACCAGGACCTCGTCGGCTGGcAGCGCCCC
CCGGGGCGCGTTCCTTGACACCATGCACCTGCGGCAGCTCGGAC
CTTTACTTGGTCACGAGGCATCGCCGATGTCATTCCGGTGCGCG
GCGGGGCGACAGCAGGGGGAGCCTACTCTCCCCCAGGCCCGTCT
CCTACTTGAAGGGCTCTTCGGGCGGTCCACTGCTCTGCCCCTCG
GGGCACGCTGTGGGCATCTTTCGGGCTGCCGTGTGCACCCGAGG
GGTTGCGAAGGCGGTGACTTTGTACCCGTCGAGTCTATCATGGT
CCACTATGCGGTCCCCGGTCTTCACGGACAACTCGTCCCCTCCG
GCCGTACCGCAGACATTCCAGGTGGCCCATCTACACGCCCTAC
TGGTAGCGGCAAGAGCACTAAGGTGCCGGCTGCGTATGCAGCCC
AAGGGTATAAGGTGCTTGTCCTGAACCCGTCCGTCGCCGCCACC
CTAGGTTTCGGGGCGTATATGTCTAAGGCACATGGTATCGACCC
TAACATCAGAACCGGGGTAAGGACCATCACCACGGGTGCCCCA
TCACGTACTCCACCTATGGCAAGTTTCTTGCCGACGGTGGTTGC
TCTGGGGGCGCCTATGACATCATCCTATGTGATGAGTGCCACTC
AACTGACTCGACCACTATCCTGGGCATCGGCACAGTCCTGGACC
AAGCGGAGACGGCTGGAGCGCGACTCGTCGTGCTCGCCACCGCT
ACGCCTCCGGGATCGGTCACCGTGCCACATCCAAACATCGAGGA
GGTGGCTCTGTCCAGCACTGGAGAAATCCCCTTTTATGGCAAAG
CCATCCCCATCGAGACCATCAAGGGGGGAGGCACCTCATTTTC
TGCCATTCCAAGAAGAAATGTGATGAGCTCGCCGCGAAGCTGTC
CGGCCTCGGACTCAATGCTGTAGCATATTACCGGGGCCTTGATG
TATCCGTCATACCAACTAGCGGAGACGTCATTGTCGTAGCAACG
GACGCTCTAATGACGGGCTTTACCGGCGATTTCGACTCAGTGAT
CGACTGCAATACATGTGTCACCCAGACAGTCGACTTCAGCCTGG
ACCCGACCTTCACCATTGAGACGACGACCGTGCCACAAGACGCG
GTGTCACGCTCGCAGCGGCGAGGCAGGACTGGTAGGGGCAGGAT
GGGCATTTACAGGTTTGTGACTCCAGGAGAACGGCCCTCGGGCA
TGTTCGATTCCTCGGTTCTGTGCGAGTGCTATGACGCGGGCTGT
GCTTGGTACGAGCTCACGCCCGCCGAGACCTCAGTTAGGTTGCG
GGCTTACCTAAACACACCAGGGTTGCCCGTCTGCCAGGACCATC
TGGAGTTCTGGGAGAGCGTCTTTACAGGCCTCACCCACATAGAC
GCCCATTTCTTGTCCCAGACTAAGCAGGCAGGAGACAACTTCCC
CTACCTGGTAGCATACCAGGCTACGGTGTGCGCCAGGGCTCAGG
CTCCACCTCCATCGTGGGACCAAATGTGGAAGTGTCTCATACGG
CTAAAGCCTACGCTGCACGGGCCAACGCCCCTGCTGTATAGGGT
GGGAGCCGTTCAAAACGAGGTTACTACCACACACCCCATAACCA
AATACATCATGGCATGCATGTCGGCTGACCTGGAGGTCGTCACG
AGCACCTGGGTGCTGGTAGGCGGAGTCCTAGCAGCTCTGGCCGC
GTATTGCCTGACAACAGGCAGCGTGGTCATTGTGGGCAGGATCA
TCTTGTCCGGAAAGCCGGCCATCATTCCCGACAGGGAAGTCCTT TACCGGGAGTTCGATGAGATGGAAGAGTGCGCCTCACACCTCCC
TTACATCGAACAGGGAATGCAGCTCGCCGAACAATTCAAACAGA
AGGCAATCGGGTTGCTGCAAACAGCCACCAAGCAAGCGGAGGCT
GCTGCTCCCGTGGTGGAATCCAAGTGGCGGACCCTCGAAGCCTT
CTGGGCGAAGCATATGTGGAATTTCATCAGCGGGATACAATATT
TAGCAGGCTTGTCCACTCTGCCTGGCAACCCCGCGATAGCATCA
CTGATGGCATTCACAGCCTCTATCACCAGCCCGCTCACCACCCA
ACATACCCTCCTGTTTAACATCCTGGGGGGATGGGTGGCCGCCC
AACTTGCTCCTCCCAGCGCTGCTTCTGCTTTCGTAGGCGCCGGC
ATCGCTGGAGCGGCTGTTGGCAGCATAGGCCTTGGGAAGGTGCT
TGTGGATATTTTGGCAGGTTATGGAGCAGGGGTGGCAGGCGCGC
TCGTGGCCTTTAAGGTCATGAGCGGCGAGATGCCCTCCACCGAG
GACCTGGTTAACCTACTCCCTGCTATCCTCTCCCCTGGCGCCCT
AGTCGTCGGGGTCGTGTGCGCAGCGATACTGCGTCGGCACGTGG
GCCCAGGGGAGGGGGCTGTGCAGTGGATGAACCGGCTGATAGCG
TTCGCTTCGCGGGGTAACCACGTCTCCCCCACGCACTATGTGCC
TGAGAGCGACGCTGCAGCACGTGTCACTCAGATCCTCTCTAGTC
TTACCATCACTCAGCTGCTGAAGAGGCTTCACCAGTGGATCAAC
GAGGACTGCTCCACGCCATGCTCCCGGCTCCGTGGCTAAGAGATGT
TTGGGATTGGATATGCACGGTGTTGACTGATTTCAAGACCTGGC
TCCAGTCCAAGCTCCTGCCGCGATTGCCGGGAGTCCCCTTCTTC
TCATGTCAACGTGGGTACAAGGGAGTCTGGCGGGGCGACGGCAT
CATGCAAACCACCTGCCCATGTGGAGCACAGATCACCGGACATG
TGAAAAACGGTTCCATGAGGATCGTGGGGCCTAGGACCTGTAGT
AACACGTGGCATGGAACATTCCCCATTAACGCGTACACCACGGG
CCCCTGCACGCCCTCCCCGGCGCCAAATTATTCTAGGGCGCTGT
GGCGGGTGGCTGCTGAGGAGTACGTGGAGGTTACGCGGGTGGGG
GATTTCCACTACGTGACGGGCATGACCACTGACAACGTAAAGTG
CCCGTGTCAGGTTCCGGCCCCCGAATTCTTCACAGAAGTGGATG
GGGTGCGGTTGCACAGGTACGCTCCAGCCGTGCAAACCCCTCCTA
CGGGAGGAGGTCACATTCCTGGTCGGGCTCAATCAATACCTGGT
TGGGTCACAGCTCCCATGCGAGCCCGAACCGGACGTAGCAGTGC
TCACTTCCATGCTCACCGACCCCTCCCACATTACGGCGGAGACG
GCTAAGCGTAGGCTGGCCAGGGGATCTCCCCCCTCCTTGGCCAG
CTCATCAGCTAtCCAGCTGTCTGCGCCTTCCTTGAAGGCAACATG
CACTACCCGTCATGACTCCCCGGACGCTGACCTCATCGAGGCCA
ACCTCCTGTGGCGGCAGGAGATGGGCGGGAACATCACCCGCGTG
GAGTCAGAAAATAAGGTAGTAATTTTGGACTCTTTCGAGCCGCT
CCAAGCGGAGGAGGTGCAGGAGAAGTATCCGTTCCGGCCGGAGA
TCCTGCGGAGGTCCAGGAAATTCCCTCGAGACGATGCCCATATG
GGCACGCCCGGATTACAACCCTCCACTGTTAGAGTCCTGGAAGG
ACCCGGACTACGTCCCTCCAGTGGTACACGGGTGTCCATTGCCG
CCTGCCAAGGCCCTCCGATACCACCTCCACGGAGGAAGAGGAC
GGTTGTCCTGTCAGAATCTACCGTGTCTTCTGCCTTGGCGGAGC
TCGCCACAAAGACCTTCGGCAGCTCCGAATCGTCGGCCGTCGAC
AGCGGCACGGCAACGGCCTCTCCTGACCAGCCCTCCGACGACGG
CGACGCGGGATCCGACGTTGAGTCGTACTCCTCCATGCCCCCCC
TTGAGGGGGAGCCGGGGGATCCCGATCTCAGCGACGGGTCTTGG
TCTACCGTAAGCGAGGAGGCTAGTGAGGACGTCGTCTGCTGCTC
GATGTAATACACATGGACAGGCGCCCTGATCACGCCATGCGCTG
CGGAGGAAACCAAGCTGCCCATCAATGCACTGAGCAACTCTTTG
CTCCGTCACCACAACTTGGTCTATGCTACAACATCTCGCAGCGC
AAGCCTGCGGCAGAAGAAGGTCACCTTTGACAGACTGCAGGTCC
TGGACGACCACTACCGGGACGTGCTCAAGGAGATGAAGGCGAAG
GCGTCCACAGTTAAGGCTAAACTTCTATCCGTGGAGGAAGCCTG
TAAGCTGACGCCCCCACATTCGGCCAGATCTAAATTTGGCTATG
GGGCAAAGGACGTCCGGAACCTATCCAGCAAGGCCGTTAACCAC
ATCCGCTCCGTGTGGAAGGACTTGCTGGAAGACACTGAGACACC
AATTGACACCACCATCATGGCAAAAAATGAGGTTTTCTGCGTCC
AACCAGAGAAGGGGGGCCGCAAGCCAGCTCGCCTTATCGTATTC
CCAGATTTGGGGGTTCGTGTTGCGAGAAAAATGGCCCTTTACGA
TGTGGTCTCCACCCTCCCTCAGGCCGTGATGGGCTCTTCATACG
GATTCCAATACTCTCCTGGACAGCGGGTCGAGTTCCTGGTGAAT
GCCTGGAAAGCGAAAAATGCCTATGGGCTTCGCATATGACAC
CCGCTGTTTTGACTCAACGGTCACTGAGAATGACATCCGTGTTG
AGGAGTCAATCTACCAATGTTGTGACTTGGCCCCCGAAGCCAGA
CAGGCCATAAGGTCGCTCACAGAGCGGCTTTACATCGGGGGCCC
CCTGACTAATTCTAAAGGGCAAACATGCGGCTATCGCCGGTGCC
GCGCGAGCGGTGTACTGACGACCAGCTGCGGTAATACCCTCACA
TGTTACTTGAAGGCCGCTGCGGCCTGTCGAGCTGCGAAGCTCCA
GGACTGCACGATGCTCGTATGCGGAGACGACCTTGTCGTTATCT
GTGAAAGCGCGGGGACCCAAGAGGACGAGGCGAGCCTACGGGCC
TTCACGGAGGCTATGACTAGATACTCTGCCCCCCCTGGGGACCC
GCCCAAACCAGAATACGACTTGGAGTTGATAACATCATGCTCCT
CCAATGTGTCAGTCGCGCACGATGCATCTGGCAAAAGGGTGTAC
TATCTCACCCGTGACCCCACCACCCCCCTTGCGCGGGCTGCGTG
GGAGACAGCTAGACACACTCCAGTCAATTCCTGGCTAGGCAACA

| SEQ ID NOs |
|---|
| TCATCATGTATGCGCCCACCTTGTGGGCAAGGATGATCCTGATG
ACTCATTTCTTCTCCATCCTTCTAGCTCAGGAACAACTTGAAAA
AGCCCTAGATTGTCAGATCTACGGGGCCTGTTACTCCATTGAGC
CACTTGACCTACCTCAGATCATTCAACGACTCCATGGCCTTAGC
GCATTTTCACTCCATAGTTACTCTCCAGGTGAGATCAATAGGGT
GGCTTCATGCCTCAGGAAACTTGGGGTACCGCCCTTGCGAGTCT
GGAGACATCGGGCCAGAAGTGTCCGCGCTAGGCTACTGTCCCAG
GGGGGGAGGGCTGCCACTTGTGGCAAGTACCTCTTCAACTGGGC
AGTAAGGACCAAGCTCAAACTCACTCCAATCCCGGCTGCGTCCC
AGTTGGATTTATCCAGCTGGTTCGTTGCTGGTTACAGCGGGGGA
GACATATATCACAGCCTGTCTCGTGCCCGACCCCGCTGGTTCAT
GTGGTGCCTACTCCTACTTTCTGTAGGGGTAGGCATCTATCTAC
TCCCCAACCGATGAACGGGGAGCTAAACACTCCAGGCCAATAGG
CCATCCTGTTTTTTCCCTTTTTTTTTTCTTTTTTTTTTTTT
TTTTTTTTTTTTTTTTCTCCTTTTTTTTTCCTCTTTTTTTCC
TTTTCTTTCCTTTGGTGGCTCCATCTTAGCCCTAGTCACGGCTA
GCTGTGAAAGGTCCGTGAGCCGCTTGACTGCAGAGAGTGCTGAT
ACTGGCCTCTCTGCAGATCAAGT
SEQ ID NO: 9: Nucleotide sequence of DNA clone of
HCV adaptive replicon II, where nucleotide changes
are in lower case and highlighted in bold GCCAGCCCCGATTGGGGCGACACTCCACCATAGATCACTCCC
CTGTGAGGAACTACTGTCTTCACGCAGAAAGCGTCTAGCCATGG
CGTTAGTATGAGTGTCGTGCAGCCTCCAGGACCCCCCTCCCGG
GAGAGCCATAGTGGTCTGCGGAACCGGTGAGTACACCGGAATTG
CCAGGACGACCGGGTCCTTTCTTGGATCAACCCGCTCAATGCCT
GGAGATTTGGGCGTGCCCCCGCGAGACTGCTAGCCGAGTAGTGT
TGGGTCGCGAAAGGCCTTGTGGTACTGCCTGATAGGGTGCTTGC
GAGTGCCCCGGGAGGTCTCGTAGACCGTGCACCATGAGCACGAA
TCCTAAACCTCAAAGAAAAACCAAAGGGCGCGCCATGATTGAAC
AAGATGGATTGCACGCAGGTTCTCCGGCCGCTTGGGTGGAGAGG
CTATTCGGCTATGACTGGGCACAACAGACAATCGGCTGCTCTGA
TGCCGCCGTGTTCCGGCTGTCAGCGCAGGGGCGCCCGGTTCTTT
TTGTCAAGACCGACCTGTCCGGTGCCCTGAATGAACTGCAGGAC
GAGGCAGCGCGGCTATCGTGGCTGGCCACGACGGGCGTTCCTTG
CGCAGCTGTGCTCGACGTTGTCACTGAAGCGGGAAGGGACTGGC
TGCTATTGGGCGAAGTGCCGGGGCAGGATCTCCTGTCATCTCAC
CTTGCTCCTGCCGAGAAAGTATCCATCATGGCTGATGCAATGCG
GCGGCTGCATACGCTTGATCCGGCTACCTGCCCATTCGACCACC
AAGCGAAACATCGCATCGAGCGAGCACGTACTCGGATGGAAGCC
GGTCTTGTCGATCAGGATGATCTGGACGAAGAGCATCAGGGGCT
CGCGCCAGCCGAACTGTTCGCCAGGCTCAAGGCGCGCATGCCCG
ACGGCGAGGATCTCGTCGTGACCCATGGCGATGCCTGCTTGCCG
AATATCATGGTGGAAAATGGCCGCTTTTCTGGATTCATCGACTG
TGGCCGGCTGGGTGTGGCGGACCGCTATCAGGACATAGCGTTGG
CTACCCGTGATATTGCTGAAGAGCTTGGCGGCGAATGGGCTGAC
CGCTTCCTCGTGCTTTACGGTATCGCCGCTCCCGATTCGCAGCG
CATCGCCTTCTATCGCCTTCTTGACGAGTTCTTCTGAGTTTAAA
CAGACCACAACGGTTTCCCTCTAGCGGGATCAATTCCGCCCCTC
TCCCTCCCCCCCCCCTAACGTTACTGGCCGAAGCCGCTTGGAAT
AAGGCCGGTGTGCGTTTGTCTATATGTTATTTTCCACCATATTG
CCGTCTTTTGGCAATGTGAGGGCCCGGAAACCTGGCCCTGTCTT
CTTGACGAGCATTCCTAGGGGTCTTTCCCCTCTCGCCAAAGGAA
TGCAAGGTCTGTTGAATGTCGTGAAGGAAGCAGTTCCTCTGGAA
GCTTCTTGAAGACAAACAACGTCTGTAGCGACCCTTTGCAGGCA
GCGGAACCCCCCACCTGGCGACAGGTGCCTCTGCGGCCAAAAGC
CACGTGTATAAGATACACCTGCAAAGGCGGCACAACCCCAGTGC
CACGTTGTGAGTTGGATAGTTGTGGAAAGAGTCAAATGGCTCTC
CTCAAGCGTATTCAACAAGGGGCTGAAGGATGCCCAGAAGGTAC
CCCATTGTATGGGATCTGATCTGGGGCCTCGGTGCACATGCTTT
ACATGTGTTTAGTCGAGGTTAAAAAACGTCTAGGCCCCCGAAC
CACGGGGACGTGGTTTTCCTTTGAAAAACACGATAATACCATGG
CGCCTATTACGGCCTACTCCCAACAGACGCAGGCCTCCGCCGTCT
TGCATCATCACTAGCCTCACAGGCGGCAGGAACCAGGTCGA
GGGGGAGGTCCAAGTGGTCTCCACCGCAACACAATCTTTCCTGG
CGACCTGCGTCAATGGCGTGTGTTGGACTGTCTATCATGGTGCC
GGCTCAAAGACCCTTGCCGGCCCAAAGGGCCCAATCACCCAAAT
GTACACCAATGTGGACCAGGACCTCGTCGGCTGGCAAGCGCCCC
CCGGGGCGCGTTCCTTGACACCATGCACCTGCGGCAGCTCGGAC
CTTTACTTGGTCACGAGGCATGCCGATGTCATTCCGGTGCGCCG
GCGGGGGCAACGACAGGGGGAGCCTACTCTCCCCCAGGCCGTCT
CCTACTTGAAGGGCTCTTCGGGCGGTCCACTGCTCTGCCCCTCG
GGGCACGCTGTGGGCATCTTTCGGGCTGCCGTGTGCACCCGAGG
GGTTGCAAGGCGGTGGACTTTGTACCCGTCGAGTCTATGGAAA
CCACTATGCGGTCCCCGGTCTTCACGGACAACTCGTCCCCTCCG
GCCGTACCGCAGACATTCCAGGTGGCCCATCTACACGCCCCTAC | TGGTAGCGGCAAGAGCACTAAGGTGCCGGCTGCGTATGCAGCCC
AAGGGTATAAGGTGCTTGTCCTGAACCCGTCCGTCGCCGCCACC
CTAGGTTTCGGGGCGTATATGTCTAAGGCACATGGTATCGACCC
TAACATCAGAACCGGGGTAAGGACCATCACCACGGGTGCCCCCA
TCACGTACTCCACCTATGGCAAGTTTCTTGCCGACGGTGGTTGC
TCTGGGGGCGCCTATGACATCATAATATGTGATGAGTGCCACTC
AACTGACTCGACCACTATCCTGGGCATCGGCACAGTCCTGGACC
AAGCGGAGACGGCTGGAGCGCGACTCGTCGTGCTCGCCACCGCT
ACGCCTCCGGGATCGGTCACCGTGCCACATCCAAACATCGAGGA
GGTGGCTCTGTCCAGCACTGGAGAAATCCCCTTTTATGGCAAAG
CCATCCCCATCGAGACCATCAAGGGGGGGAGGCACCTCATTTTC
TGCCATTCCAAGAAGAAATGTGATGAGCTCGCCGCGAAGCTGTC
CGGCCTCGGACTCAATGCTGTAGCATATTACCGGGGCCTTGATG
TATCCGTCATACCAACTAGCGGAGACGTCATTGTCGTAGCAACG
GACGCTCTAATGACGGGCTTTACCGGCGATTTCGACTCAGTGAT
CGACTGCAATACATGTGTCACCCAGACAGTCGACTTCAGCCTGG
ACCCGACCTTCACCATTGAGACGACGACCGTGCCACAAGACGCG
GTGTCACGCTCGCAGCGGCGAGGCAGGACTGGTAGGGGCAGGAT
GGGCATTTACAGGTTTGTGACTCCAGGAGAACGGCCCTCGGGCA
TGTTCGATTCCTCGGTTCTGTGCGAGTGCTATGACGCGGGCTGT
GCTTGGTACGAGCTCACGCCCGCCGAGACCTCAGTTAGGTTGCG
GGCTTACCTAAACACACCAGGGTTGCCCGTCTGCCAGGACCATC
TGGAGTTCTGGGAGAGCGTCTTTACAGGCCTCACCCACATAGAC
GCCCATTTCTTGTCCCAGACTAAGCAGGCAGGAGACAACTTCCC
CTACCTGGTAGCATACCAGGCTACGGTGTGCGCCAGGGCTCAGG
CTCCACCTCCATCGTGGGACCAAATGTGGgAGTGTCTCATACGGC
TAAAGCCTACGCTGCACGGGCCAACGCCCCTGCTGTATAGGCTG
GGAGCCGTTCAAAACGAGGTTACTACCACACACCCCATAACCAA
ATACATCATGGCATGCATGTCGGCTGACCTGGAGGTCGTCACGA
GCACCTGGGTGCTGGTAGGCGGAGTCCTAGCAGCTCTGGCCGCG
TATTGCCTGACAACAGGCACGCGTGGTGATTGTGGGCAGGATCAT
CTTGTCCGGAAAGCCGGCCATCATTCCCGACAGGGAAGTCCTTT
ACCGGGAGTTCGATGAGATGGAAGAGTGCGCCTCACACCTCCCT
TACATCGAACAGGGAATGCAGCTCGCCGAACAATTCAAACAGAA
GGCAATCGGGTTGCTGCAAACAGCCACCAAGCAAGCGGAGGCTG
CTGCTCCCGTGGTGGAATCCAAGTGGCGGACCCTCGAAGCCTTC
TGGGCGAAGCATATGTGGAATTTCATCAGCGGGATACAATATTT
AGCAGGCTTGTCCACTCTGCCTGGCAACCCCGCGATAGCATCAC
TGATGGCATTCACAGCCTCTATCACCAGCCGCTCTACCACCCAA
CATACCCTCCTGTTTAACATCCTGGGGGGATGGGTGGCCGCCCA
ACTTGCTCCTCCCAGCGCTGCTTCTGCTTTCGTAGGCGCCGGCA
TCGCTGGAGCGGCTGTTGGCAGCATAGGCCTTGGGAAGGTGCTT
GTGGATATTTTGGCAGGTTATGGAGCAGGGGTGGCAGGCGCGCT
CGTGGCCTTTAAGGTCATGAGCGGCGAGATGCCCTCCACCGAGG
ACCTGGTTAACCTACTCCCTGCTATCCTCTCCCCTGGCGCCCTA
GTCGTCGGGGTCGTGTGCGCAGCGATACTGCGTCGGCACGTGGG
CCCAGGGGAGGGGGCTGTGCAGTGGATGAACCGGCTGATAGCGT
TCGCTTCGCGGGGTAACCACGTCTCCCCCACGCACTATGTGCCT
GAGAGCGACGCTGCAGCACGTGTCACTCAGATCCTCTCTgGTCTT
ACCATCACTCAGCTGCTGAAGAGGCTTCACCAGTGGATCAACGA
GGACTGCTCCACGCCCATGCTCCGGTCCGGCTCGTGGCTAAGAGATGTTT
GGGATTGGATATGCACGGTGTTGACTGATTTCAAGACCTGGCTC
CAGTCCAAGCTCCTGCCGCGATTGCCGGGAGTCCCCTTCTTCTC
ATGTCAACGTGGGTACAAGGGAGTCTGGCGGGGCGACGGCATCA
TGCAAACCACCTGCCCATGTGGAGCACAGATCACCGGACATGTG
AAAAACGGTTCCATGAGGATCGTGGGGCCTAGGACCTGTAGTAA
CACGTGGCATGGAACATTCCCCATTAACGCGTACACCACGGGCC
CCTGCACGCCCTCCCCGGCGCCAAATTATTCTAGGGCGCTGTGG
CGGGTGGCTGCTGAGGAGTACGTGGAGGTTACGCGGGTGGGGGA
TTTCCACTACGTGACGGGGCATGACCACTGACAACGTAAGTGCCC
GTGTCAGGTTCCGGCCCCGAATTCTTCACAGAAGTGGATGGGG
TGCGGTTGCACAGGTACGCTCCAGCGTGCAAACCCCTCCTACGG
GAGGAGGTCACATTCCTGGTCGGGCTCAATCAATACCTGGTTGG
GTCACAGCTCCATGCGAGCCCGAACAGGACGTAGCAGTGCTCA
CTTCCATGCTCACCGACCCCTCCCACATTACGGCGGAGACGGCT
AAGCGTgGGGCTGGCCAGGGGATCTCCCCCTCCTTGGCCAGCT
CATCAGCTAGCCAGCTGTCTGCGCCTTCCTTGAAGGCAACATGC
ACTACCGTCCATGACTCCCCGGACGCTGACCTCATCGAGGCCAA
CCTCCTGTGGCGACAGGAGATGGGCGGGAACATCACCCGCGTGG
AGTCAGAAAATAAGGTAGTAATTTTGGACTCTTTCGAGCCGCTC
CAAGCGGAGGAGGATGAGAGGGAAGTATCCGTTCCGGCGGAGAT
CCTGCGGAGGTCCAGGAAATTCCCTCGAGCGATGCCATATGGG
CACGCCCGGATTACAAACCCTCCACTGTTAGAGTCCTGGAAGGAC
CCGGACTACGTCCCTCCAGTGGTACACGGGTGTCCATTGCCGCC
TGCCAAGGCCCCTCCGATACCACCTCCACGGAGGAAGAGGACGG
TTGTCCTGTCAGAATCTACCGTGTCTTCTGCCTTGGCGGAGCTC
GCCACAAAGACCTTCGGCAGCTCCGAATCGTCGGCCGTCGACAG |

| SEQ ID NOs |
|---|
| CGGCACGGCAACGGCCTCTCCTGACCAGCCCTCCGACGACGGCG ACGCGGGATCCGACGTTGAGTCGTACTCCTCCATGCCCCCCTT GAGGGGGAGCCGGGGGATCCCGATCTCAGCGACGGGTCTTGGTC TACCGTAAGCGAGGAGGCTAGTGAGGACGTCGTCTGCTGCTCGA TGTCCTACACATGGACAGGCGCCCTGATCACGCCATGCGCTGCG GAGGAAACCAAGCTGCCCATCAATGCACTGAGCAACTCTTTGCT CCGTCACCACAACTTGGTCTATGCTACAACATCTCGCAGCGCAA GCCTGCGGCAGAAGAAGGTCACCTTTGACAGACTGCAGGTCCTG GACGACCACTACCGGGACGTGCTCAAGGAGATGAAGGCGAAGGC GTCCACAGTTAAGGCTAAACTTCTATCCGTGGAGGAAGCCTGTA AGCTGACGCCCCCACATTCGGCCAGATCTAAATTTGGCTATGGG GCAAAGGACGTCCGGAACCTATCCAGCAAGGCCGTTAACCACAT CCGCTCCGTGTGGAAGGACTTGCTGGAAGACACTGAGACACCAA TTGACACCACCATCATGGCAAAAAAATGAGGTTTTCTGCGTCCAA CCAGAGAAGGGGGGCCGCAAGCCAGCTCGCCTTATCGTATTCCC AGATTTGGGGGTTCGTGTGTGCGAGAAAATGGCCCTTTACGATG TGGTCTCCACCCTCCCTCAGGCCGTGATGGGCTCTTCATACGGA TTCCAATACTCTCCTTGGACAGCAGGTCGAGTTCCTGGTGAATGC CTGGAAAGCGAAGAAATGCCCTATGGGCTTCGCATATGACACCC GCTGTTTTGACTCAACGGTCACTGAGAATGACATCCGTGTTGAG GAGTCAATCTACCAATGTTGTGACTTGGCCCCCGAAGCCAGACA GGCCATAAGGTCGCTCACAGAGCGGCTTTACATCGGGGGCCCC TGACTAATTCTAAAGGGCAGAACTGCGGCTATCGCCGGTGCCGC GCGAGCGGTGTACTGACGACCAGCTGCGGTAATACCCTCACATG TTACTTGAAGGCCGCTGCGGCCTGTCGAGCTGCGAAGCTCCAGG ACTGCACGATGCTCGTATGCGGAGACGACCTTGTCGTTATCTGT GAAAGCGCGGGGACCCAAGAGGACGAGGCGAGCCTACGGGCCTT CACGGAGGCTATGACTAGATACTCTGCCCCCCCTGGGGACCCGC CCAAACCAGAATACGACTTGGAGTTGATAACATCATGCTCCTCC AATGTGTCAGTCGCGCACGATGCATCTGGCAAAAGGGTGTACTA TCTCACCCGTGACCCCACCACCCCCCTTGCGCGGGCTGCGTGGG AGACAGCTAGACACACTCCAGTCAATTCCTGGCTAGGCAACATC ATCATGTATGCGCCCACCTTGTGGGCAAGGATGATCCTGATGAC TCATTTCTTCTCCATCCTTCTAGCTCAGGAACAACTTGAAAAAG CCCTAGATTGTCAGATCTACGGGGCCTGTTACTCCATTGAGCCA CTTGACCTACCTCAGATCATTCAACGACTCCATGGCCTTAGCGC ATTTTCACTCCATAGTTACTCTCCAGGTGAGATCAATAGGGTGG CTTCATGCCTCAGGAAACTTGGGGTACCGCCCTTGCGAGTCTGG AGACATCGGGCCAGAAGTGTCCGCGCTAGGCTACTGTCCCAGGG GGGGAGGGCTGCCACTTGTGGCAAGTACCTCTTCAACTGGGCAG TAAGGACCAAGCTCAAACTCACTCCAATCCCGGCTGCGTCCCAG TTGGATTTATCCAGCTGGTTCGTTGCTGGTTACAGCGGGGGAGA CATATATCACAGCCTGTCTGTGCCCGACCCCGCTGGTTCATGT GGTGCCTACTCCTACTTTCTGTAGGGGTAGGCATCTATCTACTC CCCAACCGATGAACGGGGACCTAAACACTCCAGGCCAATAGGCC ATCCTGTTTTTTTCCCTTTTTTTTTTCTTTTTTTTTTTTTTTTTT TTTTTTTTTTTTCTCCTTTTTTTTTTCCTCTTTTTTTCCTTTTCTTT CCCTTTGGTGGCTCCATCTTAGCCCTAGTCACGGCTAGCTGTGAA AGGTCCGTGAGCCGCTTGACTGCAGAGAGTGCTGATACTGGCCT CTCTGCAGATCAAGT |

SEQ ID NO: 10: Nucleotide sequence of DNA clone of HCV adaptive replicon V, where nucleotide change is in lower case and highlighted in bold GCCAGCCCCGATTGGGGGCGACACTCCACCATAGATCACTCCC CTGTGAGGAACTACTGTCTTCACGCAGAAAGCGTCTAGCCATGG CGTTAGTATGAGTGTCGTGCAGCCTCCAGGACCCCCCCTCCCGG GAGAGCCATAGTGGTCTGCGGAACCGGTGAGTACACCGGAATTG CCAGGACGACCGGGTCCTTTCTTGGATCAACCCGCTCAATGCCT GGAGATTTGGGCGTGCCCCCGCAAGACTGCTAGCCGAGTAGTGT TGGGTCGCGAAAGGCCTTGTGGTACTGAATGATAGGGTGCTTGC GAGTGCCCGGGAGGTCTCGTAGACCGTGCACCATGAGCACGAA TCCTAAACCTCAAAGAAAAACCAAAGGGCGCGCCATGATTGAAC AAGATGGATTGCACGCAGGTTCTCCGGCCGCTTGGGTGGAGAGG CTATTCGGCTATGACTGGGCACAACAGACAATCGGCTGCTCTGA TGCCGCCGTGTTCCGGCTGTCAGCGCAGGGGCGCCCGGTTCTTT TTGTCAAGACCGACCTGTCCGGTGCCCTGAATGAACTGCAGGAC GAGGCAGCGCGGCTATCGTGGCTGGCCACGACGGGCGTTCCTTG CGCAGCTGTGCTCGACGTTGTCACTGAAGCGGGAAGGGACTGGC TGCTATTGGGCGAAGTGCCGGGGCAGGATCTCCTGTCATCTCAC CTTGCTCCTGCCGAGAAAGTATCCATCATGGCTGATGCAATGCG GCGGCTGCATACGCTTGATCCGGCTACCTGCCCATTCGACCACC AAGCGAAACATCGCATCGAGCGAGCACGTACTCGGATGGAAGCC GGTCTTGTCGATCAGGATGATCTGGACGAAGAGCATCAGGGGCT CGCGCCAGCCGAACTGTTCGCCAGGCTCAAGGCGCGCATGCCCG ACGGCGAGGATCTCGTCGTGACCCATGGCGATGCCTGCTTGCCG AATATCATGGTGGAAAATGGCCGCTTTTCTGGATTCATCGACTG TGGCCGGCTGGGTGTGGCGGACCGCTATCAGGACATAGCGTTGG CTACCCGTGATATTGCTGAAGAGCTTGGCGGCGAATGGGCTGAC CGCTTCCTCGTGCTTTACGGTATCGCCGCTCCCGATTCGCAGCG CATCGCCTTCTATCGCCTTCTTGACGAGTTCTTCTGAGTTTAAA CAGACCACAACGGTTTCCCTCTAGCGGGATCAATTCCGCCCCTC TCCCTCCCCCCCCCCTAACGTTACTGGCCGAAGCCGCTTGGAAT AAGGCCGGTGTGCGTTTGTCTATATGTTATTTTCCACCATATTG CCGTCTTTTGGCAATGTGAGGGCCCGGAAACCTGGCCCTGTCTT CTTGACGAGCATTCCTAGGGGTCTTTCCCCTCTCGCCAAAGGAA TGCAAGGTCTGTTGAATGTCGTGAAGGAAGCAGTTCCTCTGGAA GCTTCTTGAAGACAAACAACGTCTGTAGCGACCCCTTTGCAGGCA GCGGAACCCCCCACCTGGCGACAGGTGCCTCTGCGGCCAAAAGC CACGTGTATAAGATACACCTGCAAAGGCGGCACAACCCCAGTGC CACGTTGTGAGTTGGATAGTTGTGGAAAAGAGTCAAATGGCTCTC CTCAAGCGTATTCAACAAGGGGCTGAAGGATGCCCAGAAGGTAC CCCATTGTATGGGATCTGATCTGGGGCCTCGGTGCACATGCTTT ACATGTGTTTAGTCGAGGTTAAAAAAACGTCTAGGCCCCCCGAAC CACGGGGACGTGGTTTTCCTTTGAAAAACACGATAATACCATGG CGCCTATTACGGCCTACTCCCAACAGACGCGAGGCCTACTTGGC TGCATCATCACTAGCCTCACAGGCCGGGACAGGAACCAGGTCGA GGGGGAGGTCCAAGTGGTCTCCACCGCAACACAATCTTTCCTGG CGACCTGCGTCAATGGCGTGTGTTGGACTGTCTATCATGGTGCC GGCTCAAAGACCCTTGCCGGCCCAAAGGGGCCCAATCACCCAAAT GTACACCAATGTGGACCAGGACCTCGTCGGCTGGCAAGCGCCCC CCGGGGCGCGTTCCTTGACACCATGCACCTGCGGCAGCTCGGAC CTTTACTTGGTCACGAGGCATGCCGATGTCATTCCGGTGCGCCG GCGGGGCGACAGCAGGGGGAGCCTACTCTCCCCCAGGCCCGTCT CCTACTTGAAGGGCTCTTCGGGCGGTCCACTGCTCTGCCCCTCG GGGCACGCTGTGGGCATCTTTCGGGCTGCCGTGTGCACCCGAGG GGTTGCGAAGGCGGTGGACTTTGTACCCGTCGAGTCTATGGAAA CCACTATGCGGTCCCCGGTCTTCACGGACAACTCGTCCCCTCCG GCCGTACCGCAGACATTCCAGGTGGCCCATCTACACGCCCCTAC TGGTAGCGGCAAGAGCACTAAGGTGCCGGCTGCGTATGCAGCCC AAGGGTATAAGGTGCTTGTCCTGAACCCGTCCGTCGCCGCCACC CTAGGTTTCGGGGCGTATATGTCTAAGGCACATGGTATCGACCC TAACATCAGAACCGGGGTAAGGACCATCACCACGGGTGCCCCCA TCACGTACTCCACCTATGGCAAGTTTCTTGCCGACGGTGGTTGC TCTGGGGGCGCCTATGACATCATAATATGTGATGAGTGCCACTC AACTGACTCGACCACTATCCTGGGCATCGGCACAGTCCTGGAGG AAGCGGAGACGGCTGGAGCGCGACTCGTCGTGCTCGCCACCGCT ACGCCTCCGGGATCGGTCACCGTGCCACATCCAAACATCGAGGA GGTGGCTCTGTCCAGCACTGGAGAAATCCCCTTTTATGGCAAAG CCATCCCCATCGAGACCATCAAGGGGGGGAGGCACCTCATTTTC TGCCATTCCAAGAAGAAATGTGATGAGCTCGCCGCGAAGCTGTC CGGCCTCGGACTCAATGCTGTAGCATATTACCGGGGCCTTGATG TATCCGTCATACCAACTAGCGGAGACGTCATTGTCGTAGCAACG GACGCTCTAATGACGGGCTTTACCGGCGATTTCGACTCAGTGAT CGACTGCAATACATGTGTCACCCAGACAGTCGACTTCAGCCTGG ACCCGACCTTCACCATTGAGACGACGACCGTGCCACAAGACGCG GTGTCACGCTCGCAGCGGCGAGGCAGGACTGGTAGGGGCAGGAT GGGCATTTACAGGTTTGTGACTCCAGGAGAACGGCCCTCGGGCA TGTTCGATTCCTCGGTTCTGTGCGAGTGCTATGACGCGGCTGT GCTTGGTACGAGCTCACGCCCGCCGAGACCTCAGTTAGGTTGCG GGCTTACCTAAACACACCAGGGTTGCCCGTCTGCCAGGACCATC TGGAGTTCTGGGAGAGCGTCTTTACAGGCCTCACCCACATAGAC GCCCATTTCTTGTCCCAGACTAAGCAGGCAGGAGACAACTTCCC CTACCTGGTAGCATACCAGGCTACGGTGTGCGCCAGGGCTCAGG CTCCACCTCCATCGTGGGACCAAATGTGGAAGTGTCTCATACGG CTAAAGCCTACGCTGCACGGGCCAACGCCCCTGCTGTATAGGCT GGGAGCCGTTCAAAACGAGGTTACTACCACACCCCATAACCA AATACATCATGCCATGCATGTCGGCTGACCTGGAGGTCGTCACG AGCACCTGGGTGCTGGTAGGCGGAGTCCTAGCAGCTCTGGCCGC GTATTGCCTGACAACAGGCAGCGTGGTCATTGTGGGCAGGATCA TCTTGTCCGGAAAGCCGGCCATCATTCCCGACAGGGAAGTCCTT TACCGGGAGTTCGATGAGATGGAAGAGTGCGCCTCACACCTCCC TTACATCGAACAGGGAATGCAGCTCGCCGAACAATTCAAACAGA AGGCAATCGGGTTGCTGCAAACAGCCACCAAGCAAGCGGAGGCT GCTGCTCCCGTGGTGGAATCCAAGTGGCGGACCCTCGAAGCCTT CTGGGCGAAGCATATGTGGAATTTCATCAGCGGGATACAATATT TAGCAGGCTTGTCCACTCTGCCTGGCAACCCCGCGATAGCATCA CTGATGGCATTCACAGCCTCTATCACCAGCCCGCTCACCACCCA ACATACCCTCCTGTTTAACATCCTGGGGGATTGGGTGGCCGCCC AACTTGCTCCTCCCAGCGCTGCTTCTGCTTTCGTAGGCGCCGGC ATCGCTGGAGCGGCTGTTGGCAGCATAGGCCTTGGGAAGGTGCT TGTGGATATTTTGGCAGGTTATGGAGCAGGGGTGGCAGGCGCGC TCGTGGCCTTTAAGGTCATGAGCGGCGAGATGCCCTCCACCGAG GACCTGGTTAACCTACTCCCTGCTATCCTCTCCCCTGGCGCCCT -continued SEQ ID NOs AGTCGTCGGGGTCGTGTGCGCAGCGATACTGCGTCGGCACGTGG
GCCCAGGGGAGGGGGCTGTGCAGTGGATGAACCGGCTGATAGCG
TTCGCTTCGCGGGGTAACCACGTCTCCCCCACGCACTATGTCC
TGAGAGCGACGCTGCAGCACGTGTCACTCAGATCCTCTCTAGTC
TTACCATCACTCAGCTGCTGAAGAGGCTTCACCAGTGGATCAAC
GAGGACTGCTCCACGCCATGCTCCGGCTCGTGGCTAAGAGATGT
TTGGGATTGGATATGCACGGTGTTGACTGATTTCAAGACCTGGC
TCCAGTCCAAGCTCCTGCCGCGATTGCCGGGAGTCCCCTTCTTC
TCATGTCAACGTGGGTACAAGGGAGTCTGGCGGGGCGACGGCAT
CATGCAAACCACCTGCCCATGTGGAGCACAGATCACCGGACATG
TGAAAAACGGTTCCATGAGGATCGTGGGGCCTAGGACCTGTAGT
AACACGTGGCATGGAACATTCCCCATTAACGCGTACACCACGGG
CCCCTGCACGCCCTCCCCGGCGCCAAATTATTCTAGGGCGCTGT
GGCGGGTGGCTGCTGAGGAGTACGTGGAGGTTACGCGGGTGGGG
GATTTCCACTACGTGACGGGCATGACCACTGACAACGTAAAGTG
CCCGTGTCAGGTTCCGGCCCCCGAATTCTTCACAGAAGTGGATG
GGGTGCGGTTGCACAGGTACGCTCCAGCGTGCAAACCCCTCCTA
CGGGAGGAGGTCACATTCCTGGTCGGGCTCAATCAATACCTGGT
TGGGTCACAGCTCCCATGCGAGCCCGAACCGGACGTAGCAGTGC
TCACTTCCATGCTCACCGACCCCTCCCACATTACGGCGGAGACG
GCTAAGCGTAGGCTGGCCAGGGGATCTCCCCCCTCCTTGtCCAGC
TCATCAGCTAGCCAGCTGTCTGCGCCTTCCTTGAAGGCAACATG
CACTACCCGTCATGACTCCCCGGACGCTGACCTCATCGAGGCCA
ACCTCCTGTGGCGGCAGGAGATGGGCGGGAACATCACCCGCGTG
GAGTCAGAAAATAAGGTAGTAATTTTGGACTCTTTCGAGCCGCT
CCAAGCGGAGGAGGATGAGAGGGAAGTATCCGTTCCGGCGGAGA
TCCTGCGGAGGTCCAGGAAATTCCCTCGAGCGATGCCCATATGG
GCACGCCCGGATTACAACCCTCCACTGTTAGAGTCCTGGAAGGA
CCCGGACTACGTCCCTCCAGTGGTACACGGGTGTCCATTGCCGC
CTGCCAAGGCCCCTCCGATACCACCTCCACGGAGGAAGAGGACG
GTTGTCCTGTCAGAATCTACCGTGTCTTCTGCCTTGGCGGAGCT
CGCCACAAAGACCTTCGGCAGCTCCGAATCGTCGGCCGTCGACA
GCGGCACGGCAACGGCCTCTCCTGACCAGCCCTCCGACGACGGC
GACGCGGGATCCGACGTTGAGTCGTACTCCTCCATGCCCCCCCT
TGAGGGGGAGCCGGGGGATCCCGATCTCAGCGACGGGTCTTGGT
CTACCGTAAGCGAGGAGGCTAGTGAGGACGTCGTCTGCTGCTCG
ATGTCCTACACATGGACAGGCGCCCTGATCACGCCATGCGCTGC
GGAGGAAACCAAGCTGCCCATCAATGCACTGAGCAACTCTTTGC
TCCGTCACCACAACTTGGTCTATGCTACAACATCTCGCAGCGCA
AGCCTGCGGCAGAAGAAGGTCACCTTTGACAGACTGCAGGTCCT
GGACGACCACTACCGGGACGTGCTCAAGGAGATGAAGGCGAAGG
CGTCCACAGTTAAGGCTAAACTTCTATCCGTGGAGGAAGCCTGT
AAGCTGACGCCCCCACATTCGGCCAGATCTAAATTTGGCTATGG
GGCAAAGGACGTCCGGAACCTATCCAGCAAGGCCGTTAACCACA
TCCGCTCCGTGTGGAAGGACTTGCTGGAAGACACTGAGACACCA
ATTGACACCACCATCATGGCAAAAAATGAGGTTTTCTGCGTCCA
ACCAGAGAAGGGGGGCCGCAAGCCAGCTCGCCTTATCGTATTCC
CAGATTTGGGGGTTCGTGTGTGCGAGAAAATGGCCCTTTACGAT
GTGGTCTCCACCCTCCCTCAGGCCGTGATGGGCTCTTCATACGG
ATTCCAATACTCTCCTGGACAGCGGGTCGAGTTCCTGGTGAATG
CCTGGAAAGCGAAGAAATGCCCTATGGGCTTCGCATATGACACC
CGCTGTTTTGACTCAACGGTCACTGAGAATGACATCCGTGTTGA
GGAGTCAATCTACCAATGTTGTGACTTGGCCCCCGAAGCCAGAC
AGGCCATAAGGTCGCTCACAGAGCGGCTTTACATCGGGGGCCCC
CTGACTAATTCTAAAGGGCAGAACTGCGGCTATCGCCGGTGCCG
CGCGAGCGGTGTACTGACGACCAGCTGCGGTAATACCCTCACAT
GTTACTTGAAGGCCGCTGCGGCCTGTCGAGCTGCGAAGCTCCAG
GACTGCACGATGCTCGTATGCGGAGACGACCTTGTCGTTATCTG
TGAAAGCGCGGGGACCCAAGAGGACGAGGCGAGCCTACGGGCCT
TCACGGAGGCTATGACTAGATACTCTGCCCCCCCTGGGGACCCG
CCCAAACCAGAATACGACTTGGAGTTGATAACATCATGCTCCTC
CAATGTGTCAGTCGCGCACGATGCATCTGGCAAAAGGGTGTACT
ATCTCACCCGTGACCCCACCACCCCCCTTGCGCGGGCTGCGTGG
GAGACAGCTAGACACACTCCAGTCAATTCCTGGCTAGGCAACAT
CATCATGTATGCGCCCACCTTGTGGGCAAGGATGATCCTGATGA
CTCATTTCTTCTCCATCCTTCTAGCTCAGGAACAACTTGAAAAA
GCCCTAGATTGTCAGATCTACGGGGCCTGTTACTCCATTGAGCC
ACTTGACCTACCTCAGATCATTCAACGACTCCATGGCCTTAGCG
CATTTTCACTCCATAGTTACTCTCCAGGTGAGATCAATAGGGTG
GCTTCATGCCTCAGGAAACTTGGGGTACCGCCCTTGCGAGTCTG
GAGACATCGGGCCAGAAGTGTCCGCGCTAGGCTACTGTCCCAGG
GGGGGAGGGCTGCCACTTGTGGCAAGTACCTCTTCAACTGGGCA
GTAAGGACCAAGCTCAAACTCACTCCAATCCCGGCTGCGTCCCA
GTTGGATTTATCCAGCTGGTTCGTTGCTGGTTACAGCGGGGGAG
ACATATATCACAGCCTGTCTCCGTGCCCGACCCCGCTGGTTCAT
GTGGTGCCTACTCCTACTTTCTGTAGGGGTAGGCATCTATCTAC
TCCCCAACCGATGAACGGGGACCTAAACACTCCAGGCCAATAGG -continued SEQ ID NOs CCATCCTGTTTTTTTCCCTTTTTTTTTTTCTTTTTTTTTTTTTTTTT
TTTTTTTTTTTTTTTTTCTCCTTTTTTTTTCCTCTTTTTTTCCTTTTCT
TTCCTTTGGTGGCTCCATCTTAGCCCTAGTCACGGCTAGCTGTG
AAAGGTCCGTGAGCCGCTTGACTGCAGAGAGTGCTGATACTGGC
CTCTCTGCAGATCAAGT SEQ ID NO: 11: NS5A gene of DNA clone of HCV adaptive replicon IV, where nucleotide change is in lower case and highlighted in bold TCCGGCTCGTGGCTAAGAGATGTTTGGGATTGGATATGCACGGT
GTTGACTGATTTCAAGACCTGGCTCCAGTCCAAGCTCCTGCCGC
GATTGCCGGGAGTCCCCTTCTTCTCATGTCAACGTGGGTACAAG
GGAGTCTGGCGGGGCGACGGCATCATGCAAACCACCTGCCCATG
TGGAGCACAGATCACCGGACATGTGAAAAACGGTTCCATGAGGA
TCGTGGGGCCTAGGACCTGTAGTAACACGTGGCATGGAACATTC
CCCATTAACGCGTACACCACGGGCCCCTGCACGCCCTCCCCGGC
GCCAAATTATTCTAGGGCGCTGTGGCGGGTGGCTGCTGAGGAGT
ACGTGGAGGTTACGCGGGTGGGGGATTTCCACTACGTGACGGGC
ATGACCACTGACAACGTAAAGTGCCCGTGTCAGGTTCCGGCCCC
CGAATTCTTCACAGAAGTGGATGGGGTGCGGTTGCACAGGTACG
CTCCAGCGTGCAAACCCCTCCTACGGGAGGAGGTCACATTCCTG
GTCGGGCTCAATCAATACCTGGTTGGGTCACAGCTCCCATGCGA
GCCCGAACCGGACGTAGCAGTGCTCACTTCCATGCTCACCGACC
CCTCCCACATTACGGCGGAGACGGCTAAGCGTAGGCTGGCCAGG
GGATCTCCCCCCTgCTTGGCCAGCTCATCAGCTAGCCAGCTGTCT
GCGCCTTCCTTGAAGGCAACATGCACTACCCGTCATGACTCCCC
GGACGCTGACCTCATCGAGGCCAACCTCCTGTGGCGGCAGGAGA
TGGGCGGGAACATCACCCGCGTGGAGTCAGAAAATAAGGTAGTA
ATTTTGGACTCTTTCGAGCCGCTCCAAGCGGAGGAGGATGAGAG
GGAAGTATCCGTTCCGGCGGAGATCCTGCGGAGGTCCAGGAAAT
TCCCTCGAGCGATGCCCATATGGGCACGCCCGGATTACAACCCT
CCACTGTTAGAGTCCTGGAAGGACCCGGACTACGTCCCTCCAGT
GGTACACGGGTGTCCATTGCCGCCTGCCAAGGCCCCTCCGATAC
CACCTCCACGGAGGCCGAGGACGGTTGTCCTGTCAGAATCTACC
GTGTCTTCTGCCTTGGCGGAGCTCGCCACAAAGACCTTCGGCAG
CTCCGAATCGTCGGCCGTCGACAGCGGCACGGCAACGGCCTCTC
CTGACCAGCCCTCCGACGACGGCGACGCGGGATCCGACGTTGAG
TCGTACTCCTCCATGCCCCCCCTTGAGGGGGAGCCGGGGGATCC
CGATCTCAGCGACGGGTCTTGGTCTACCGTAAGCGAGGAGGCTA
GTGAGGACGTCGTCTGCTGC SEQ ID NO: 12: NS5A gene of HCV adaptive replicon III, where nucleotide change is in lower case and highlighted in bold TCCGGCTCGTGGCTAAGAGATGTTTGGGATTGGATATGCACGGT
GTTGACTGATTTCAAGACCTGGCTCCAGTCCAAGCTCCTGCCGC
GATTGCCGGGAGTCCCCTTCTTCTCATGTCAACGTGGGTACAAG
GGAGTCTGGCGGGGCGACGGCATCATGCAAACCACCTGCCCATG
TGGAGCACAGATCACCGGACATGTGAAAAACGGTTCCATGAGGA
TCGTGGGGCCTAGGACCTGTAGTAACACGTGGCATGGAACATTC
CCCATTAACGCGTACACCACGGGCCCCTGCACGCCCTCCCCGGC
GCCAAATTATTCTAGGGCGCTGTGGCGGGTGGCTGCTGAGGAGT
ACGTGGAGGTTACGCGGGTGGGGGATTTCCACTACGTGACGGGC
ATGACCACTGACAACGTAAAGTGCCCGTGTCAGGTTCCGGCCCC
CGAATTCTTCACAGAAGTGGATGGGGTGCGGTTGCACAGGTACG
CTCCAGCGTGCAAACCCCTCCTACGGGAGGAGGTCACATTCCTG
GTCGGGCTCAATCAATACCTGGTTGGGTCACAGCTCCCATGCGA
GCCCGAACCGGACGTAGCAGTGCTCACTTCCATGCTCACCGACC
CCTCCCACATTACGGCGGAGACGGCTAAGCGTAGGCTGGCCAGG
GGATCTCCCCCCcCCTTGGCCAGCTCATCAGCTAGCCAGCTGTCT
GCGCCTTCCTTGAAGGCAACATGCACTACCCGTCATGACTCCCC
GGACGCTGACCTCATCGAGGCCAACCTCCTGTGGCGGCAGGAGA
TGGGCGGGAACATCACCCGCGTGGAGTCAGAAAATAAGGTAGTA
ATTTTGGACTCTTTCGAGCCGCTCCAAGCGGAGGAGGATGAGAG
GGAAGTATCCGTTCCGGCGGAGATCCTGCGGAGGTCCAGGAAAT
TCCCTCGAGCGATGCCCATATGGGCACGCCCGGATTACAACCCT
CCACTGTTAGAGTCCTGGAAGGACCCGGACTACGTCCCTCCAGT
GGTACACGGGTGTCCATTGCCGCCTGCCAAGGCCCCTCCGATAC
CACCTCCACGGAGGAAGAGGGACGGTTGTCCTGTCAGAATCTAC
CGTGTCTTCTGCCTTGGCGGAGCTCGCCACAAAGACCTTCGGCA
GCTCCGAATCGTCGGCCGTCGACAGCGGCACGGCAACGGCCTCT
CCTGACCAGCCCTCCGACGACGGCGACGCGGGATCCGACGTTGA
GTCGTACTCCTCCATGCCCCCCCTTGAGGGGGAGCCGGGGGATC
CCGATCTCAGCGACGGGTCTTGGTCTACCGTAAGCGAGGAGGCT
AGTGAGGACGTCGTCTGCTGC SEQ ID NO: 13: Nucleotide sequence of DNA clone of HCV adaptive replicon VII, where nucleotide change is in lower case and highlighted in bold -continued SEQ ID NOs CCTGGAAAGCGAAGAAATGCCCTATGGGCTTCGCATATGACACC
CGCTGTTTTGACTCAACGGTCACTGAGAATGACATCCGTGTTGA
GGAGTCAATCTACCAATGTTGTGACTTGGCCCCCGAAGCCAGAC
AGGCCATAAGGTCGCTCACAGAGCGGCTTTACATCGGGGGCCCC
CTGACTAATTCTAAAGGGCAGAACTGCGGCTATCGCCGGTGCCG
CGCGAGCGGTGTACTGACGACCAGCTGCGGTAATACCCTCACAT
GTTACTTGAAGGCCGCTGCGGCCTGTCGAGCTGCGAAGCTCCAG
GACTGCACGATGCTCGTATGCGGAGACGACCTTGTCGTTATCTG
TGAAAGCGCGGGGACCCAAGAGGACGAGGCGAGCCTACGGGCCT
TCACGGAGCGTATGACTAGATACTCTGCCCCCCCCTGGGGACCCG
CCCAAACCAGAATACGACTTGGAGTTGATAACATCATGCTCCTC
CAATGTGTCAGTCGCGCACGATGCATCTGGCAAAAGGGTGTACT
ATCTCACCCGTGACCCCACCACCCCCCTTGCGCGGGCTGCGTGG
GAGACAGCTAGACACACTCCAGTCAATTCCTGGCTAGGCAACAT
CATCATGTATGCGCCCACCTTGTGGGCAAGGATGATCCTGATGA
CTCATTTCTTCTCCATCCTTCTAGCTCAGGAACAACTTGAAAAA
GCCCTAGATTGTCAGATCTACGGGGCCTGTTACTCCATTGAGCC
ACTTGACCTACCTCAGATCATTCAACGACTCCATGGCCTTAGCG
CATTTTCACTCCATAGTTACTCTCCAGGTGAGATCAATAGGGTG
GCTTCATGCCTCAGGAAACTTGGGGTACCGCCCTTGCGAGTCTG
GAGACATCGGGCCAGAAGTGTCCGCGCTAGGCTACTGTCCCAGG
GGGGGAGGGCTGCCACTTGTGGCAAGTACCTCTTCAACTGGGCA
GTAAGGACCAAGCTCAAACTCACTCCAATCCCGGCTGCGTCCCA
GTTGGATTATCCAGCTGGTTCGTTGCTGGTTACAGCGGGGGAG
ACATATATCACAGCCTGTCTCGTGCCCGACCCCGCTGGTTCATG
TGGTGCCTACTCCTACTTTCTGTAGGGGTAGGCATCTATCTACT
CCCCAACCGATGAACGGGGAGCTAAACACTCCAGGCCAATAGGC
CATCCTGTTTTTTTCCCTTTTTTTTTTCTTTTTTTTTTTTTTTTTT
TTTTTTTTTTTTCTCCTTTTTTTTTCCTCTTTTTTTCCTTTTCTTTC
CTTTGGTGGCTCCATCTTAGCCCTAGTCACGGCTAGCTGTGAAA
GGTCCGTGAGCCGCTTGACTGCAGAGAGTGCTGATACTGGCCTC
TCTGCAGATCAAGT SEQ ID NO: 14: Amino acid sequence of the NS5A protein of HCV adaptive replicon I, where amino acid generated is highlighted in bold SGSWLRDVWDWICTVLTDFKTWLQSKLLPRLPGVPFFSCQRGYKG
VWRGDGIMQTTCPCGAQITGHVKNGSMRIVGPRTCSNTWHGTFPI
NAYTTGPCTPSPAPNYSRALWRVAAEEYVEVTRVGDFHYVTGMTT
DNVKCPCQVPAPEFFTEVDGVRLHRYAPACKPLLREEVTFLVGLNQ
YLVGSQLPCEPEPDVAVLTSMLTDPSHITAETAKRRLARGSPPSLA
SSSASQLYSFEPLQAEEDEREVSVPAEILRRSRKFPRAMPIWARPDY
NPPLLESWKDPDYVPPVVHGCPLPPAKAPPIPPPRRKRTVVLSESTV
SSALAELATKTFGSSESSAVDSGTATASPDQPSDDGDAGSDVESYSS
MPPLEGEPGDPDLSDGSWSTVSEEASEDVVCC SEQ ID NO: 15: Amino acid sequence of the polyprotein coding region of HCV adaptive replicon VI, where amino acid changes are highlighted in bold MAPITAYSQQTRGLLGCIITSLTGRDRNQVEGEVQVVSTATQSFLAT
CVNGVCWTVYHGAGSKTLAGPKGPITQMYTNVDQDLVGWRAPP
GARSLTPCTCGSSDLYLVTRHADVIPVRRRGDSRGSLLSPRPVSYLK
GSSGGPLLCPSGHAVGIFRAAVCTRGVAKAVDFVPVESMETTMRSP
VFTDNSSPPAVPQTFQVAHLHAPTGSGKSTKVPAAYAAQGYKVLV
LNPSVAATLGFGAYMSKAHGIDPNIRTGVRTITTGAPITYSTYHKFL
ADGGCSGGAYDIIICDECHISTDSTTILGIGTVLDQAETAGARLVVLA
TATPPGSVTVPHPNIEEVALSSTGEJIPFYGKAIPIETIKGGRHLIFCHS
KKKCDELAAKLSGLGLNAVAYYRGLDVSVIPTSGDVIVVATDALM
TGFTGDFDSVIDCNTCVTQTVDFSLDPTFTIETTTVPQDAVSRSQRR
GRTGRGRMGIYRFVTPGERPSGMFDSSVLCECYDAGCAWYELTPA
ETSVRLRAYLNTPGLPVCQDHLEFWESVFTGLTHIDAHFLSQTKQA
GDNFPYLVAYQATVCARAQAPPPSWDQMWKCLIRLKPTLHGPTPL
LYRLGAVQNEVTTTHPITKYIMACMSADLEVVTSTWVLVGGVLAA
LAAYCLTTGSVVIVGRIILSGKPAIIPDREVLYREFDEMEECASHLPY
IEQGMQLAEQFKQKAIGLLQTATKQAEAAAPVVESKWRTLEAFWA
KHMWNFISGIQYLAGLSTLPGNPAIASLMAFTASITSPLTTWHTLLF
NILGGWVAAQLAPPSAASAFVGAGIAGAAVGSIGLGKVLVDILAGY
GAGVAGALVAFKVMSGEMPSTEDLVNLLPAILSPGALVVGVVCAA
ILRRHVGPGEGAVQWMNRLIAFASRGNHVSPTHYVPESDAAARVT
QILSSLTITQLLKRLHQWINEDCSTPCSGSQLRDVWDWICTVLTDFK
TWLQSKLLPRLPGVPFFSCQRGYKGVWRGDGIMQTTCPCGAQITG
HVKNGSMRIVGPRTCSNTWHGTFPINAYTTGPCTPSPAPNYSRALW
RVAAEEYVEVTRVGDFHYVTGMTTDNVKCPCQVPAPEFFTEVDGV
RLHRYAPACKPLLREEVTFLVGLNQYLVGSQLPCEPEPDVAVLTSM
LTDPSHITAETAKRRLARGSPPSLASSSAIQLSAPSLKATCTTRHDSP DADLIEANLLWRQEMGGNITRVESENKVVILDSFEPLQAEEDEREV
SVPAEILRRSRKFPRAMPIWARPDYNPPLLESWKDPDYVPPVVHGC
PLPPAKAPPIPPPRRKRTVVLSESTVSSALAELATKTFGSSESSAVDS
GTATASPDQPSDDGDAGSDVESYSSMPPLEGEPGDPDLSDGSWSTV
SEEASEDVVCCSMSYTWTGALITPCAAEETKLPINALSNSLLRHHNL
VYATTSRSASLRQKKVTFDRLQVLDDHYRDVLKEMKAKASTVKA
KLLSVEEACKLTPPHSARSKFGYGAKDVRNLSSKAVNHIRSVWKD
LLEDTETPIDTTIMAKNEVFCVQPEKGGRKPARLIVFPDLGVRVCEK
MALYDVVSTLPQAVMGSSYGFQYSPGQRVEFLVNAWKAKKCPMG
FAYDTRCFDSTVTENDIRVEESIYQCCDLAPEARQAIRSLTERLYIGG
PLTNSKGQNCGYRRCRASGVLTTSCGNTLTCYLKAAAACRAAKLQ
DCTMLVCGDDLVVICESAGTQEDEASLRAFTEAMTRYSAPPGDPPK
PEYDLELITSCSSNVSVAHDASGKRVYYLTRDPTTPLARAAWETAR
HTPVNSWLGNIIMYAPTLWARMILMTHFFSILLAQEQLEKALDCQI
YGACYSIEPLDLPQIIQRLHGLSAFSLHSYSPGEINRVASCLRKLGVP
PLRVWRHRARSVRARLLSQGGRAATCGKYLFNWAVRTKLKLTPIP
AASQLDLSSWFVAGYSGGDIYHSLSRARPRWFMWCLLLLSVGVGI
YLLPNR SEQ ID NO: 16: Amino acid sequence of the NS5A protein of HCV adaptive replicon VII, where amino acid change is highlighted in bold SGSWLRDVWDWICTVLTDFKTWLQSKLLPRLPGVPFFSCQRGYKG
VWRGDGIMQTTCPCGAQITGHVKNGSMRIVGPRTCSNTWHGTFPI
NAYTTGPCTPSPAPNYSRALWRVAAEEYVEVTRVGDFHYVTGMTT
DNVKCPCQVPAPEFFTEVDGVRLHRYAPACKPLLREEVTFLVGLNQ
YLVGSQLPCEPEPDVAVLTSMLTDPSHITAETAKRRLARGSPPSLA
SSSAIQLSAPSLKATCTTRHDSPDADLIEANLLWRQEMGGNITRVES
ENKVVILDSFEPLQAEEDEREVSVPAEILRRSRKFPRAMPIWARPDY
NPPLLESWKDPDYVPPVVHGCPLPPAKAPPIPPPRRKRTVVLSESTV
SSALAELATKTFGSSESSAVDSGTATASPDQPSDDGDAGSDVESYSS
MPPLEGEPGDPDLSDGSWSTVSEEASEDVVCC SEQ ID NO: 17: Amino acid sequence of the polyprotein of HCV adaptive replicon II, where amino acid changes are highlighted in bold MAPITAYSQQTRGLLGCIITSLTGRDRNQVEGEVQVVSTATQSFLAT
CVNGVCWTVYHGAGSKTLAGPKGPITQMYTNVDQDLVGWQAPPG
ARSLTPCTCGSSDLYLVTRHADVIPVRRRGDSRGSLLSPRPVSYLKG
SSGGPLLCPSGHAVGIFRAAVCTRGVAKAVDFVPVESMETTMRSPV
FTDNSSPPAVPQTFQVAHLHAPTGSGKSTKVPAAYAAQGYKVLVL
NPSVAATLGFGAYMSKAHGIDPNIRTGVRTITTGAPITYSTYGKFLA
DGGCSGGAYDIIICDECHSTDSTTILGIGTVLDQAETAGARLVVLAT
ATPPGSVTVPHPNIEEVALSSTGEIPFYGKAIPIETIKGGRHLIFCHSK
KKCDELAAKLSGLGLNAVAYYRGLDVSVIPTSGDVIVVATDALMT
GFTGDFDSVIDCNTCVTQTVDFSLDPTFTIETTTVPQDAVSRSQRRG
RTGRGRMGIYRFVTPGERPSGMFDSSVLCECYDAGCAWYELTPAE
TSVRLRAYLNTPGLPVCQDHLEFWESVFTGLTHIDAHFLSQTKQAG
DNFPYLVAYQATVCARAQAPPPSWDQMWECLIRLKPTLHGPTPLL
YRLGAVQNEVTTTHPITKYIMACMSADLEVVTSTWVLVGGVLAAL
AAYCLTTGSVVIVGRIILCGKPAIIPDREVLYREFDEMEECASHLPYI
EQGMQLAEQFKQKAIGLLQTATKQAEAAPVVESKWRTLEAFWAK
HMWNFISGIQYLAGLSTLPGNPAIASLMAFTASITSPLTTQHTLLFNI
LGGWVAAQLAPPSAASAFVGAGIAGAAVGSIGLGKVLVDILAGYG
AGVAGALVAFKVMSGEMPSTEDLVNLLPAILSPGALVVGVVCAAI
LRRHVGPGEGAVQWMNRLIAFASRGNHVSPTHYVPESDAAARVTQ
ILSGLTITQLLKRLHQWINEDCSTPCSGSWLRDVWDWICTVLTDFK
TWLQSKLLPRLPGVPFFSCQRGYKGVRGDGIMQTTCPCGAQITGHV
KNGSMRIVGPRTCSNTWHGTFPINAYTTGPCTPSPAPNYSRALWRV
AAEEYVEVTRVGDFHYVTGMTTDNVKCPCQVPAPEFFTEVDGVRL
HRYAPACKPLLREEVTFLVGLNQYLVGSQLPCEPEPDVAVLTSMLT
DPSHITAETAKRGLARGSPPSLASSSASQLSAPSLKATCTTRHDSPD
ADLIEANLLWRQEMGGNITRVESENKVVILDSFEPLQAEEDEREVS
VPAEILRRSRKFPRAMPIWARPDYNPPLLESWKDPDYVPPVVHGCP
LPPAKAPPIPPPRRKRTVVLSESTVSSALAELATKTFGSSESSAVDSG
TATASPDQPSDDGDAGSDVESYSSMPPLEGEPGDPDLSDGSWSTVS
EEASEDVVCCSMSYTWTGALITPCAAEETKLPINALSNSLLRHHNL
VYATTSRSASLRQKKVTFDRLQVLDDHYRDVLKEMKAKASTVKA
KLLSVEEACKLTPPHSARSKFGYGAKDVRNLSSKAVNHIRSVWKD
LLEDTETPIDTTIMAKNEVFCVQPEKGGRKPARLIVFPDLGVRVCEK
MALYDVVSTLPQAVMGSSYGFQYSPGQRVEFLVNAWKAKKCPMG
FAYDTRCFDSTVTENDIRVEESIYQCCDLAPEARQAIRSLTERLYIGG
PLTNSKGQNCGYRRCRASGVLTTSCGNTLTCYLKAAAACRAAKLQ
DCTMLVCGDDLVVICESAGTQEDEASLRAFTEAMTRYSAPPGDPPK
PEYDLELITSCSSNVSVAHDASGKRVYYLTRDPTTPLARAAWETAR

SEQ ID NOs

HTPVNSWLGNIIMYAPTLWARMILMTHFFSILLAQEQLEKALDCQI
YGACYSIEPLDLPQIIQRLHGLSAFSLHSYSPGEINRVASCLRKLGVP
PLRVWRHRARSVRARLLSQGGRAATCGKYLFNWAVRTKLKLTPIP
AASQLDLSSWFVAGYSGGDIYHSLSRARPRWFMWCLLLLSVGVGI
YLLPNR
SEQ ID NO: 18: Amino acid sequence of the NS5A protein
of HCV adaptive replicon II, where amino acid change
is highlighted in bold SGSWLRDVWDWICTVLTDFKTWLQSKLLPRLPGVPFFSCQRGYKG
VWRGDGIMQTTCPCGAQITGHVKNGSMRIVGPRTCSNTWHGTFPI
NAYTTGPCTPSPAPNYSRALWRVAAEEYVEVTRVGDFHYVTGMTT
DNVKCPCQVPAPEFFTEVDGVRLHRYAPACKPLLREEVTFLVGLNQ
YLVGSQLPCEPEPDVAVLTSMLTDPSHITAETAKRGLARGSPPSLA
SSSASQLSAPSLKATCTTRHDSPDADLIEANLLWRQEMGGNITRVES
ENKVVILDSFEPLQAEEDEREVSVPAEILRRSRKFPRAMPIWARPDY
NPPLLESWKDPDYVPPVVHGCPLPPAKAPPIPPPRRKRTVVLSESTV
SSALAELATKTFGSSESSAVDSGTATASPDQPSDDGDAGSDVESYSS
MPPLEGEPGDPDLSDGSWSTVSEEASEDVVCC
SEQ ID NO: 19: Amino acid sequence of the NS5A protein
of HCV adaptive replicon V, where amino acid change
is highlighted in bold SGSWLRDVWDWICTVLTDFKTWLQSKLLPRLPGVPFFSCQRGYKG
VWRGDGIMQTTCPCGAQITGHVKNGSMRIVGPRTCSNTWHGTFPI
NAYTTGPCTPSPAPNYSRALWRVAAEEYVEVTRVGDFHYVTGMTT
DNVKCPCQVPAPEFFTEVDGVRLHRYAPACKPLLREEVTFLVGLNQ
YLVGSQLPCEPEPDVAVLTSMLTDPSHITAETAKRRLARGSPPSLSS
SSASQLSAPSLKATCTTRHDSPDADLIEANLLWRQEMGGNITRVESE
NKVVILDSFEPLQAEEDEREVSVPAEILRRSRKFPRAMPIWARPDYN
PPLLESWKDPDYVPPVVHGCPLPPAKAPPIPPPRRKRTVVLSESTVSS
ALAELATKTFGSSESSAVDSGTATASPDQPSDDGDAGSDVESYSSM
PPLEGEPGDPDLSDGSWSTVSEEASEDVVCC
SEQ ID NO: 20: Amino acid sequence of the NS5A protein
of HCV adaptive replicon IV, where amino acid change
is highlighted in bold SGSWLRDVWDWICTVLTDFKTWLQSKLLPRLPGVPFFSCQRGYKG
VWRGDGIMQTTCPCGAQITGHVKNGSMRIVGPRTCSNTWHGTFPI
NAYTTGPCTPSPAPNYSRALWRVAAEEYVEVTRVGDFHYVTGMTT
DNVKCPCQVPAPEFFTEVDGVRLHRYAPACKPLLREEVTFLVGLNQ
YLVGSQLPCEPEPDVAVLTSMLTDPSHITAETAKRRLARGSPPCLA
SSSASQLSAPSLKATCTTRHDSPDADLIEANLLWRQEMGGNITRVES
ENKVVILDSFEPLQAEEDEREVSVPAEILRRSRKFPRAMPIWARPDY
NPPLLESWKDPDYVPPVVHGCPLPPAKAPPIPPPRRKRTVVLSESTV
SSALAELATKTFGSSESSAVDSGTATASPDQPSDDGDAGSDVESYSS
MPPLEGEPGDPDLSDGSWSTVSEEASEDVVCC
SEQ ID NO: 21: Amino acid sequence of the NS5A protein
of HCV adaptive replicon III, where amino acid change
is highlighted in bold SGSWLRDVWDWICTVLTDFKTWLQSKLLPRLPGVPFFSCQRGYKG
VWRGDGIMQTTCPCGAQITGHVKNGSMRIVGPRTCSNTWHGTFPI
NAYTTGPCTPSPAPNYSRALWRVAAEEYVEVTRVGDFHYVTGMTT
DNVKCPCQVPAPEFFTEVDGVRLHRYAPACKPLLREEVTFLVGLNQ
YLVGSQLPCEPEPDVAVLTSMLTDPSHITAETAKRRLARGSPPLA
SSSASQLSAPSLKATCTTRHDSPDADLIEANLLWRQEMGGNITRVES
ENKVVILDSFEPLQAEEDEREVSVPAEILRRSRKFPRAMPIWARPDY
NPPLESWKDPDYVPPVVHGCPLPPAKAPPIPPPRRKRTVVLSESTVS
SALAELATKTFGSSESSAVDSGTATASPDQPSDDGDAGSDVESYSS
MPPLEGEPGDPDLSDGSWSTVSEEASEDVVCC
SEQ ID NO: 22: Nucleotide sequence of DNA clone of
HCV adaptive replicon HCVrep/NS2-5B (see FIG. 9)

GCCAGCCCCCGATTGGGGCGACACTCCACCATAGATCACTCCC
CTGTGAGGAACTACTGTCTTCACGCAGAAAGCGTCTAGCCATGG
CGTTAGTATGAGTGTCGTGCAGCCTCCAGGACCCCCCCTCCCGG
GAGAGCCATAGTGGTCTGCGGAACCGGTGAGTACACCGGAATTG
CCAGGACGACCGGGTCCTTTCTTGGATCAACCCGCTCAATGCCT
GGAGATTTGGGCGTGCCCCCGCGAGACTGCTAGCCGAGTAGTGT
TGGGTCGCGAAAGGCCTTGTGGTACTGCCTGATAGGGTGCTTGC
GAGTGCCCCGGGAGGTCTCGTAGACCGTGCACCATGAGCACAACG
GTTTCCCTCTAGCGGGATCAATTCCGCCCTCTCCCTCCCCCCC
CCCTAACGTTACTGGCCGAAGCCGCTTGGAATAAGGCCGGTGTG
CGTTTGTCTATATGTTATTTTCCACCATATTGCCGTCTTTTGGC
AATGTGAGGGCCCGGAAACCTGGCCCTGTCTTCTTGACGAGCAT
TCCTAGGGGTCTTTCCCCTCTCGCCAAAGGAATGCAAGGTCTGT

TGAATGTCGTGAAGGAAGCAGTTCCTCTGGAAGCTTCTTGAAGA
CAAACAACGTCTGTAGCGACCCTTTGCAGGCAGCGGAACCCCCC
ACCTGGCGACAGGTGCCTCTGCGGCCAAAAGCCACGTGTATAAG
ATACACCTGCAAAGGCGGCACAACCCCAGTGCCACGTTGTGAGT
TGGATAGTTGTGGAAAGAGTCAAATGGCTCTCCTCAAGCGTATT
CAACAAGGGGCTGAAGGATGCCCAGAAGGTACCCCATTGTATGG
GATCTGATCTGGGGCCTCGGTGCACATGCTTTACATGTGTTTAG
TCGAGGTTAAAAAACGTCTAGGCCCCCCGAACCACGGGGACGTG
GTTTTCCTTTGAAAAACACGATAATACCATGGACCGGGAGATGG
CAGCATCGTGCGGAGGCGCGGTTTTCGTAGGTCTGATACTCTTG
ACCTTGTCACCGCACTATAAGCTGTTCCTCGCTAGGCTCATATG
GTGGTTACAATATTTTATCACCAGGGCCGAGGCACACTTGCAAG
TGTGGATCCCCCCCCTCAACGTTCGGGGGGGCCGCGATGCCGTC
ATCCTCCTCACGTGCGCGATCCACCCAGAGCTAATCTTTACCAT
CACCAAAATCTTGCTCGCCATACTCGGTCCACTCATGGTGCTCC
AGGCTGGTATAACCAAAGTGCCGTACTTCGTGCGCGCACACGGG
CTCATTCGTGCATGCATGCTGGTGCGGAAGGTTGCTGGGGGTCA
TTATGTCCAAATGGCTCTCATGAAGTTGGCCGCACTGACAGGTA
CGTACGTTTATGACCATCTCACCCCACTGCGGGACTGGGCCCAC
GCGGGCCTACGAGACCTTGCGGTGGCAGTTGAGCCCGTCGTCTT
CTCTGATATGGAGACCAAGGTTATCACCTGGGGGGCAGACACCG
CGGCGTGTGGGGACATCATCTTGGGCCTGCCCGTCTCCGCCCGC
AGGGGGAGGGAGATACATCTGGGACCGGCAGACAGCCTTGAAGG
GCAGGGGTGGCGACTCCTCGCGCCTATTACGGCCTACTCCCAAC
AGACGCGAGGCCTACTTGGCTGCATCATCACTAGCCTCACAGGC
CGGGACAGGAACCAGGTCGAGGGGGAGGTCCAAGTGGTCTCCAC
CGCAACACAATCTTTCCTGGCGACCTGCGTCAATGGCGTGTGTT
GGACTGTCTATCATGGTGCCGGCTCAAAGACCCTTGCCGGCCCA
AAGGGCCCAATCACCCAAATGTACACCAATGTGGACCAGGACCT
CGTCGGCTGGCAAGCGCCCCCCGGGGCGCGTTCCTTGACACCAT
GCACCTGCGGCAGCTCGGACCTTTACTTGGTCACGAGGCATGCC
GATGTCATTCCGGTGCGCCGGCGGGACGACAGCAGGGGGAGCCT
ACTCTCCCCAGGCCCGTCTCCTACTTGAAGGGCTCTTCGGGCG
GTCCACTGCTCTGCCCCTCGGGGCACGCTGTGGGCATCTTTCGG
GCTGCCGTGTGCACCCGAGGGGTTGCGAAGGCGGTGGACTTTGT
ACCCGTCGAGTCTATGGAAACCACTATGCGGTCCCCGGTCTTCA
CGGACAACTCGTCCCCTCCGGCCGTACCGCAGACATTCCAGGTG
GCCCATCTACACGCCCCTACTGGTAGCGGCAAGAGCACTAAGGT
GCCGGCTGCGTATGCAGCCCAAGGGTATAAGGTGCTTGTCCTGA
ACCCGTCGTCGCCGCCACCCTAGGTTTCGGGGGCGTATATGTCT
AAGGCACATGGTATCGACCCTAACATCAGAACCGGGGTAAGGAC
CATCACCACGGGTGCCCCATCACGTACTCCACCTATGGCAAGT
TTCTTGCCGACGGTGGTTGCTCTGGGGGCGCCTATGACATCATA
ATATGTGATGAGTGCCACTCAACTGACTCGACCACTATCCTGGG
CATCGGCACAGTCCTGGACCAAGCGGAGACGGCTGGAGCGCGAC
TCGTCGTGCTCGCCACCGCTACGCCTCCGGGATCGGTCACCGTG
CCACATCCAAACATCGAGGAGGTGGCTCTGTCCAGCACTGGAGA
AATCCCCTTTTATGCAAAGCCATCCCCATCGAGACCATCAAGG
GGGGAGGCACCTCATTTTCTGCCATTCCAAGAAGAAATGTGAT
GAGCTCGCCGCGAAGCTGTCCGGCCTCGGACTCAATGCTGTAGC
ATATTACCGGGGCCTTGATGTATCCGTCATACCAACTAGCGGAG
ACGTCATTGTCGTAGCAACGGACGCTCTAATGACGGGCTTTACC
GGCGATTTCGACTCAGTGATCGACTGCAATACATGTGTCACCCA
GACAGTCGACTTCAGCCTGGACCCGACCTTCACCATTGAGACGA
CGACCGTGCCACAAGACGCGGTGTCACGCTCGCAGCGGCGAGGC
AGGACTGGTAGGGGCAGGATGGGCATTTACAGGTTTGTGACTCC
AGGAGAACGGCCCTCGGGCATGTTCGATTCCTCGGTTCTGTGCG
AGTGCTATGACGCGGGCTGTGCTTGGTACGAGCTCACGCCCGCC
GAGACCTCAGTTAGGTTGCGGGCTTACCTAAACACACCAGGGTT
GCCCGTCTGCCAGGACCATCTGGAGTTCTGGGAGAGCGTCTTTA
CAGGCCTCACCCACATAGACGCCCATTTCTTGTCCCAGACTAAG
CAGGCAGGAGACAACTTCCCCTACCTGGTAGCATACCAGGCTAC
GGTGTGCGCCAGGGCTCAGGCTCCACCTCCATCGTGGGACCAAA
TGTGGAAGTGTCTCATACGGCTAAAGCCTACGCTGCACGGGCCA
ACGCCCCTGCTGTATAGGCTGGGAGCCGTTCAAAACGAGGTTAC
TACCACACACCCCATAACCAAATACATCATGGCATGCATGTCGG
CTGACCTGGAGGTCGTCACGAGCACCTGGGTGCTGGTAGGCGGA
GTCCTAGCAGCTCTGCCGCGATCTTGCCTGACAACAGGCAGCGT
GGTCATTGTGGGCAGGATCATCTTGTCCGGAAAGCCGGCCATCA
TTCCCGACAGGGAAGTCCTTTACCGGGAGTTCGATGAGATGGAA
GAGTGCGCCTCACACCTCCCTTACATCGAACAGGGAATGCAGCT
CGCCGAACAATTCAAACAGAAGGCAATCGGGTTGCTGCAAACAG
CCACCAAGCAAGCGGAGGCTGCTGCTCCCGTGGTGGAATCCAAG
TGGCGGACCCTCGAAGCCTTCTGGGCGAAGCATATGTGGAATTT
CATCAGCGGGATACAATATTTAGCAGGCTTGTCCACTCTGCCTG
GCAACCCCGCCGATAGCATCACTGATGGCATTCACAGCCTCTATC
ACCAGCCCGCTCACCACCCAACATACCCTCCTGTTTAACATCCT

| SEQ ID NOs |
|---|
| GGGGGGATGGGTGGCCGCCCAACTTGCTCCTCCCAGCGCTGCTT
CTGCTTTCGTAGGCGCCGGCATCGCTGGAGCGGCTGTTGGCAGC
ATAGGCCTTGGGAAGGTGCTTGTGGATATTTTGGCAGGTTATGG
AGCAGGGGTGGCAGGCGCGCTCGTGGCCTTTAAGGTCATGAGCG
GCGAGATGCCCTCCACCGAGGACCTGGTTAACCTACTCCCTGCT
ATCCTCTCCCCTGGCGCCCTAGTCGTCGGGGTCGTGTGCGCAGC
GATACTGCGTCGGCACGTGGGCCCAGGGGAGGGGGCTGTGCAGT
GGATGAACCGGCTGATAGCGTTCGCTTCGCGGGGTAACCACGTC
TCCCCCACGCACTATGTGCCTGAGAGCGACGCTGCAGCACGTGT
CACTCAGATCCTCTCTAGTCTTACCATCACTCAGCTGCTGAAGA
GGCTTCACCAGTGGATCAACGAGGACTGCTCCACGCCATGCTCC
GGCTCGTGGCTAAGAGATGTTTGGGATTGGATATGCACGGTGTT
GACTGATTTCAAGACCTGGCTCCAGTCCAAGCTCCTGCCGCGAT
TGCCGGGAGTCCCCTTCTTCTCATGTCAACGTGGGTACAAGGGA
GTCTGGCGGGGCGACGGCATCATGCAAACCACCTGCCCATGTGG
AGCACAGATCACCGGACATGTGAAAAACGGTTGGATGAGGATCG
TGGGGCCTAGGACCTGTAGTAACACGTGGCATGGAACATTCCCC
ATTAACGCGTACACCACGGGCCCCTGCACGCCCTCCCCGGCGCC
AAATTATTCTAGGGCGCTGTGGCGGGTGGCTGCTGAGGAGTACG
TGGAGGTTACGCGGGTGGGGGATTTCCACTACGTGACGGGCATG
ACCACTGACAACGTAAAGTGCCCGTGTCAGGTTCCGGCCCCCGA
ATTCTTCACAGAAGTGGATGGGGTGCGGTTGCACAGGTACGCTC
CAGCGTGCAAACCCCTCCTACGGGAGGAGGTCACATTCCTGGTC
GGGCTCAATCAATACCTGGTTGGGTCACAGCTCCCATGCGAGCC
CGAACCGGACGTAGCAGTGCTCACTTCCATGCTCACCGACCCCT
CCCACATTACGGCGGAGACGGCTAAGCGTAGGCTGGCCAGGGGA
TCTCCCCCCTCCTTGGCCAGCTCATCAGCTATCCAGCTGTCTGC
GCCTTCCTTGAAGGCAACATGCACTACCCGTCATGACTCCCCGG
ACGCTGACCTCATCGAGGCCAACCTCCTGTGGCGGCAGGAGATG
GGCGGGAACATCACCCGCGTGGAGTCAGAAAATAAGGTAGTAAT
TTTGGACTCTTTCGAGCCGCTCCAAGCGGAGGAGGATGAGAGGG
AAGTATCCGTTCCGGCGGAGATCCTGCGGAGGTCCAGGAAATTC
CCTCGAGCGATGCCCATATGGGCACGCCCGGATTACAACCCTCC
ACTGTTAGAGTCCTGGAAGGACCCGGACTACGTCCCTCCAGTGG
TACACGGGTGTCCATTGCCGCCTGCCAAGGCCCCTCCGATACCA
CCTCCACGGAGGAAGAGGACGGTTGTCCTGTCAGAATCTACCGT
GTCTTCTGCCTTGGCGGAGCTCGCCACAAAGACCTTCGGCAGCT
CCGAATCGTCGGCCGTCGACAGCGGCACGGCAACGGCCTCTCCT
GACCAGCCCTCCGACGACGGCGACGCGGGATCCGACGTTGAGTC
GTACTCCTCCATGCCCCCCCTTGAGGGGGGAGCCGGGGGGATCCCG
ATCTCAGCGACGGGTCTTGGTCTACCGTAAGCGAGGAGGCTAGT
GAGGACGTCGTCTGCTGCTCGATGTCCTACACATGGACAGGCGC
CCTGATCACGCCATGCGCTGCGGAGGAAACCAAGGCTGCCCATCA
ATGCACTGAGCAACTCTTTGCTCCGTCACCACAACTTGGTCTAT
GCTACAACATCTCGCAGCGCAAGCCTGCGGCAGAAGAAGGTCAC
CTTTGACAGACTGCAGGTCCTGGACGACCACTACCGGGACGTGC
TCAAGGAGATGAAGGCGAAGGCGTCCACAGGTTAAGGCTAAACTT
CTATCCGTGGAGGAAGCCTGTAAGCTGACGCCCCCACATTCGGC
CAGATCTAAATTTGGCTATGGGGCAAAGGACGTCCGGAACCTAT
CCAGCAAGGCCGTTAACCACATCCGCTCCGTGTGGAAGGACTTG
CTGGAAGACACTGAGACACCAATTGACACCACCATCATGGCAAA
AAATGAGGTTTTCTGCGTCCAACCAGAGAAGGGGGGCCGCAAGC
CAGCTCGCCTTATCGTATTCCCAGATTTGGGGGTTCGTGTGTGC
GAGAAAATGGCCCTTTACGATGTGGTCTCCACCCTCCCTCAGGC
CGTGATGGGCTCTTCATACGGATTCCAATACTCTCCTGGACAGC
GGGTCGAGTTCCTGGTGAATGCCTGGAAAGCGAAGAAATGCCCT
ATGGGCTTCGCATATGACACCCGTCTGTTTTGACTCAACGGTCAC
TGAGAATGACATCCGTGTTGAGGAGTCAATCTACCAATGTTGTG
ACTTGGCCCCGAAGCCAGACAGGCCATAAGGTCGCTCACAGAG
CGGCTTTACATCGGGGGCCCCCTGACTAATTCTAAAGGGCAGAA
CTGCGGCTATCGCCGGTGCCGCGCGAGCGGTGTACTGACGACCA
GCTGCGGTAATACCCTCACATGTTACTTGAAGGCCGCTGCGGCC
TGTCGAGCTGCAAGCTCCAGGACTGCACGATGCTCGTATGCGG
AGACGACCTTGTCGTTATCTGTGAAAGCGCGGGGACCCAAGAGG
ACGAGGCGAGCCTACGGGCCTTCACGGAGGCTATGACTAGATAC
TCTGCCCCCCCTGGGGACCCGCCCAAACCAGAATACGACTTGGA
GTTGATAACATCATGCTCCTCCAATGTGTCAGTCGCGCACGATG
CATCTGGCAAAAGGGTGTACTATCTCACCCGTGACCCCACCACC
CCCCTTGCGCGGGCTGCGTGGGAGACAGCTAGACACACTCCAGT
CAATTCCTGGCTAGGCAACATCATCATGTATGCGCCCACCTTGT
GGGCAAGGATGATCCTGATGACTCATTTCTTCTCCATCCTTCTA
GCTCAGGAACAACTTGAAAAAGCCCTAGATTGTCAGATCTACGG
GGCCTGTTACTCCATTGGCAGCCACTTGACCTACCTCAGATCATTC
AACGACTCCATGGCCTTAGCGCATTTTCACTCCATAGTTACTCT
CCAGGTGAGATCAATAGGGTGGCTTCATGCCTCAGGAAACTTGG
GGTACCGCCCTTGCGAGTCTGGAGACATCGGGCCAGAAGTGTCC
GCGCTAGGCTACTGTCCCAGGGGGGGAGGGCTGCCACTTGTGGC | AAGTACCTCTTCAACTGGGCAGTAAGGACCAAGCTCAAACTCAC
TCCAATCCCGGCTGCGTCCCAGTTGGATTTATCCAGCTGGTTCG
TTGCTGGTTACAGCGGGGGAGACATATATCACAGCCTGTCTCGT
GGCCCGACCCCGCTGGTTCATGTGGTGCCTACTCCTACTTTCTG
TAGGGGTAGGCATCTATCTACTCCCCAACCGATGAACGGGGACC
TAAACACTCCAGGCCAATAGGCCATCCTGTTTTTTTCCCTTTTTTT
TTTTCTTTTTTTTTTTTTTTTTTTTTTTTTTTTTTTTTCTCCTTTTTT
TTTCCTCTTTTTTTTCCTTTTCTTTCCTTTGGTGGCTCCATCTTAGCC
CTAGTCACGGCTAGCTGTGAAAGGTCCGTGAGCCGCTTGACTGC
AGAGAGTGCTGATACTGGCCTCTCTGCAGATCAAGT
SEQ ID NO: 23: Nucleotide sequence of full-length
HCV cDNA clone containing the mutation that results
in Ser to Ile at position 1179 of SEQ ID NO: 3, and
where the 5' NTR is fused to the neomycin
phosphotransferase gene and the EMCV IRES is inserted
upstream of the HCV open reading frame (see FIG. 9)

GCCAGCCCCGATTGGGGGCGACACTCCACCATAGATCACTCCC
CTGTGAGGAACTACTGTCTTCACGCAGAAAGCGTCTAGCCATGG
CGTTAGTATGAGTGTCGTGCAGCCTCCAGGACCCCCCCTCCCGG
GAGAGCCATAGTGGTCTGCGGAACCGGTGAGTACACCGGAATTG
CCAGGACGACCGGGTCCTTTCTTGGATCAACCCGCTCAATGCCT
GGAGATTTGGGCGTGCCCCCGCGAGACTGCTAGCCGAGTAGTGT
TGGGTCGCGAAAGGCCTTGTGGTACTGCCTGATAGGGTGCTTGC
GAGTGCCCCGGGAGGTCTCGTAGACCGTGCACCATGAGCACGAA
TCCTAAACCTCAAAGAAAAACCAAAGGGCGCGCCATGATTGAAC
AAGATGGATTGCACGCAGGTTCTCCGGCCGCTTGGGTGGAAGAGG
CTATTCGGCTATGACTGGGCACAACAGACAATCGGCTGCTCTGA
TGCCGCCGTGTTCCGGCTGTCAGCGCAGGGGCGCCCGGTTCTTT
TTGTCAAGACCGACCTGTCCGGTGCCCTGAATGAACTGCAGGAC
GAGGCAGCGCGGCTATCGTGGCTGGCCACGACGGGCGTTCCTTG
CGCAGCTGTGCTCGACGTTGTCACTGAAGCGGGAAGGGACTGGC
TGCTATTGGGCGAAGTGCCGGGGCAGGATCTCCTGTCATCTCAC
CTTGCTCCTGCCGAGAAAGTATCCATCATGGCTGATGCAATGCG
GCGGCTGCATACGCTTGATCCGGCTACCTGCCCATTCGACCACC
AAGCGAAACATCGCATCGAGCGAGCACGTACTCGGATGGAAGCC
GGTCTTGTCGATCAGGATGATCTGGACGAAGAGCATCAGGGGCT
CGCGCCAGCCGAACTGTTCGCCAGGCTCAAGGCGCGCATGCCCG
ACGGCGAGGATCTCGTCGTGACCCATGGCGATGCCTGCTTGCCG
AATATCATGGTGGAAAATGGCCGCTTTTCTGGATTCATCGACTG
TGGCCGGCTGGGTGTGGCGGACCGCTATCAGGACATAGCGTTGG
CTACCCGTGATATTGCTGAAGAGCTTGGCGGCGAATGGGCTGAC
CGCTTCCTCGTGCTTTACGGTATCGCCGCTCCCGATTCGCAGCG
CATCGCCTTCTATCGCCTTCTTGACGAGTTCTTCTGAGTTTAAA
CAGACCACAACGGTTTCCCTCTAGCGGGATCAATTCCGCCCCTC
TCCCTCCCCCCCCCCTAACGTTACTGGCCGAAGCCGCTTGGAAT
AAGGCCGGTGTGCGTTTGTCTATATGTTATTTTCCACCATATTG
CCGTCTTTTGGCAATGTGAGGGCCCGGAAACCTGGCCCTGTCTT
CTTGACGAGCATTCCTAGGGGTCTTTCCCCTCTCGCCAAAGGAA
TGCAAGGTCTGTTGAATGTCGTGAAGGAAGCAGTTCCTCTGGAA
GCTTCTTGAAGACAAACAAACGTCTGTAGCGACCCTTTGCAGGCA
GCGGAACCCCCCACCTGGCGACAGGTGCCTCTGCGGCCAAAAGC
CACGTGTATAAGATACACCTGCAAAGGCGGCACAACCCCAGTGC
CACGTTGTGAGTTGGATAGTTGTGGAAAGAGTCAAATGGCTCTC
CTCAAGCGTATTCAACAAGGGGCTGAAGGATGCCCAGAAGGTAC
CCCATTGTATGGGATCTGATCTGGGGCCTCGGTGCACATGCTTT
ACATGTGTTTAGTCGAGGTTAAAAAACGTCTAGGCCCCCCGAAC
CACGGGGACGTGGTTTTCCTTTGAAAAACACGATAATAATGAGC
ACGAATCCTAAACCTCAAAGAAAAACCAAACGTAACACCAACCG
CCGCCCACAGGACGTCAAGTTCCCGGGCGGTGGTCAGATCGTCG
GTGGAGTTTACCTGTTGCCGCGCAGGGGCCCAGGTTGGGTGTG
CGCGCGACTAGGAAGACTTCCGAGCGGTCGCAACCTCGTGGAAG
GCGACAACCTATCCCCAAGGCTCGCCAGCCCGAGGGTAGGGCCT
GGGCTCAGCCCGGGTACCCCTGGCCCCTCTATGGCAATGAGGGC
TTGGGGTGGGCAGGATGGCTCCTGTCACCCCGTGGCTCTCGGCC
TAGTTGGGGCCCACGGACCCCCGGCGTAGGTCGCGCAATTTGG
GTAAGGTCATCGATACCCTCACGTGCGGCTTCGCCGATCTCATG
GGGTACATTCCGCTCGTCGGCGCCCTCCTAGGGGGCGCTGCCAG
GGCCCTGGCGCATGGCGTCCGGGTTCTGGAGGACGGCGTGAACT
ATGCAACAGGGAATCTGCCCGGTTGCTCCTTTTCTATCTTCCTT
TTGGCTTTGCTGTCCTGTTTGACCATCCCAGCTTCCGCTTATGA
AGTGCGCAACGTATCCGGAGTGTACCATGTCACGAACGACTGCT
CCAACGCAAGCATTGTGTATGAGGCAGCGGACATGATCATGCAT
ACCCCCGGGTGCGTGCCCTGCGTTCGGGAGAACAACTCCTCCCG
CTGCTGGGTAGCGCTCACTCCCACGCTCGCGGCCAGGAACGCTA
GCGTCCCCACTACGACGATACGACGCCATGTCGATTTGCTCGTT
GGGGCGGCTGCTCTCTGCTCCGCTATGTACGTGGGAGATCTCTG |

CGGATCTGTTTTCCTCGTCGCCCAGCTGTTCACCTTCTCGCCTC
GCCGGCACGAGACAGTACAGGACTGCAATTGCTCAATATATCCC
GGCCACGTGACAGGTCACCGTATGGCTTGGGATATGATGATGAA
CTGGTCACCTACAGCAGCCCTAGTGGTATCGCAGTTACTCCGGA
TCCCACAAGCTGTCGTGGATATGGTGGCGGGGGCCCATTGGGGA
GTCCTAGCGGGCCTTGCCTACTATTCCATGGTGGGGAACTGGGC
TAAGGTTCTGATTGTGATGCTACTCTTTGCCGGCGTTGACGGGG
GAACCTATGTGACAGGGGGGACGATGGCCAAAAACACCCTCGGG
ATTACGTCCCTCTTTTCACCCGGGTCATCCCAGAAAATCCAGCT
TGTAAACACCAACGGCAGCTGGCACATCAACAGGACTGCCCTGA
ACTGCAATGACTCCCTCAACACTGGGTTCCTTGCTGCGCTGTTC
TACGTGCACAAGTTCAACTCATCTGGATGCCCAGAGCGCATGGC
CAGCTGCAGCCCCATCGACGCGTTCGCTCAGGGGTGGGGGCCCA
TCACTTACAATGAGTCACACAGCTCGGACCAGAGGCCTTATTGT
TGGCACTACGCACCCCGGCCGTGCGGTATCGTACCCGCGGCGCA
GGTGTGTGGTCCAGTGTACTGCTTCACCCCAAGCCCTGTCGTGG
TGGGGACGACCGACCGGTTCGGCGTCCCTACGTACAGTTGGGGG
GAGAATGAGACGGACGTGCTGCTTCTTAACAACACGCGGCCGCC
GCAAGGCAACTGGTTTGGCTGTACATGGATGAATAGCACTGGGT
TCACCAAGACGTGCGGGGGCCCCCGTGTAACATCGGGGGGATC
GGCAATAAAACCTTGACCTGCCCCACGGACTGCTTCCGGAAGCA
CCCCGAGGCCACTTACACCAAGTGTGGTTCGGGGCCTTGGTTGA
CACCCAGATGCTTGGTCCACTACCCATACAGGCTTTGGCACTAC
CCCTGCACTGTCAACTTTACCATCTTCAAGGTTAGGATGTACGT
GGGGGGAGTGGAGCACAGGCTCGAAGCCGCATGCAATTGGACTC
GAGGAGAGCGTTGTAACCTGGAGGACAGGGACAGATCAGAGCTT
AGCCCGCTGCTGCTGCTACAACGGAGTGGCAGGTATTGCCCTG
TTCCTTCACCACCCTACCGGCTCTGTCCACTGGTTTGATCCATC
TCCATCAGAACGTCGTGGACGTACAATACCTGTACGGTATAGGG
TCGGCGGTTGTCTCCTTTGCAATCAAATGGGAGTATGTCCTGTT
GCTCTTCCTTCTTCTGGCGGACGCGCGCGTCTGTGCCTGCTTGT
GGATGATGCTGCTGATAGCTCAAGCTGAGGCCGCCCTAGAGAAC
CTGGTGGTCCTCAACGCGGCATCCGTGGCCGGGGCGCATGGCAT
TCTCTCCTTCCTCGTGTTCTTCTGTGCTGCCTGGTACATCAAGG
GCAGGCTGGTCCCTGGGGCGGCATATGCCCTCTACGGCGTATGG
CCGCTACTCCTGCTCCTGCTGGCGTTACCACCACGAGCATACGC
CATGGACCGGGAGATGGCAGCATCGTGCGGAGGCGCGGTTTCG
TAGGTCTGATACTCTTGACCTTGTCACCGCACTATAAGCTGTTC
CTCGCTAGGCTCATATGGTGGTTACAATATTTTATCACCAGGGC
CGAGGCACACTTGCAAGTGTGGATCCCCCCCCTCAACGTTCGGG
GGGGCCGCGATGCCGTCATCCTCCTCACGTGCGCGATCCACCCA
GAGCTAATCTTTACCATCACCAAAATCTTGCTCGCCATACTCGG
TCCACTCATGGTGCTCCAGGCTGGTATAACCAAAGTGCCGTACT
TCGTGCGCGCACACGGCTCATTCGTGCATGCATGCTGGTGCGG
AAGGTTGCTGGGGGTCATTATGTCCAAATGGCTCTCATGAAGTT
GGCCGCACTGACAGGTACGTACGTTTATGACCATGTGACCCCAC
TGCGGGACTGGGCCCACGCGGGCCTACGAGACCTTGCGGTGGCA
GTTGAGCCCGTCGTCTTCTCTGATATGGAGACCAAGGTTATCAC
CTGGGGGGCAGACACCGCGGCGTGTGGGGACATCATCTTGGGCC
TGCCCGTCCGCCCGCAGGGGGAGGGAGATACATCTGGGACCG
GCAGACAGCCTTGAAGGGCAGGGGTGGCGACTCCTCGCGCCTAT
TACGGCCTACTCCCAACAGACGCGAGGCCTACTTGGCTGCATCA
TCACTAGCCTCACAGGCCGGGACAGGAACCAGGTCGAGGGGGAG
GTCCAAGTGGTCTCCACCGCAACACAATCTTTCCTGGCGACCTG
CGTCAATGGCGTGTGTTGGACTGTCTATCATGGTGCCGGCTCAA
AGACCCTTGCCGGCCCAAAGGGCCCAATCACCCAAATGTACACC
AATGTGGACCAGGACCTCGTCGGCTGGCAAGCGCCCCCCGGGGC
GCGTTCCTTGACACCATGCACCTGCGGCAGCTCGGACCTTTACT
TGGTCACGAGGCATGCCGATGTCATTCCGGTGCGCCGGCGGGGC
GACAGCAGGGGGAGCCTACTCTCCCCAGGCCCGTCTCCTACTT
GAAGGGCTCTTCGGGCGGTCCACTGCTCTGCCCCTCGGGGCACG
CTGTGGGCATCTTTCGGGCTGCCGTGTGCACCCGAGGGGTTGCG
AAGGCGGTGGACTTTGTACCCGTCGAGTCTATGGAAACCACTAT
GCGGTCCCCGGTCTTCACGGACAACTCGTTCCCCTCCGGCGTAC
CGCAGACATTCCAGGTGGCCCATCTACACGCCCTACTGGTAGC
GGCAAGAGCACTAAGGTGCCGGCTGCGTATGCAGCCCAAGGGTA
TAAGGTGCTTGTCCTGAACCCGTCCGTCGCCGCCACCCTAGGTT
TCGGGGCGTATATGTCTAAGGCACATGGTATCGACCCTAACATC
AGAACCGGGGTAAGGACCATCACCACGGGTGCCCCCATCACGTA
CTCCACCTATGGCAAGTTTCTTGCCGACGGTGGTTGCTCTGGGG
GCGCCTATGACATCATAAATATGTGATGAGTGCCACTCAACTGAC
TCGACCACTATCCTGGGCATCGACAGTCCTGGACCAAGGGGA
GACGGCTGGAGCGCGACTCGTCGTGCTCGCCACCGCTACGCCTC
CGGGATCGGTCACCGTGCCACATCCAAACATCGAGGAGGTGGCT
CTGTCCAGCACTGGAGAAATCCCCTTTTATGGCAAAGCCATCCC
CATCGAGACCATCAAGGGGGGAGGCACCTCATTTTCTGCCATT
CCAAGAAGAAATGTGATGAGCTCGCCGCGAAGCTGTCCGGCCTC

GGACTCAATGCTGTAGCATATTACCGGGGCCTTGATGTATCCGT
CATACCAACTAGCGGAGACGTCATTGTCGTAGCAACGGACGCTC
TAATGACGGGCTTTACCGGCGATTTCGACTCAGTGATCGACTGC
AATACATGTGTCACCCAGACAGTCGACTTCAGCCTGGACCCGAC
CTTCACCATTGAGACGACGACCGTGCCACAAGACGCGGTGTCAC
GCTCGCAGCGGCGAGGCAGGACTGGTAGGGGCAGGATGGGCATT
TACAGGTTTGTGACTCCAGGAGAACGGCCCTCGGGCATGTTCGA
TTCCTCGGTTCTGTGCGACTGCTATGACGCGGGCTGTGCTTGGT
ACGAGCTCACGCCCGCCGAGACCTCAGTTAGGTTGCGGGCTTAC
CTAAACACACCAGGGTTGCCCGTCTGCCAGGACCATCTGGAGTT
CTGGGAGAGCGTCTTTACAGGCCTCACCCACATAGACGCCCATT
TCTTGTCCCAGACTAAGCAGGCAGGAGACAACTTCCCCTACCTG
GTAGCATACCAGGCTACGGTGTGCGCCAGGGCTCAGGCTCCACC
TCCATCGTGGGACCAAATGTGGAAGTGTCTCATACGGCTAAAGC
CTACGCTGCACGGGCCAACGCCCCTGCTGTATAGGCTGGGAGCC
GTTCAAAACGAGGTTACTACCACACACCCCATAACCAAATACAT
CATGGCATGCATGTCGGCTGACCTGGAGGTCGTCACGAGCACCT
GGGTGCTGGTAGGCGGAGTTCCTAGCAGCTCTGGCCGCGTATTGC
CTGACAACAGGCAGCGTGGTCATTGTGGGCAGGATCATCTTGTC
CGGAAAGCCGGCCATCATTCCCGACAGGGAAGTCCTTTACCGGG
AGTTCGATGAGATGGAAGAGTGCGCCTCACACCTCCCTTACATC
GAACAGGGAATGCAGCTCGCCGAACAATTCAAACAGAAGGCAAT
CGGGTTGCTGCAAACAGCCACCAAGCAAGCGGAGGCTGCTGCTC
CCGTGGTGGAATCCAAGTGGCGGACCCTCGAAGCCTTCTGGGCG
AAGCATATGTGGAATTTCATCAGCGGGATACAATATTTAGCAGG
CTTGTCCACTCTGCCCTGGCCAACCCCGCGATAGCATCACTGATGG
CATTCACGCCTCTATCACCAGCCCGCTCACCACCCAACATACC
CTCCTGTTTAACATCCTGGGGGGATGGGTGGCCGCCCAACTTGC
TCCTCCCAGCGCTGCTTCTGCTTTCGTAGGCGCCGGCATCGCTG
GAGCGGCTGTTGGCAGCATAGGCCTTGGGAAGGTGCTTGTGGAT
ATTTTGGCAGGTTATGGAGCAGGGGTGGCAGGCGCGCTCGTGGC
CTTTAAGGTCATGAGCGGCGAGATGCCCTCCACCGAGGACCTGG
TTAACCTACTCCCTGCTATCCTCTCCCCTGGCGCCCTAGTCGTC
GGGGTCGTGTGCGCAGCGATACTGCGTCGGCACGTGGGCCCAGG
GGAGGGGGCTGTGCAGTGGATGAACCGGCTGATAGCGTTCGCTT
CGCGGGGTAACCACGTCTCCCCCACGCACTATGTGCCTGAGAGC
GACGCTGCAGCACGTGTCACTCAGATCCTCTCTAGTCTTACCAT
CACTCAGCTGCTGAAGAGGCTTCACCAGTGGATCAACGAGGACT
GCTCCACGCCATGCTCCGGCTCGTGGCTAAGAGATGTTTGGGAT
TGGATATGCACGGTGTTGACTGATTTCAAGACCTGGCTCCAGTC
CAAGCTCCTGCCGCGATTGCCGGGAGTCCCCTTCTTCTCATGTC
AACGTGGGTACAAGGGAGTCTGGCGGGGCGACGGCATCATGCAA
ACCACCTGCCCATGTGGAGCACAGATCACCGGACATGTGAAAAA
CGGTTCCATGAGGATCGTGGGGCCTAGGACCTGTAGTAACACGT
GGCATGGAACATTCCCCATTAACGCGTACACCACGGGCCCCTGC
ACGCCCTCCCCGGCGCCAAATTATTCTAGGGCGCTGTGGCGGGT
GGCTGCTGAGGAGTACGTGGAGGTTACGCGGGTGGGGGATTTCC
ACTACGTGACGGGCATGACCACTGACAACGTAAAGTGCCCGTGT
CAGGTTCCGGCCCCGAATTCTTCACAGAAGTGGATGGGGTGCG
GTTGCACAGGTACGCTCCAGCGTGCAAACCCCTCCTACGGGAGG
AGGTCACATTCCTGGTCGGGCTCAATCAATACCTGGTTGGGTCA
CAGCTCCCATGCGAGCCCGAACCGGACGTAGCAGTGCTCACTTC
CATGCTCACCGACCCCTCCCACATTACGGCGGAGACGGCTAAGC
GTAGGCTGGCCAGGGGATCTCCCCCCTCCTTGGCCAGCTCATCA
GCTATCCAGCTGTCTGCGCCTTCCTTGAAGGCAACATGCACTAC
CCGTCATGACTCCCCGGACGCTGACCTCATCGAGGCCAACCTCC
TGTGGCGCCAGGAGATGGGCGGGAACATCACCCGCGTGGAGTCA
GAAAATAAGGTAGTAATTTTGGACTCTTTCGAGCGCTCCAAGC
GGAGGAGGATGAGAGGGAAGTATCCGTTCCGGCGGAGATCCTGC
GGAGGTCCAGGAAATTCCCTCGAGCGATGCCCATATGGGCACGC
CCGGATTACAACCCTCCACTGTTAGAGTCCTGGAAGGACCCGGA
CTACGTCCTCCAGTGGTACACGGGTGTCCATTGCCGCCTGCCA
AGGCCCCTCCGATACCACCTCCACGGAGGAAGAGGACGGTTGTC
CTGTCAGAATCTACCGTGTCTTCTGCCTTGGCGGAGCTCGCCAC
AAAGACCTTCGGCAGCTCCGAATCGTCGGCCGTCGACAGCGGCA
CGGCAACGGCCTCTCCTGACCAGCCCTCCGACGACGGCGACGCG
GGATCCGACGTTGAGTCGTACTCCTCCATGCCCCCCTTGAGGG
GGAGCCGGGGGATCCCGATCTCAGCGACGGGTCTTGGTCTACCG
TAAGCGAGGAGGCTAGTGAGGACGTCGTCTGCTGCTCGATGTCC
TACACATGGACAGGCGCCCTGATCACGCCATGCGCTGCGGAGGA
AACCAAGCTGCCCATCAATGCACTGAGCAACTCTTTGCTCCGTC
ACCACAACTTGGTCTATGCTACAACATCTCGCAGCGCAAGCCTG
CGGCAGAAGAAGGTCACCTTTGACAGACTGCAGGTCCTGGACGA
CCACTACCGGGACGTGCTCAAGGAGATGAAGGCGAAGGCGTCCA
CAGTTAAGGCTAAACTTCTATCCGTGGAGGAAGCCTGTAAGCTG
ACGCCCCCACATTCGGCCAGATCTAAATTTGGCTATGGGGCAAA
GGACGTCCGGAACCTATCCAGCAAGGCCGTTAACCACATCCGCT

| SEQ ID NOs | |
|---|---|
| 5 | CCGTGTGGAAGGACTTGCTGGAAGACACTGAGACACCAATTGAC ACCACCATCATGGCAAAAAATGAGGTTTTCTGCGTCCAACCAGA GAAGGGGGGCCGCAAGCCAGCTCGCCTTATCGTATTCCCAGATT TGGGGGTTCGTGTGTGCGAGAAAATGGCCCTTTACGATGTGGTC TCCACCCTCCCTCAGGCCGTGATGGGCTCTTCATACGGATTCCA ATACTCTCCTGGACAGCGGGTCGAGTTCCTGGTGAATGCCTGGA AAGCGAAGAAATGCCCTATGGGCTTCGCATATGACACCCGCTGT TTTGACTCAACGGTCACTGAGAATGACATCCGTGTTGAGGAGTC AATCTACCAATGTTGTGACTTGGCCCCCGAAGCCAGACAGGCCA TAAGGTCGCTCACAGAGCGGCTTTACATCGGGGGCCCCCTGACT AATTCTAAAGGGCAGAACTGCGGCTATCGCCGGTGCCGCGCGAG CGGTGTACTGACGACCAGCTGCGGTAATACCCTCACATGTTACT TGAAGGCCGCTGCGGCCTGTCGAGCTGCGAAGCTCCAGGACTGC ACGATGCTCGTATGCGGGAGACGACCTTGTCGTTATCTGTGAAAG CGCGGGGACCCAAGAGGACGAGGCGAGCCTACGGGCCTTCACGG AGGCTATGACTAGATACTCTGCCCCCCCTGGGGACCCGCCCAAA CCAGAATACGACTTGGAGTTGATAACATCATGCTCCTCCAATGT GTCAGTCGCGCACGATGCATCTGGCAAAAGGGTGTACTATCTCA CCCGTGACCCCACCACCCCCCTTGCGCGGGCTGCGTGGGAGACA GCTAGACACACTCCAGTCAATTCCTGGCTAGGCAACATCATCAT GTATGCGCCCACCTTGTGGGCAAGGATGATCCTGATGACTCATT TCTTCTCCATCCTTCTAGCTCAGGAACAACTTGAAAAAGCCCTA GATTGTCAGATCTACGGGGCCTGTTACTCCATTGAGCCACTTGA CCTACCTCAGATCATTCAACGACTCCATGGCCTTAGCGCATTTT CACTCCATAGTTACTCTCCAGGTGAGATCAATAGGGTGGCTTCA TGCCTCAGGAAACTTGGGGTACCGCCCTTGCGAGTCTGGAGACA TCGGGGCCAGAAGTGTCCGCGCTAGGCTACTGTCCCAGGGGGGGA GGGCTGCCACTTGTGGCAAGTACCTCTTCAACTGGGCAGTAAGG ACCAAGCTCAAACTCACTCCAATCCCGGCTGCGTCCCAGTTGGA TTTATCCAGCTGGTTCGTTGCTGGTTACAGCGGGGGAGACATAT ATCACAGCCTGTCTCGTGCCCGACCCCGCTGGTTCATGTGGTGC CTACTCCTACTTTCTGTAGGGGTAGGCATCTATCTACTCCCCAA CCGATGAACGGGGACCTAAACACTCCAGGCCAATAGGCCATCCT GTTTTTTTCCCTTTTTTTTTTCTTTTTTTTTTTTTTTTTTTTTT TTTTTTTTCTCCTTTTTTTTCCTCTTTTTTCCTTTTCTTTCTTTG GTGGCTCCATCTTAGCCCTAGTCACGGCTAGCTGTGAAAGGTCC GTGAGCCGCTTGACTGCAGAGAGTGCTGATACTGGCCTCTCTGC AGATCAAGT SEQ ID NO: 24: Nucleotide sequence of full-length HCV cDNA clone containing the mutation that results in Ser to Ile at position 1179 of SEQ ID NO: 3 (see FIG. 9) GCCAGCCCCCGATTGGGGGCGACACTCCACCATAGATCACTCCC CTGTGAGGAACTACTGTCTTCACGCAGAAAGCGTCTAGCCATGG CGTTAGTATGAGTGTCGTGCAGCCTCCAGGACCCCCCCTCCCGG GAGAGCCATAGTGGTCTGCGGAACCGGTGAGTACACCGGAATTG CCAGGACGACCGGGTCCTTTCTTGGATCAACCCGCTCAATGCCT GGAGATTTGGGCGTGCCCCCGCGAGACTGCTAGCCGAGTAGTGT TGGGTCGCGAAAGGCCTTGTGGTACTGCCTGATAGGGTGCTTGC GAGTGCCCCGGGAGGTCTCGTAGACCGTGCACCATGAGCACGAA TCCTAAACCTCAAAGAAAAACCAAACGTAACACCAACCGCCGCC CACAGGACGTCAAGTTCCCGGGCGGTGGTCAGATCGTCGGTGGA GTTTACCTGTTGCCGCGCAGGGGCCCCAGGTTGGGTGTGCGCGC GACTAGGAAGACTTCCGAGCGGTCGCAACCTCGTGGAAGGCGAC AACCTATCCCCAAGGCTCGCCAGCCCGAGGGTAGGGCCTGGGCT CAGCCCGGGTACCCCTGGCCCCTCTATGGCAATGAGGGCTTGGG GTGGGCAGGATGGCTCCTGTCACCCCGTGGCTCTCGGCCTAGTT GGGGCCCCACGGACCCCCGGCGTAGGTCGCGCAATTTGGGTAAG GTCATCGATACCCTCACGTGCGGCTTCGCCGATCTCATGGGGTA CATTCCGCTCGTCGGCGCCCCCCTAGGGGGCGCTGCCAGGGCCC TGGCGCATGGCGTCCGGGTTCTGGAGGACGGCGTGAACTATGCA ACAGGGAATCTGCCCGGTTGCTCCTTTTCTATCTTCCTTTTGGC TTTGCTGTCTGTTTGACCATCCCAGCTTCCGCTTATGAAGTGC GCAACGTATCCGGAGTGTACCATGTCACGAACGACTGCTCCAAC GCAAGCATTGTGTATGAGGCAGCGGACATGATCATGCATACCCC CGGGTGCGTGCCCTGCGTTCGGGAGAACAACTCCTCCCGCTGCT GGGTAGCGCTCACTCCCACCGCTGCGGCCAGGAACGCTAGCGTC CCCACTACGACGATACGACGCCATGTCGATTTGCTCGTTGGGGC GGCTGCTCTCTGCTCCGCTATGTACGTGGGAGATCTCTGCCGGAT CTGTTTTCCTCGTCGCCCAGCTGTTCACCTTCTCGCCTCGCCGG CACGAGACAGTACAGGCATGCAATTGCTCAATATATCCCGACTA CGTGACAGGTCACCGTATGGCTTGGGATATGATGATGAACTGGT CACCTACAGCAGCCCAGTGGTATCGCAGTTACTCCGGATCCCA CAAGCTGTCGTGGATATGGTGGCGGGGGCCCATTGGGGAGTCCT AGCGGGCCTTGCCTACTATTCCATGGTGGGGAACTGGGCTAAGG TTCTGATTGTGATGCTACTCTTTGCCGGCGTTGACGGGGGAACC | TATGTGACAGGGGGGACGATGGCCAAAAACACCCTCGGGATTAC GTCCCTCTTTTCACCCGGGTCATCCCAGAAAATCCAGCTTGTAA ACACCAACGGCAGCTGGCACATCAACAGGACTGCCCCTGAACTGC AATGACTCCCTCAACACTGGGTTCCTTGCTGCGCTGTTCTACGT GCACAAGTTCAACTCATCTGGATGCCCAGAGCGCATGGCCAGCT GCAGCCCCATCGACGCGTTCGCTCAGGGGTGGGGGCCCATCACT TACAATGAGTCACACAGCTCGGACCAGAGGCCTTATTGTTGGCA CTACGCACCCCGGCCGTGCGGTATCGTACCCGCGGCGCAGGTGT GTGGTCCAGTGTACTGCTTCACCCCAAGCCCTGTCGTGGTGGGG ACGACCGACCGGTTCGGCGTCCCTACGTACAGTTGGGGGGGAGAA TGAGACGGACGTGCTGCTTCTTAACAACACGCGGCCGCCGCAAG GCAACTGGTTTGGCTGTACATGGATGAATAGCACTGGGTTCACC AAGACGTGCGGGGGCCCCCCGTGTAACATCGGGGGGATCGGCAA TAAAACCTTGACCTGCCCCACGGACTGCTTCCGGAAGCACCCCG AGGCCACTTACACCAAGTGTGGTTCGGGGCCTTGGTTGACACCC AGATGCTTGGTCCACTACCCATACAGGCTTTGGCACTACCCCTG CACTGTCAACTTTACCATCTTCAAGGTTAGGATGTACGTGGGGG GAGTGGAGCACAGGCTCGAAGCCGCATGCAATTGGACTCGAGGA GAGCGTTGTAACCTGGAGGACAGGGACAGATCAGAGCTTAGCCC GCTGCTGCTGTCTACAACGGAGTGGCAGGTATTGCCCTGTTCCT TCACCACCCTACCGGCTCTGTCCACTGGTTTGATCCATCTCCAT CAGAACGTCGTGGACGTACAATACCTGTACGGTATAGGGTCGGC GGTTGTCTCCCTTTGCAATCAAATGGGAGTATGTCCTGTTGCTCT TCCTTCTTCTGGCGGACGCGCGCGTCTGTGCCTGCTTGTGGATG ATGCTGCTGATAGCTCAAGCTGAGGCCGCCCTAGAGAACCTGGT GGTCCTCAACGCGGCATCCGTGGCCGGGGCGCATGGCATTCTCT CCTTCCTCGTGTTCTTCTGTGCTGCCTGGTACATCAAGGGCAGG CTGGTCCCTGGGCGGCATATGCCCTCTACGGCGTATGGCCGCT ACTCCTGCTCCTGCTGGCGTTACCACCACGAGCATACGCCATGG ACCGGGAGATGGCAGCATCGTGCGGAGGCGCGGTTTTCGTAGGT CTGATACTCTTGACCTTGTCACCGCACTATAAGCTGTTCCTCGC TAGGCTCATATGGTGGTTACAATATTTTATCACCAGGGCCGAGG CACACTTGCAAGTGTGGATCCCCCCCCTCAACGTTCGGGGGGGC CGCGATGCCGTCATCCTCCTCACGTGCGCGATCCACCCAGAGCT AATCTTTACCATCACCAAAATCTTGCTCGCCATACTCGGTCCAC TCATGGTGCTCCAGGCTGGTATAACCAAAGTGCCGTACTTCGTG CGCGCACACGGGCTCATTCGTCATGCATGCTGGTGCGGAAGGT TGCTGGGGGTCATTATGTCCAAATGGCTCTCATGAAGTTGGCCG CACTGACAGGTACGTACGTTTATGACCATCTCACCCCACTGCGG GACTGGGCCCACGCGGCCTACGAGACCTTGCGTGGCAGTTGA GCCCGTCGTCTTCTCTGATATGGAGACCAAGGTTATCACCTGGG GGGCAGACACCGCGGCGTGTGGGGACATCATCTTGGGCCTGCCC GTCTCCGCCCGCAGGGGGAGGGAGATACATCTGGGACCGGCAGA CAGCCTTGAAGGGCAGGGGTTGGCGACTCCTCGCGCCTATTACGG CCTACTCCCAACAGACGCGAGGCCTACTTGGCTGCATCATCACT AGCCTCACAGGCCGGGACAGGAACCAGGTCGAGGGGGGAGGTCCA AGTGGTCTCCACCGCAACACAATCTTTCCTGGCGACCTGCCTCA ATGGCGTGTGTTGGACTGTCTATCATGGTGCCGGCTCAAAGACC CTTGCCGGCCCAAAGGGCCCAATCACCCAAATGTACACCAATGT GGACCAGGACCTCGTCGGCTGGCAAGCGCCCCCCGGGGCGCGTT CCTTGACACCATGCCACCTGCGGCAGCTCGGACCTTTACTTGGTC ACGAGGCATGCCGATGTCATTCCGGTGCGCGCGGGGGCGACAG CAGGGGGAGCCTACTCTCCCCAGGCCCGTCTCCTACTTGAAGG GCTCTTCGGGCGGTCCACTGCTCTGCCCCTCGGGGCACGCTGTG GGCATCTTTCGGGCTGCCGTGTGCACCCGAGGGGTTGCGAAGGC GGTGGACTTTGTACCCGTCGAGTCTATGGAAACCACTATGCGGT CCCCGGTCTTCACGGACAACTCGTCCCCTCCGGCCGTACCGCAG ACATTCCAGGTGGCCCATCTACACGCCCTACTGGTAGCGGCAA GAGCACTAAGGTGCCGGCTGCGTATGCAGCCCAAGGGTATAAGG TGCTTGTCCTGAACCCGTCCGTCGCGCCACCCTAGGTTTCGGG GCGTATATGTCTAAGGCACATGGTATCGACCCTAACATCAGAAC CGGGGTAAGGACCATCACCACGGGTGCCCCCATCACGTACTCCA CCTATGGCAAGTTTCTTGCCGACGGTGGTTGCTCTGGGGGCGCC TATGACATCATAATATGTGATGAGTGCCACTCAACTGACTGGAC CACTATCCTGGGCATCGGCACAGTCCTGGACCAAGCGGAGACGG CTGGAGCGCGACTCGTCGTGCTCGCCACCGCTACGCCTCCGGGA TCGGTCACCGTGCCACATCCAAACATCGAGGAGGTGGCTCTGTC CAGCACTGGAGAAATCCCCTTTTATGGCAAAGCCATCCCCATCG AGACCATCAAGGGGGGAGGCCACCTCATTTTCTGCCATTCCAAG AAGAAATGTGATGAGCTCGCCGCGAAGCTGTCCGGCCTCGGACT CAATGCTGTAGCATATTACCGGGGCCTTGATGTATCCGTCATAC CAACTAGCGGAGACGTCATTGTCGTAGCAACGGACGCTCTAATG ACGGGCTTTACCGGCGATTTCGACTCAGTGATCGACTGCAATAC ATGTGTCACCCAGACAGTCGACTTCAGCCTGGACCCGACCTTCA CCATTGAGACGACGACCGTGCCACAAGACGCGGTGTCACGCTCG CAGCGGCGAGGCAGGACTGGTAGGGCAGGATGGGCATTTACAG GTTTGTGACTCCAGGAGAACGGCCCTCGGGCATGTTCGATTCCT |

SEQ ID NOs

CGGTTCTGTGCGAGTGCTATGACGCGGGCTGTGCTTGGTACGAG
CTCACGCCCGCCGAGACCTCAGTTAGGTTGCGGGCTTACCTAAA
CACACCAGGGTTGCCCGT

-continued

SEQ ID NOs

CTGGAGCGCGACTCGTCGTGCTCGCCACCGCTACGCCTCCGGGA
TCGGTCACCGTGCCACATCCAAACATCGAGGAGGTGGCTCTGTC
CAGCACTGGAGAAATCCCCTTTTATGGCAAAGCCATCCCCATCG
AGACCATCAAGGGGGGGAGGCACCTCATTTTCTGCCATTCCAAG
AAGAAATGTGATGAGCTCGCCGCGAAGCTGTCCGGCCTCGGACT
CAATGCTGTAGCATATTACCGGGGCCTTGATGTATCCGTCATAC
CAACTAGCGGAGACGTCATTGTCGTAGCAACGGACGCTCTAATG
ACGGGCTTTACCGGCGATTTCGACTCAGTGATCGACTGCAATAC
ATGTGTCACCCAGACAGTCGACTTCAGCCTGGACCCGACCTTCA
CCATTGAGACGACGACCGTGCCACAAGACGCGGTGTCACGCTCG
CAGCGGCGAGGCAGGACTGGTAGGGGCAGGATGGGCATTTACAG
GTTTGTGACTCCAGGAGAACGGCCCTCGGGCATGTTCGATTCCT
CGGTTCTGTGCGAGTGCTATGACGCGGGCTGTGCTTGGTACGAG
CTCACGCCCGCCGAGACCTCAGTTAGGTTGCGGGCTTACCTAAA
CACACCAGGGTTGCCCGTCTGCCAGGACCATCTGGAGTTCTGGG
AGAGCGTCTTTACAGGCCTCACCCACATAGACGCCCATTTCTTG
TCCCAGACTAAGCAGGCAGGAGACAACTTCCCCTACCTGGTAGC
ATACCAGGCTACGGTGTGCGCCAGGGCTCAGGCTCCACCTCCAT
CGTGGGACCAAATGTGGAAGTGTCTCATACGGCTAAAGCCTACG
CTGCACGGGCCAACGCCCCTGCTGTATAGGCTGGGAGCCGTTCA
AAACGAGGTTACTACCACACACCCCATAACCAAATACATCATGG
CATGCATGTCGGCTGACCTGGAGGTCGTCACGAGCACCTGGGTG
CTGGTAGGCGGAGTCCTAGCAGCTCTGGCCGCGTATTGCCTGAC
AACAGGCAGCGTGGTCATTGTGGGCAGGATCATCTTGTCCGGAA
AGCCGGCCATCATTCCCGACAGGGAAGTCCTTTACCGGGAGTTC
GATGAGATGGAAGAGTGCGCCTCACACCTCCCTTACATCGAACA
GGGAATGCAGCTCGCCGAACAATTCAAACAGAAGGCAATCGGGT
TGCTGCAAACAGCCACCAAGCAAGCGGAGGCTGCTGCTCCCGTG
GTGGAATCCAAGTGGCGGACCCTCGAAGCCTTCTGGGCGAAGCA
TATGTGGAATTTCATCAGCGGGATACAATATTTAGCAGGCTTGT
CCACTCTGCCTGGCAACCCCGCGATAGCATCACTGATGGCATTC
ACAGCCTCTATCACCAGCCCGCTCACCACCCAACATACCCTCCT
GTTTAACATCCTGGGGGGATGGGTGGCCGCCCAACTTGCTCCTC
CCAGCGCTGCTTCTGCTTTCGTAGGCGCCGGCATCGCTGGAGCG
GCTGTTGGCAGCATAGGCCTTGGGAAGGTGCTTGTGGATATTTT
GGCAGGTTATGGAGCAGGGGTGGCAGGCGCGCTCGTGGCCTTTA
AGGTCATGAGCGGCGAGATGCCCTCCACCGAGGACCTGGTTAAC
CTACTCCCTGCTATCCTCTCCCCTGGCGCCCTAGTCGTCGGGGT
CGTGTGCGCAGCGATACTGCGTCGGCACGTGGGCCCAGGGGAGG
GGGCTGTGCAGTGGATGAACCGGCTGATAGCGTTCGCTTCGCGG
GGTAACCACGTGTCCCCCACGCACTATGTGCCTGAGAGCGACGC
TGCAGCACGTGTCACTCAGATCCTCTCTAGTCTTACCATCACTC
AGCTGCTGAAGAGGCTTCACCAGTGGATCAACGAGGACTGCTCC
ACGCCATGCTCCGGCTCGTGGCTAAGAGATGTTTGGGATTGGAT
ATGCACGGTGTTGACTGATTTCAAGACCTGGCTCCAGTCCAAGC
TCCTGCCGCGATTGCCGGGAGTCCCCTTCTTCTCATGTCAACGT
GGGTACAAGGGAGTCTGGCGGGGCGACGGCATCATGCAAACCAC
CTGCCCATGTGGAGCACAGATCACCGGACATGTGAAAAACGGTT
CCATGAGGATCGTGGGGCCTAGGACCTGTAGTAACACGTGGCAT
GGAACATTCCCCATTAACGCGTACACCACGGGCCCTGCACGCC
CTCCCCGGCGCCAAATTATTCTAGGGCGCTGTGGCGGGTGGCTG
CTGAGGAGTACGTGGAGGTTACGCGGGTGGGGATTTCCACTAC
GTGACGGGCATGACCACTGACAACGTAAAGTGCCCGTGTCAGGT
TCCGGCCCCCGAATTCTTCACAGAAGTGGATGGGGTGCGGTTGC
ACAGGTACGCTCCAGCGTGCAAACCCCTCCTACGGGAGGAGGTC
ACATTCCTGGTCGGGCTCAATCAATACCTGGTTGGGTCACAGCT
CCCATGCGAGCCCGAACCGGACGTAGCAGTGCTCACTTCCATGC
TCACCGACCCCTCCCACATTACGGCGGAGACGGCTAAGCGTAGG
CTGGCCAGGGGATCTCCCCCCTCCTTGGCCAGCTCATCAGCTAT
CCAGCTGTCTGCGCCTTCCTTGAAGGCAACATGCACTACCCGTC
ATGACTCCCCGGACGCTGACCTCATCGAGGCCAACCTCCTGTGG
CGGCAGGAGATGGGCGGGAACATCACCCGCGTGGAGTCAGAAAA

-continued

SEQ ID NOs

TAAGGTAGTAATTTTGGACTCTTTCGAGCCGCTCCAAGCGGAGG
AGGATGAGAGGGAAGTATCCGTTCCGGCGGAGATCCTGCGGAGG
TCCAGGAAATTCCCTCGAGCGATGCCCATATGGGCACGCCCGGA
TTACAACCCTCCACTGTTAGAGTCCTGGAAGGACCCGGACTACG
TCCCTCCAGTGGTACACGGGTGTCCATTGCCGCCTGCCAAGGCC
CCTCCGATACCACCTCCACGGAGGAAGAGGACGGTTGTCCTGTC
AGAATCTACCGTGTCTTCTGCCTTGGCGGAGCTCGCCACAAAGA
CCTTCGGCAGCTCCGAATCGTCGGCCGTCGACAGCGGCACGGCA
ACGGCCTCTCCTGACCAGCCCTCCGACGACGGCGACGCGGGATC
CGACGTTGAGTCGTACTCCTCCATGCCCCCCCTTGAGGGGGAGC
CGGGGGATCCCGATCTCAGCGACGGGTCTTGGTCTACCGTAAGC
GAGGAGGCTAGTGAGGACGTCGTCTGCTGCTCGATGTCCTACAC
ATGGACAGGCGCCCTGATCACGCCATGCGCTGCGGAGGAAACCA
AGCTGCCCATCAATGCACTGAGCAACTCTTTGCTCCGTCACCAC
AACTTGGTCTATGCTACAACATCTCGCAGCGCAAGCCTGCGGCA
GAAGAAGGTCACCTTTGACAGACTGCAGGTCCTGGACGACCACT
ACCGGGACGTGCTCAAGGAGATGAAGGCGAAGGCGTCCACAGTT
AAGGCTAAACTTCTATCCGTGGAGGAAGCCTGTAAGCTGACGCC
CCCACATTCGGCCAGATCTAAATTTGGCTATGGGGCAAAGGACG
TCCGGAACCTATCCAGCAAGGCCGTTAACCACATCCGCTCCGTG
TGGAAGGACTTGCTGGAAGACACTGAGACACCAATTGACACCAC
CATCATGGCAAAAAATGAGGTTTTCTGCGTCCAACCAGAGAAGG
GGGGCCGCAAGCCAGCTCGCCTTATCGTATTCCCAGATTTGGGG
GTTCGTGTGTGCGAGAAAATGGCCCTTTACGATGTGGTCTCCAC
CCTCCCTCAGGCCGTGATGGGCTCTTCATACGGATTCCAATACT
CTCCTGGACAGCGGGTCGAGTTCCTGGTGAATGCCTGGAAAGCG
AAGAAATGCCCTATGGGCTTCGCATATGACACCCGCTGTTTTGA
CTCAACGGTCACTGAGAATGACATCCGTGTTGAGGAGTCAATCT
ACCAATGTTGTGACTTGGCCCCCGAAGCCAGACAGGCCATAAGG
TCGCTCACAGAGCGGCTTTACATCGGGGGCCCCCTGACTAATTC
TAAAGGGCAGAACTGCGGCTATCGCCGGTGCCGCGCGAGCGGTG
TACTGACGACCAGCTGCGGTAATACCCTCACATGTTACTTGAAG
GCCGCTGCGGCCTGTCGAGCTGCGAAGCTCCAGGACTGCACGAT
GCTCGTATGCGGAGACGACCTTGTCGTTATCTGTGAAAGCGCGG
GGACCCAAGAGGACGAGGCGAGCCTACGGGCCTTCACGGAGGCT
ATGACTAGATACTCTGCCCCCCCTGGGGACCCGCCCAAACCAGA
ATACGACTTGGAGTTGATAACATCATGCTCCTCCAATGTGTCAG
TCGCGCACGATGCATCTGGCAAAAGGGTGTACTATCTCACCCGT
GACCCCACCACCCCCCTTGCGCGGGCTGCGTGGGAGACAGCTAG
ACACACTCCAGTCAATTCCTGGCTAGGCAACATCATCATGTATG
CGCCCACCTTGTGGGCAAGGATGATCCTGATGACTCATTTCTTC
TCCATCCTTCTAGCTCAGGAACAACTTGAAAAAGCCCTAGATTG
TCAGATCTACGGGGCCTGTTACTCCATTGAGCCACTTGACCTAC
CTCAGATCATTCAACGACTCCATGGCCTTAGCGCATTTTCACTC
CATAGTTACTCTCCAGGTGAGATCAATAGGGTGGCTTCATGCCT
CAGGAAACTTGGGGTACCGCCCTTGCGAGTCTGGAGACATCGGG
CCAGAAGTGTCCGCGCTAGGCTACTGTCCCAGGGGGGGAGGGCT
GCCACTTGTGGCAAGTACCTCTTCAACTGGGCAGTAAGGACCAA
GCTCAAACTCACTCCAATCCCGGCTGCGTCCCAGTTGGATTTAT
CCAGCTGGTTCGTTGCTGGTTACAGCGGGGGAGACATATATCAC
AGCCTGTCTCGTGCCCGACCCCGCTGGTTCATGTGGTGCCTACT
CCTACTTTCTGTAGGGGTAGGCATCTATCTACTCCCCAACCGCT
GAACGGGACCTAAACACTCCAGGCCAATAGGCCATCCTGTTTTT
TTTCCCTTTTTTTTTTTCTTTTTTTTTTTTTTTTTTTTTTTTT
TTTCTCCTTTTTTTTTCCTCTTTTTTTCCTTTTCTTTCCTTTGGTGG
CTCCATCTTAGCCCTAGTCACGGCTAGCTGTGAAAGGTCCGTGA
GCCGCTTGACTGCAGAGAGTGCTGATACTGGCCTCTCTGCAGAT
CAAGT

What is claimed is:

1. A method of testing a compound for inhibiting HCV replication, comprising the steps of:
   (a) treating an Huh7 or Huh7 derived host cell comprising an HCV subtype 1b full length clone or replicon sequence having at least one adaptive mutation that is capable of productive HCV RNA replication in a host cell, or is capable of being transcribed into an HCV subtype 1b full length clone or replicon sequence that is capable of productive HCV RNA replication in a host cell, wherein the HCV subtype 1b full length clone or replicon sequence comprises, from 5' to 3' on the positive-sense nucleic acid, a functional 5' non-translated region (5' NTR) sequence, wherein said HCV 5'NTR sequence comprises at the 5' terminus at least one of GCCAGCC; GGCCAGCC; UGCCAGCC; AGCCAGCC; AAGCCAGCC; GAGCCAGCC; GUGCCAGCC; and GCGCCAGCC; one or more protein coding regions, including at least one polyprotein coding region consensus sequence comprising a NS3 serine proteinase/helicase through NS5B RNA-dependent RNA polymerase encoding region that is capable of replicating HCV RNA; and a functional HCV 3' non-translated region (3' NTR) that comprises a poly (u/c) tract of variable length and an HCV extreme 3' terminal conserved sequence of about 98 nucleotides with the compound, and wherein said HCV subtype 1b replicon is deficient in some or all of the structural genes C, E1, and E2; and
   (b) evaluating the treated host cell for reduced HCV replication, wherein reduced HCV replication indicates the ability of the compound to inhibit HCV replication.

2. The method of claim 1, wherein said HCV subtype 1b full length clone or replicon comprises an adaptive mutation encoding an amino acid change corresponding to an amino acid change of Ser (1179) to Ile of SEQ ID NO:3.

3. The method of claim 2, wherein said polynucleotide is SEQ ID NO:24.

* * * * *

SEQUENCE LISTING

<160> NUMBER OF SEQ ID NOS: 24

<210> SEQ ID NO 1
<211> LENGTH: 21
<212> TYPE: DNA
<213> ORGANISM: Hepatitis C virus

<400> SEQUENCE: 1
ggcgacactc caccatagat c                                            21

<210> SEQ ID NO 2
<211> LENGTH: 99
<212> TYPE: DNA
<213> ORGANISM: Hepatitis C virus

<400> SEQUENCE: 2
tggtggctcc atcttagccc tagtcacggc tagctgtgaa aggtccgtga gccgcatgac    60
tgcagagagt gctgatactg gcctctctgc tgatcatgt                           99

<210> SEQ ID NO 3
<211> LENGTH: 1985
<212> TYPE: PRT
<213> ORGANISM: Hepatitis C virus

<400> SEQUENCE: 3

Met Ala Pro Ile Thr Ala Tyr Ser Gln Gln Thr Arg Gly Leu Leu Gly
1               5                   10                  15

Cys Ile Ile Thr Ser Leu Thr Gly Arg Asp Arg Asn Gln Val Glu Gly
            20                  25                  30

Glu Val Gln Val Val Ser Thr Ala Thr Gln Ser Phe Leu Ala Thr Cys
        35                  40                  45

Val Asn Gly Val Cys Trp Thr Val Tyr His Gly Ala Gly Ser Lys Thr
    50                  55                  60

Leu Ala Gly Pro Lys Gly Pro Ile Thr Gln Met Tyr Thr Asn Val Asp
65                  70                  75                  80

Gln Asp Leu Val Gly Trp Gln Ala Pro Pro Gly Ala Arg Ser Leu Thr
                85                  90                  95

Pro Cys Thr Cys Gly Ser Ser Asp Leu Tyr Leu Val Thr Arg His Ala
            100                 105                 110

Asp Val Ile Pro Val Arg Arg Arg Gly Asp Ser Arg Gly Ser Leu Leu
        115                 120                 125

Ser Pro Arg Pro Val Ser Tyr Leu Lys Gly Ser Ser Gly Gly Pro Leu
    130                 135                 140

Leu Cys Pro Ser Gly His Ala Val Gly Ile Phe Arg Ala Ala Val Cys
145                 150                 155                 160

Thr Arg Gly Val Ala Lys Ala Val Asp Phe Val Pro Val Glu Ser Met
                165                 170                 175

Glu Thr Thr Met Arg Ser Pro Val Phe Thr Asp Asn Ser Ser Pro Pro
            180                 185                 190

Ala Val Pro Gln Thr Phe Gln Val Ala His Leu His Ala Pro Thr Gly
        195                 200                 205

Ser Gly Lys Ser Thr Lys Val Pro Ala Ala Tyr Ala Ala Gln Gly Tyr
    210                 215                 220

Lys Val Leu Val Leu Asn Pro Ser Val Ala Ala Thr Leu Gly Phe Gly
225                 230                 235                 240

-continued

```
Ala Tyr Met Ser Lys Ala His Gly Ile Asp Pro Asn Ile Arg Thr Gly
            245                 250                 255

Val Arg Thr Ile Thr Thr Gly Ala Pro Ile Thr Tyr Ser Thr Tyr Gly
        260                 265                 270

Lys Phe Leu Ala Asp Gly Gly Cys Ser Gly Ala Tyr Asp Ile Ile
    275                 280                 285

Ile Cys Asp Glu Cys His Ser Thr Asp Ser Thr Thr Ile Leu Gly Ile
290                 295                 300

Gly Thr Val Leu Asp Gln Ala Glu Thr Ala Gly Ala Arg Leu Val Val
305                 310                 315                 320

Leu Ala Thr Ala Thr Pro Pro Gly Ser Val Thr Val Pro His Pro Asn
                325                 330                 335

Ile Glu Glu Val Ala Leu Ser Ser Thr Gly Glu Ile Pro Phe Tyr Gly
            340                 345                 350

Lys Ala Ile Pro Ile Glu Thr Ile Lys Gly Gly Arg His Leu Ile Phe
        355                 360                 365

Cys His Ser Lys Lys Lys Cys Asp Glu Leu Ala Ala Lys Leu Ser Gly
    370                 375                 380

Leu Gly Leu Asn Ala Val Ala Tyr Tyr Arg Gly Leu Asp Val Ser Val
385                 390                 395                 400

Ile Pro Thr Ser Gly Asp Val Ile Val Val Ala Thr Asp Ala Leu Met
                405                 410                 415

Thr Gly Phe Thr Gly Asp Phe Asp Ser Val Ile Asp Cys Asn Thr Cys
            420                 425                 430

Val Thr Gln Thr Val Asp Phe Ser Leu Asp Pro Thr Phe Thr Ile Glu
        435                 440                 445

Thr Thr Thr Val Pro Gln Asp Ala Val Ser Arg Ser Gln Arg Arg Gly
    450                 455                 460

Arg Thr Gly Arg Gly Arg Met Gly Ile Tyr Arg Phe Val Thr Pro Gly
465                 470                 475                 480

Glu Arg Pro Ser Gly Met Phe Asp Ser Ser Val Leu Cys Glu Cys Tyr
                485                 490                 495

Asp Ala Gly Cys Ala Trp Tyr Glu Leu Thr Pro Ala Glu Thr Ser Val
            500                 505                 510

Arg Leu Arg Ala Tyr Leu Asn Thr Pro Gly Leu Pro Val Cys Gln Asp
        515                 520                 525

His Leu Glu Phe Trp Glu Ser Val Phe Thr Gly Leu Thr His Ile Asp
    530                 535                 540

Ala His Phe Leu Ser Gln Thr Lys Gln Ala Gly Asp Asn Phe Pro Tyr
545                 550                 555                 560

Leu Val Ala Tyr Gln Ala Thr Val Cys Ala Arg Ala Gln Ala Pro Pro
                565                 570                 575

Pro Ser Trp Asp Gln Met Trp Lys Cys Leu Ile Arg Leu Lys Pro Thr
            580                 585                 590

Leu His Gly Pro Thr Pro Leu Leu Tyr Arg Leu Gly Ala Val Gln Asn
        595                 600                 605

Glu Val Thr Thr Thr His Pro Ile Thr Lys Tyr Ile Met Ala Cys Met
    610                 615                 620

Ser Ala Asp Leu Glu Val Val Thr Ser Thr Trp Val Leu Val Gly Gly
625                 630                 635                 640

Val Leu Ala Ala Leu Ala Ala Tyr Cys Leu Thr Thr Gly Ser Val Val
                645                 650                 655

Ile Val Gly Arg Ile Ile Leu Ser Gly Lys Pro Ala Ile Ile Pro Asp
```

-continued

```
            660             665             670
Arg Glu Val Leu Tyr Arg Glu Phe Asp Glu Met Glu Cys Ala Ser
        675             680             685
His Leu Pro Tyr Ile Glu Gln Gly Met Gln Leu Ala Glu Gln Phe Lys
        690             695             700
Gln Lys Ala Ile Gly Leu Leu Gln Thr Ala Thr Lys Gln Ala Glu Ala
705             710             715             720
Ala Ala Pro Val Val Glu Ser Lys Trp Arg Thr Leu Glu Ala Phe Trp
                725             730             735
Ala Lys His Met Trp Asn Phe Ile Ser Gly Ile Gln Tyr Leu Ala Gly
        740             745             750
Leu Ser Thr Leu Pro Gly Asn Pro Ala Ile Ala Ser Leu Met Ala Phe
        755             760             765
Thr Ala Ser Ile Thr Ser Pro Leu Thr Thr Gln His Thr Leu Leu Phe
        770             775             780
Asn Ile Leu Gly Gly Trp Val Ala Ala Gln Leu Ala Pro Pro Ser Ala
785             790             795             800
Ala Ser Ala Phe Val Gly Ala Gly Ile Ala Gly Ala Ala Val Gly Ser
                805             810             815
Ile Gly Leu Gly Lys Val Leu Val Asp Ile Leu Ala Gly Tyr Gly Ala
                820             825             830
Gly Val Ala Gly Ala Leu Val Ala Phe Lys Val Met Ser Gly Glu Met
                835             840             845
Pro Ser Thr Glu Asp Leu Val Asn Leu Leu Pro Ala Ile Leu Ser Pro
        850             855             860
Gly Ala Leu Val Val Gly Val Val Cys Ala Ala Ile Leu Arg Arg His
865             870             875             880
Val Gly Pro Gly Glu Gly Ala Val Gln Trp Met Asn Arg Leu Ile Ala
                885             890             895
Phe Ala Ser Arg Gly Asn His Val Ser Pro Thr His Tyr Val Pro Glu
                900             905             910
Ser Asp Ala Ala Ala Arg Val Thr Gln Ile Leu Ser Ser Leu Thr Ile
        915             920             925
Thr Gln Leu Leu Lys Arg Leu His Gln Trp Ile Asn Glu Asp Cys Ser
        930             935             940
Thr Pro Cys Ser Gly Ser Trp Leu Arg Asp Val Trp Asp Trp Ile Cys
945             950             955             960
Thr Val Leu Thr Asp Phe Lys Thr Trp Leu Gln Ser Lys Leu Leu Pro
                965             970             975
Arg Leu Pro Gly Val Pro Phe Phe Ser Cys Gln Arg Gly Tyr Lys Gly
                980             985             990
Val Trp Arg Gly Asp Gly Ile Met  Gln Thr Thr Cys Pro  Cys Gly Ala
        995             1000            1005
Gln Ile  Thr Gly His Val Lys  Asn Gly Ser Met Arg  Ile Val Gly
        1010            1015            1020
Pro Arg  Thr Cys Ser Asn Thr  Trp His Gly Thr Phe  Pro Ile Asn
        1025            1030            1035
Ala Tyr  Thr Thr Gly Pro Cys  Thr Pro Ser Pro Ala  Pro Asn Tyr
        1040            1045            1050
Ser Arg  Ala Leu Trp Arg Val  Ala Ala Glu Glu Tyr  Val Glu Val
        1055            1060            1065
Thr Arg  Val Gly Asp Phe His  Tyr Val Thr Gly Met  Thr Thr Asp
        1070            1075            1080
```

-continued

```
Asn Val Lys Cys Pro Cys Gln Val Pro Ala Pro Glu Phe Phe Thr
1085                1090                1095

Glu Val Asp Gly Val Arg Leu His Arg Tyr Ala Pro Ala Cys Lys
1100                1105                1110

Pro Leu Leu Arg Glu Glu Val Thr Phe Leu Val Gly Leu Asn Gln
1115                1120                1125

Tyr Leu Val Gly Ser Gln Leu Pro Cys Glu Pro Glu Pro Asp Val
1130                1135                1140

Ala Val Leu Thr Ser Met Leu Thr Asp Pro Ser His Ile Thr Ala
1145                1150                1155

Glu Thr Ala Lys Arg Arg Leu Ala Arg Gly Ser Pro Pro Ser Leu
1160                1165                1170

Ala Ser Ser Ala Ser Gln Leu Ser Ala Pro Ser Leu Lys Ala
1175                1180                1185

Thr Cys Thr Thr Arg His Asp Ser Pro Asp Ala Asp Leu Ile Glu
1190                1195                1200

Ala Asn Leu Leu Trp Arg Gln Glu Met Gly Gly Asn Ile Thr Arg
1205                1210                1215

Val Glu Ser Glu Asn Lys Val Val Ile Leu Asp Ser Phe Glu Pro
1220                1225                1230

Leu Gln Ala Glu Glu Asp Glu Arg Glu Val Ser Val Pro Ala Glu
1235                1240                1245

Ile Leu Arg Arg Ser Arg Lys Phe Pro Arg Ala Met Pro Ile Trp
1250                1255                1260

Ala Arg Pro Asp Tyr Asn Pro Pro Leu Leu Glu Ser Trp Lys Asp
1265                1270                1275

Pro Asp Tyr Val Pro Pro Val His Gly Cys Pro Leu Pro Pro
1280                1285                1290

Ala Lys Ala Pro Pro Ile Pro Pro Pro Arg Arg Lys Arg Thr Val
1295                1300                1305

Val Leu Ser Glu Ser Thr Val Ser Ser Ala Leu Ala Glu Leu Ala
1310                1315                1320

Thr Lys Thr Phe Gly Ser Ser Glu Ser Ser Ala Val Asp Ser Gly
1325                1330                1335

Thr Ala Thr Ala Ser Pro Asp Gln Pro Ser Asp Asp Gly Asp Ala
1340                1345                1350

Gly Ser Asp Val Glu Ser Tyr Ser Ser Met Pro Pro Leu Glu Gly
1355                1360                1365

Glu Pro Gly Asp Pro Asp Leu Ser Asp Gly Ser Trp Ser Thr Val
1370                1375                1380

Ser Glu Glu Ala Ser Glu Asp Val Val Cys Cys Ser Met Ser Tyr
1385                1390                1395

Thr Trp Thr Gly Ala Leu Ile Thr Pro Cys Ala Ala Glu Glu Thr
1400                1405                1410

Lys Leu Pro Ile Asn Ala Leu Ser Asn Ser Leu Leu Arg His His
1415                1420                1425

Asn Leu Val Tyr Ala Thr Thr Ser Arg Ser Ala Ser Leu Arg Gln
1430                1435                1440

Lys Lys Val Thr Phe Asp Arg Leu Gln Val Leu Asp Asp His Tyr
1445                1450                1455

Arg Asp Val Leu Lys Glu Met Lys Ala Lys Ala Ser Thr Val Lys
1460                1465                1470
```

-continued

```
Ala Lys Leu Leu Ser Val Glu Ala Cys Lys Leu Thr Pro Pro
    1475            1480            1485

His Ser Ala Arg Ser Lys Phe Gly Tyr Gly Ala Lys Asp Val Arg
    1490            1495            1500

Asn Leu Ser Ser Lys Ala Val Asn His Ile Arg Ser Val Trp Lys
    1505            1510            1515

Asp Leu Leu Glu Asp Thr Glu Thr Pro Ile Asp Thr Thr Ile Met
    1520            1525            1530

Ala Lys Asn Glu Val Phe Cys Val Gln Pro Glu Lys Gly Gly Arg
    1535            1540            1545

Lys Pro Ala Arg Leu Ile Val Phe Pro Asp Leu Gly Val Arg Val
    1550            1555            1560

Cys Glu Lys Met Ala Leu Tyr Asp Val Val Ser Thr Leu Pro Gln
    1565            1570            1575

Ala Val Met Gly Ser Ser Tyr Gly Phe Gln Tyr Ser Pro Gly Gln
    1580            1585            1590

Arg Val Glu Phe Leu Val Asn Ala Trp Lys Ala Lys Lys Cys Pro
    1595            1600            1605

Met Gly Phe Ala Tyr Asp Thr Arg Cys Phe Asp Ser Thr Val Thr
    1610            1615            1620

Glu Asn Asp Ile Arg Val Glu Glu Ser Ile Tyr Gln Cys Cys Asp
    1625            1630            1635

Leu Ala Pro Glu Ala Arg Gln Ala Ile Arg Ser Leu Thr Glu Arg
    1640            1645            1650

Leu Tyr Ile Gly Gly Pro Leu Thr Asn Ser Lys Gly Gln Asn Cys
    1655            1660            1665

Gly Tyr Arg Arg Cys Arg Ala Ser Gly Val Leu Thr Thr Ser Cys
    1670            1675            1680

Gly Asn Thr Leu Thr Cys Tyr Leu Lys Ala Ala Ala Cys Arg
    1685            1690            1695

Ala Ala Lys Leu Gln Asp Cys Thr Met Leu Val Cys Gly Asp Asp
    1700            1705            1710

Leu Val Val Ile Cys Glu Ser Ala Gly Thr Gln Glu Asp Glu Ala
    1715            1720            1725

Ser Leu Arg Ala Phe Thr Glu Ala Met Thr Arg Tyr Ser Ala Pro
    1730            1735            1740

Pro Gly Asp Pro Pro Lys Pro Glu Tyr Asp Leu Glu Leu Ile Thr
    1745            1750            1755

Ser Cys Ser Ser Asn Val Ser Val Ala His Asp Ala Ser Gly Lys
    1760            1765            1770

Arg Val Tyr Tyr Leu Thr Arg Asp Pro Thr Thr Pro Leu Ala Arg
    1775            1780            1785

Ala Ala Trp Glu Thr Ala Arg His Thr Pro Val Asn Ser Trp Leu
    1790            1795            1800

Gly Asn Ile Ile Met Tyr Ala Pro Thr Leu Trp Ala Arg Met Ile
    1805            1810            1815

Leu Met Thr His Phe Phe Ser Ile Leu Leu Ala Gln Glu Gln Leu
    1820            1825            1830

Glu Lys Ala Leu Asp Cys Gln Ile Tyr Gly Ala Cys Tyr Ser Ile
    1835            1840            1845

Glu Pro Leu Asp Leu Pro Gln Ile Ile Gln Arg Leu His Gly Leu
    1850            1855            1860

Ser Ala Phe Ser Leu His Ser Tyr Ser Pro Gly Glu Ile Asn Arg
```

```
                1865                1870                1875

Val Ala Ser Cys Leu Arg Lys Leu Gly Val Pro Pro Leu Arg Val
        1880                1885                1890

Trp Arg His Arg Ala Arg Ser Val Arg Ala Arg Leu Leu Ser Gln
        1895                1900                1905

Gly Gly Arg Ala Ala Thr Cys Gly Lys Tyr Leu Phe Asn Trp Ala
        1910                1915                1920

Val Arg Thr Lys Leu Lys Leu Thr Pro Ile Pro Ala Ala Ser Gln
        1925                1930                1935

Leu Asp Leu Ser Ser Trp Phe Val Ala Gly Tyr Ser Gly Gly Asp
        1940                1945                1950

Ile Tyr His Ser Leu Ser Arg Ala Arg Pro Arg Trp Phe Met Trp
        1955                1960                1965

Cys Leu Leu Leu Leu Ser Val Gly Val Gly Ile Tyr Leu Leu Pro
        1970                1975                1980

Asn Arg
    1985

<210> SEQ ID NO 4
<211> LENGTH: 447
<212> TYPE: PRT
<213> ORGANISM: Hepatitis C virus

<400> SEQUENCE: 4

Ser Gly Ser Trp Leu Arg Asp Val Trp Asp Trp Ile Cys Thr Val Leu
1               5                   10                  15

Thr Asp Phe Lys Thr Trp Leu Gln Ser Lys Leu Leu Pro Arg Leu Pro
            20                  25                  30

Gly Val Pro Phe Phe Ser Cys Gln Arg Gly Tyr Lys Gly Val Trp Arg
        35                  40                  45

Gly Asp Gly Ile Met Gln Thr Thr Cys Pro Cys Gly Ala Gln Ile Thr
    50                  55                  60

Gly His Val Lys Asn Gly Ser Met Arg Ile Val Gly Pro Arg Thr Cys
65                  70                  75                  80

Ser Asn Thr Trp His Gly Thr Phe Pro Ile Asn Ala Tyr Thr Thr Gly
                85                  90                  95

Pro Cys Thr Pro Ser Pro Ala Pro Asn Tyr Ser Arg Ala Leu Trp Arg
            100                 105                 110

Val Ala Ala Glu Glu Tyr Val Glu Val Thr Arg Val Gly Asp Phe His
        115                 120                 125

Tyr Val Thr Gly Met Thr Thr Asp Asn Val Lys Cys Pro Cys Gln Val
    130                 135                 140

Pro Ala Pro Glu Phe Phe Thr Glu Val Asp Gly Val Arg Leu His Arg
145                 150                 155                 160

Tyr Ala Pro Ala Cys Lys Pro Leu Leu Arg Glu Glu Val Thr Phe Leu
                165                 170                 175

Val Gly Leu Asn Gln Tyr Leu Val Gly Ser Gln Leu Pro Cys Glu Pro
            180                 185                 190

Glu Pro Asp Val Ala Val Leu Thr Ser Met Leu Thr Asp Pro Ser His
        195                 200                 205

Ile Thr Ala Glu Thr Ala Lys Arg Arg Leu Ala Arg Gly Ser Pro Pro
    210                 215                 220

Ser Leu Ala Ser Ser Ser Ala Ser Gln Leu Ser Ala Pro Ser Leu Lys
225                 230                 235                 240
```

```
Ala Thr Cys Thr Thr Arg His Asp Ser Pro Asp Ala Asp Leu Ile Glu
            245                 250                 255
Ala Asn Leu Leu Trp Arg Gln Glu Met Gly Gly Asn Ile Thr Arg Val
        260                 265                 270
Glu Ser Glu Asn Lys Val Val Ile Leu Asp Ser Phe Glu Pro Leu Gln
    275                 280                 285
Ala Glu Glu Asp Glu Arg Glu Val Ser Val Pro Ala Glu Ile Leu Arg
290                 295                 300
Arg Ser Arg Lys Phe Pro Arg Ala Met Pro Ile Trp Ala Arg Pro Asp
305                 310                 315                 320
Tyr Asn Pro Pro Leu Leu Glu Ser Trp Lys Asp Pro Asp Tyr Val Pro
                325                 330                 335
Pro Val Val His Gly Cys Pro Leu Pro Pro Ala Lys Ala Pro Pro Ile
            340                 345                 350
Pro Pro Pro Arg Arg Lys Arg Thr Val Val Leu Ser Glu Ser Thr Val
        355                 360                 365
Ser Ser Ala Leu Ala Glu Leu Ala Thr Lys Thr Phe Gly Ser Ser Glu
    370                 375                 380
Ser Ser Ala Val Asp Ser Gly Thr Ala Thr Ala Ser Pro Asp Gln Pro
385                 390                 395                 400
Ser Asp Asp Gly Asp Ala Gly Ser Asp Val Glu Ser Tyr Ser Ser Met
                405                 410                 415
Pro Pro Leu Glu Gly Glu Pro Gly Asp Pro Asp Leu Ser Asp Gly Ser
            420                 425                 430
Trp Ser Thr Val Ser Glu Glu Ala Ser Glu Asp Val Val Cys Cys
        435                 440                 445

<210> SEQ ID NO 5
<211> LENGTH: 7987
<212> TYPE: DNA
<213> ORGANISM: Hepatitis C virus

<400> SEQUENCE: 5
gccagccccc gattgggggc gacactccac catagatcac tcccctgtga ggaactactg      60
tcttcacgca gaaagcgtct agccatggcg ttagtatgag tgtcgtgcag cctccaggac     120
ccccctccc gggagagcca tagtggtctg cggaaccggt gagtacaccg gaattgccag     180
gacgaccggg tcctttcttg gatcaacccg ctcaatgcct ggagatttgg gcgtgccccc     240
gcgagactgc tagccgagta gtgttgggtc gcgaaaggcc ttgtggtact gcctgatagg     300
gtgcttgcga gtgccccggg aggtctcgta gaccgtgcac catgagcacg aatcctaaac     360
ctcaaagaaa aaccaaaggg cgcgccatga ttgaacaaga tggattgcac gcaggttctc     420
cggccgcttg ggtggagagg ctattcggct atgactgggc acaacagaca atcggctgct     480
ctgatgccgc cgtgttccgg ctgtcagcgc agggcgcccc ggttcttttt gtcaagaccg     540
acctgtccgg tgccctgaat gaactgcagg acgaggcagc gcggctatcg tggctggcca     600
cgacgggcgt tccttgcgca gctgtgctcg acgttgtcac tgaagcggga agggactggc     660
tgctattggg cgaagtgccg gggcaggatc tcctgtcatc tcaccttgct cctgccgaga     720
aagtatccat catggctgat gcaatgcggc ggctgcatac gcttgatccg gctacctgcc     780
cattcgacca ccaagcgaaa catcgcatcg agcgagcacg tactcggatg gaagccggtc     840
ttgtcgatca ggatgatctg gacgaagagc atcaggggct cgcgccagcc gaactgttcg     900
ccaggctcaa ggcgcgcatg cccgacggcg aggatctcgt cgtgacccat ggcgatgcct     960
```

```
gcttgccgaa tatcatggtg gaaaatggcc gcttttctgg attcatcgac tgtggccggc    1020
tgggtgtggc ggaccgctat caggacatag cgttggctac ccgtgatatt gctgaagagc    1080
ttggcggcga atgggctgac cgcttcctcg tgctttacgg tatcgccgct cccgattcgc    1140
agcgcatcgc cttctatcgc cttcttgacg agttcttctg agtttaaaca gaccacaacg    1200
gtttccctct agcgggatca attccgcccc tctccctccc cccccctaa cgttactggc    1260 cgaagccgct tggaataagg ccggtgtgcg tttgtctata tgttattttc caccatattg    1320
ccgtcttttg gcaatgtgag ggcccggaaa cctggccctg tcttcttgac gagcattcct    1380
aggggtcttt cccctctcgc caaggaatg caaggtctgt tgaatgtcgt gaaggaagca    1440
gttcctctgg aagcttcttg aagacaaaca acgtctgtag cgacccttg caggcagcgg    1500 aaccccccac ctggcgacag gtgcctctgc ggccaaaagc cacgtgtata agatacacct    1560
gcaaaggcgg cacaacccca gtgccacgtt gtgagttgga tagttgtgga aagagtcaaa    1620
tggctctcct caagcgtatt caacaagggg ctgaaggatg cccagaaggt accccattgt    1680
atgggatctg atctggggcc tcggtgcaca tgctttacat gtgtttagtc gaggttaaaa    1740
aacgtctagg ccccccgaac cacggggacg tggttttcct ttgaaaaaca cgataatacc    1800
atggcgccta ttacggccta ctcccaacag acgcgaggcc tacttggctg catcatcact    1860
agcctcacag gccgggacag gaaccaggtc gaggggagg tccaagtggt ctccaccgca    1920
acacaatctt tcctggcgac ctgcgtcaat ggcgtgtgtt ggactgtcta tcatggtgcc    1980
ggctcaaaga cccttgccgg cccaaagggc ccaatcaccc aaatgtacac caatgtggac    2040
caggacctcg tcggctggca agcgccccc ggggcgcgtt ccttgacacc atgcacctgc    2100
ggcagctcgg acctttactt ggtcacgagg catgccgatg tcattccggt gcgccggcgg    2160
ggcgacagca gggggagcct actctccccc aggcccgtct cctacttgaa gggctcttcg    2220
ggcggtccac tgctctgccc ctcggggcac gctgtgggca tctttcgggc tgccgtgtgc    2280
acccgagggg ttgcgaaggc ggtggacttt gtacccgtcg agtctatgga aaccactatg    2340
cggtccccgg tcttcacgga caactcgtcc cctccggccg taccgcagac attccaggtg    2400
gcccatctac acgcccctac tggtagcggc aagagcacta aggtgccggc tgcgtatgca    2460
gcccaagggt ataaggtgct tgtcctgaac ccgtccgtcg ccgccaccct aggtttcggg    2520
gcgtatatgt ctaaggcaca tggtatcgac cctaacatca gaaccggggt aaggaccatc    2580
accacgggtg cccccatcac gtactccacc tatggcaagt tcttgccga cggtggttgc    2640 tctgggggcg cctatgacat cataatatgt gatgagtgcc actcaactga ctcgaccact    2700
atcctgggca tcggcacagt cctgaccaa gcggagacgg ctggagcgcg actcgtcgtg    2760
ctcgccaccg ctacgcctcc gggatcggtc accgtgccac atccaaacat cgaggaggtg    2820
gctctgtcca gcactggaga aatccccttt tatggcaaag ccatccccat cgagaccatc    2880 aagggggga ggcacctcat tttctgccat tccaagaaga aatgtgatga gctcgccgcg    2940
aagctgtccg gcctcggact caatgctgta gcatattacc ggggccttga tgtatccgtc    3000
ataccaacta gcggagacgt cattgtcgta gcaacggacg ctctaatgac gggctttacc    3060
ggcgatttcg actcagtgat cgactgcaat acatgtgtca cccagacagt cgacttcagc    3120
ctggacccga ccttcaccat tgagacgacg accgtgccac aagacgcggt gtcacgctcg    3180
cagcggcgag gcaggactgg taggggcagg atgggcattt acaggtttgt gactccagga    3240
gaacggccct cgggcatgtt cgattcctcg gttctgtgcg agtgctatga cgcgggctgt    3300
gcttggtacg agctcacgcc cgccgagacc tcagttaggt tgcgggctta cctaaacaca    3360
```

| | |
|---|---|
| ccagggttgc ccgtctgcca ggaccatctg gagttctggg agagcgtctt tacaggcctc | 3420 |
| acccacatag acgcccattt cttgtcccag actaagcagg caggagacaa cttcccctac | 3480 |
| ctggtagcat accaggctac ggtgtgcgcc agggctcagg ctccacctcc atcgtgggac | 3540 |
| caaatgtgga agtgtctcat acggctaaag cctacgctgc acgggccaac gcccctgctg | 3600 |
| tataggctgg gagccgttca aaacgaggtt actaccacac accccataac caaatacatc | 3660 |
| atggcatgca tgtcggctga cctggaggtc gtcacgagca cctgggtgct ggtaggcgga | 3720 |
| gtcctagcag ctctggccgc gtattgcctg acaacaggca gcgtggtcat tgtgggcagg | 3780 |
| atcatcttgt ccggaaagcc ggccatcatt cccgacaggg aagtccttta ccgggagttc | 3840 |
| gatgagatgg aagagtgcgc ctcacacctc ccttacatcg aacagggaat gcagctcgcc | 3900 |
| gaacaattca aacagaaggc aatcgggttg ctgcaaacag ccaccaagca agcggaggct | 3960 |
| gctgctcccg tggtggaatc caagtggcgg accctcgaag ccttctgggc gaagcatatg | 4020 |
| tggaatttca tcagcgggat acaatattta gcaggcttgt ccactctgcc tggcaacccc | 4080 |
| gcgatagcat cactgatggc attcacagcc tctatcacca gcccgctcac cacccaacat | 4140 |
| accctcctgt ttaacatcct gggggatgg gtggccgccc aacttgctcc tcccagcgct | 4200 |
| gcttctgctt tcgtaggcgc cggcatcgct ggagcggctg ttggcagcat aggccttggg | 4260 |
| aaggtgcttg tggatatttt ggcaggttat ggagcagggg tggcaggcgc gctcgtggcc | 4320 |
| tttaaggtca tgagcggcga gatgccctcc accgaggacc tggttaacct actccctgct | 4380 |
| atcctctccc ctggcgccct agtcgtcggg gtcgtgtgcg cagcgatact gcgtcggcac | 4440 |
| gtgggcccag gggagggggc tgtgcagtgg atgaaccggc tgatagcgtt cgcttcgcgg | 4500 |
| ggtaaccacg tctcccccac gcactatgtg cctgagagcg acgctgcagc acgtgtcact | 4560 |
| cagatcctct ctagtcttac catcactcag ctgctgaaga ggcttcacca gtggatcaac | 4620 |
| gaggactgct ccacgccatg ctccggctcg tggctaagag atgtttggga ttggatatgc | 4680 |
| acggtgttga ctgatttcaa gacctggctc cagtccaagc tcctgccgcg attgccggga | 4740 |
| gtcccctttc tctcatgtca acgtgggtac aaggagtct ggcggggcga cggcatcatg | 4800 |
| caaaccacct gcccatgtgg agcacagatc accggacatg tgaaaaacgg ttccatgagg | 4860 |
| atcgtggggc ctaggacctg tagtaacacg tggcatggaa cattccccat taacgcgtac | 4920 |
| accacgggcc cctgcacgcc ctccccggcg ccaaattatt ctagggcgct gtggcgggtg | 4980 |
| gctgctgagg agtacgtgga ggttacgcgg gtggggatt tccactacgt gacgggcatg | 5040 |
| accactgaca acgtaaagtg cccgtgtcag gttccggccc ccgaattctt cacagaagtg | 5100 |
| gatgggtgc ggttgcacag gtacgctcca gcgtgcaaac ccctcctacg ggaggaggtc | 5160 |
| acattcctgg tcgggctcaa tcaataccctg gttgggtcac agctcccatg cgagcccgaa | 5220 |
| ccggacgtag cagtgctcac ttccatgctc accgaccct cccacattac ggcggagacg | 5280 |
| gctaagcgta ggctggccag gggatctccc ccctccttgg ccagctcatc agctagccag | 5340 |
| ctgtctgcgc cttccttgaa ggcaacatgc actacccgtc atgactcccc ggacgctgac | 5400 |
| ctcatcgagg ccaacctcct gtggcggcag gagatgggcg gaacatcac ccgcgtggag | 5460 |
| tcagaaaata aggtagtaat tttggactct ttcgagccgc tccaagcgga ggaggatgag | 5520 |
| agggaagtat ccgttccggc ggagatcctg cggaggtcca ggaaattccc tcgagcgatg | 5580 |
| cccatatggg cacgcccgga ttacaaccct ccactgttag agtcctggaa ggacccggac | 5640 |
| tacgtccctc cagtggtaca cgggtgtcca ttgccgcctg ccaaggcccc tccgatacca | 5700 |

-continued

```
cctccacgga ggaagaggac ggttgtcctg tcagaatcta ccgtgtcttc tgccttggcg    5760
gagctcgcca caaagacctt cggcagctcc gaatcgtcgg ccgtcgacag cggcacggca    5820
acggcctctc ctgaccagcc ctccgacgac ggcgacgcgg gatccgacgt tgagtcgtac    5880
tcctccatgc ccccccttga gggggagccg gggatcccg atctcagcga cgggtcttgg     5940
tctaccgtaa gcgaggaggc tagtgaggac gtcgtctgct gctcgatgtc ctacacatgg    6000
acaggcgccc tgatcacgcc atgcgctgcg gaggaaacca agctgcccat caatgcactg    6060
agcaactctt tgctccgtca ccacaacttg gtctatgcta caacatctcg cagcgcaagc    6120
ctgcggcaga agaaggtcac ctttgacaga ctgcaggtcc tggacgacca ctaccgggac    6180
gtgctcaagg agatgaaggc gaaggcgtcc acagttaagg ctaaacttct atccgtggag    6240
gaagcctgta agctgacgcc cccacattcg gccagatctca aatttggcta tggggcaaag   6300
gacgtccgga acctatccag caaggccgtt aaccacatcc gctccgtgtg aaggacttg     6360 ctggaagaca ctgagacacc aattgacacc accatcatgg caaaaaatga ggttttctgc    6420
gtccaaccag agaaggggg ccgcaagcca gctcgcctta tcgtattccc agatttgggg     6480
gttcgtgtgt gcgagaaaat ggcccttac gatgtggtct ccaccctccc tcaggccgtg     6540
atgggctctt catacggatt ccaatactct cctggacagc gggtcgagtt cctggtgaat    6600
gcctggaaag cgaagaaatg ccctatgggc ttcgcatatg acaccccgctg ttttgactca   6660 acggtcactg agaatgacat ccgtgttgag gagtcaatct accaatgttg tgacttggcc    6720
cccgaagcca gacaggccat aaggtcgctc acagagcggc tttacatcgg gggccccctg    6780
actaattcta aagggcagaa ctgcggctat cgccggtgcc gcgcgagcgg tgtactgacg    6840
accagctgcg gtaataccct cacatgttac ttgaaggccg ctgcggcctg tcgagctgcg    6900
aagctccagg actgcacgat gctcgtatgc ggagacgacc ttgtcgttat ctgtgaaagc    6960
gcggggaccc aagaggacga ggcgagccta cgggccttca cggaggctat gactagatac    7020 tctgccccc ctggggaccc gcccaaacca gaatacgact tggagttgat aacatcatgc     7080
tcctccaatg tgtcagtcgc gcacgatgca tctggcaaaa gggtgtacta tctcacccgt    7140
gaccccacca cccccccttgc gcgggctgcg tgggagacag ctagacacac tccagtcaat   7200
tcctggctag caacatcat catgtatgcg cccaccttgt gggcaaggat gatcctgatg     7260
actcatttct tctccatcct tctagctcag gaacaacttg aaaaagccct agattgtcag    7320
atctacgggg cctgttactc cattgagcca cttgacctac ctcagatcat tcaacgactc    7380
catggcctta gcgcatttc actccatagt tactctccag gtgagatcaa tagggtggct    7440
tcatgcctca ggaaacttgg ggtaccgccc ttgcgagtct ggagacatcg ggccagaagt    7500
gtccgcgcta ggctactgtc ccaggggggg agggctgcca cttgtggcaa gtacctcttc    7560
aactgggcag taaggaccaa gctcaaactc actccaatcc cggctgcgtc ccagttggat    7620
ttatccagct ggttcgttgc tggttacagc ggggagaca tatatcacag cctgtctcgt     7680
gcccgacccc gctggttcat gtggtgccta ctcctacttt ctgtagggtg aggcatctat    7740
ctactcccca accgatgaac ggggagctaa acactccagg ccaataggcc atcctgtttt    7800 tttcccttt tttttttctt ttttttttt tttttttttt tttttttttt ctcctttttt      7860
tttcctcttt ttttccttt ctttcctttg gtggctccat cttagcccta gtcacggcta    7920
gctgtgaaag gtccgtgagc cgcttgactg cagagagtgc tgatactggc ctctctgcag    7980
atcaagt                                                               7987
```

<210> SEQ ID NO 6
<211> LENGTH: 7989
<212> TYPE: DNA
<213> ORGANISM: Hepatitis C virus

<400> SEQUENCE: 6

```
gccagccccc gattgggggc gacactccac catagatcac tcccctgtga ggaactactg      60
tcttcacgca gaaagcgtct agccatggcg ttagtatgag tgtcgtgcag cctccaggac     120 ccccctccc gggagagcca tagtggtctg cggaaccggt gagtacaccg gaattgccag      180
gacgaccggg tcctttcttg gatcaacccg ctcaatgcct ggagatttgg gcgtgccccc     240
gcgagactgc tagccgagta gtgttgggtc gcgaaaggcc ttgtggtact gcctgatagg     300
gtgcttgcga gtgccccggg aggtctcgta gaccgtgcac catgagcacg aatcctaaac     360
ctcaaagaaa aaccaaaggg cgcgccatga ttgaacaaga tggattgcac gcaggttctc     420
cggccgcttg ggtggagagg ctattcggct atgactgggc acaacagaca atcggctgct     480
ctgatgccgc cgtgttccgg ctgtcagcgc agggggcgccc ggttcttttt gtcaagaccg     540
acctgtccgg tgccctgaat gaactgcagg acgaggcagc gcggctatcg tggctggcca     600
cgacgggcgt tccttgcgca gctgtgctcg acgttgtcac tgaagcggga agggactggc     660
tgctattggg cgaagtgccg gggcaggatc tcctgtcatc tcaccttgct cctgccgaga     720
aagtatccat catggctgat gcaatgcggc ggctgcatac gcttgatccg gctacctgcc     780
cattcgacca ccaagcgaaa catcgcatcg agcgagcacg tactcggatg aagccggtc      840 ttgtcgatca ggatgatctg gacgaagagc atcaggggct cgcgccagcc gaactgttcg     900
ccaggctcaa ggcgcgcatg cccgacggcg aggatctcgt cgtgacccat ggcgatgcct     960
gcttgccgaa tatcatggtg gaaaatggcc gcttttctgg attcatcgac tgtggccggc    1020
tgggtgtggc ggaccgctat caggacatag cgttggctac ccgtgatatt gctgaagagc    1080
ttggcggcga atgggctgac cgcttcctcg tgctttacgg tatcgccgct cccgattcgc    1140
agcgcatcgc cttctatcgc cttcttgacg agttcttctg agtttaaaca gaccacaacg    1200
gtttccctct agcgggatca attccgcccc tctccctccc ccccccctaa cgttactggc    1260
cgaagccgct tggaataagg ccggtgtgcg tttgtctata tgttattttc caccatattg    1320
ccgtcttttg gcaatgtgag ggcccggaaa cctggccctg tcttcttgac gagcattcct    1380
aggggtcttt cccctctcgc caaaggaatg caaggtctgt tgaatgtcgt gaaggaagca    1440
gttcctctgg aagcttcttg aagacaaaca acgtctgtag cgaccctttg caggcagcgg    1500
aaccccccac ctggcgacag tgcctctgc ggccaaaagc cacgtgtata agatacacct    1560
gcaaaggcgg cacaacccca gtgccacgtt gtgagttgga tagttgtgga aagagtcaaa    1620
tggctctcct caagcgtatt caacaagggg ctgaaggatg cccagaaggt accccattgt    1680
atgggatctg atctggggcc tcggtgcaca tgctttacat gtgtttagtc gaggttaaaa    1740
aacgtctagg ccccccgaac cacggggacg tggttttcct ttgaaaaaca cgataatacc    1800
atggcgccta ttacggccta ctcccaacag acgcgaggcc tacttggctg catcatcact    1860
agcctcacag gccgggacag gaaccaggtc gagggggagg tccaagtggt ctccaccgca    1920
acacaatctt tcctggcgac ctgcgtcaat ggcgtgtgtt ggactgtcta tcatggtgcc    1980
ggctcaaaga cccttgccgg cccaaagggc caatcaccc aaatgtacac caatgtggac    2040
caggacctcg tcggctggca agcgcccccc ggggcgcgtt ccttgacacc atgcacctgc    2100
ggcagctcgg acctttactt ggtcacgagg catgccgatg tcattccggt gcgccggcgg    2160
```

```
ggcgacagca ggggagcct actctccccc aggcccgtct cctacttgaa gggctcttcg    2220
ggcggtccac tgctctgccc ctcggggcac gctgtgggca tctttcgggc tgccgtgtgc    2280
acccgagggg ttgcgaaggc ggtggacttt gtacccgtcg agtctatgga aaccactatg    2340
cggtccccgg tcttcacgga caactcgtcc cctccggccg taccgcagac attccaggtg    2400
gcccatctac acgcccctac tggtagcggc aagagcacta aggtgccggc tgcgtatgca    2460
gcccaagggt ataaggtgct tgtcctgaac ccgtccgtcg ccgccaccct aggtttcggg    2520
gcgtatatgt ctaaggcaca tggtatcgac cctaacatca gaaccggggt aaggaccatc    2580
accacgggtg cccccatcac gtactccacc tatggcaagt ttcttgccga cggtggttgc    2640
tctgggggcg cctatgacat cataatatgt gatgagtgcc actcaactga ctcgaccact    2700
atcctgggca tcggcacagt cctggaccaa gcggagacgg ctggagcgcg actcgtcgtg    2760
ctcgccaccg ctacgcctcc gggatcggtc accgtgccac atccaaacat cgaggaggtg    2820
gctctgtcca gcactggaga atccccttt tatggcaaag ccatccccat cgagaccatc    2880
aaggggggga ggcacctcat tttctgccat tccaagaaga aatgtgatga gctcgccgcg    2940
aagctgtccg gcctcggact caatgctgta gcatattacc ggggccttga tgtatccgtc    3000
ataccaacta gcggagacgt cattgtcgta gcaacggacg ctctaatgac gggctttacc    3060
ggcgatttcg actcagtgat cgactgcaat acatgtgtca cccagacagt cgacttcagc    3120
ctggacccga ccttcaccat tgagacgacg accgtgccac aagacgcggt gtcacgctcg    3180
cagcggcgag gcaggactgg taggggcagg atgggcattt acaggtttgt gactccagga    3240
gaacggccct cgggcatgtt cgattcctcg gttctgtgcg agtgctatga cgcgggctgt    3300
gcttggtacg agctcacgcc cgccgagacc tcagttaggt tgcgggctta cctaaacaca    3360
ccagggttgc ccgtctgcca ggaccatctg gagttctggg agagcgtctt tacaggcctc    3420
acccacatag acgcccattt cttgtcccag actaagcagg caggagacaa cttcccctac    3480
ctggtagcat accaggctac ggtgtgcgcc agggctcagg ctccacctcc atcgtgggac    3540
caaatgtgga agtgtctcat acggctaaag cctacgctgc acgggccaac gcccctgctg    3600
tataggctgg gagccgttca aaacgaggtt actaccacac accccataac caaatacatc    3660
atggcatgca tgtcggctga cctggaggtc gtcacgagca cctgggtgct ggtaggcgga    3720
gtcctagcag ctctggccgc gtattgcctg acaacaggca cgtggtcat tgtgggcagg    3780 atcatcttgt ccggaaagcc ggccatcatt cccgacaggg aagtccttta ccgggagttc    3840
gatgagatgg aagagtgcgc ctcacacctc ccttacatcg aacagggaat gcagctcgcc    3900
gaacaattca acagaaggc aatcgggttg ctgcaaacag ccaccaagca agcggaggct    3960
gctgctcccg tggtggaatc caagtggcgg accctcgaag ccttctgggc gaagcatatg    4020
tggaatttca tcagcgggat acaatattta gcaggcttgt ccactctgcc tggcaacccc    4080
gcgatagcat cactgatggc attcacagcc tctatcacca gcccgctcac cacccaacat    4140
accctcctgt ttaacatcct gggggatgg gtggccgccc aacttgctcc tcccagcgct    4200
gcttctgctt tcgtaggcgc cggcatcgct ggagcggctg ttggcagcat aggccttggg    4260
aaggtgcttg tggatatttt ggcaggttat ggagcagggg tggcaggcgc gctcgtggcc    4320
tttaaggtca tgagcggcga gatgccctcc accgaggacc tggttaacct actccctgct    4380
atcctctccc ctggcgccct agtcgtcggg gtcgtgtgcg cagcgatact cgtcggcac    4440 gtgggcccag ggggagggggc tgtgcagtgg atgaaccggc tgatagcgtt cgcttcgcgg    4500
ggtaaccacg tctcccccac gcactatgtg cctgagagcg acgctgcagc acgtgtcact    4560
```

```
cagatcctct ctagtcttac catcactcag ctgctgaaga ggcttcacca gtggatcaac    4620
gaggactgct ccacgccatg ctccggctcg tggctaagag atgtttggga ttggatatgc    4680
acggtgttga ctgatttcaa gacctggctc cagtccaagc tcctgccgcg attgccggga    4740 gtcccttct tctcatgtca acgtgggtac aagggagtct ggcggggcga cggcatcatg    4800
caaaccacct gcccatgtgg agcacagatc accggacatg tgaaaaacgg ttccatgagg    4860
atcgtggggc ctaggacctg tagtaacacg tggcatggaa cattccccat taacgcgtac    4920
accacgggcc cctgcacgcc ctccccggcg ccaaattatt ctaggcgct gtggcgggtg     4980 gctgctgagg agtacgtgga ggttacgcgg gtgggggatt tccactacgt gacgggcatg    5040
accactgaca acgtaaagtg cccgtgtcag gttccggccc ccgaattctt cacagaagtg    5100
gatggggtgc ggttgcacag gtacgctcca gcgtgcaaac ccctcctacg ggaggaggtc    5160
acattcctgg tcgggctcaa tcaatacctg gttgggtcac agctcccatg cgagcccgaa    5220
ccggacgtag cagtgctcac ttccatgctc accgacccct cccacattac ggcggagacg    5280
gctaagcgta ggctgccag gggatctccc cctccttgg ccagctcatc agctagccag      5340
ctgtctgcgc cttccttgaa ggcaacatgc actacccgtc atgactcccc ggacgctgac    5400
ctcatcgagg ccaacctcct gtggcggcag gagatgggcg ggaacatcac ccgcgtggag    5460
tcagaaaata aggtagtaat tttggactct ttcgagccgc tccaagcgga ggaggatgag    5520
agggaagtat ccgttccggc ggagatcctg cggaggtcca ggaaattccc tcgagcgatg    5580
cccatatggg cacgccgga ttacaaccct ccactgttag agtcctggaa ggaccccgga     5640
tacgtccctc cagtggtaca cgggtgtcca ttgccgcctg ccaaggcccc tccgatacca    5700
cctccacgga ggaagaggac ggttgtcctg tcagaatcta ccgtgtcttc tgccttggcg    5760
gagctcgcca caaagaccct cggcagctcc gaatcgtcgg ccgtcgacag cggcacggca    5820
acggcctctc ctgaccagcc ctccgacgac ggcgacgcgg gatccgacgt tgagtcgtac    5880
tcctccatgc cccccttga ggggagccg ggggatcccg atctcagcga cgggtcttgg      5940
tctaccgtaa gcgaggaggc tagtgaggac gtcgtctgct gctcgatgtc ctacacatgg    6000
acaggcgccc tgatcacgcc atgcgctgcg gaggaaacca agctgcccat caatgcactg    6060
agcaactctt tgctccgtca ccacaacttg gtctatgcta caacatctcg cagcgcaagc    6120
ctgcggcaga agaaggtcac ctttgacaga ctgcaggtcc tggacgacca ctaccgggac    6180
gtgctcaagg agatgaaggc gaaggcgtcc acagttaagg ctaaacttct atccgtggag    6240
gaagcctgta agctgacgcc cccacattcg gccagatcta aatttggcta tggggcaaag    6300
gacgtccgga acctatccag caaggccgtt aaccacatcc gctccgtgtg gaaggacttg    6360
ctggaagaca ctgagacacc aattgacacc accatcatgg caaaaaatga ggttttctgc    6420
gtccaaccag agaagggggg ccgcaagcca gctcgcctta tcgtattccc agatttgggg    6480
gttcgtgtgt gcgagaaaat ggcccttac gatgtggtct ccaccctccc tcaggccgtg    6540
atgggctctt catacggatt ccaatactct cctggacagc gggtcgagtt cctggtgaat    6600
gcctggaaag cgaagaaatg ccctatgggc ttcgcatatg acacccgctg ttttgactca    6660
acggtcactg agaatgacat ccgtgttgag gagtcaatct accaatgttg tgacttggcc    6720
cccgaagcca gacaggccat aaggtcgctc acagagcggc tttacatcgg ggcccccctg    6780
actaattcta aagggcagaa ctgcggctat cgccggtgcc gcgcgagcgg tgtactgacg    6840
accagctgcg gtaatacccct cacatgttac ttgaaggccg ctgcggcctg tcgagctgcg    6900
```

-continued

| | |
|---|---|
| aagctccagg actgcacgat gctcgtatgc ggagacgacc ttgtcgttat ctgtgaaagc | 6960 |
| gcggggaccc aagaggacga ggcgagccta cgggccttca cggaggctat gactagatac | 7020 |
| tctgccccc ctggggaccc gcccaaacca gaatacgact tggagttgat aacatcatgc | 7080 |
| tcctccaatg tgtcagtcgc gcacgatgca tctggcaaaa gggtgtacta tctcacccgt | 7140 |
| gaccccacca ccccccttgc gcgggctgcg tgggagacag ctagacacac tccagtcaat | 7200 |
| tcctggctag gcaacatcat catgtatgcg cccaccttgt gggcaaggat gatcctgatg | 7260 |
| actcatttct tctccatcct tctagctcag gaacaacttg aaaaagccct agattgtcag | 7320 |
| atctacgggg cctgttactc cattgagcca cttgacctac tcagatcat tcaacgactc | 7380 |
| catggcctta gcgcattttc actccatagt tactctccag gtgagatcaa tagggtggct | 7440 |
| tcatgcctca ggaaacttgg ggtaccgccc ttgcgagtct ggagacatcg gccagaagt | 7500 |
| gtccgcgcta ggctactgtc ccagggggg agggctgcca cttgtggcaa gtacctcttc | 7560 |
| aactgggcag taaggaccaa gctcaaactc actccaatcc cggctgcgtc ccagttggat | 7620 |
| ttatccagct ggttcgttgc tggttacagc gggggagaca tatatcacag cctgtctcgt | 7680 |
| gcccgacccc gctggttcat gtggtgccta ctcctacttt ctgtaggggt aggcatctat | 7740 |
| ctactcccca accgatgaac ggggacctaa acactccagg ccaataggcc atcctgtttt | 7800 |
| tttccctttt ttttttttctt ttttttttttt tttttttttt tttttttttt ttctcctttt | 7860 |
| tttttcctct ttttttccttt ttcttccctt tggtggctcc atcttagccc tagtcacggc | 7920 |
| tagctgtgaa aggtccgtga gccgcttgac tgcagagagt gctgatactg gcctctctgc | 7980 |
| agatcaagt | 7989 |

```
<210> SEQ ID NO 7
<211> LENGTH: 7848
<212> TYPE: DNA
<213> ORGANISM: Hepatitis C virus

<400> SEQUENCE: 7
```

| | |
|---|---|
| gccagcccc gattgggggc gacactccac catagatcac tccctgtga ggaactactg | 60 |
| tcttcacgca gaaagcgtct agccatggcg ttagtatgag tgtcgtgcag cctccaggac | 120 |
| ccccctccc gggagagcca tagtggtctg cggaaccggt gagtacaccg gaattgccag | 180 |
| gacgaccggg tcctttcttg gatcaacccg ctcaatgcct ggagatttgg gcgtgccccc | 240 |
| gcgagactgc tagccgagta gtgttgggtc gcgaaaggcc ttgtggtact gcctgatagg | 300 |
| gtgcttgcga gtgccccggg aggtctcgta gaccgtgcac catgagcacg aatcctaaac | 360 |
| ctcaaagaaa aaccaaaggg cgcgccatga ttgaacaaga tggattgcac gcaggttctc | 420 |
| cggccgcttg ggtggagagg ctattcggct atgactggga caacagaca atcggctgct | 480 |
| ctgatgccgc cgtgttccgg ctgtcagcgc aggggcgccc ggttcttttt gtcaagaccg | 540 |
| acctgtccgg tgccctgaat gaactgcagg acgaggcagc gcggctatcg tggctggcca | 600 |
| cgacgggcgt tccttgcgca gctgtgctcg acgttgtcac tgaagcggga agggactggc | 660 |
| tgctattggg cgaagtgccg gggcaggatc tcctgtcatc tcaccttgct cctgccgaga | 720 |
| aagtatccat catggctgat gcaatgcggc ggctgcatac gcttgatccg gctacctgcc | 780 |
| cattcgacca ccaagcgaaa catcgcatcg agcgagcacg tactcggatg gaagccggtc | 840 |
| ttgtcgatca ggatgatctg gacgaagagc atcaggggct cgcgccagcc gaactgttcg | 900 |
| ccaggctcaa ggcgcgcatg cccgacggcg aggatctcgt cgtgacccat ggcgatgcct | 960 |
| gcttgccgaa tatcatggtg gaaaatggcc gcttttctgg attcatcgac tgtggccggc | 1020 |

```
tgggtgtggc ggaccgctat caggacatag cgttggctac ccgtgatatt gctgaagagc    1080
ttggcggcga atgggctgac cgcttcctcg tgctttacgg tatcgccgct cccgattcgc    1140
agcgcatcgc cttctatcgc cttcttgacg agttcttctg agtttaaaca gaccacaacg    1200
gtttccctct agcgggatca attccgcccc tctccctccc cccccctaa cgttactggc     1260 cgaagccgct tggaataagg ccggtgtgcg tttgtctata tgttattttc caccatattg    1320
ccgtcttttg gcaatgtgag ggcccggaaa cctggccctg tcttcttgac gagcattcct    1380
aggggtcttt cccctctcgc caaaggaatg caaggtctgt tgaatgtcgt gaaggaagca    1440
gttcctctgg aagcttcttg aagacaaaca acgtctgtag cgacccttg caggcagcgg     1500 aaccccccac ctggcgacag gtgcctctgc ggccaaaagc cacgtgtata agatacacct    1560
gcaaaggcgg cacaacccca gtgccacgtt gtgagttgga tagttgtgga aagagtcaaa    1620
tggctctcct caagcgtatt caacaagggg ctgaaggatg cccagaaggt accccattgt    1680
atgggatctg atctggggcc tcggtgcaca tgctttacat gtgtttagtc gaggttaaaa    1740
aacgtctagg ccccccgaac cacgggacg tggttttcct ttgaaaaaca cgataatacc     1800
atggcgccta ttacggccta ctcccaacag acgcgaggcc tacttggctg catcatcact    1860
agcctcacag gccgggacag gaaccaggtc gagggggagg tccaagtggt ctccaccgca    1920
acacaatctt tcctggcgac ctgcgtcaat ggcgtgtgtt ggactgtcta tcatggtgcc    1980
ggctcaaaga cccttgccgg cccaaagggc ccaatcaccc aaatgtacac caatgtggac    2040
caggacctcg tcggctggca agcgcccccc ggggcgcgtt ccttgacacc atgcacctgc    2100
ggcagctcgg acctttactt ggtcacgagg catgccgatg tcattccggt gcgccggcgg    2160
ggcgacagca gggggagcct actctccccc aggcccgtct cctacttgaa gggctcttcg    2220
ggcggtccac tgctctgccc ctcggggcac gctgtgggca tctttcgggc tgccgtgtgc    2280
acccgagggg ttgcgaaggc ggtggacttt gtacccgtcg agtctatgga aaccactatg    2340
cggtccccgg tcttcacgga caactcgtcc cctccggccg taccgcagac attccaggtg    2400
gcccatctac acgcccctac tggtagcggc aagagcacta aggtgccggc tgcgtatgca    2460
gcccaagggt ataaggtgct tgtcctgaac ccgtccgtcg ccgccaccct aggtttcggg    2520
gcgtatatgt ctaaggcaca tggtatcgac cctaacatca gaaccggggt aaggaccatc    2580
accacgggtg ccccccatca gtactccacc tatggcaagt tccttgccga cggtggttgc    2640
tctgggggcg cctatgacat cataatatgt gatgagtgcc actcaactga ctcgaccact    2700
atcctgggca tcggcacagt cctggaccaa gcggagacgg ctggagcgcg actcgtcgtg    2760
ctcgccaccg ctacgcctcc gggatcggtc accgtgccac atccaaacat cgaggaggtg    2820
gctctgtcca gcactggaga aatccccttt tatggcaaag ccatccccat cgagaccatc    2880 aagggggga ggcacctcat tttctgccat tccaagaaga aatgtgatga gctcgccgcg     2940
aagctgtccg gcctcggact caatgctgta gcatattacc ggggccttga tgtatccgtc    3000
ataccaacta gcggagacgt cattgtcgta gcaacggacg ctctaatgac gggctttacc    3060
ggcgatttcg actcagtgat cgactgcaat acatgtgtca cccagacagt cgacttcagc    3120
ctggacccga ccttcaccat tgagacgacg accgtgccac aagacgcggt gtcacgctcg    3180
cagcggcgag gcaggactgg tagggcagg atgggcattt acaggtttgt gactccagga     3240
gaacggccct cgggcatgtt cgattcctcg gttctgtgcg agtgctatga cgcgggctgt    3300
gcttggtacg agctcacgcc cgccgagacc tcagttaggt tgcgggctta cctaaacaca    3360
```

```
ccagggttgc ccgtctgcca ggaccatctg gagttctggg agagcgtctt tacaggcctc    3420
acccacatag acgcccattt cttgtcccag actaagcagg caggagacaa cttcccctac    3480
ctggtagcat accaggctac ggtgtgcgcc agggctcagg ctccacctcc atcgtgggac    3540
caaatgtgga agtgtctcat acggctaaag cctacgctgc acgggccaac gcccctgctg    3600
tataggctgg gagccgttca aaacgaggtt actaccacac accccataac caaatacatc    3660
atggcatgca tgtcggctga cctggaggtc gtcacgagca cctgggtgct ggtaggcgga    3720
gtcctagcag ctctggccgc gtattgcctg acaacaggca gcgtggtcat tgtgggcagg    3780
atcatcttgt ccggaaagcc ggccatcatt cccgacaggg aagtccttta ccgggagttc    3840
gatgagatgg aagagtgcgc ctcacacctc ccttacatcg aacagggaat gcagctcgcc    3900
gaacaattca aacagaaggc aatcggggttg ctgcaaacag ccaccaagca agcggaggct    3960
gctgctcccg tggtggaatc caagtggcgg accctcgaag ccttctgggc gaagcatatg    4020
tggaatttca tcagcgggat acaatattta gcaggcttgt ccactctgcc tggcaacccc    4080
gcgatagcat cactgatggc attcacagcc tctatcacca gcccgctcac cacccaacat    4140
accctcctgt ttaacatcct gggggatggg gtggccgccc aacttgctcc tcccagcgct    4200
gcttctgctt tcgtaggcgc cggcatcgct ggagcggctg ttggcagcat aggccttggg    4260
aaggtgcttg tggatatttt ggcaggttat ggagcagggg tggcaggcgc gctcgtggcc    4320
tttaaggtca tgagcggcga gatgcctcc accgaggacc tggttaacct actccctgct    4380
atcctctccc ctggcgccct agtcgtcggg gtcgtgtgcg cagcgatact gcgtcggcac    4440
gtgggcccag ggggaggggc tgtgcagtgg atgaaccggc tgatagcgtt cgcttcgcgg    4500
ggtaaccacg tctcccccac gcactatgtg cctgagagcg acgctgcagc acgtgtcact    4560
cagatcctct ctagtcttac catcactcag ctgctgaaga ggcttcacca gtggatcaac    4620
gaggactgct ccacgccatg ctccggctcg tggctaagag atgtttggga ttggatatgc    4680
acggtgttga ctgatttcaa gacctggctc cagtccaagc tcctgccgcg attgccggga    4740 gtcccccttct tctcatgtca acgtgggtac aagggagtct ggcggggcga cggcatcatg    4800
caaaccacct gcccatgtgg agcacagatc accggacatg tgaaaaacgg ttccatgagg    4860
atcgtggggc ctaggacctg tagtaacacg tggcatggaa cattccccat taacgcgtac    4920
accacgggcc cctgcacgcc ctcccccggcg ccaaattatt ctagggcgct gtggcgggtg    4980
gctgctgagg agtacgtgga ggttacgcgg gtgggggatt tccactacgt gacgggcatg    5040
accactgaca acgtaaagtg cccgtgtcag gttccggccc ccgaattctt cacagaagtg    5100
gatggggtgc ggttgcacag gtacgctcca cgcgtgcaaa ccctcctacg ggaggaggtc    5160
acattcctgg tcgggctcaa tcaatacctg gttgggtcac agctcccatg cgagcccgaa    5220
ccggacgtag cagtgctcac ttccatgctc accgacccct cccacattac ggcggagacg    5280
gctaagcgta ggctggccag gggatctccc ccctccttgg ccagctcatc agctagccag    5340
ctgtactctt tcgagccgct ccaagcggag gaggatgaga gggaagtatc cgttccggcg    5400
gagatcctgc ggaggtccag gaaattccct cgagcgatgc ccatatgggc acgcccggat    5460
tacaaccctc cactgttaga gtcctggaag gacccggact acgtccctcc agtggtacac    5520
gggtgtccat tgccgcctgc caaggcccct ccgataccac ctccacgag gaagaggacg    5580 gttgtcctgt cagaatctac cgtgtcttct gccttggcgg agctcgccac aaagaccttc    5640
ggcagctccg aatcgtcggc cgtcgacagc ggcacggcaa cggcctctcc tgaccagccc    5700
tccgacgacg gcgacgcggg atccgacgtt gagtcgtact cctccatgcc ccccttgag    5760
```

```
ggggagccgg gggatcccga tctcagcgac gggtcttggt ctaccgtaag cgaggaggct    5820
agtgaggacg tcgtctgctg ctcgatgtcc tacacatgga caggcgccct gatcacgcca    5880
tgcgctgcgg aggaaaccaa gctgccatc  aatgcactga gcaactcttt gctccgtcac    5940
cacaacttgg tctatgctac aacatctcgc agcgcaagcc tgcgcagaa  gaaggtcacc    6000 tttgacagac tgcaggtcct ggacgaccac taccgggacg tgctcaagga gatgaaggcg    6060
aaggcgtcca cagttaaggc taaacttcta tccgtggagg aagcctgtaa gctgacgccc    6120
ccacattcgg ccagatctaa atttggctat ggggcaaagg acgtccggaa cctatccagc    6180
aaggccgtta accacatccg ctccgtgtgg aaggacttgc tggaagacac tgagacacca    6240
attgacacca ccatcatggc aaaaaatgag gttttctgcg tccaaccaga aaggggggc     6300 cgcaagccag ctcgccttat cgtattccca gatttggggg ttcgtgtgtg cgagaaaatg    6360 gcccttacg  atgtggtctc caccctccct caggccgtga tgggctcttc atacggattc    6420
caatactctc ctggacagcg ggtcgagttc ctggtgaatg cctggaaagc gaagaaatgc    6480
cctatgggct tcgcatatga cacccgctgt tttgactcaa cggtcactga gaatgacatc    6540
cgtgttgagg agtcaatcta ccaatgttgt gacttggccc ccgaagccag acaggccata    6600
aggtcgctca cagagcggct ttacatcggg ggccccctga ctaattctaa agggcagaac    6660
tgcggctatc gccggtgccg cgcgagcggt gtactgacga ccagctgcgg taataccctc    6720
acatgttact tgaaggccgc tgcggcctgt cgagctgcga agctccagga ctgcacgatg    6780
ctcgtatgcg gagacgacct tgtcgttatc tgtgaaagcg cggggaccca agaggacgag    6840
gcgagcctac gggccttcac ggaggctatg actagatact ctgcccccc  tggggacccg    6900 cccaaaccaa aatacgactt ggagttgata acatcatgct cctccaatgt gtcagtcgcg    6960
cacgatgcat ctggcaaaag ggtgtactat ctcacccgtg accccaccac ccccccttgcg    7020 cgggctgcgt gggagacagc tagacacact ccagtcaatt cctggctagg caacatcatc    7080
atgtatgcgc ccaccttgtg ggcaaggatg atcctgatga ctcatttctt ctccatcctt    7140
ctagctcagg aacaacttga aaaagcccta gattgtcaga tctacggggc ctgttactcc    7200
attgagccac ttgacctacc tcagatcatt caacgactcc atggccttag cgcattttca    7260
ctccatagtt actctccagg tgagatcaat agggtggctt catgcctcag gaaacttggg    7320
gtaccgccct tgcgagtctg gagacatcgg gccagaagtg tccgcgctag gctactgtcc    7380
caggggggga gggctgccac ttgtggcaag tacctcttca actgggcagt aaggaccaag    7440
ctcaaactca ctccaatccc ggctgcgtcc cagttggatt tatccagctg gttcgttgct    7500
ggttacagcg gggagacat  atatcacagc ctgtctcgtg cccgaccccg ctggttcatg    7560
tggtgcctac tcctactttc tgtaggggta ggcatctatc tactccccaa ccgatgaacg    7620
gggacctaaa cactccaggc caataggcca tcctgttttt ttccctttt  ttttttcttt    7680 tttttttttt tttttttttt tttttttttt tctccttttt ttttcctctt ttttccttt     7740 tctttccttt ggtggctcca tcttagccct agtcacggct agctgtgaaa ggtccgtgag    7800
ccgcttgact gcagagagtg ctgatactgg cctctctgca gatcaagt               7848
```

<210> SEQ ID NO 8
<211> LENGTH: 7987
<212> TYPE: DNA
<213> ORGANISM: Hepatitis C virus

<400> SEQUENCE: 8

```
gccagccccc gattgggggc gacactccac catagatcac tccnctgtga ggaactactg    60
tcttcacgca gaaagcgtct agccatggcg ttagtatgag tgtcgtgcag cctccaggac   120
ccccctccc gggagagcca tagtggtctg cggaaccggt gagtacaccg gaattgccag    180
gacgaccggg tcctttcttg gatcaacccg ctcaatgcct ggagatttgg gcgtgccccc   240
gcgagactgc tagccgagta gtgttgggtc gcgaaaggcc ttgtggtact gcctgatagg   300
gtgcttgcga gtgcccnggg aggtctcgta gaccgtgcac catgagcacg aatcctaaac   360
ctcaaagaaa aaccaaaggg cgcgccatga ttgaacaaga tggattgcac gcaggttctc   420
cggccgcttg ggtggagagg ctattcggct atgactgggc acaacagaca atcggctgct   480
ctgatgccgc cgtgttccgg ctgtcagcgc aggggcgccc ggttcttttt gtcaagaccg   540
acctgtccgg tgccctgaat gaactgcagg acgaggcagc gcggctatcg tggctggcca   600
cgacgggcgt tccttgcgca gctgtgctcg acgttgtcac tgaagcggga agggactggc   660
tgctattggg cgaagtgccg gggcaggatc tcctgtcatc tcaccttgct cctgccgaga   720
aagtatccat catggctgat gcaatgcggc ggctgcatac gcttgatccg gctacctgcc   780
cattcgacca ccaagcgaaa catcgcatcg agcgagcacg tactcggatg aagccggtc    840
ttgtcgatca ggatgatctg gacgaagagc atcaggggct cgcgccagcc gaactgttcg   900
ccaggctcaa ggcgcgcatg cccgacggcg aggatctcgt cgtgacccat ggcgatgcct   960
gcttgccgaa tatcatggtg gaaaatggcc gcttttctgg attcatcgac tgtggccggc  1020
tgggtgtggc ggaccgctat caggacatag cgttggctac ccgtgatatt gctgaagagc  1080
ttggcggcga atgggctgac cgcttcctcg tgctttacgg tatcgccgct cccgattcgc  1140
agcgcatcgc cttctatcgc cttcttgacg agttcttctg agtttaaaca gaccacaacg  1200
gtttccctct agcgggatca attccgcccc tctccctccc ccccctaa cgttactggc    1260
cgaagccgct tggaataagg ccggtgtgcg tttgtctata tgttattttc caccatattg  1320
ccgtcttttg gcaatgtgag ggcccggaaa cctggccctg tcttcttgac gagcattcct  1380
aggggtcttt cccctctcgc caaaggaatg caaggtctgt tgaatgtcgt gaaggaagca  1440
gttcctctgg aagcttcttg aagacaaaca acgtctgtag cgaccctttg caggcagcgg  1500
aaccccccac ctggcgacag tgcctctgc ggccaaaagc cacgtgtata agatacacct   1560
gcaaaggcgg cacaacccca gtgccacgtt gtgagttgga tagttgtgga aagagtcaaa  1620
tggctctcct caagcgtatt caacaagggg ctgaaggatg cccagaaggt accccattgt  1680
atgggatctg atctggggcc tcggtgcaca tgctttacat gtgtttagtc gaggttaaaa  1740
aacgtctagg ccccccgaac cacggggacg tggttttcct ttgaaaaaca cgataatacc  1800
atggcgccta ttacggccta ctcccaacag acgcgaggcc tacttggctg catcatcact  1860
agcctcacag gccgggacag gaaccaggtc gagggggagg tccaagtggt ctccaccgca  1920
acacaatctt tcctggcgac ctgcgtcaat ggcgtgtgtt ggactgtcta tcatggtgcc  1980
ggctcaaaga cccttgccgg cccaagggc caatcaccc aaatgtacac caatgtggac    2040
caggacctcg tcggctggcg agcgcccccc ggggcgcgtt ccttgacacc atgcacctgc  2100
ggcagctcgg accttactt ggtcacgagg catgccgatg tcattccggt gcgccggcgg   2160
ggcgacagca gggggagcct actctccccc aggcccgtct cctacttgaa gggctcttcg  2220
ggcggtccac tgctctgccc ctcggggcac gctgtgggca tctttcgggc tgccgtgtgc  2280
acccgagggg ttgcgaaggc ggtggacttt gtaccgtcg agtctatgga aaccactatg    2340
cggtccccgg tcttcacgga caactcgtcc cctccggccg taccgcagac attccaggtg  2400
```

```
gcccatctac acgcccctac tggtagcggc aagagcacta aggtgccggc tgcgtatgca    2460
gcccaagggt ataaggtgct tgtcctgaac ccgtccgtcg ccgccaccct aggtttcggg    2520
gcgtatatgt ctaaggcaca tggtatcgac cctaacatca gaaccggggt aaggaccatc    2580 accacggtg cccccatcac gtactccacc tatggcaagt ttcttgccga cggtggttgc     2640
tctgggggcg cctatgacat cataatatgt gatgagtgcc actcaactga ctcgaccact    2700
atcctgggca tcggcacagt cctggaccaa gcggagacgg ctggagcgcg actcgtcgtg    2760
ctcgccaccg ctacgcctcc gggatcggtc accgtgccac atccaaacat cgaggaggtg    2820
gctctgtcca gcactggaga atccccttt tatggcaaag ccatcccat cgagaccatc      2880 aagggggga ggcacctcat tttctgccat tccaagaaga aatgtgatga gctcgccgcg     2940
aagctgtccg gcctcggact caatgctgta gcatattacc ggggccttga tgtatccgtc    3000
ataccaacta gcggagacgt cattgtcgta gcaacggacg ctctaatgac gggctttacc    3060
ggcgatttcg actcagtgat cgactgcaat acatgtgtca cccagacagt cgacttcagc    3120
ctggacccga ccttcaccat tgagacgacg accgtgccac aagacgcggt gtcacgctcg    3180
cagcggcgag gcaggactgg taggggcagg atgggcattt acaggtttgt gactccagga    3240 gaacggcct cgggcatgtt cgattcctcg gttctgtgcg agtgctatga cgcgggctgt     3300
gcttggtacg agctcacgcc cgccgagacc tcagttaggt tgcgggctta cctaaacaca    3360
ccagggttgc ccgtctgcca ggaccatctg gagttctggg agagcgtctt tacaggcctc    3420
acccacatag acgcccattt cttgtcccag actaagcagg caggagacaa cttcccctac    3480
ctggtagcat accaggctac ggtgtgcgcc agggctcagg ctccacctcc atcgtgggac    3540
caaatgtgga agtgtctcat acggctaaag cctacgctgc acgggccaac gcccctgctg    3600
tataggctgg gagccgttca aaacgaggtt actaccacac accccataac caaatacatc    3660
atggcatgca tgtcggctga cctggaggtc gtcacgagca cctgggtgct ggtaggcgga    3720
gtcctagcag ctctggccgc gtattgcctg acaacaggca gcgtggtcat tgtgggcagg    3780
atcatcttgt ccggaaagcc ggccatcatt cccgacaggg aagtccttta ccgggagttc    3840
gatgagatgg aagagtgcgc ctcacacctc ccttacatcg aacagggaat gcagctcgcc    3900
gaacaattca aacagaaggc aatcgggttg ctgcaaacag ccaccaagca agcggaggct    3960
gctgctcccg tggtggaatc caagtggcgg accctcgaag ccttctgggc gaagcatatg    4020 tggaattca tcagcgggat acaatattta gcaggcttgt ccactctgcc tggcaacccc     4080
gcgatagcat cactgatggc attcacagcc tctatcacca gcccgctcac cacccaacat    4140
accctcctgt ttaacatcct gggggatgg gtggccgccc aacttgctcc tcccagcgct     4200
gcttctgctt tcgtaggcgc cggcatcgct ggagcggctg ttggcagcat aggccttggg    4260
aaggtgcttg tggatatttt ggcaggttat ggagcagggg tggcaggcgc gctcgtggcc    4320
tttaaggtca tgagcggcga gatgcctc accgaggacc tggttaacct actccctgct     4380
atcctctccc ctggcgccct agtcgtcggg gtcgtgtgcg cagcgatact gcgtcggcac    4440
gtgggcccag gggagggggc tgtgcagtgg atgaaccggc tgatagcgtt cgcttcgcgg    4500
ggtaaccacg tctcccccac gcactatgtg cctgagagcg acgctgcagc acgtgtcact    4560
cagatcctct ctagtcttac catcactcag ctgctgaaga ggcttcacca gtggatcaac    4620
gaggactgct ccacgccatg ctccggctcg tggctaagag atgtttggga ttggatatgc    4680
acggtgttga ctgatttcaa gacctggctc cagtccaagc tcctgccgcg attgccggga    4740
```

```
gtcccttct tctcatgtca acgtgggtac aagggagtct ggcggggcga cggcatcatg    4800
caaaccacct gcccatgtgg agcacagatc accggacatg tgaaaaacgg ttccatgagg    4860 atcgtgggc ctaggacctg tagtaacacg tggcatggaa cattccccat taacgcgtac    4920
accacgggcc cctgcacgcc ctccccggcg ccaaattatt ctagggcgct gtggcgggtg    4980
gctgctgagg agtacgtgga ggttacgcgg gtgggggatt tccactacgt gacgggcatg    5040
accactgaca acgtaaagtg cccgtgtcag gttccggccc ccgaattctt cacagaagtg    5100
gatggggtgc ggttgcacag gtacgctcca gcgtgcaaac ccctcctacg ggaggaggtc    5160
acattcctgg tcgggctcaa tcaataccctg gttgggtcac agctcccatg cgagcccgaa    5220
ccggacgtag cagtgctcac ttccatgctc accgacccct ccacattac ggcggagacg    5280 gctaagcgta ggctggccag gggatctccc ccctccttgg ccagctcatc agctatccag    5340
ctgtctgcgc cttccttgaa ggcaacatgc actacccgtc atgactcccc ggacgctgac    5400
ctcatcgagg ccaacctcct gtggcggcag gagatgggcg ggaacatcac ccgcgtggag    5460
tcagaaaata aggtagtaat tttggactct ttcgagccgc tccaagcgga ggaggatgag    5520
agggaagtat ccgttccggc ggagatcctg cggaggtcca ggaaattccc tcgagcgatg    5580
cccatatggg cacgcccgga ttacaaccct ccactgttag agtcctggaa ggacccggac    5640
tacgtccctc cagtggtaca cgggtgtcca ttgccgcctg ccaaggcccc tccgatacca    5700
cctccacgga ggaagaggac ggttgtcctg tcagaatcta ccgtgtcttc tgccttggcg    5760
gagctcgcca caaagacctt cggcagctcc gaatcgtcgg ccgtcgacag cggcacggca    5820
acggcctctc ctgaccagcc ctccgacgac ggcgacgcgg gatccgacgt tgagtcgtac    5880
tcctccatgc ccccccttga gggggagccg ggggatcccg atctcagcga cgggtcttgg    5940
tctaccgtaa gcgaggaggc tagtgaggac gtcgtctgct gctcgatgtc ctacacatgg    6000
acaggcgccc tgatcacgcc atgcgctgcg gaggaaacca agctgcccat caatgcactg    6060
agcaactctt tgctccgtca ccacaacttg gtctatgcta caacatctcg cagcgcaagc    6120
ctgcggcaga agaaggtcac ctttgacaga ctgcaggtcc tggacgacca ctaccgggac    6180
gtgctcaagg agatgaaggc gaaggcgtcc acagttaagg ctaaacttct atccgtggag    6240
gaagcctgta agctgacgcc cccacattcg gccagatcta aatttggcta tgggcaaag    6300 gacgtccgga acctatccag caaggccgtt aaccacatcc gctccgtgtg gaaggacttg    6360
ctggaagaca ctgagacacc aattgacacc accatcatgg caaaaaatga ggttttctgc    6420
gtccaaccag agaagggggg ccgcaagcca gctcgcctta tcgtattccc agatttgggg    6480
gttcgtgtgt gcgagaaaat ggccctttac gatgtggtct ccaccctccc tcaggccgtg    6540
atgggctctt catacggatt ccaatactct cctggacagc gggtcgagtt cctggtgaat    6600
gcctggaaag cgaagaaatg ccctatgggc ttcgcatatg acaccccgctg ttttgactca    6660 acggtcactg agaatgacat ccgtgttgag gagtcaatct accaatgttg gacttggcc    6720 cccgaagcca gacaggccat aaggtcgctc acagagcggc tttacatcgg ggcccctg    6780 actaattcta aagggcagaa ctgccggtat cgccggtgcc gcgcgagcgg tgtactgacg    6840
accagctgcg gtaatacccct cacatgttac ttgaaggccg ctgcggcctg tcgagctgcg    6900
aagctccagg actgcacgat gctcgtatgc ggagacgacc ttgtcgttat ctgtgaaagc    6960
gcggggaccc aagaggacga ggcgagccta cgggccttca cggaggctat gactagatac    7020 tctgccccc ctgggaccc gcccaaacca gaatacgact tggagttgat aacatcatgc    7080
tcctccaatg tgtcagtcgc gcacgatgca tctggcaaaa gggtgtacta tctcacccgt    7140
```

-continued

```
gaccccacca cccccttgc gcgggctgcg tgggagacag ctagacacac tccagtcaat    7200
tcctggctag gcaacatcat catgtatgcg cccaccttgt gggcaaggat gatcctgatg    7260
actcatttct tctccatcct tctagctcag gaacaacttg aaaaagcccct agattgtcag    7320
atctacgggg cctgttactc cattgagcca cttgacctac ctcagatcat tcaacgactc    7380
catggcctta gcgcattttc actccatagt tactctccag gtgagatcaa tagggtggct    7440
tcatgcctca ggaaacttgg ggtaccgccc ttgcgagtct ggagacatcg ggccagaagt    7500
gtccgcgcta ggctactgtc ccaggggggg agggctgcca cttgtggcaa gtacctcttc    7560
aactgggcag taaggaccaa gctcaaactc actccaatcc cggctgcgtc ccagttggat    7620
ttatccagct ggttcgttgc tggttacagc ggggagaca tatatcacag cctgtctcgt    7680
gcccgacccc gctggttcat gtggtgccta ctcctacttt ctgtagggt aggcatctat    7740
ctactcccca accgatgaac ggggagctaa acactccagg ccaataggcc atcctgtttt    7800
tttccttttt ttttttttctt tttttttttt tttttttttt tttttttttt ctccttttttt    7860
tttcctcttt ttttccttt ctttcctttg gtggctccat cttagcccta gtcacggcta    7920
gctgtgaaag gtccgtgagc cgcttgactg cagagagtgc tgatactggc ctctctgcag    7980
atcaagt                                                              7987
```

<210> SEQ ID NO 9
<211> LENGTH: 7989
<212> TYPE: DNA
<213> ORGANISM: Hepatitis C virus

<400> SEQUENCE: 9

```
gccagccccc gattgggggc gacactccac catagatcac tcccctgtga ggaactactg      60
tcttcacgca gaaagcgtct agccatggcg ttagtatgag tgtcgtgcag cctccaggac     120
ccccctccc gggagagcca tagtggtctg cggaaccggt gagtacaccg gaattgccag     180
gacgaccggg tcctttcttg atcaacccg ctcaatgcct ggagatttgg gcgtgcccccc     240
gcgagactgc tagccgagta gtgttgggtc gcgaaaggcc ttgtggtact gcctgatagg     300
gtgcttgcga gtgccccggg aggtctcgta gaccgtgcac catgagcacg aatcctaaac     360
ctcaaagaaa aaccaaaggg cgcgccatga ttgaacaaga tggattgcac gcaggttctc     420
cggccgcttg ggtggagagg ctattcggct atgactgggc acaacagaca atcggctgct     480
ctgatgccgc cgtgttccgg ctgtcagcgc aggggcgccc ggttcttttt gtcaagaccg     540
acctgtccgg tgccctgaat gaactgcagg acgaggcagc gcggctatcg tggctggcca     600
cgacgggcgt tccttgcgca gctgtgctcg acgttgtcac tgaagcggga agggactggc     660
tgctattggg cgaagtgccg gggcaggatc tcctgtcatc tcaccttgct cctgccgaga     720
aagtatccat catggctgat gcaatgcggc ggctgcatac gcttgatccg gctacctgcc     780
cattcgacca ccaagcgaaa catcgcatcg agcgagcacg tactcggatg gaagccggtc     840
ttgtcgatca ggatgatctg gacgaagagc atcagggggct cgcgccagcc gaactgttcg     900
ccaggctcaa ggcgcgcatg cccgacggcg aggatctcgt cgtgacccat ggcgatgcct     960
gcttgccgaa tatcatggtg gaaaatggcc gcttttctgg attcatcgac tgtggccggc    1020
tgggtgtggc ggaccgctat caggacatag cgttggctac ccgtgatatt gctgaagagc    1080
ttggcggcga atgggctgac cgcttcctcg tgctttacgg tatcgccgct cccgattcgc    1140
agcgcatcgc cttctatcgc cttcttgacg agttcttctg agtttaaaca gaccacaacg    1200
```

```
gtttccctct agcgggatca attccgcccc tctccctccc cccccccta acgttactggc    1260
cgaagccgct tggaataagg ccggtgtgcg tttgtctata tgttattttc caccatattg    1320
ccgtcttttg gcaatgtgag ggcccggaaa cctggccctg tcttcttgac gagcattcct    1380
aggggtcttt cccctctcgc caaaggaatg caaggtctgt tgaatgtcgt gaaggaagca    1440
gttcctctgg aagcttcttg aagacaaaca acgtctgtag cgacccttg caggcagcgg     1500
aaccccccac ctggcgacag gtgcctctgc ggccaaaagc cacgtgtata agatacacct    1560
gcaaaggcgg cacaacccca gtgccacgtt gtgagttgga tagttgtgga aagagtcaaa    1620
tggctctcct caagcgtatt caacaagggg ctgaaggatg cccagaaggt accccattgt    1680
atgggatctg atctggggcc tcggtgcaca tgctttacat gtgtttagtc gaggttaaaa    1740
aacgtctagg cccccgaac cacggggacg tggttttcct ttgaaaaaca cgataatacc     1800
atggcgccta ttacggccta ctcccaacag acgcgaggcc tacttggctg catcatcact    1860
agcctcacag gccgggacag gaaccaggtc gaggggagg tccaagtggt ctccaccgca     1920
acacaatctt tcctggcgac ctgcgtcaat ggcgtgtgtt ggactgtcta tcatggtgcc    1980
ggctcaaaga cccttgccgg cccaaagggc ccaatcaccc aaatgtacac caatgtggac    2040
caggacctcg tcggctggca agcgcccccc ggggcgcgtt ccttgacacc atgcacctgc    2100
ggcagctcgg acctttactt ggtcacgagg catgccgatg tcattccggt cgcccggcgg    2160
ggcgacagca gggggagcct actctccccc aggcccgtct cctacttgaa gggctcttcg    2220
ggcggtccac tgctctgccc ctcggggcac gctgtgggca tctttcgggc tgccgtgtgc    2280
acccgagggg ttgcgaaggc ggtggacttt gtacccgtcg agtctatgga aaccactatg    2340
cggtccccgg tcttcacgga caactcgtcc cctccggccg taccgcagac attccaggtg    2400
gcccatctac acgcccctac tggtagcggc aagagcacta aggtgccggc tgcgtatgca    2460
gcccaagggt ataaggtgct tgtcctgaac ccgtccgtcg ccgccaccct aggtttcggg    2520
gcgtatatgt ctaaggcaca tggtatcgac cctaacatca gaaccggggt aaggaccatc    2580
accacgggtg cccccatcac gtactccacc tatggcaagt tcttgccga cggtggttgc     2640
tctgggggcg cctatgacat cataatatgt gatgagtgcc actcaactga ctcgaccact    2700
atcctgggca tcggcacagt cctggaccaa gcggagacgg ctggagcgcg actcgtcgtg    2760
ctcgccaccg ctacgcctcc gggatcggtc accgtgccac atccaaacat cgaggaggtg    2820
gctctgtcca gcactggaga aatccccttt tatggcaaag ccatccccat cgagaccatc    2880
aagggggga ggcacctcat tttctgccat tccaagaaga atgtgatga gctcgccgcg      2940
aagctgtccg gcctcggact caatgctgta gcatattacc ggggccttga tgtatccgtc    3000
ataccaacta gcggagacgt cattgtcgta gcaacggacg ctctaatgac gggctttacc    3060
ggcgatttcg actcagtgat cgactgcaat acatgtgtca cccagacagt cgacttcagc    3120
ctggacccga ccttcaccat tgagacgacg accgtgccac aagacgcggt gtcacgctcg    3180
cagcggcgag gcaggactgg tagggggcagg atgggcattt acaggtttgt gactccagga    3240
gaacggcccc tcggcatgtt cgattcctcg gttctgtgcg agtgctatga cgcgggctgt    3300
gcttggtacg agctcacgcc cgccgagacc tcagttaggt tgcgggctta cctaaacaca    3360
ccagggttgc ccgtctgcca ggaccatctg gagttctggg agagcgtctt tacaggcctc    3420
acccacatag acgcccattt cttgtcccag actaagcagg caggagacaa cttcccctac    3480
ctggtagcat accaggctac ggtgtgcgcc agggctcagg ctccacctcc atcgtgggac    3540
caaatgtggg agtgtctcat acggctaaag cctacgctgc acgggccaac gcccctgctg    3600
```

-continued

```
tataggctgg gagccgttca aaacgaggtt actaccacac accccataac caaatacatc    3660
atggcatgca tgtcggctga cctggaggtc gtcacgagca cctgggtgct ggtaggcgga    3720
gtcctagcag ctctggccgc gtattgcctg acaacaggca gcgtggtcat tgtgggcagg    3780
atcatcttgt ccggaaagcc ggccatcatt cccgacaggg aagtccttta ccgggagttc    3840
gatgagatga aagagtgcgc ctcacacctc ccttacatcg aacagggaat gcagctcgcc    3900
gaacaattca aacagaaggc aatcgggttg ctgcaaacag ccaccaagca agcggaggct    3960
gctgctcccg tggtggaatc caagtggcgg accctcgaag ccttctgggc gaagcatatg    4020
tggaatttca tcagcgggat acaatattta gcaggcttgt ccactctgcc tggcaacccc    4080
gcgatagcat cactgatggc attcacagcc tctatcacca gcccgctcac cacccaacat    4140
accctcctgt ttaacatcct gggggggatgg gtggccgccc aacttgctcc tcccagcgct    4200
gcttctgctt tcgtaggcgc cggcatcgct ggagcggctg ttggcagcat aggccttggg    4260
aaggtgcttg tggatatttt ggcaggttat ggagcagggg tggcaggcgc gctcgtggcc    4320
tttaaggtca tgagcggcga gatgccctcc accgaggacc tggttaacct actccctgct    4380
atcctctccc ctggcgccct agtcgtcggg gtcgtgtgcg cagcgatact gcgtcggcac    4440
gtgggcccag gggaggggc tgtgcagtgg atgaaccggc tgatagcgtt cgcttcgcgg    4500
ggtaaccacg tctcccccac gcactatgtg cctgagagcg acgctgcagc acgtgtcact    4560
cagatcctct ctggtcttac catcactcag ctgctgaaga ggcttcacca gtggatcaac    4620
gaggactgct ccacgccatg ctccggctcg tggctaagag atgtttggga ttggatatgc    4680
acggtgttga ctgatttcaa gacctggctc cagtccaagc tcctgccgcg attgccggga    4740
gtccccttct tctcatgtca acgtgggtac aagggagtct ggcggggcga cggcatcatg    4800
caaaccacct gcccatgtgg agcacagatc accggacatg tgaaaaacgg ttccatgagg    4860
atcgtggggc ctaggacctg tagtaacacg tggcatggaa cattccccat taacgcgtac    4920
accacgggcc cctgcacgcc ctccccggcg ccaaattatt ctagggcgct gtggcgggtg    4980
gctgctgagt agtacgtgga ggttacgcgg gtggggatt tccactacgt gacgggcatg    5040
accactgaca acgtaaagtg cccgtgtcag gttccggccc ccgaattctt cacagaagtg    5100
gatggggtgc ggttgcacag gtacgctcca gcgtgcaaac ccctcctacg ggaggaggtc    5160
acattcctgg tcgggctcaa tcaatacctg gttgggtcac agctcccatg cgagcccgaa    5220
ccggacgtag cagtgctcac ttccatgctc accgacccct cccacattac ggcggagacg    5280
gctaagcgtg ggctggccag gggatctccc ccctccttgg ccagctcatc agctagccag    5340
ctgtctgcgc cttccttgaa ggcaacatgc actaccgtc atgactcccc ggacgctgac    5400
ctcatcgagg ccaacctcct gtggcggcag gagatgggcg gaacatcac ccgcgtggag    5460 tcagaaaata aggtagtaat tttggactct ttcgagccgc tccaagcgga ggaggatgag    5520
agggaagtat ccgttccggc ggagatcctg cggaggtcca ggaaattccc tcgagcgatg    5580
cccatatggg cacgcccgga ttacaaccct ccactgttag agtcctggaa ggacccggac    5640
tacgtccctc cagtggtaca cgggtgtcca ttgccgcctg caaggcccc tccgatacca    5700 cctccacgga ggaagaggac ggttgtcctg tcagaatcta ccgtgtcttc tgccttggcg    5760
gagctcgcca caaagacctt cggcagctcc gaatcgtcgc ccgtcgacag cggcacggca    5820
acggcctctc ctgaccagcc ctccgacgac ggcgacgcgg gatccgacgt tgagtcgtac    5880
tcctccatgc ccccccttga gggggagccg ggggatcccg atctcagcga cgggtcttgg    5940
```

```
tctaccgtaa gcgaggaggc tagtgaggac gtcgtctgct gctcgatgtc ctacacatgg    6000
acaggcgccc tgatcacgcc atgcgctgcg gaggaaacca agctgcccat caatgcactg    6060
agcaactctt tgctccgtca ccacaacttg gtctatgcta caacatctcg cagcgcaagc    6120
ctgcggcaga agaaggtcac ctttgacaga ctgcaggtcc tggacgacca ctaccgggac    6180
gtgctcaagg agatgaaggc gaaggcgtcc acagttaagg ctaaacttct atccgtggag    6240
gaagcctgta agctgacgcc cccacattcg gccagatcta aatttggcta tggggcaaag    6300
gacgtccgga acctatccag caaggccgtt aaccacatcc gctccgtgtg aaggacttg    6360 ctggaagaca ctgagacacc aattgacacc accatcatgg caaaaaatga ggttttctgc    6420
gtccaaccag agaaggggg ccgcaagcca gctcgcctta cgtattccc agatttgggg    6480 gttcgtgtgt gcgagaaaat gccctttac gatgtggtct ccaccctccc tcaggccgtg    6540
atgggctctt catacggatt ccaatactct cctggacagc gggtcgagtt cctggtgaat    6600
gcctggaaag cgaagaaatg ccctatgggc ttcgcatatg acaccgcctg ttttgactca    6660
acggtcactg agaatgacat ccgtgttgag gagtcaatct accaatgttg tgacttggcc    6720
cccgaagcca gacaggccat aagggtcgctc acagagcggc tttacatcgg ggccccctg    6780 actaattcta agggcagaa ctgcggctat cgccggtgcc gcgcgagcgg tgtactgacg    6840
accagctgcg gtaataccct cacatgttac ttgaaggccg ctgcggcctg tcgagctgcg    6900
aagctccagg actgcacgat gctcgtatgc ggagacgacc ttgtcgttat ctgtgaaagc    6960
gcggggaccc aagaggacga ggcgagccta cgggccttca cggaggctat gactagatac    7020
tctgcccccc ctgggaccc gcccaaacca gaatacgact tggagttgat aacatcatgc    7080
tcctccaatg tgtcagtcgc gcacgatgca tctggcaaaa gggtgtacta tctcacccgt    7140
gaccccacca cccccttgc gcgggctgcg tgggagacag ctagacacac tccagtcaat    7200
tcctggctag caacatcat catgtatgcg cccaccttgt gggcaaggat gatcctgatg    7260
actcatttct tctccatcct tctagctcag gaacaacttg aaaaagccct agattgtcag    7320
atctacgggg cctgttactc cattgagcca cttgacctac ctcagatcat tcaacgactc    7380
catggcctta gcgcattttc actccatagt tactctccag gtgagatcaa tagggtggct    7440
tcatgcctca ggaaacttgg ggtaccgccc ttgcgagtct ggagacatcg gccagaagt    7500 gtccgcgcta ggctactgtc ccaggggggg agggctgcca cttgtggcaa gtacctcttc    7560
aactgggcag taaggaccaa gctcaaactc actccaatcc cggctgcgtc ccagttggat    7620
ttatccagct ggttcgttgc tggttacagc ggggagaca tatatcacag cctgtctcgt    7680
gcccgacccc gctggttcat gtggtgccta ctcctacttt ctgtaggggt aggcatctat    7740
ctactcccca accgatgaac ggggacctaa acactccagg ccaataggcc atcctgtttt    7800 tttcccttt tttttttctt tttttttttt tttttttttt tttttttttt ttctcctttt    7860
tttttcctct tttttcctt ttcttttcctt tggtggctcc atcttagccc tagtcacggc    7920
tagctgtgaa aggtccgtga gccgcttgac tgcagagagt gctgatactg gcctctctgc    7980
agatcaagt                                                               7989

<210> SEQ ID NO 10
<211> LENGTH: 7989
<212> TYPE: DNA
<213> ORGANISM: Hepatitis C virus

<400> SEQUENCE: 10
gccagccccc gattggggc gacactccac catagatcac tcccctgtga ggaactactg      60
```

-continued

| | |
|---|---|
| tcttcacgca gaaagcgtct agccatggcg ttagtatgag tgtcgtgcag cctccaggac | 120 |
| ccccctccc gggagagcca tagtggtctg cggaaccggt gagtacaccg gaattgccag | 180 |
| gacgaccggg tcctttcttg gatcaacccg ctcaatgcct ggagatttgg gcgtgccccc | 240 |
| gcgagactgc tagccgagta gtgttgggtc gcgaaaggcc ttgtggtact gcctgatagg | 300 |
| gtgcttgcga gtgccccggg aggtctcgta gaccgtgcac catgagcacg aatcctaaac | 360 |
| ctcaaagaaa aaccaaaggg cgcgccatga ttgaacaaga tggattgcac gcaggttctc | 420 |
| cggccgcttg ggtggagagg ctattcggct atgactgggc acaacagaca atcggctgct | 480 |
| ctgatgccgc cgtgttccgg ctgtcagcgc agggggcgccc ggttcttttt gtcaagaccg | 540 |
| acctgtccgg tgccctgaat gaactgcagg acgaggcagc gcggctatcg tggctggcca | 600 |
| cgacgggcgt tccttgcgca gctgtgctcg acgttgtcac tgaagcggga agggactggc | 660 |
| tgctattggg cgaagtgccg gggcaggatc tcctgtcatc tcaccttgct cctgccgaga | 720 |
| aagtatccat catggctgat gcaatgcggc ggctgcatac gcttgatccg gctacctgcc | 780 |
| cattcgacca ccaagcgaaa catcgcatcg agcgagcacg tactcggatg gaagccggtc | 840 |
| ttgtcgatca ggatgatctg gacgaagagc atcaggggct cgcgccagcc gaactgttcg | 900 |
| ccaggctcaa ggcgcgcatg cccgacggcg aggatctcgt cgtgacccat ggcgatgcct | 960 |
| gcttgccgaa tatcatggtg gaaaatggcc gcttttctgg attcatcgac tgtggccggc | 1020 |
| tgggtgtggc ggaccgctat caggacatag cgttggctac ccgtgatatt gctgaagagc | 1080 |
| ttggcggcga atgggctgac cgcttcctcg tgctttacgg tatcgccgct cccgattcgc | 1140 |
| agcgcatcgc cttctatcgc cttcttgacg agttcttctg agtttaaaca gaccacaacg | 1200 |
| gtttccctct agcgggatca attccgcccc tctccctccc cccccctaa cgttactggc | 1260 |
| cgaagccgct tggaataagg ccggtgtgcg tttgtctata tgttattttc caccatattg | 1320 |
| ccgtctttg gcaatgtgag ggcccggaaa cctggccctg tcttcttgac gagcattcct | 1380 |
| aggggtcttt cccctctcgc caaaggaatg caaggtctgt tgaatgtcgt gaaggaagca | 1440 |
| gttcctctgg aagcttcttg aagacaaaca acgtctgtag cgacccttg caggcagcgg | 1500 |
| aacccccac ctggcgacag gtgcctctgc ggccaaaagc cacgtgtata agatacacct | 1560 |
| gcaaaggcgg cacaacccca gtgccacgtt gtgagttgga tagttgtgga aagagtcaaa | 1620 |
| tggctctcct caagcgtatt caacaagggg ctgaaggatg cccagaaggt accccattgt | 1680 |
| atgggatctg atctggggcc tcggtgcaca tgctttacat gtgtttagtc gaggttaaaa | 1740 |
| aacgtctagg ccccccgaac cacggggacg tggttttcct ttgaaaaaca cgataatacc | 1800 |
| atggcgccta ttacggccta ctcccaacag acgcgaggcc tacttggctg catcatcact | 1860 |
| agcctcacag gccgggacag gaaccaggtc gaggggggagg tccaagtggt ctccaccgca | 1920 |
| acacaatctt tcctggcgac ctgcgtcaat ggcgtgtgtt ggactgtcta tcatggtgcc | 1980 |
| ggctcaaaga cccttgccgg cccaaagggc ccaatcaccc aaatgtacac caatgtggac | 2040 |
| caggacctcg tcggctggca agcgcccccc ggggcgcgtt ccttgacacc atgcacctgc | 2100 |
| ggcagctcgg acctttactt ggtcacgagg catgccgatg tcattccggt gcgccggcgg | 2160 |
| ggcgacagca gggggagcct actctccccc aggcccgtct cctacttgaa gggctcttcg | 2220 |
| ggcggtccac tgctctgccc ctcggggcac gctgtgggca tctttcgggc tgccgtgtgc | 2280 |
| acccgagggg ttgcgaaggc ggtggacttt gtaccgtcg agtctatgga aaccactatg | 2340 |
| cggtccccgg tcttcacgga caactcgtcc cctccggccg taccgcagac attccaggtg | 2400 |

```
gcccatctac acgcccctac tggtagcggc aagagcacta aggtgccggc tgcgtatgca    2460
gcccaagggt ataaggtgct tgtcctgaac ccgtccgtcg ccgccaccct aggtttcggg    2520
gcgtatatgt ctaaggcaca tggtatcgac cctaacatca gaaccggggt aaggaccatc    2580 accacggggtg cccccatcac gtactccacc tatggcaagt ttcttgccga cggtggttgc    2640
tctgggggcg cctatgacat cataatatgt gatgagtgcc actcaactga ctcgaccact    2700
atcctgggca tcggcacagt cctggaccaa gcggagacgg ctggagcgcg actcgtcgtg    2760
ctcgccaccg ctacgcctcc gggatcggtc accgtgccac atccaaacat cgaggaggtg    2820
gctctgtcca gcactggaga aatccccttt tatggcaaag ccatccccat cgagaccatc    2880 aagggggggga ggcacctcat tttctgccat tccaagaaga aatgtgatga gctcgccgcg    2940
aagctgtccg gcctcggact caatgctgta gcatattacc ggggccttga tgtatccgtc    3000
ataccaacta gcggagacgt cattgtcgta gcaacggacg ctctaatgac gggctttacc    3060
ggcgatttcg actcagtgat cgactgcaat acatgtgtca cccagacagt cgacttcagc    3120
ctggacccga ccttcaccat tgagacgacg accgtgccac aagacgcggt gtcacgctcg    3180
cagcggcgag gcaggactgg taggggcagg atgggcattt acaggtttgt gactccagga    3240
gaacggccct cgggcatgtt cgattcctcg gttctgtgcg agtgctatga cgcgggctgt    3300
gcttggtacg agctcacgcc cgccgagacc tcagttaggt tgcgggctta cctaaacaca    3360
ccagggttgc ccgtctgcca ggaccatctg gagttctggg agagcgtctt tacaggcctc    3420
acccacatag acgcccattt cttgtcccag actaagcagg caggagacaa cttcccctac    3480
ctggtagcat accaggctac ggtgtgcgcc agggctcagg ctccacctcc atcgtgggac    3540
caaatgtgga agtgtctcat acggctaaag cctacgctgc acgggccaac gccctgctg    3600 tataggctgg gagccgttca aaacgaggtt actaccacac accccataac caaatacatc    3660
atggcatgca tgtcggctga cctggaggtc gtcacgagca cctgggtgct ggtaggcgga    3720
gtcctagcag ctctggccgc gtattgcctg acaacaggca gcgtggtcat tgtgggcagg    3780
atcatcttgt ccggaaagcc ggccatcatt cccgacaggg aagtccttta ccgggagttc    3840
gatgagatgg aagagtgcgc ctcacacctc ccttacatcg aacagggaat gcagctcgcc    3900
gaacaattca acagaaggc aatcgggttg ctgcaaacag ccaccaagca agcggaggct    3960
gctgctcccg tggtggaatc caagtggcgg accctcgaag ccttctgggc gaagcatatg    4020
tggaatttca tcagcgggat acaatattta gcaggcttgt ccactctgcc tggcaacccc    4080
gcgatagcat cactgatggc attcacagcc tctatcacca gcccgctcac cacccaacat    4140
accctcctgt ttaacatcct gggggggatgg gtggccgccc aacttgctcc tcccagcgct    4200
gcttctgctt tcgtaggcgc cggcatcgct ggagcggctg ttggcagcat aggccttggg    4260
aaggtgcttg tggatatttt ggcaggttat ggagcagggg tggcaggcgc gctcgtggcc    4320
tttaaggtca tgagcggcga gatgcccctcc accgaggacc tggttaacct actccctgct    4380
atcctctccc ctggcgccct agtcgtcggg gtcgtgtgcg cagcgatact gcgtcggcac    4440
gtgggcccag gggagggggc tgtgcagtgg atgaaccggc tgatagcgtt cgcttcgcgg    4500
ggtaaccacg tctcccccac gcactatgtg cctgagagcg acgctgcagc acgtgtcact    4560
cagatcctct ctagtcttac catcactcag ctgctgaaga ggcttcacca gtggatcaac    4620
gaggactgct ccacgccatg ctccggctcg tggctaagag atgtttggga ttggatatgc    4680
acggtgttga ctgatttcaa gacctggctc cagtccaagc tcctgccgcg attgccggga    4740
gtccccttct tctcatgtca acgtgggtac aagggagtct ggcggggcga cggcatcatg    4800
```

```
caaaccacct gcccatgtgg agcacagatc accggacatg tgaaaaacgg ttccatgagg   4860
atcgtggggc ctaggacctg tagtaacacg tggcatggaa cattccccat taacgcgtac   4920
accacgggcc cctgcacgcc ctccccggcg ccaaattatt ctagggcgct gtggcgggtg   4980
gctgctgagg agtacgtgga ggttacgcgg gtggggatt tccactacgt gacgggcatg    5040
accactgaca acgtaaagtg cccgtgtcag gttccggccc ccgaattctt cacagaagtg   5100
gatggggtgc ggttgcacag gtacgctcca gcgtgcaaac ccctcctacg ggaggaggtc   5160
acattcctgg tcgggctcaa tcaatacctg gttgggtcac agctcccatg cgagcccgaa   5220
ccggacgtag cagtgctcac ttccatgctc accgacccct ccacattac ggcggagacg    5280
gctaagcgta ggctggccag gggatctccc ccctccttgt ccagctcatc agctagccag   5340
ctgtctgcgc cttccttgaa ggcaacatgc actacccgtc atgactcccc ggacgctgac   5400
ctcatcgagg ccaacctcct gtggcggcag gagatgggcg gaacatcac ccgcgtggag    5460
tcagaaaata aggtagtaat tttggactct ttcgagccgc tccaagcgga ggaggatgag   5520
agggaagtat ccgttccggc ggagatcctg cggaggtcca ggaaattccc tcgagcgatg   5580
cccatatggg cacgcccgga ttacaaccct ccactgttag agtcctggaa ggacccggac   5640
tacgtccctc cagtggtaca cgggtgtcca ttgccgcctg ccaaggcccc tccgatacca   5700
cctccacgga ggaagaggac ggttgtcctg tcagaatcta ccgtgtcttc tgccttggcg   5760
gagctcgcca caaagacctt cggcagctcc gaatcgtcgg ccgtcgacag cggcacggca   5820
acggcctctc ctgaccagcc ctccgacgac ggcgacgcgg gatccgacgt tgagtcgtac   5880
tcctccatgc ccccccttga ggggagccg ggggatcccg atctcagcga cgggtcttgg    5940
tctaccgtaa gcgaggaggc tagtgaggac gtcgtctgct gctcgatgtc ctacacatgg   6000
acaggcgccc tgatcacgcc atgcgctgcg gaggaaacca agctgcccat caatgcactg   6060
agcaactctt tgctccgtca ccacaacttg gtctatgcta caacatctcg cagcgcaagc   6120
ctgcggcaga agaaggtcac ctttgacaga ctgcaggtcc tggacgacca ctaccgggac   6180
gtgctcaagg agatgaaggc gaaggcgtcc acagttaagg ctaaacttct atccgtggag   6240
gaagcctgta agctgacgcc cccacattcg gccagatcta aatttggcta tggggcaaag   6300
gacgtccgga acctatccag caaggccgtt aaccacatcc gctccgtgtg gaaggacttg   6360
ctggaagaca ctgagacacc aattgacacc accatcatgg caaaaaatga ggttttctgc   6420
gtccaaccag agaaggggg ccgcaagcca gctcgcctta tcgtattccc agatttgggg    6480
gttcgtgtgt gcgagaaaat ggcccttac gatgtggtct ccaccctccc tcaggccgtg    6540
atgggctctt catacggatt ccaatactct cctggacagc gggtcgagtt cctggtgaat   6600
gcctggaaag cgaagaaatg ccctatgggc ttcgcatatg acacccgctg ttttgactca   6660
acggtcactg agaatgacat ccgtgttgag gagtcaatct accaatgttg tgacttggcc   6720
cccgaagcca gacaggccat aaggtcgctc acagagcggc tttacatcgg ggcccctg     6780
actaattcta aagggcagaa ctgccggtat cgccggtgcc gcgcgagcgg tgtactgacg   6840
accagctgcg gtaataccct cacatgttac ttgaaggccg ctgcggcctg tcgagctgcg   6900
aagctccagg actgcacgat gctcgtatgc ggagacgacc ttgtcgttat ctgtgaaagc   6960
gcggggaccc aagaggacga ggcgagccta cgggccttca cggaggctat gactagatac   7020
tctgcccccc ctgggacccc gcccaaacca gaatacgact tggagttgat aacatcatgc   7080
tcctccaatg tgtcagtcgc gcacgatgca tctggcaaaa gggtgtacta tctcacccgt   7140
```

-continued

| | |
|---|---|
| gaccccacca cccccttgc gcgggctgcg tgggagacag ctagacacac tccagtcaat | 7200 |
| tcctggctag gcaacatcat catgtatgcg cccaccttgt gggcaaggat gatcctgatg | 7260 |
| actcatttct tctccatcct tctagctcag gaacaacttg aaaaagccct agattgtcag | 7320 |
| atctacgggg cctgttactc cattgagcca cttgacctac ctcagatcat tcaacgactc | 7380 |
| catggcctta gcgcattttc actccatagt tactctccag gtgagatcaa tagggtggct | 7440 |
| tcatgcctca ggaaacttgg ggtaccgccc ttgcgagtct ggagacatcg ggccagaagt | 7500 |
| gtccgcgcta ggctactgtc ccagggggg agggctgcca cttgtggcaa gtacctcttc | 7560 |
| aactgggcag taaggaccaa gctcaaactc actccaatcc cggctgcgtc ccagttggat | 7620 |
| ttatccagct ggttcgttgc tggttacagc gggggagaca tatatcacag cctgtctcgt | 7680 |
| gcccgacccc gctggttcat gtggtgccta ctcctacttt ctgtaggggt aggcatctat | 7740 |
| ctactcccca accgatgaac ggggacctaa acactccagg ccaataggcc atcctgtttt | 7800 |
| tttccctttt tttttttctt tttttttttt tttttttttt tttttttttt ttctcctttt | 7860 |
| ttttcctct tttttccctt ttctttcctt tggtggctcc atcttagccc tagtcacggc | 7920 |
| tagctgtgaa aggtccgtga gccgcttgac tgcagagagt gctgatactg gcctctctgc | 7980 |
| agatcaagt | 7989 |

<210> SEQ ID NO 11
<211> LENGTH: 1341
<212> TYPE: DNA
<213> ORGANISM: Hepatitis C virus
<400> SEQUENCE: 11

| | |
|---|---|
| tccggctcgt ggctaagaga tgtttgggat tggatatgca cggtgttgac tgatttcaag | 60 |
| acctggctcc agtccaagct cctgccgcga ttgccgggag tcccttcctt ctcatgtcaa | 120 |
| cgtgggtaca agggagtctg gcggggcgac ggcatcatgc aaaccacctg cccatgtgga | 180 |
| gcacagatca ccggacatgt gaaaaacggt tccatgagga tcgtggggcc taggacctgt | 240 |
| agtaacacgt ggcatggaac attccccatt aacgcgtaca ccacgggccc ctgcacgccc | 300 |
| tccccggcgc aaattattc tagggcgctg tggcgggtgg ctgctgagga gtacgtggag | 360 |
| gttacgcggg tggggatt ccactacgtg acgggcatga ccactgacaa cgtaaagtgc | 420 |
| ccgtgtcagg ttccggcccc cgaattcttc acagaagtgg atggggtgcg gttgcacagg | 480 |
| tacgctccag cgtgcaaacc cctcctacgg gaggaggtca cattcctggt cgggctcaat | 540 |
| caatacctgg ttgggtcaca gctcccatgc gagcccgaac cggacgtagc agtgctcact | 600 |
| tccatgctca ccgaccccctc ccacattacg gcggagacgg ctaagcgtag gctggccagg | 660 |
| ggatctcccc cctgcttggc cagctcatca gctagccagc tgtctgcgcc ttccttgaag | 720 |
| gcaacatgca ctacccgtca tgactccccg gacgctgacc tcatcgaggc caacctcctg | 780 |
| tggcggcagg agatgggcgg gaacatcacc gcgtgagt cagaaaataa ggtagtaatt | 840 |
| ttggactctt tcgagccgct ccaagcggag gaggatgaga ggaagtatc cgttccggcg | 900 |
| gagatcctgc ggaggtccag gaaattccct cgagcgatgc ccatatgggc acgcccggat | 960 |
| tacaaccctc cactgttaga gtcctggaag gacccggact acgtccctcc agtggtacac | 1020 |
| gggtgtccat gccgcctgc caaggccct ccgataccac ctccacgag gaagaggacg | 1080 |
| gttgtcctgt cagaatctac cgtgtcttct gccttggcgg agctcgccac aaagaccttc | 1140 |
| ggcagctccg aatcgtcggc cgtcgacagc ggcacggcaa cggcctctcc tgaccagccc | 1200 |
| tccgacgacg gcgacgcggg atccgacgtt gagtcgtact cctccatgcc cccccttgag | 1260 |

```
ggggagccgg gggatcccga tctcagcgac gggtcttggt ctaccgtaag cgaggaggct    1320
agtgaggacg tcgtctgctg c                                              1341

<210> SEQ ID NO 12
<211> LENGTH: 1341
<212> TYPE: DNA
<213> ORGANISM: Hepatitis C virus

<400> SEQUENCE: 12
tccggctcgt ggctaagaga tgtttgggat tggatatgca cggtgttgac tgatttcaag      60
acctggctcc agtccaagct cctgccgcga ttgccgggag tccccttctt ctcatgtcaa     120
cgtgggtaca agggagtctg gcggggcgac ggcatcatgc aaaccacctg cccatgtgga     180
gcacagatca ccggacatgt gaaaaacggt tccatgagga tcgtggggcc taggacctgt     240
agtaacacgt ggcatggaac attccccatt aacgcgtaca ccacgggccc ctgcacgccc     300
tccccggcgc caaattattc tagggcgctg tggcggtgg ctgctgagga gtacgtggag     360
gttacgcggg tgggggattt ccactacgtg acgggcatga ccactgacaa cgtaaagtgc     420
ccgtgtcagg ttccggcccc cgaattcttc acagaagtgg atggggtgcg gttgcacagg     480
tacgctccag cgtgcaaacc cctcctacgg gaggaggtca cattcctggt cgggctcaat     540
caatacctgg ttgggtcaca gctcccatgc gagcccgaac cggacgtagc agtgctcact     600
tccatgctca ccgacccctc ccacattacg gcggagacgg ctaagcgtag gctggccagg     660
ggatctcccc cccccttggc cagctcatca gctagccagc tgtctgcgcc ttccttgaag     720
gcaacatgca ctacccgtca tgactccccg gacgctgacc tcatcgaggc caacctcctg     780
tggcggcagg agatgggcgg gaacatcacc gcgtgagt cagaaaataa ggtagtaatt     840
ttggactctt tcgagccgct ccaagcggag gaggatgaga gggaagtatc cgttccggcg     900
gagatcctgc ggaggtccag gaaattccct cgagcgatgc ccatatgggc acgcccggat     960
tacaaccctc cactgttaga gtcctggaag gacccggact acgtccctcc agtggtacac    1020
gggtgtccat tgccgcctgc caaggcccct ccgataccac ctccacgag gaagaggacg    1080 gttgtcctgt cagaatctac cgtgtcttct gccttggcgg agctcgccac aaagaccttc    1140
ggcagctccg aatcgtcggc cgtcgacagc ggcacggcaa cggcctctcc tgaccagccc    1200
tccgacgacg gcgacgcggg atccgacgtt gagtcgtact cctccatgcc cccccttgag    1260
ggggagccgg gggatcccga tctcagcgac gggtcttggt ctaccgtaag cgaggaggct    1320
agtgaggacg tcgtctgctg c                                              1341

<210> SEQ ID NO 13
<211> LENGTH: 7987
<212> TYPE: DNA
<213> ORGANISM: Hepatitis C virus

<400> SEQUENCE: 13
gccagccccc gattgggggc gacactccac catagatcac tcccctgtga ggaactactg      60
tcttcacgca gaaagcgtct agccatggcg ttagtatgag tgtcgtgcag cctccaggac     120
cccccctccc gggagagcca tagtggtctg cggaaccggt gagtacaccg gaattgccag     180
gacgaccggg tcctttcttg gatcaacccg ctcaatgcct ggagatttgg gcgtgccccc     240
gcgagactgc tagccgagta gtgttgggtc gcgaaaggcc ttgtggtact gcctgatagg     300
gtgcttgcga gtgccccggg aggtctcgta gaccgtgcac catgagcacg aatcctaaac     360
```

| | |
|---|---|
| ctcaaagaaa aaccaaaggg cgcgccatga ttgaacaaga tggattgcac gcaggttctc | 420 |
| cggccgcttg ggtggagagg ctattcggct atgactgggc acaacagaca atcggctgct | 480 |
| ctgatgccgc cgtgttccgg ctgtcagcgc aggggcgccc ggttctttttt gtcaagaccg | 540 |
| acctgtccgg tgccctgaat gaactgcagg acgaggcagc gcggctatcg tggctggcca | 600 |
| cgacgggcgt tccttgcgca gctgtgctcg acgttgtcac tgaagcggga agggactggc | 660 |
| tgctattggg cgaagtgccg gggcaggatc tcctgtcatc tcaccttgct cctgccgaga | 720 |
| aagtatccat catggctgat gcaatgcggc ggctgcatac gcttgatccg gctacctgcc | 780 |
| cattcgacca ccaagcgaaa catcgcatcg agcgagcacg tactcggatg gaagccggtc | 840 |
| ttgtcgatca ggatgatctg gacgaagagc atcaggggct cgcgccagcc gaactgttcg | 900 |
| ccaggctcaa ggcgcgcatg cccgacggcg aggatctcgt cgtgacccat ggcgatgcct | 960 |
| gcttgccgaa tatcatggtg gaaaatggcc gcttttctgg attcatcgac tgtggccggc | 1020 |
| tgggtgtggc ggaccgctat caggacatag cgttggctac ccgtgatatt gctgaagagc | 1080 |
| ttggcggcga atgggctgac cgcttcctcg tgctttacgg tatcgccgct cccgattcgc | 1140 |
| agcgcatcgc cttctatcgc cttcttgacg agttcttctg agtttaaaca gaccacaacg | 1200 |
| gtttccctct agcgggatca attccgcccc tctccctccc cccccctaa cgttactggc | 1260 |
| cgaagccgct tggaataagg ccggtgtgcg tttgtctata tgttattttc caccatattg | 1320 |
| ccgtcttttg gcaatgtgag ggcccggaaa cctggccctg tcttcttgac gagcattcct | 1380 |
| aggggtcttt cccctctcgc caaggaatg caaggtctgt tgaatgtcgt gaaggaagca | 1440 |
| gttcctctgg aagcttcttg aagacaaaca acgtctgtag cgacccttg caggcagcgg | 1500 |
| aaccccccac ctggcgacag gtgcctctgc ggccaaaagc cacgtgtata agatacacct | 1560 |
| gcaaaggcgg cacaacccca gtgccacgtt gtgagttgga tagttgtgga aagagtcaaa | 1620 |
| tggctctcct caagcgtatt caacaagggg ctgaaggatg cccagaaggt accccattgt | 1680 |
| atgggatctg atctggggcc tcggtgcaca tgctttacat gtgtttagtc gaggttaaaa | 1740 |
| aacgtctagg cccccccgaac cacggggacg tggttttcct ttgaaaaaca cgataatacc | 1800 |
| atggcgccta ttacggccta ctcccaacag acgcgaggcc tacttggctg catcatcact | 1860 |
| agcctcacag gccgggacag gaaccaggtc gaggggagg tccaagtggt ctccaccgca | 1920 |
| acacaatctt tcctggcgac ctgcgtcaat ggcgtgtgtt ggactgtcta tcatggtgcc | 1980 |
| ggctcaaaga cccttgccgg cccaaagggc ccaatcaccc aaatgtacac caatgtggac | 2040 |
| caggacctcg tcgctggca agcgcccccc ggggcgcgtt ccttgacacc atgcacctgc | 2100 |
| ggcagctcgg acctttactt ggtcacgagg catgccgatg tcattccggt gcgccggcgg | 2160 |
| ggcgacagca gggggagcct actctccccc aggcccgtct cctacttgaa gggctcttcg | 2220 |
| ggcggtccac tgctctgccc ctcggggcac gctgtgggca tctttcgggc tgccgtgtgc | 2280 |
| acccgagggg ttgcgaaggc ggtggacttt gtacccgtcg agtctatgga aaccactatg | 2340 |
| cggtccccgg tcttcacgga caactcgtcc cctccggccg taccgcagac attccaggtg | 2400 |
| gcccatctac acgcccctac tggtagcggc aagagcacta aggtgccggc tgcgtatgca | 2460 |
| gcccaagggt ataaggtgct tgtcctgaac ccgtccgtcg ccgccaccct aggtttcggg | 2520 |
| gcgtatatgt ctaaggcaca tggtatcgac cctaacatca gaaccggggt aaggaccatc | 2580 |
| accacgggtg cccccatcac gtactccacc tatggcaagt ttcttgccga cggtggttgc | 2640 |
| tctgggggcg cctatgacat cataatatgt gatgagtgcc actcaactga ctcgaccact | 2700 |
| atcctgggca tcggcacagt cctggaccaa gcggagacgg ctggagcgcg actcgtcgtg | 2760 |

```
ctcgccaccg ctacgcctcc gggatcggtc accgtgccac atccaaacat cgaggaggtg    2820
gctctgtcca gcactggaga atccccttt tatggcaaag ccatccccat cgagaccatc     2880
aaggggggga ggcacctcat tttctgccat tccaagaaga aatgtgatga gctcgccgcg    2940
aagctgtccg gcctcggact caatgctgta gcatattacc ggggccttga tgtatccgtc    3000
ataccaacta gcggagacgt cattgtcgta gcaacggacg ctctaatgac gggctttacc    3060
ggcgatttcg actcagtgat cgactgcaat acatgtgtca cccagacagt cgacttcagc    3120
ctggacccga ccttcaccat tgagacgacg accgtgccac aagacgcggt gtcacgctcg    3180
cagcggcgag gcaggactgg tagggcagg atgggcattt acaggtttgt gactccagga     3240
gaacggccct cgggcatgtt cgattcctcg gttctgtgcg agtgctatga cgcgggctgt    3300
gcttggtacg agctcacgcc cgccgagacc tcagttaggt tgcgggctta cctaaacaca    3360
ccagggttgc ccgtctgcca ggaccatctg gagttctggg agagcgtctt tacaggcctc    3420
acccacatag acgcccattt cttgtcccag actaagcagg caggagacaa cttccctac    3480 ctggtagcat accaggctac ggtgtgcgcc agggctcagg ctccacctcc atcgtgggac    3540
caaatgtgga agtgtctcat acggctaaag cctacgctgc acgggccaac gcccctgctg    3600
tataggctgg gagccgttca aaacgaggtt actaccacac accccataac caaatacatc    3660
atggcatgca tgtcggctga cctggaggtc gtcacgagca cctgggtgct ggtaggcgga    3720
gtcctagcag ctctggccgc gtattgcctg caacaggca gcgtggtcat tgtgggcagg     3780
atcatcttgt ccggaaagcc ggccatcatt cccgacaggg aagtccttta ccgggagttc    3840
gatgagatgg aagagtgcgc ctcacacctc ccttacatcg aacagggaat gcagctcgcc    3900
gaacaattca acagaaggc aatcgggttg ctgcaaacag ccaccaagca agcggaggct     3960
gctgctcccg tggtggaatc caagtggcgg accctcgaag ccttctgggc gaagcatatg    4020
tggaatttca tcagcgggat acaatattta gcaggcttgt ccactctgcc tggcaacccc    4080
gcgatagcat cactgatggc attcacagcc tctatcacca gcccgctcac cacccaacat    4140
accctcctgt ttaacatcct gggggatgg gtggccgccc aacttgctcc tcccagcgct     4200
gcttctgctt tcgtaggcgc cggcatcgct ggagcggctg ttggcagcat aggccttggg    4260
aaggtgcttg tggatatttt ggcaggttat ggagcagggg tggcaggcgc gctcgtggcc    4320
tttaaggtca tgagcggcga gatgcctcc accgaggacc tggttaacct actccctgct     4380
atcctctccc ctggcgccct agtcgtcggg gtcgtgtgcg cagcgatact gcgtcggcac    4440
gtgggcccag gggaggggc tgtgcagtgg atgaaccggc tgatagcgtt cgcttcgcgg    4500
ggtaaccacg tctcccccac gcactatgtg cctgagagcg acgctgcagc acgtgtcact    4560
cagatcctct ctagtcttac catcactcag ctgctgaaga ggcttcacca gtggatcaac    4620
gaggactgct ccacgccatg ctccggctcg tggctaagag atgtttggga ttggatatgc    4680
acggtgttga ctgatttcaa gacctggctc cagtccaagc tcctgccgcg attgccggga    4740
gtccccttct tctcatgtca acgtgggtac aagggagtct ggcggggcga cggcatcatg    4800
caaaccacct gcccatgtgg agcacagatc accggacatg tgaaaacgg ttccatgagg     4860 atcgtggggc ctaggacctg tagtaacacg tggcatggaa cattccccat taacgcgtac    4920
accacgggcc cctgcacgcc ctccccggcg ccaaattatt ctagggcgct gtggcgggtg    4980
gctgctgagg agtacgtgga ggttacgcg gtgggggatt ccactacgt gacgggcatg     5040 accactgaca acgtaaagtg cccgtgtcag gttccggccc ccgaattctt cacagaagtg    5100
```

```
gatggggtgc ggttgcacag gtacgctcca gcgtgcaaac ccctcctacg ggaggaggtc    5160
acattcctgg tcgggctcaa tcaatacctg gttgggtcac agctcccatg cgagcccgaa    5220
ccggacgtag cagtgctcac ttccatgctc accgacccct cccacattac ggcggagacg    5280
gctaagcgta ggctggccag gggatctccc ccctccttgg ccagctcatc agctatccag    5340
ctgtctgcgc cttccttgaa ggcaacatgc actacccgtc atgactcccc ggacgctgac    5400
ctcatcgagg ccaacctcct gtggcggcag agatgggcg gaacatcac ccgcgtggag      5460
tcagaaaata aggtagtaat tttggactct ttcgagccgc tccaagcgga ggaggatgag    5520
agggaagtat ccgttccggc ggagatcctg cggaggtcca ggaaattccc tcgagcgatg    5580
cccatatggg cacgcccgga ttacaaccct ccactgttag agtcctggaa ggacccggac    5640
tacgtccctc cagtggtaca cgggtgtcca ttgccgcctg ccaaggcccc tccgatacca    5700
cctccacgga ggaagaggac ggttgtcctg tcagaatcta ccgtgtcttc tgccttggcg    5760
gagctcgcca caaagacctt cggcagctcc gaatcgtcgg ccgtcgacag cggcacggca    5820
acggcctctc ctgaccagcc ctccgacgac ggcgacgcgg gatccgacgt tgagtcgtac    5880
tcctccatgc ccccccttga gggggagccg ggggatcccg atctcagcga cgggtcttgg    5940
tctaccgtaa gcgaggaggc tagtgaggac gtcgtctgct gctcgatgtc ctacacatgg    6000
acaggcgccc tgatcacgcc atgcgctgcg gaggaaacca agctgcccat caatgcactg    6060
agcaactctt tgctccgtca ccacaacttg gtctatgcta caacatctcg cagcgcaagc    6120
ctgcggcaga agaaggtcac ctttgacaga ctgcaggtcc tggacgacca ctaccgggac    6180
gtgctcaagg agatgaaggc gaaggcgtcc acagttaagg ctaaacttct atccgtggag    6240
gaagcctgta agctgacgcc cccacattcg gccagatcta aatttggcta tggggcaaag    6300
gacgtccgga acctatccag caaggccgtt aaccacatcc gctccgtgtg gaaggacttg    6360
ctggaagaca ctgagacacc aattgacacc accatcatgg caaaaaatga ggttttctgc    6420
gtccaaccag agaaggggg ccgcaagcca gctcgcctta tcgtattccc agatttgggg    6480
gttcgtgtgt gcgagaaaat ggcccttta cgatgtggtct ccaccctccc tcaggccgtg    6540
atgggctctt catacggatt ccaatactct cctggacagc gggtcgagtt cctggtgaat    6600
gcctggaaag cgaagaaatg ccctatgggc ttcgcatatg acacccgctg ttttgactca    6660
acggtcactg agaatgacat ccgtgttgag gagtcaatct accaatgttg tgacttggcc    6720
cccgaagcca gacaggccat aaggtcgctc acagagcggc tttacatcgg ggcccctg     6780
actaattcta aagggcagaa ctgcggctat cgccggtgcc gcgcgagcgg tgtactgacg    6840
accagctgcg gtaataccct cacatgttac ttgaaggccg ctgcggcctg tcgagctgcg    6900
aagctccagg actgcacgat gctcgtatgc ggagacgacc ttgtcgttat ctgtgaaagc    6960
gcggggaccc aagaggacga ggcgagccta cgggccttca cggaggctat gactagatac    7020
tctgcccccc ctgggaccc gcccaaacca gaatacgact ggagttgat aacatcatgc     7080
tcctccaatg tgtcagtcgc gcacgatgca tctggcaaaa gggtgtacta tctcacccgt    7140
gaccccacca ccccccttgc gcgggctgcg tgggagacag ctagacacac tccagtcaat    7200
tcctggctag caacatcat catgtatgcg cccaccttgt gggcaaggat gatcctgatg     7260
actcatttct tctccatcct tctagctcag gaacaacttg aaaaagccct agattgtcag    7320
atctacgggg cctgttactc cattgagcca cttgacctac ctcagatcat tcaacgactc    7380
catggcctta gcgcattttc actccatagt tactctccag gtgagatcaa tagggtggct    7440
tcatgcctca ggaaacttgg ggtaccgccc ttgcgagtct ggagacatcg ggccagaagt    7500
```

-continued

```
gtccgcgcta ggctactgtc ccagggggggg agggctgcca cttgtggcaa gtacctcttc    7560
aactgggcag taaggaccaa gctcaaactc actccaatcc cggctgcgtc ccagttggat    7620
ttatccagct ggttcgttgc tggttacagc gggggagaca tatatcacag cctgtctcgt    7680
gcccgacccc gctggttcat gtggtgccta ctcctacttt ctgtaggggt aggcatctat    7740
ctactcccca accgatgaac ggggagctaa acactccagg ccaataggcc atcctgtttt    7800 tttcccttttt ttttttttctt ttttttttttt ttttttttttt ttttttttttt ctccttttttt    7860 tttcctctttt ttttccttttt ctttccttttg gtggctccat cttagcccta gtcacggcta    7920
gctgtgaaag gtccgtgagc cgcttgactg cagagagtgc tgatactggc ctctctgcag    7980
atcaagt                                                              7987
```

<210> SEQ ID NO 14
<211> LENGTH: 400
<212> TYPE: PRT
<213> ORGANISM: Hepatitis C virus

<400> SEQUENCE: 14

```
Ser Gly Ser Trp Leu Arg Asp Val Trp Asp Trp Ile Cys Thr Val Leu
1               5                   10                  15

Thr Asp Phe Lys Thr Trp Leu Gln Ser Lys Leu Leu Pro Arg Leu Pro
                20                  25                  30

Gly Val Pro Phe Phe Ser Cys Gln Arg Gly Tyr Lys Gly Val Trp Arg
            35                  40                  45

Gly Asp Gly Ile Met Gln Thr Thr Cys Pro Cys Gly Ala Gln Ile Thr
        50                  55                  60

Gly His Val Lys Asn Gly Ser Met Arg Ile Val Gly Pro Arg Thr Cys
65                  70                  75                  80

Ser Asn Thr Trp His Gly Thr Phe Pro Ile Asn Ala Tyr Thr Thr Gly
                85                  90                  95

Pro Cys Thr Pro Ser Pro Ala Pro Asn Tyr Ser Arg Ala Leu Trp Arg
            100                 105                 110

Val Ala Ala Glu Glu Tyr Val Glu Val Thr Arg Val Gly Asp Phe His
        115                 120                 125

Tyr Val Thr Gly Met Thr Thr Asp Asn Val Lys Cys Pro Cys Gln Val
    130                 135                 140

Pro Ala Pro Glu Phe Phe Thr Glu Val Asp Gly Val Arg Leu His Arg
145                 150                 155                 160

Tyr Ala Pro Ala Cys Lys Pro Leu Leu Arg Glu Glu Val Thr Phe Leu
                165                 170                 175

Val Gly Leu Asn Gln Tyr Leu Val Gly Ser Gln Leu Pro Cys Glu Pro
            180                 185                 190

Glu Pro Asp Val Ala Val Leu Thr Ser Met Leu Thr Asp Pro Ser His
        195                 200                 205

Ile Thr Ala Glu Thr Ala Lys Arg Arg Leu Ala Arg Gly Ser Pro Pro
    210                 215                 220

Ser Leu Ala Ser Ser Ser Ala Ser Gln Leu Tyr Ser Phe Glu Pro Leu
225                 230                 235                 240

Gln Ala Glu Glu Asp Glu Arg Glu Val Ser Val Pro Ala Glu Ile Leu
                245                 250                 255

Arg Arg Ser Arg Lys Phe Pro Arg Ala Met Pro Ile Trp Ala Arg Pro
            260                 265                 270

Asp Tyr Asn Pro Pro Leu Leu Glu Ser Trp Lys Asp Pro Asp Tyr Val
```

-continued

```
                275                 280                 285
Pro Pro Val Val His Gly Cys Pro Leu Pro Pro Ala Lys Ala Pro Pro
            290                 295                 300
Ile Pro Pro Pro Arg Arg Lys Arg Thr Val Val Leu Ser Glu Ser Thr
305                 310                 315                 320
Val Ser Ser Ala Leu Ala Glu Leu Ala Thr Lys Thr Phe Gly Ser Ser
                325                 330                 335
Glu Ser Ser Ala Val Asp Ser Gly Thr Ala Thr Ala Ser Pro Asp Gln
            340                 345                 350
Pro Ser Asp Asp Gly Asp Ala Gly Ser Asp Val Glu Ser Tyr Ser Ser
        355                 360                 365
Met Pro Pro Leu Glu Gly Glu Pro Gly Asp Pro Asp Leu Ser Asp Gly
    370                 375                 380
Ser Trp Ser Thr Val Ser Glu Glu Ala Ser Glu Asp Val Val Cys Cys
385                 390                 395                 400

<210> SEQ ID NO 15
<211> LENGTH: 1985
<212> TYPE: PRT
<213> ORGANISM: Hepatitis C virus

<400> SEQUENCE: 15

Met Ala Pro Ile Thr Ala Tyr Ser Gln Gln Thr Arg Gly Leu Leu Gly
1               5                   10                  15
Cys Ile Ile Thr Ser Leu Thr Gly Arg Asp Arg Asn Gln Val Glu Gly
                20                  25                  30
Glu Val Gln Val Val Ser Thr Ala Thr Gln Ser Phe Leu Ala Thr Cys
            35                  40                  45
Val Asn Gly Val Cys Trp Thr Val Tyr His Gly Ala Gly Ser Lys Thr
        50                  55                  60
Leu Ala Gly Pro Lys Gly Pro Ile Thr Gln Met Tyr Thr Asn Val Asp
65                  70                  75                  80
Gln Asp Leu Val Gly Trp Arg Ala Pro Pro Gly Ala Arg Ser Leu Thr
                85                  90                  95
Pro Cys Thr Cys Gly Ser Ser Asp Leu Tyr Leu Val Thr Arg His Ala
            100                 105                 110
Asp Val Ile Pro Val Arg Arg Arg Gly Asp Ser Arg Gly Ser Leu Leu
        115                 120                 125
Ser Pro Arg Pro Val Ser Tyr Leu Lys Gly Ser Ser Gly Gly Pro Leu
    130                 135                 140
Leu Cys Pro Ser Gly His Ala Val Gly Ile Phe Arg Ala Ala Val Cys
145                 150                 155                 160
Thr Arg Gly Val Ala Lys Ala Val Asp Phe Val Pro Val Glu Ser Met
                165                 170                 175
Glu Thr Thr Met Arg Ser Pro Val Phe Thr Asp Asn Ser Ser Pro Pro
            180                 185                 190
Ala Val Pro Gln Thr Phe Gln Val Ala His Leu His Ala Pro Thr Gly
        195                 200                 205
Ser Gly Lys Ser Thr Lys Val Pro Ala Ala Tyr Ala Ala Gln Gly Tyr
    210                 215                 220
Lys Val Leu Val Leu Asn Pro Ser Val Ala Ala Thr Leu Gly Phe Gly
225                 230                 235                 240
Ala Tyr Met Ser Lys Ala His Gly Ile Asp Pro Asn Ile Arg Thr Gly
                245                 250                 255
```

-continued

```
Val Arg Thr Ile Thr Thr Gly Ala Pro Ile Thr Tyr Ser Thr Tyr Gly
                260                 265                 270

Lys Phe Leu Ala Asp Gly Gly Cys Ser Gly Gly Ala Tyr Asp Ile Ile
            275                 280                 285

Ile Cys Asp Glu Cys His Ser Thr Asp Ser Thr Thr Ile Leu Gly Ile
        290                 295                 300

Gly Thr Val Leu Asp Gln Ala Glu Thr Ala Gly Ala Arg Leu Val Val
305                 310                 315                 320

Leu Ala Thr Ala Thr Pro Pro Gly Ser Val Thr Val Pro His Pro Asn
                325                 330                 335

Ile Glu Glu Val Ala Leu Ser Ser Thr Gly Glu Ile Pro Phe Tyr Gly
            340                 345                 350

Lys Ala Ile Pro Ile Glu Thr Ile Lys Gly Gly Arg His Leu Ile Phe
        355                 360                 365

Cys His Ser Lys Lys Cys Asp Glu Leu Ala Ala Lys Leu Ser Gly
        370                 375                 380

Leu Gly Leu Asn Ala Val Ala Tyr Tyr Arg Gly Leu Asp Val Ser Val
385                 390                 395                 400

Ile Pro Thr Ser Gly Asp Val Ile Val Ala Thr Asp Ala Leu Met
            405                 410                 415

Thr Gly Phe Thr Gly Asp Phe Asp Ser Val Ile Asp Cys Asn Thr Cys
            420                 425                 430

Val Thr Gln Thr Val Asp Phe Ser Leu Asp Pro Thr Phe Thr Ile Glu
        435                 440                 445

Thr Thr Thr Val Pro Gln Asp Ala Val Ser Arg Ser Gln Arg Arg Gly
    450                 455                 460

Arg Thr Gly Arg Gly Arg Met Gly Ile Tyr Arg Phe Val Thr Pro Gly
465                 470                 475                 480

Glu Arg Pro Ser Gly Met Phe Asp Ser Ser Val Leu Cys Glu Cys Tyr
                485                 490                 495

Asp Ala Gly Cys Ala Trp Tyr Glu Leu Thr Pro Ala Glu Thr Ser Val
            500                 505                 510

Arg Leu Arg Ala Tyr Leu Asn Thr Pro Gly Leu Pro Val Cys Gln Asp
        515                 520                 525

His Leu Glu Phe Trp Glu Ser Val Phe Thr Gly Leu Thr His Ile Asp
        530                 535                 540

Ala His Phe Leu Ser Gln Thr Lys Gln Ala Gly Asp Asn Phe Pro Tyr
545                 550                 555                 560

Leu Val Ala Tyr Gln Ala Thr Val Cys Ala Arg Ala Gln Ala Pro Pro
                565                 570                 575

Pro Ser Trp Asp Gln Met Trp Lys Cys Leu Ile Arg Leu Lys Pro Thr
            580                 585                 590

Leu His Gly Pro Thr Pro Leu Leu Tyr Arg Leu Gly Ala Val Gln Asn
        595                 600                 605

Glu Val Thr Thr Thr His Pro Ile Thr Lys Tyr Ile Met Ala Cys Met
    610                 615                 620

Ser Ala Asp Leu Glu Val Val Thr Ser Thr Trp Val Leu Val Gly Gly
625                 630                 635                 640

Val Leu Ala Ala Leu Ala Ala Tyr Cys Leu Thr Thr Gly Ser Val Val
                645                 650                 655

Ile Val Gly Arg Ile Ile Leu Ser Gly Lys Pro Ala Ile Ile Pro Asp
            660                 665                 670

Arg Glu Val Leu Tyr Arg Glu Phe Asp Glu Met Glu Glu Cys Ala Ser
```

-continued

```
            675                 680                 685
His Leu Pro Tyr Ile Glu Gln Gly Met Gln Leu Ala Glu Gln Phe Lys
690                 695                 700
Gln Lys Ala Ile Gly Leu Leu Gln Thr Ala Thr Lys Gln Ala Glu Ala
705                 710                 715                 720
Ala Ala Pro Val Val Glu Ser Lys Trp Arg Thr Leu Glu Ala Phe Trp
            725                 730                 735
Ala Lys His Met Trp Asn Phe Ile Ser Gly Ile Gln Tyr Leu Ala Gly
                740                 745                 750
Leu Ser Thr Leu Pro Gly Asn Pro Ala Ile Ala Ser Leu Met Ala Phe
            755                 760                 765
Thr Ala Ser Ile Thr Ser Pro Leu Thr Gln His Thr Leu Leu Phe
770                 775                 780
Asn Ile Leu Gly Gly Trp Val Ala Ala Gln Leu Ala Pro Pro Ser Ala
785                 790                 795                 800
Ala Ser Ala Phe Val Gly Ala Gly Ile Ala Gly Ala Ala Val Gly Ser
                805                 810                 815
Ile Gly Leu Gly Lys Val Leu Val Asp Ile Leu Ala Gly Tyr Gly Ala
                820                 825                 830
Gly Val Ala Gly Ala Leu Val Ala Phe Lys Val Met Ser Gly Glu Met
                835                 840                 845
Pro Ser Thr Glu Asp Leu Val Asn Leu Leu Pro Ala Ile Leu Ser Pro
850                 855                 860
Gly Ala Leu Val Val Gly Val Val Cys Ala Ala Ile Leu Arg Arg His
865                 870                 875                 880
Val Gly Pro Gly Glu Gly Ala Val Gln Trp Met Asn Arg Leu Ile Ala
                885                 890                 895
Phe Ala Ser Arg Gly Asn His Val Ser Pro Thr His Tyr Val Pro Glu
                900                 905                 910
Ser Asp Ala Ala Arg Val Thr Gln Ile Leu Ser Ser Leu Thr Ile
                915                 920                 925
Thr Gln Leu Leu Lys Arg Leu His Gln Trp Ile Asn Glu Asp Cys Ser
930                 935                 940
Thr Pro Cys Ser Gly Ser Trp Leu Arg Asp Val Trp Asp Trp Ile Cys
945                 950                 955                 960
Thr Val Leu Thr Asp Phe Lys Thr Trp Leu Gln Ser Lys Leu Leu Pro
                965                 970                 975
Arg Leu Pro Gly Val Pro Phe Phe Ser Cys Gln Arg Gly Tyr Lys Gly
                980                 985                 990
Val Trp Arg Gly Asp Gly Ile Met  Gln Thr Thr Cys Pro  Cys Gly Ala
                995                 1000                1005
Gln Ile  Thr Gly His Val Lys  Asn Gly Ser Met Arg  Ile Val Gly
    1010                1015                1020
Pro Arg  Thr Cys Ser Asn Thr  Trp His Gly Thr Phe  Pro Ile Asn
    1025                1030                1035
Ala Tyr  Thr Thr Gly Pro Cys  Thr Pro Ser Pro Ala  Pro Asn Tyr
    1040                1045                1050
Ser Arg  Ala Leu Trp Arg Val  Ala Ala Glu Glu Tyr  Val Glu Val
    1055                1060                1065
Thr Arg  Val Gly Asp Phe His  Tyr Val Thr Gly Met  Thr Thr Asp
    1070                1075                1080
Asn Val  Lys Cys Pro Cys Gln  Val Pro Ala Pro Glu  Phe Phe Thr
    1085                1090                1095
```

-continued

```
Glu Val Asp Gly Val Arg Leu His Arg Tyr Ala Pro Ala Cys Lys
    1100                1105                1110

Pro Leu Leu Arg Glu Glu Val Thr Phe Leu Val Gly Leu Asn Gln
    1115                1120                1125

Tyr Leu Val Gly Ser Gln Leu Pro Cys Glu Pro Glu Pro Asp Val
    1130                1135                1140

Ala Val Leu Thr Ser Met Leu Thr Asp Pro Ser His Ile Thr Ala
    1145                1150                1155

Glu Thr Ala Lys Arg Arg Leu Ala Arg Gly Ser Pro Pro Ser Leu
    1160                1165                1170

Ala Ser Ser Ser Ala Ile Gln Leu Ser Ala Pro Ser Leu Lys Ala
    1175                1180                1185

Thr Cys Thr Thr Arg His Asp Ser Pro Asp Ala Asp Leu Ile Glu
    1190                1195                1200

Ala Asn Leu Leu Trp Arg Gln Glu Met Gly Gly Asn Ile Thr Arg
    1205                1210                1215

Val Glu Ser Glu Asn Lys Val Val Ile Leu Asp Ser Phe Glu Pro
    1220                1225                1230

Leu Gln Ala Glu Glu Asp Glu Arg Glu Val Ser Val Pro Ala Glu
    1235                1240                1245

Ile Leu Arg Arg Ser Arg Lys Phe Pro Arg Ala Met Pro Ile Trp
    1250                1255                1260

Ala Arg Pro Asp Tyr Asn Pro Pro Leu Leu Glu Ser Trp Lys Asp
    1265                1270                1275

Pro Asp Tyr Val Pro Pro Val His Gly Cys Pro Leu Pro Pro
    1280                1285                1290

Ala Lys Ala Pro Pro Ile Pro Pro Arg Arg Lys Arg Thr Val
    1295                1300                1305

Val Leu Ser Glu Ser Thr Val Ser Ser Ala Leu Ala Glu Leu Ala
    1310                1315                1320

Thr Lys Thr Phe Gly Ser Ser Glu Ser Ser Ala Val Asp Ser Gly
    1325                1330                1335

Thr Ala Thr Ala Ser Pro Asp Gln Pro Ser Asp Asp Gly Asp Ala
    1340                1345                1350

Gly Ser Asp Val Glu Ser Tyr Ser Ser Met Pro Pro Leu Glu Gly
    1355                1360                1365

Glu Pro Gly Asp Pro Asp Leu Ser Asp Gly Ser Trp Ser Thr Val
    1370                1375                1380

Ser Glu Glu Ala Ser Glu Asp Val Val Cys Cys Ser Met Ser Tyr
    1385                1390                1395

Thr Trp Thr Gly Ala Leu Ile Thr Pro Cys Ala Ala Glu Glu Thr
    1400                1405                1410

Lys Leu Pro Ile Asn Ala Leu Ser Asn Ser Leu Leu Arg His His
    1415                1420                1425

Asn Leu Val Tyr Ala Thr Thr Ser Arg Ser Ala Ser Leu Arg Gln
    1430                1435                1440

Lys Lys Val Thr Phe Asp Arg Leu Gln Val Leu Asp Asp His Tyr
    1445                1450                1455

Arg Asp Val Leu Lys Glu Met Lys Ala Lys Ala Ser Thr Val Lys
    1460                1465                1470

Ala Lys Leu Leu Ser Val Glu Glu Ala Cys Lys Leu Thr Pro Pro
    1475                1480                1485
```

-continued

```
His Ser Ala Arg Ser Lys Phe Gly Tyr Gly Ala Lys Asp Val Arg
    1490            1495                1500

Asn Leu Ser Ser Lys Ala Val Asn His Ile Arg Ser Val Trp Lys
    1505            1510                1515

Asp Leu Leu Glu Asp Thr Glu Thr Pro Ile Asp Thr Thr Ile Met
    1520            1525                1530

Ala Lys Asn Glu Val Phe Cys Val Gln Pro Glu Lys Gly Gly Arg
    1535            1540                1545

Lys Pro Ala Arg Leu Ile Val Phe Pro Asp Leu Gly Val Arg Val
    1550            1555                1560

Cys Glu Lys Met Ala Leu Tyr Asp Val Val Ser Thr Leu Pro Gln
    1565            1570                1575

Ala Val Met Gly Ser Ser Tyr Gly Phe Gln Tyr Ser Pro Gly Gln
    1580            1585                1590

Arg Val Glu Phe Leu Val Asn Ala Trp Lys Ala Lys Lys Cys Pro
    1595            1600                1605

Met Gly Phe Ala Tyr Asp Thr Arg Cys Phe Asp Ser Thr Val Thr
    1610            1615                1620

Glu Asn Asp Ile Arg Val Glu Ser Ile Tyr Gln Cys Cys Asp
    1625            1630                1635

Leu Ala Pro Glu Ala Arg Gln Ala Ile Arg Ser Leu Thr Glu Arg
    1640            1645                1650

Leu Tyr Ile Gly Gly Pro Leu Thr Asn Ser Lys Gly Gln Asn Cys
    1655            1660                1665

Gly Tyr Arg Arg Cys Arg Ala Ser Gly Val Leu Thr Thr Ser Cys
    1670            1675                1680

Gly Asn Thr Leu Thr Cys Tyr Leu Lys Ala Ala Ala Cys Arg
    1685            1690                1695

Ala Ala Lys Leu Gln Asp Cys Thr Met Leu Val Cys Gly Asp Asp
    1700            1705                1710

Leu Val Val Ile Cys Glu Ser Ala Gly Thr Gln Glu Asp Glu Ala
    1715            1720                1725

Ser Leu Arg Ala Phe Thr Glu Ala Met Thr Arg Tyr Ser Ala Pro
    1730            1735                1740

Pro Gly Asp Pro Pro Lys Pro Glu Tyr Asp Leu Glu Leu Ile Thr
    1745            1750                1755

Ser Cys Ser Ser Asn Val Ser Val Ala His Asp Ala Ser Gly Lys
    1760            1765                1770

Arg Val Tyr Tyr Leu Thr Arg Asp Pro Thr Thr Pro Leu Ala Arg
    1775            1780                1785

Ala Ala Trp Glu Thr Ala Arg His Thr Pro Val Asn Ser Trp Leu
    1790            1795                1800

Gly Asn Ile Ile Met Tyr Ala Pro Thr Leu Trp Ala Arg Met Ile
    1805            1810                1815

Leu Met Thr His Phe Phe Ser Ile Leu Leu Ala Gln Glu Gln Leu
    1820            1825                1830

Glu Lys Ala Leu Asp Cys Gln Ile Tyr Gly Ala Cys Tyr Ser Ile
    1835            1840                1845

Glu Pro Leu Asp Leu Pro Gln Ile Ile Gln Arg Leu His Gly Leu
    1850            1855                1860

Ser Ala Phe Ser Leu His Ser Tyr Ser Pro Gly Glu Ile Asn Arg
    1865            1870                1875

Val Ala Ser Cys Leu Arg Lys Leu Gly Val Pro Pro Leu Arg Val
```

-continued

```
                1880                1885                1890

Trp Arg His Arg Ala Arg Ser Val Arg Ala Arg Leu Leu Ser Gln
    1895                1900                1905

Gly Gly Arg Ala Ala Thr Cys Gly Lys Tyr Leu Phe Asn Trp Ala
    1910                1915                1920

Val Arg Thr Lys Leu Lys Leu Thr Pro Ile Pro Ala Ala Ser Gln
    1925                1930                1935

Leu Asp Leu Ser Ser Trp Phe Val Ala Gly Tyr Ser Gly Gly Asp
    1940                1945                1950

Ile Tyr His Ser Leu Ser Arg Ala Arg Pro Arg Trp Phe Met Trp
    1955                1960                1965

Cys Leu Leu Leu Leu Ser Val Gly Val Gly Ile Tyr Leu Leu Pro
    1970                1975                1980

Asn Arg
    1985

<210> SEQ ID NO 16
<211> LENGTH: 447
<212> TYPE: PRT
<213> ORGANISM: Hepatitis C virus

<400> SEQUENCE: 16

Ser Gly Ser Trp Leu Arg Asp Val Trp Asp Trp Ile Cys Thr Val Leu
1               5                   10                  15

Thr Asp Phe Lys Thr Trp Leu Gln Ser Lys Leu Leu Pro Arg Leu Pro
                20                  25                  30

Gly Val Pro Phe Phe Ser Cys Gln Arg Gly Tyr Lys Gly Val Trp Arg
            35                  40                  45

Gly Asp Gly Ile Met Gln Thr Thr Cys Pro Cys Gly Ala Gln Ile Thr
        50                  55                  60

Gly His Val Lys Asn Gly Ser Met Arg Ile Val Gly Pro Arg Thr Cys
65                  70                  75                  80

Ser Asn Thr Trp His Gly Thr Phe Pro Ile Asn Ala Tyr Thr Thr Gly
                85                  90                  95

Pro Cys Thr Pro Ser Pro Ala Pro Asn Tyr Ser Arg Ala Leu Trp Arg
            100                 105                 110

Val Ala Ala Glu Glu Tyr Val Glu Val Thr Arg Val Gly Asp Phe His
        115                 120                 125

Tyr Val Thr Gly Met Thr Thr Asp Asn Val Lys Cys Pro Cys Gln Val
    130                 135                 140

Pro Ala Pro Glu Phe Phe Thr Glu Val Asp Gly Val Arg Leu His Arg
145                 150                 155                 160

Tyr Ala Pro Ala Cys Lys Pro Leu Leu Arg Glu Glu Val Thr Phe Leu
                165                 170                 175

Val Gly Leu Asn Gln Tyr Leu Val Gly Ser Gln Leu Pro Cys Glu Pro
            180                 185                 190

Glu Pro Asp Val Ala Val Leu Thr Ser Met Leu Thr Asp Pro Ser His
        195                 200                 205

Ile Thr Ala Glu Thr Ala Lys Arg Arg Leu Ala Arg Gly Ser Pro Pro
    210                 215                 220

Ser Leu Ala Ser Ser Ser Ala Ile Gln Leu Ser Ala Pro Ser Leu Lys
225                 230                 235                 240

Ala Thr Cys Thr Thr Arg His Asp Ser Pro Asp Ala Asp Leu Ile Glu
                245                 250                 255
```

```
Ala Asn Leu Leu Trp Arg Gln Glu Met Gly Gly Asn Ile Thr Arg Val
            260                 265                 270

Glu Ser Glu Asn Lys Val Val Ile Leu Asp Ser Phe Glu Pro Leu Gln
            275                 280                 285

Ala Glu Glu Asp Glu Arg Glu Val Ser Val Pro Ala Glu Ile Leu Arg
290                 295                 300

Arg Ser Arg Lys Phe Pro Arg Ala Met Pro Ile Trp Ala Arg Pro Asp
305                 310                 315                 320

Tyr Asn Pro Pro Leu Leu Glu Ser Trp Lys Asp Pro Asp Tyr Val Pro
                325                 330                 335

Pro Val Val His Gly Cys Pro Leu Pro Pro Ala Lys Ala Pro Pro Ile
            340                 345                 350

Pro Pro Pro Arg Arg Lys Arg Thr Val Val Leu Ser Glu Ser Thr Val
            355                 360                 365

Ser Ser Ala Leu Ala Glu Leu Ala Thr Lys Thr Phe Gly Ser Ser Glu
370                 375                 380

Ser Ser Ala Val Asp Ser Gly Thr Ala Thr Ala Ser Pro Asp Gln Pro
385                 390                 395                 400

Ser Asp Asp Gly Asp Ala Gly Ser Asp Val Glu Ser Tyr Ser Ser Met
                405                 410                 415

Pro Pro Leu Glu Gly Glu Pro Gly Asp Pro Asp Leu Ser Asp Gly Ser
            420                 425                 430

Trp Ser Thr Val Ser Glu Glu Ala Ser Glu Asp Val Val Cys Cys
            435                 440                 445

<210> SEQ ID NO 17
<211> LENGTH: 1985
<212> TYPE: PRT
<213> ORGANISM: Hepatitis C virus

<400> SEQUENCE: 17

Met Ala Pro Ile Thr Ala Tyr Ser Gln Gln Thr Arg Gly Leu Leu Gly
1               5                   10                  15

Cys Ile Ile Thr Ser Leu Thr Gly Arg Asp Arg Asn Gln Val Glu Gly
            20                  25                  30

Glu Val Gln Val Val Ser Thr Ala Thr Gln Ser Phe Leu Ala Thr Cys
        35                  40                  45

Val Asn Gly Val Cys Trp Thr Val Tyr His Gly Ala Gly Ser Lys Thr
    50                  55                  60

Leu Ala Gly Pro Lys Gly Pro Ile Thr Gln Met Tyr Thr Asn Val Asp
65                  70                  75                  80

Gln Asp Leu Val Gly Trp Gln Ala Pro Pro Gly Ala Arg Ser Leu Thr
                85                  90                  95

Pro Cys Thr Cys Gly Ser Ser Asp Leu Tyr Leu Val Thr Arg His Ala
            100                 105                 110

Asp Val Ile Pro Val Arg Arg Arg Gly Asp Ser Arg Gly Ser Leu Leu
        115                 120                 125

Ser Pro Arg Pro Val Ser Tyr Leu Lys Gly Ser Ser Gly Gly Pro Leu
    130                 135                 140

Leu Cys Pro Ser Gly His Ala Val Gly Ile Phe Arg Ala Ala Val Cys
145                 150                 155                 160

Thr Arg Gly Val Ala Lys Ala Val Asp Phe Val Pro Val Glu Ser Met
                165                 170                 175

Glu Thr Thr Met Arg Ser Pro Val Phe Thr Asp Asn Ser Ser Pro Pro
            180                 185                 190
```

-continued

```
Ala Val Pro Gln Thr Phe Gln Val Ala His Leu His Ala Pro Thr Gly
            195                 200                 205

Ser Gly Lys Ser Thr Lys Val Pro Ala Ala Tyr Ala Ala Gln Gly Tyr
            210                 215                 220

Lys Val Leu Val Leu Asn Pro Ser Val Ala Ala Thr Leu Gly Phe Gly
225                 230                 235                 240

Ala Tyr Met Ser Lys Ala His Gly Ile Asp Pro Asn Ile Arg Thr Gly
            245                 250                 255

Val Arg Thr Ile Thr Thr Gly Ala Pro Ile Thr Tyr Ser Thr Tyr Gly
            260                 265                 270

Lys Phe Leu Ala Asp Gly Gly Cys Ser Gly Gly Ala Tyr Asp Ile Ile
            275                 280                 285

Ile Cys Asp Glu Cys His Ser Thr Asp Ser Thr Thr Ile Leu Gly Ile
            290                 295                 300

Gly Thr Val Leu Asp Gln Ala Glu Thr Ala Gly Ala Arg Leu Val Val
305                 310                 315                 320

Leu Ala Thr Ala Thr Pro Pro Gly Ser Val Thr Val Pro His Pro Asn
            325                 330                 335

Ile Glu Glu Val Ala Leu Ser Ser Thr Gly Glu Ile Pro Phe Tyr Gly
            340                 345                 350

Lys Ala Ile Pro Ile Glu Thr Ile Lys Gly Gly Arg His Leu Ile Phe
            355                 360                 365

Cys His Ser Lys Lys Lys Cys Asp Glu Leu Ala Ala Lys Leu Ser Gly
            370                 375                 380

Leu Gly Leu Asn Ala Val Ala Tyr Tyr Arg Gly Leu Asp Val Ser Val
385                 390                 395                 400

Ile Pro Thr Ser Gly Asp Val Ile Val Ala Thr Asp Ala Leu Met
            405                 410                 415

Thr Gly Phe Thr Gly Asp Phe Asp Ser Val Ile Asp Cys Asn Thr Cys
            420                 425                 430

Val Thr Gln Thr Val Asp Phe Ser Leu Asp Pro Thr Phe Thr Ile Glu
            435                 440                 445

Thr Thr Thr Val Pro Gln Asp Ala Val Ser Arg Ser Gln Arg Arg Gly
450                 455                 460

Arg Thr Gly Arg Gly Arg Met Gly Ile Tyr Arg Phe Val Thr Pro Gly
465                 470                 475                 480

Glu Arg Pro Ser Gly Met Phe Asp Ser Ser Val Leu Cys Glu Cys Tyr
            485                 490                 495

Asp Ala Gly Cys Ala Trp Tyr Glu Leu Thr Pro Ala Glu Thr Ser Val
            500                 505                 510

Arg Leu Arg Ala Tyr Leu Asn Thr Pro Gly Leu Pro Val Cys Gln Asp
            515                 520                 525

His Leu Glu Phe Trp Glu Ser Val Phe Thr Gly Leu Thr His Ile Asp
            530                 535                 540

Ala His Phe Leu Ser Gln Thr Lys Gln Ala Gly Asp Asn Phe Pro Tyr
545                 550                 555                 560

Leu Val Ala Tyr Gln Ala Thr Val Cys Ala Arg Ala Gln Ala Pro Pro
            565                 570                 575

Pro Ser Trp Asp Gln Met Trp Glu Cys Leu Ile Arg Leu Lys Pro Thr
            580                 585                 590

Leu His Gly Pro Thr Pro Leu Leu Tyr Arg Leu Gly Ala Val Gln Asn
            595                 600                 605
```

-continued

```
Glu Val Thr Thr Thr His Pro Ile Thr Lys Tyr Ile Met Ala Cys Met
    610                 615                 620
Ser Ala Asp Leu Glu Val Val Thr Ser Thr Trp Val Leu Val Gly Gly
625                 630                 635                 640
Val Leu Ala Ala Leu Ala Ala Tyr Cys Leu Thr Thr Gly Ser Val Val
                645                 650                 655
Ile Val Gly Arg Ile Ile Leu Ser Gly Lys Pro Ala Ile Ile Pro Asp
            660                 665                 670
Arg Glu Val Leu Tyr Arg Glu Phe Asp Glu Met Glu Glu Cys Ala Ser
        675                 680                 685
His Leu Pro Tyr Ile Glu Gln Gly Met Gln Leu Ala Glu Gln Phe Lys
    690                 695                 700
Gln Lys Ala Ile Gly Leu Leu Gln Thr Ala Thr Lys Gln Ala Glu Ala
705                 710                 715                 720
Ala Ala Pro Val Val Glu Ser Lys Trp Arg Thr Leu Glu Ala Phe Trp
                725                 730                 735
Ala Lys His Met Trp Asn Phe Ile Ser Gly Ile Gln Tyr Leu Ala Gly
            740                 745                 750
Leu Ser Thr Leu Pro Gly Asn Pro Ala Ile Ala Ser Leu Met Ala Phe
        755                 760                 765
Thr Ala Ser Ile Thr Ser Pro Leu Thr Thr Gln His Thr Leu Leu Phe
    770                 775                 780
Asn Ile Leu Gly Gly Trp Val Ala Ala Gln Leu Ala Pro Pro Ser Ala
785                 790                 795                 800
Ala Ser Ala Phe Val Gly Ala Gly Ile Ala Gly Ala Ala Val Gly Ser
                805                 810                 815
Ile Gly Leu Gly Lys Val Leu Val Asp Ile Leu Ala Gly Tyr Gly Ala
            820                 825                 830
Gly Val Ala Gly Ala Leu Val Ala Phe Lys Val Met Ser Gly Glu Met
        835                 840                 845
Pro Ser Thr Glu Asp Leu Val Asn Leu Leu Pro Ala Ile Leu Ser Pro
    850                 855                 860
Gly Ala Leu Val Val Gly Val Val Cys Ala Ala Ile Leu Arg Arg His
865                 870                 875                 880
Val Gly Pro Gly Glu Gly Ala Val Gln Trp Met Asn Arg Leu Ile Ala
                885                 890                 895
Phe Ala Ser Arg Gly Asn His Val Ser Pro Thr His Tyr Val Pro Glu
            900                 905                 910
Ser Asp Ala Ala Ala Arg Val Thr Gln Ile Leu Ser Gly Leu Thr Ile
        915                 920                 925
Thr Gln Leu Leu Lys Arg Leu His Gln Trp Ile Asn Glu Asp Cys Ser
    930                 935                 940
Thr Pro Cys Ser Gly Ser Trp Leu Arg Asp Val Trp Asp Trp Ile Cys
945                 950                 955                 960
Thr Val Leu Thr Asp Phe Lys Thr Trp Leu Gln Ser Lys Leu Leu Pro
                965                 970                 975
Arg Leu Pro Gly Val Pro Phe Phe Ser Cys Gln Arg Gly Tyr Lys Gly
            980                 985                 990
Val Trp Arg Gly Asp Gly Ile Met Gln Thr Thr Cys Pro Cys Gly Ala
        995                 1000                1005
Gln Ile Thr Gly His Val Lys Asn Gly Ser Met Arg Ile Val Gly
    1010                1015                1020
Pro Arg Thr Cys Ser Asn Thr Trp His Gly Thr Phe Pro Ile Asn
```

-continued

```
                1025                1030                1035

Ala Tyr Thr Thr Gly Pro Cys Thr Pro Ser Pro Ala Pro Asn Tyr
            1040                1045                1050

Ser Arg Ala Leu Trp Arg Val Ala Ala Glu Glu Tyr Val Glu Val
            1055                1060                1065

Thr Arg Val Gly Asp Phe His Tyr Val Thr Gly Met Thr Thr Asp
            1070                1075                1080

Asn Val Lys Cys Pro Cys Gln Val Pro Ala Pro Glu Phe Phe Thr
            1085                1090                1095

Glu Val Asp Gly Val Arg Leu His Arg Tyr Ala Pro Ala Cys Lys
            1100                1105                1110

Pro Leu Leu Arg Glu Glu Val Thr Phe Leu Val Gly Leu Asn Gln
            1115                1120                1125

Tyr Leu Val Gly Ser Gln Leu Pro Cys Glu Pro Glu Pro Asp Val
            1130                1135                1140

Ala Val Leu Thr Ser Met Leu Thr Asp Pro Ser His Ile Thr Ala
            1145                1150                1155

Glu Thr Ala Lys Arg Gly Leu Ala Arg Gly Ser Pro Pro Ser Leu
            1160                1165                1170

Ala Ser Ser Ser Ala Ser Gln Leu Ser Ala Pro Ser Leu Lys Ala
            1175                1180                1185

Thr Cys Thr Thr Arg His Asp Ser Pro Asp Ala Asp Leu Ile Glu
            1190                1195                1200

Ala Asn Leu Leu Trp Arg Gln Glu Met Gly Gly Asn Ile Thr Arg
            1205                1210                1215

Val Glu Ser Glu Asn Lys Val Val Ile Leu Asp Ser Phe Glu Pro
            1220                1225                1230

Leu Gln Ala Glu Glu Asp Glu Arg Glu Val Ser Val Pro Ala Glu
            1235                1240                1245

Ile Leu Arg Arg Ser Arg Lys Phe Pro Arg Ala Met Pro Ile Trp
            1250                1255                1260

Ala Arg Pro Asp Tyr Asn Pro Pro Leu Leu Glu Ser Trp Lys Asp
            1265                1270                1275

Pro Asp Tyr Val Pro Pro Val His Gly Cys Pro Leu Pro Pro
            1280                1285                1290

Ala Lys Ala Pro Pro Ile Pro Pro Arg Arg Lys Arg Thr Val
            1295                1300                1305

Val Leu Ser Glu Ser Thr Val Ser Ser Ala Leu Ala Glu Leu Ala
            1310                1315                1320

Thr Lys Thr Phe Gly Ser Ser Glu Ser Ser Ala Val Asp Ser Gly
            1325                1330                1335

Thr Ala Thr Ala Ser Pro Asp Gln Pro Ser Asp Asp Gly Asp Ala
            1340                1345                1350

Gly Ser Asp Val Glu Ser Tyr Ser Ser Met Pro Pro Leu Glu Gly
            1355                1360                1365

Glu Pro Gly Asp Pro Asp Leu Ser Asp Gly Ser Trp Ser Thr Val
            1370                1375                1380

Ser Glu Glu Ala Ser Glu Asp Val Val Cys Cys Ser Met Ser Tyr
            1385                1390                1395

Thr Trp Thr Gly Ala Leu Ile Thr Pro Cys Ala Ala Glu Glu Thr
            1400                1405                1410

Lys Leu Pro Ile Asn Ala Leu Ser Asn Ser Leu Leu Arg His His
            1415                1420                1425
```

-continued

| | | | | | | | | | | | |
|---|---|---|---|---|---|---|---|---|---|---|---|
| Asn | Leu | Val | Tyr | Ala | Thr | Thr | Ser | Arg | Ser | Ala | Ser | Leu | Arg | Gln |
| | | 1430 | | | | 1435 | | | | 1440 | |
| Lys | Lys | Val | Thr | Phe | Asp | Arg | Leu | Gln | Val | Leu | Asp | Asp | His | Tyr |
| | 1445 | | | | 1450 | | | | | 1455 | |
| Arg | Asp | Val | Leu | Lys | Glu | Met | Lys | Ala | Lys | Ala | Ser | Thr | Val | Lys |
| 1460 | | | | | 1465 | | | | | 1470 | |
| Ala | Lys | Leu | Leu | Ser | Val | Glu | Glu | Ala | Cys | Lys | Leu | Thr | Pro | Pro |
| 1475 | | | | | 1480 | | | | | 1485 | |
| His | Ser | Ala | Arg | Ser | Lys | Phe | Gly | Tyr | Gly | Ala | Lys | Asp | Val | Arg |
| 1490 | | | | | 1495 | | | | | 1500 | |
| Asn | Leu | Ser | Ser | Lys | Ala | Val | Asn | His | Ile | Arg | Ser | Val | Trp | Lys |
| 1505 | | | | | 1510 | | | | | 1515 | |
| Asp | Leu | Leu | Glu | Asp | Thr | Glu | Thr | Pro | Ile | Asp | Thr | Thr | Ile | Met |
| 1520 | | | | | 1525 | | | | | 1530 | |
| Ala | Lys | Asn | Glu | Val | Phe | Cys | Val | Gln | Pro | Glu | Lys | Gly | Gly | Arg |
| 1535 | | | | | 1540 | | | | | 1545 | |
| Lys | Pro | Ala | Arg | Leu | Ile | Val | Phe | Pro | Asp | Leu | Gly | Val | Arg | Val |
| 1550 | | | | | 1555 | | | | | 1560 | |
| Cys | Glu | Lys | Met | Ala | Leu | Tyr | Asp | Val | Val | Ser | Thr | Leu | Pro | Gln |
| 1565 | | | | | 1570 | | | | | 1575 | |
| Ala | Val | Met | Gly | Ser | Ser | Tyr | Gly | Phe | Gln | Tyr | Ser | Pro | Gly | Gln |
| 1580 | | | | | 1585 | | | | | 1590 | |
| Arg | Val | Glu | Phe | Leu | Val | Asn | Ala | Trp | Lys | Ala | Lys | Lys | Cys | Pro |
| 1595 | | | | | 1600 | | | | | 1605 | |
| Met | Gly | Phe | Ala | Tyr | Asp | Thr | Arg | Cys | Phe | Asp | Ser | Thr | Val | Thr |
| 1610 | | | | | 1615 | | | | | 1620 | |
| Glu | Asn | Asp | Ile | Arg | Val | Glu | Glu | Ser | Ile | Tyr | Gln | Cys | Cys | Asp |
| 1625 | | | | | 1630 | | | | | 1635 | |
| Leu | Ala | Pro | Glu | Ala | Arg | Gln | Ala | Ile | Arg | Ser | Leu | Thr | Glu | Arg |
| 1640 | | | | | 1645 | | | | | 1650 | |
| Leu | Tyr | Ile | Gly | Gly | Pro | Leu | Thr | Asn | Ser | Lys | Gly | Gln | Asn | Cys |
| 1655 | | | | | 1660 | | | | | 1665 | |
| Gly | Tyr | Arg | Arg | Cys | Arg | Ala | Ser | Gly | Val | Leu | Thr | Thr | Ser | Cys |
| 1670 | | | | | 1675 | | | | | 1680 | |
| Gly | Asn | Thr | Leu | Thr | Cys | Tyr | Leu | Lys | Ala | Ala | Ala | Cys | Arg |
| 1685 | | | | | 1690 | | | | | 1695 | |
| Ala | Ala | Lys | Leu | Gln | Asp | Cys | Thr | Met | Leu | Val | Cys | Gly | Asp | Asp |
| 1700 | | | | | 1705 | | | | | 1710 | |
| Leu | Val | Val | Ile | Cys | Glu | Ser | Ala | Gly | Thr | Gln | Glu | Asp | Glu | Ala |
| 1715 | | | | | 1720 | | | | | 1725 | |
| Ser | Leu | Arg | Ala | Phe | Thr | Glu | Ala | Met | Thr | Arg | Tyr | Ser | Ala | Pro |
| 1730 | | | | | 1735 | | | | | 1740 | |
| Pro | Gly | Asp | Pro | Pro | Lys | Pro | Glu | Tyr | Asp | Leu | Glu | Leu | Ile | Thr |
| 1745 | | | | | 1750 | | | | | 1755 | |
| Ser | Cys | Ser | Ser | Asn | Val | Ser | Val | Ala | His | Asp | Ala | Ser | Gly | Lys |
| 1760 | | | | | 1765 | | | | | 1770 | |
| Arg | Val | Tyr | Tyr | Leu | Thr | Arg | Asp | Pro | Thr | Thr | Pro | Leu | Ala | Arg |
| 1775 | | | | | 1780 | | | | | 1785 | |
| Ala | Ala | Trp | Glu | Thr | Ala | Arg | His | Thr | Pro | Val | Asn | Ser | Trp | Leu |
| 1790 | | | | | 1795 | | | | | 1800 | |
| Gly | Asn | Ile | Ile | Met | Tyr | Ala | Pro | Thr | Leu | Trp | Ala | Arg | Met | Ile |
| 1805 | | | | | 1810 | | | | | 1815 | |

```
Leu Met Thr His Phe Phe Ser Ile Leu Leu Ala Gln Glu Gln Leu
    1820                1825                1830

Glu Lys Ala Leu Asp Cys Gln Ile Tyr Gly Ala Cys Tyr Ser Ile
    1835                1840                1845

Glu Pro Leu Asp Leu Pro Gln Ile Ile Gln Arg Leu His Gly Leu
    1850                1855                1860

Ser Ala Phe Ser Leu His Ser Tyr Ser Pro Gly Glu Ile Asn Arg
    1865                1870                1875

Val Ala Ser Cys Leu Arg Lys Leu Gly Val Pro Pro Leu Arg Val
    1880                1885                1890

Trp Arg His Arg Ala Arg Ser Val Arg Ala Arg Leu Leu Ser Gln
    1895                1900                1905

Gly Gly Arg Ala Ala Thr Cys Gly Lys Tyr Leu Phe Asn Trp Ala
    1910                1915                1920

Val Arg Thr Lys Leu Lys Leu Thr Pro Ile Pro Ala Ala Ser Gln
    1925                1930                1935

Leu Asp Leu Ser Ser Trp Phe Val Ala Gly Tyr Ser Gly Gly Asp
    1940                1945                1950

Ile Tyr His Ser Leu Ser Arg Ala Arg Pro Arg Trp Phe Met Trp
    1955                1960                1965

Cys Leu Leu Leu Leu Ser Val Gly Val Gly Ile Tyr Leu Leu Pro
    1970                1975                1980

Asn Arg
    1985

<210> SEQ ID NO 18
<211> LENGTH: 447
<212> TYPE: PRT
<213> ORGANISM: Hepatitis C virus

<400> SEQUENCE: 18

Ser Gly Ser Trp Leu Arg Asp Val Trp Asp Trp Ile Cys Thr Val Leu
1               5                   10                  15

Thr Asp Phe Lys Thr Trp Leu Gln Ser Lys Leu Leu Pro Arg Leu Pro
                20                  25                  30

Gly Val Pro Phe Phe Ser Cys Gln Arg Gly Tyr Lys Gly Val Trp Arg
            35                  40                  45

Gly Asp Gly Ile Met Gln Thr Thr Cys Pro Cys Gly Ala Gln Ile Thr
        50                  55                  60

Gly His Val Lys Asn Gly Ser Met Arg Ile Val Gly Pro Arg Thr Cys
65                  70                  75                  80

Ser Asn Thr Trp His Gly Thr Phe Pro Ile Asn Ala Tyr Thr Thr Gly
                85                  90                  95

Pro Cys Thr Pro Ser Pro Ala Pro Asn Tyr Ser Arg Ala Leu Trp Arg
            100                 105                 110

Val Ala Ala Glu Glu Tyr Val Glu Val Thr Arg Val Gly Asp Phe His
        115                 120                 125

Tyr Val Thr Gly Met Thr Thr Asp Asn Val Lys Cys Pro Cys Gln Val
130                 135                 140

Pro Ala Pro Glu Phe Phe Thr Glu Val Asp Gly Val Arg Leu His Arg
145                 150                 155                 160

Tyr Ala Pro Ala Cys Lys Pro Leu Leu Arg Glu Glu Val Thr Phe Leu
                165                 170                 175

Val Gly Leu Asn Gln Tyr Leu Val Gly Ser Gln Leu Pro Cys Glu Pro
            180                 185                 190
```

-continued

Glu Pro Asp Val Ala Val Leu Thr Ser Met Leu Thr Asp Pro Ser His
        195                 200                 205

Ile Thr Ala Glu Thr Ala Lys Arg Gly Leu Ala Arg Gly Ser Pro Pro
    210                 215                 220

Ser Leu Ala Ser Ser Ala Ser Gln Leu Ser Ala Pro Ser Leu Lys
225                 230                 235                 240

Ala Thr Cys Thr Thr Arg His Asp Ser Pro Asp Ala Asp Leu Ile Glu
                245                 250                 255

Ala Asn Leu Leu Trp Arg Gln Glu Met Gly Gly Asn Ile Thr Arg Val
            260                 265                 270

Glu Ser Glu Asn Lys Val Val Ile Leu Asp Ser Phe Glu Pro Leu Gln
        275                 280                 285

Ala Glu Glu Asp Glu Arg Glu Val Ser Val Pro Ala Glu Ile Leu Arg
    290                 295                 300

Arg Ser Arg Lys Phe Pro Arg Ala Met Pro Ile Trp Ala Arg Pro Asp
305                 310                 315                 320

Tyr Asn Pro Pro Leu Leu Glu Ser Trp Lys Asp Pro Asp Tyr Val Pro
                325                 330                 335

Pro Val Val His Gly Cys Pro Leu Pro Pro Ala Lys Ala Pro Pro Ile
            340                 345                 350

Pro Pro Pro Arg Arg Lys Arg Thr Val Val Leu Ser Glu Ser Thr Val
        355                 360                 365

Ser Ser Ala Leu Ala Glu Leu Ala Thr Lys Thr Phe Gly Ser Ser Glu
    370                 375                 380

Ser Ser Ala Val Asp Ser Gly Thr Ala Thr Ala Ser Pro Asp Gln Pro
385                 390                 395                 400

Ser Asp Asp Gly Asp Ala Gly Ser Asp Val Glu Ser Tyr Ser Ser Met
                405                 410                 415

Pro Pro Leu Glu Gly Glu Pro Gly Asp Pro Asp Leu Ser Asp Gly Ser
            420                 425                 430

Trp Ser Thr Val Ser Glu Glu Ala Ser Glu Asp Val Val Cys Cys
        435                 440                 445

<210> SEQ ID NO 19
<211> LENGTH: 447
<212> TYPE: PRT
<213> ORGANISM: Hepatitis C virus

<400> SEQUENCE: 19

Ser Gly Ser Trp Leu Arg Asp Val Trp Asp Trp Ile Cys Thr Val Leu
1               5                   10                  15

Thr Asp Phe Lys Thr Trp Leu Gln Ser Lys Leu Leu Pro Arg Leu Pro
            20                  25                  30

Gly Val Pro Phe Phe Ser Cys Gln Arg Gly Tyr Lys Gly Val Trp Arg
        35                  40                  45

Gly Asp Gly Ile Met Gln Thr Thr Cys Pro Cys Gly Ala Gln Ile Thr
    50                  55                  60

Gly His Val Lys Asn Gly Ser Met Arg Ile Val Gly Pro Arg Thr Cys
65                  70                  75                  80

Ser Asn Thr Trp His Gly Thr Phe Pro Ile Asn Ala Tyr Thr Thr Gly
                85                  90                  95

Pro Cys Thr Pro Ser Pro Ala Pro Asn Tyr Ser Arg Ala Leu Trp Arg
            100                 105                 110

Val Ala Ala Glu Glu Tyr Val Glu Val Thr Arg Val Gly Asp Phe His

-continued

```
                115                 120                 125
Tyr Val Thr Gly Met Thr Thr Asp Asn Val Lys Cys Pro Cys Gln Val
            130                 135                 140
Pro Ala Pro Glu Phe Phe Thr Glu Val Asp Gly Val Arg Leu His Arg
145                 150                 155                 160
Tyr Ala Pro Ala Cys Lys Pro Leu Leu Arg Glu Val Thr Phe Leu
                165                 170                 175
Val Gly Leu Asn Gln Tyr Leu Val Gly Ser Gln Leu Pro Cys Glu Pro
            180                 185                 190
Glu Pro Asp Val Ala Val Leu Thr Ser Met Leu Thr Asp Pro Ser His
            195                 200                 205
Ile Thr Ala Glu Thr Ala Lys Arg Arg Leu Ala Arg Gly Ser Pro Pro
        210                 215                 220
Ser Leu Ser Ser Ser Ser Ala Ser Gln Leu Ser Ala Pro Ser Leu Lys
225                 230                 235                 240
Ala Thr Cys Thr Thr Arg His Asp Ser Pro Asp Ala Asp Leu Ile Glu
                245                 250                 255
Ala Asn Leu Leu Trp Arg Gln Glu Met Gly Gly Asn Ile Thr Arg Val
            260                 265                 270
Glu Ser Glu Asn Lys Val Val Ile Leu Asp Ser Phe Glu Pro Leu Gln
        275                 280                 285
Ala Glu Glu Asp Glu Arg Glu Val Ser Val Pro Ala Glu Ile Leu Arg
    290                 295                 300
Arg Ser Arg Lys Phe Pro Arg Ala Met Pro Ile Trp Ala Arg Pro Asp
305                 310                 315                 320
Tyr Asn Pro Pro Leu Leu Glu Ser Trp Lys Asp Pro Asp Tyr Val Pro
                325                 330                 335
Pro Val Val His Gly Cys Pro Leu Pro Pro Ala Lys Ala Pro Pro Ile
            340                 345                 350
Pro Pro Pro Arg Arg Lys Arg Thr Val Val Leu Ser Glu Ser Thr Val
        355                 360                 365
Ser Ser Ala Leu Ala Glu Leu Ala Thr Lys Thr Phe Gly Ser Ser Glu
    370                 375                 380
Ser Ser Ala Val Asp Ser Gly Thr Ala Thr Ala Ser Pro Asp Gln Pro
385                 390                 395                 400
Ser Asp Asp Gly Asp Ala Gly Ser Asp Val Glu Ser Tyr Ser Ser Met
                405                 410                 415
Pro Pro Leu Glu Gly Glu Pro Gly Asp Pro Asp Leu Ser Asp Gly Ser
            420                 425                 430
Trp Ser Thr Val Ser Glu Glu Ala Ser Glu Asp Val Val Cys Cys
        435                 440                 445

<210> SEQ ID NO 20
<211> LENGTH: 447
<212> TYPE: PRT
<213> ORGANISM: Hepatitis C virus

<400> SEQUENCE: 20

Ser Gly Ser Trp Leu Arg Asp Val Trp Asp Trp Ile Cys Thr Val Leu
1               5                   10                  15
Thr Asp Phe Lys Thr Trp Leu Gln Ser Lys Leu Leu Pro Arg Leu Pro
                20                  25                  30
Gly Val Pro Phe Phe Ser Cys Gln Arg Gly Tyr Lys Gly Val Trp Arg
            35                  40                  45
```

-continued

```
Gly Asp Gly Ile Met Gln Thr Thr Cys Pro Cys Gly Ala Gln Ile Thr
 50                  55                  60
Gly His Val Lys Asn Gly Ser Met Arg Ile Val Gly Pro Arg Thr Cys
 65                  70                  75                  80
Ser Asn Thr Trp His Gly Thr Phe Pro Ile Asn Ala Tyr Thr Thr Gly
                 85                  90                  95
Pro Cys Thr Pro Ser Pro Ala Pro Asn Tyr Ser Arg Ala Leu Trp Arg
            100                 105                 110
Val Ala Ala Glu Glu Tyr Val Glu Val Thr Arg Val Gly Asp Phe His
        115                 120                 125
Tyr Val Thr Gly Met Thr Thr Asp Asn Val Lys Cys Pro Cys Gln Val
130                 135                 140
Pro Ala Pro Glu Phe Phe Thr Glu Val Asp Gly Val Arg Leu His Arg
145                 150                 155                 160
Tyr Ala Pro Ala Cys Lys Pro Leu Leu Arg Glu Glu Val Thr Phe Leu
                165                 170                 175
Val Gly Leu Asn Gln Tyr Leu Val Gly Ser Gln Leu Pro Cys Glu Pro
            180                 185                 190
Glu Pro Asp Val Ala Val Leu Thr Ser Met Leu Thr Asp Pro Ser His
        195                 200                 205
Ile Thr Ala Glu Thr Ala Lys Arg Arg Leu Ala Arg Gly Ser Pro Pro
210                 215                 220
Cys Leu Ala Ser Ser Ala Ser Gln Leu Ser Ala Pro Ser Leu Lys
225                 230                 235                 240
Ala Thr Cys Thr Thr Arg His Asp Ser Pro Asp Ala Asp Leu Ile Glu
                245                 250                 255
Ala Asn Leu Leu Trp Arg Gln Glu Met Gly Gly Asn Ile Thr Arg Val
            260                 265                 270
Glu Ser Glu Asn Lys Val Val Ile Leu Asp Ser Phe Glu Pro Leu Gln
        275                 280                 285
Ala Glu Glu Asp Glu Arg Glu Val Ser Val Pro Ala Glu Ile Leu Arg
290                 295                 300
Arg Ser Arg Lys Phe Pro Arg Ala Met Pro Ile Trp Ala Arg Pro Asp
305                 310                 315                 320
Tyr Asn Pro Pro Leu Leu Glu Ser Trp Lys Asp Pro Asp Tyr Val Pro
                325                 330                 335
Pro Val Val His Gly Cys Pro Leu Pro Pro Ala Lys Ala Pro Pro Ile
            340                 345                 350
Pro Pro Pro Arg Arg Lys Arg Thr Val Val Leu Ser Glu Ser Thr Val
        355                 360                 365
Ser Ser Ala Leu Ala Glu Leu Ala Thr Lys Thr Phe Gly Ser Ser Glu
370                 375                 380
Ser Ser Ala Val Asp Ser Gly Thr Ala Thr Ala Ser Pro Asp Gln Pro
385                 390                 395                 400
Ser Asp Asp Gly Asp Ala Gly Ser Asp Val Glu Ser Tyr Ser Ser Met
                405                 410                 415
Pro Pro Leu Glu Gly Glu Pro Gly Asp Pro Asp Leu Ser Asp Gly Ser
            420                 425                 430
Trp Ser Thr Val Ser Glu Glu Ala Ser Glu Asp Val Val Cys Cys
        435                 440                 445

<210> SEQ ID NO 21
<211> LENGTH: 447
<212> TYPE: PRT
```

<213> ORGANISM: Hepatitis C virus

<400> SEQUENCE: 21

```
Ser Gly Ser Trp Leu Arg Asp Val Trp Asp Trp Ile Cys Thr Val Leu
1               5                   10                  15

Thr Asp Phe Lys Thr Trp Leu Gln Ser Lys Leu Leu Pro Arg Leu Pro
                20                  25                  30

Gly Val Pro Phe Phe Ser Cys Gln Arg Gly Tyr Lys Gly Val Trp Arg
            35                  40                  45

Gly Asp Gly Ile Met Gln Thr Thr Cys Pro Cys Gly Ala Gln Ile Thr
        50                  55                  60

Gly His Val Lys Asn Gly Ser Met Arg Ile Val Gly Pro Arg Thr Cys
65                  70                  75                  80

Ser Asn Thr Trp His Gly Thr Phe Pro Ile Asn Ala Tyr Thr Thr Gly
                85                  90                  95

Pro Cys Thr Pro Ser Pro Ala Pro Asn Tyr Ser Arg Ala Leu Trp Arg
            100                 105                 110

Val Ala Ala Glu Glu Tyr Val Glu Val Thr Arg Val Gly Asp Phe His
        115                 120                 125

Tyr Val Thr Gly Met Thr Thr Asp Asn Val Lys Cys Pro Cys Gln Val
    130                 135                 140

Pro Ala Pro Glu Phe Phe Thr Glu Val Asp Gly Val Arg Leu His Arg
145                 150                 155                 160

Tyr Ala Pro Ala Cys Lys Pro Leu Leu Arg Glu Glu Val Thr Phe Leu
                165                 170                 175

Val Gly Leu Asn Gln Tyr Leu Val Gly Ser Gln Leu Pro Cys Glu Pro
            180                 185                 190

Glu Pro Asp Val Ala Val Leu Thr Ser Met Leu Thr Asp Pro Ser His
        195                 200                 205

Ile Thr Ala Glu Thr Ala Lys Arg Arg Leu Ala Arg Gly Ser Pro Pro
    210                 215                 220

Pro Leu Ala Ser Ser Ser Ala Ser Gln Leu Ser Ala Pro Ser Leu Lys
225                 230                 235                 240

Ala Thr Cys Thr Thr Arg His Asp Ser Pro Asp Ala Asp Leu Ile Glu
                245                 250                 255

Ala Asn Leu Leu Trp Arg Gln Glu Met Gly Gly Asn Ile Thr Arg Val
            260                 265                 270

Glu Ser Glu Asn Lys Val Val Ile Leu Asp Ser Phe Glu Pro Leu Gln
        275                 280                 285

Ala Glu Glu Asp Glu Arg Glu Val Ser Val Pro Ala Glu Ile Leu Arg
    290                 295                 300

Arg Ser Arg Lys Phe Pro Arg Ala Met Pro Ile Trp Ala Arg Pro Asp
305                 310                 315                 320

Tyr Asn Pro Pro Leu Leu Glu Ser Trp Lys Asp Pro Asp Tyr Val Pro
                325                 330                 335

Pro Val Val His Gly Cys Pro Leu Pro Pro Ala Lys Ala Pro Pro Ile
            340                 345                 350

Pro Pro Pro Arg Arg Lys Arg Thr Val Val Leu Ser Glu Ser Thr Val
        355                 360                 365

Ser Ser Ala Leu Ala Glu Leu Ala Thr Lys Thr Phe Gly Ser Ser Glu
    370                 375                 380

Ser Ser Ala Val Asp Ser Gly Thr Ala Thr Ala Ser Pro Asp Gln Pro
385                 390                 395                 400
```

```
Ser Asp Asp Gly Asp Ala Gly Ser Asp Val Glu Ser Tyr Ser Ser Met
            405                 410                 415

Pro Pro Leu Glu Gly Glu Pro Gly Asp Pro Asp Leu Ser Asp Gly Ser
            420                 425                 430

Trp Ser Thr Val Ser Glu Glu Ala Ser Glu Asp Val Val Cys Cys
            435                 440                 445

<210> SEQ ID NO 22
<211> LENGTH: 7789
<212> TYPE: DNA
<213> ORGANISM: Hepatitis C virus

<400> SEQUENCE: 22
gccagccccc gattggggc gacactccac catagatcac tccctgtga ggaactactg        60 tcttcacgca gaaagcgtct agccatggcg ttagtatgag tgtcgtgcag cctccaggac     120
cccccctccc gggagagcca tagtggtctg cggaaccggt gagtacaccg gaattgccag     180
gacgaccggg tcctttcttg gatcaacccg ctcaatgcct ggagatttgg gcgtgccccc     240
gcgagactgc tagccgagta gtgttgggtc gcgaaaggcc ttgtggtact gcctgatagg     300
gtgcttgcga gtgccccggg aggtctcgta gaccgtgcac cagaccacaa cggtttccct     360
ctagcgggat caattccgcc cctctcccctc cccccccct aacgttactg gccgaagccg     420
cttggaataa ggccggtgtg cgtttgtcta tatgttattt tccaccatat tgccgtcttt     480
tggcaatgtg agggcccgga aacctggccc tgtcttcttg acgagcattc ctagggggtct     540 ttcccctctc gccaaaggaa tgcaaggtct gttgaatgtc gtgaaggaag cagttcctct     600
ggaagcttct tgaagacaaa caacgtctgt agcgaccctt gcaggcagc ggaaccccc      660 acctggcgac aggtgcctct gcggccaaaa gccacgtgta taagatacac ctgcaaaggc     720
ggcacaaccc cagtgccacg ttgtgagttg gatagttgtg gaaagagtca aatggctctc     780
ctcaagcgta ttcaacaagg ggctgaagga tgcccagaag gtacccatt gtatgggatc     840 tgatctgggg cctcggtgca catgctttac atgtgtttag tcgaggttaa aaaacgtcta     900 ggcccccga accacgggga cgtggttttc ctttgaaaaa cacgataata ccatggaccg     960
ggagatggca gcatcgtgcg gaggcgcggt tttcgtaggt ctgatactct tgaccttgtc    1020
accgcactat aagctgttcc tcgctaggct catatggtgg ttacaatatt ttatcaccag    1080
ggccgaggca cacttgcaag tgtggatccc ccccctcaac gttcgggggg ccgcgatgc     1140 cgtcatcctc ctcacgtgcg cgatccaccc agagctaatc tttaccatca ccaaaatctt    1200
gctcgccata ctcggtccac tcatggtgct ccaggctggt ataaccaaag tgccgtactt    1260
cgtgcgcgca cacgggctca ttcgtgcatg catgctggtg cggaaggttg ctggggtca    1320 ttatgtccaa atggctctca tgaagttggc cgcactgaca ggtacgtacg tttatgacca    1380 tctcaccca ctgcgggact gggcccacgc gggcctacga gaccttgcgg tggcagttga    1440
gcccgtcgtc ttctctgata tggagaccaa ggttatcacc tgggggcag acaccgcggc     1500 gtgtgggac atcatcttgg gcctgccgt ctccgcccgc agggggaggg agatacatct      1560
gggaccggca gacagccttg aagggcaggg gtggcgactc ctcgcgccta ttacggccta    1620
ctcccaacag acgcgaggcc tacttggctg catcatcact agcctcacag gccgggacag    1680
gaaccaggtc gaggggagg tccaagtggt ctccaccgca acacaatctt tcctggcgac     1740
ctgcgtcaat ggcgtgtgtt ggactgtcta tcatggtgcc ggctcaaaga cccttgccgg    1800
cccaaagggc ccaatcaccc aaatgtacac caatgtggac caggacctcg tcggctggca    1860
```

-continued

```
agcgccccc   ggggcgcgtt   ccttgacacc   atgcacctgc   ggcagctcgg   acctttactt   1920
ggtcacgagg  catgccgatg   tcattccggt   gcgccggcgg   ggcgacagca   gggggagcct   1980
actctccccc  aggcccgtct   cctacttgaa   gggctcttcg   ggcggtccac   tgctctgccc   2040
ctcggggcac  gctgtgggca   tctttcgggc   tgccgtgtgc   acccgagggg   ttgcgaaggc   2100
ggtggacttt  gtacccgtcg   agtctatgga   aaccactatg   cggtcccgg    tcttcacgga   2160
caactcgtcc  cctccggccg   taccgcagac   attccaggtg   gcccatctac   acgccctac    2220
tggtagcggc  aagagcacta   aggtgccggc   tgcgtatgca   gcccaagggt   ataaggtgct   2280
tgtcctgaac  ccgtccgtcg   ccgccaccct   aggtttcggg   gcgtatatgt   ctaaggcaca   2340
tggtatcgac  cctaacatca   gaaccggggt   aaggaccatc   accacgggtg   ccccatcac    2400
gtactccacc  tatggcaagt   ttcttgccga   cggtggttgc   tctgggggcg   cctatgacat   2460
cataatatgt  gatgagtgcc   actcaactga   ctcgaccact   atcctgggca   tcggcacagt   2520
cctggaccaa  gcgagacgg    ctggagcgcg   actcgtcgtg   ctcgccaccg   ctacgcctcc   2580
gggatcggtc  accgtgccac   atccaaacat   cgaggaggtg   gctctgtcca   gcactggaga   2640
aatccccttt  tatggcaaag   ccatccccat   cgagaccatc   aagggggga    ggcacctcat   2700
tttctgccat  tccaagaaga   aatgtgatga   gctcgccgcg   aagctgtccg   gcctcggact   2760
caatgctgta  gcatattacc   ggggccttga   tgtatccgtc   ataccaacta   gcggagacgt   2820
cattgtcgta  gcaacggacg   ctctaatgac   gggctttacc   ggcgatttcg   actcagtgat   2880
cgactgcaat  acatgtgtca   cccagacagt   cgacttcagc   ctggacccga   ccttcaccat   2940
tgagacgacg  accgtgccac   aagacgcggt   gtcacgctcg   cagcggcgag   gcaggactgg   3000
taggggcagg  atgggcattt   acaggtttgt   gactccagga   gaacggccct   cgggcatgtt   3060
cgattcctcg  gttctgtgcg   agtgctatga   cgcgggctgt   gcttggtacg   agctcacgcc   3120
cgccgagacc  tcagttaggt   tgcgggctta   cctaaacaca   ccagggttgc   ccgtctgcca   3180
ggaccatctg  gagttctggg   agagcgtctt   tacaggcctc   acccacatag   acgcccattt   3240
cttgtcccag  actaagcagg   caggagacaa   cttcccctac   ctggtagcat   accaggctac   3300
ggtgtgcgcc  agggctcagg   ctccacctcc   atcgtgggac   caaatgtgga   agtgtctcat   3360
acggctaaag  cctacgctgc   acgggccaac   gcccctgctg   tataggctgg   agccgttca    3420
aaacgaggtt  actaccacac   accccataac   caaatacatc   atggcatgca   tgtcggctga   3480
cctggaggtc  gtcacgagca   cctgggtgct   ggtaggcgga   gtcctagcag   ctctggccgc   3540
gtattgcctg  acaacaggca   gcgtggtcat   tgtgggcagg   atcatcttgt   ccggaaagcc   3600
ggccatcatt  cccgacaggg   aagtcccttta  ccgggagttc   gatgagatgg   aagagtgcgc   3660
ctcacacctc  ccttacatcg   aacagggaat   gcagctcgcc   gaacaattca   aacagaaggc   3720
aatcgggttg  ctgcaaacag   ccaccaagca   agcggaggct   gctgctcccg   tggtggaatc   3780
caagtggcgg  accctcgaag   ccttctgggc   gaagcatatg   tggaatttca   tcagcgggat   3840
acaatattta  gcaggcttgt   ccactctgcc   tggcaacccc   gcgatagcat   cactgatggc   3900
attcacagcc  tctatcacca   gcccgctcac   cacccaacat   accctcctgt   ttaacatcct   3960
ggggggatgg  gtggccgccc   aacttgctcc   tcccagcgct   gcttctgctt   tcgtaggcgc   4020
cggcatcgct  ggagcggctg   ttggcagcat   aggccttggg   aaggtgcttg   tggatatttt   4080
ggcaggttat  ggagcagggg   tggcaggcgc   gctcgtggcc   tttaaggtca   tgagcggcga   4140
gatgccctcc  accgaggacc   tggttaacct   actccctgct   atcctctccc   ctggcgccct   4200
agtcgtcggg  gtcgtgtgcg   cagcgatact   gcgtcggcac   gtgggcccag   ggagggggc    4260
```

```
tgtgcagtgg atgaaccggc tgatagcgtt cgcttcgcgg ggtaaccacg tctcccccac    4320
gcactatgtg cctgagagcg acgctgcagc acgtgtcact cagatcctct ctagtcttac    4380
catcactcag ctgctgaaga ggcttcacca gtggatcaac gaggactgct ccacgccatg    4440
ctccggctcg tggctaagag atgtttggga ttggatatgc acggtgttga ctgatttcaa    4500
gacctggctc cagtccaagc tcctgccgcg attgccggga gtcccttct tctcatgtca     4560 acgtgggtac aagggagtct ggcggggcga cggcatcatg caaaccacct gcccatgtgg    4620
agcacagatc accggacatg tgaaaaacgg ttccatgagg atcgtggggc ctaggacctg    4680
tagtaacacg tggcatggaa cattccccat taacgcgtac accacgggcc cctgcacgcc    4740
ctccccggcg ccaaattatt ctagggcgct gtggcgggtg gctgctgagg agtacgtgga    4800
ggttacgcgg gtgggggatt tccactacgt gacgggcatg accactgaca acgtaaagtg    4860
cccgtgtcag gttccggccc ccgaattctt cacagaagtg gatggggtgc ggttgcacag    4920
gtacgctcca gcgtgcaaac ccctcctacg ggaggaggtc acattcctgg tcgggctcaa    4980
tcaatacctg gttgggtcac agctcccatg cgagcccgaa ccggacgtag cagtgctcac    5040
ttccatgctc accgaccect cccacattac ggcggagacg gctaagcgta ggctggccag    5100
gggatctccc ccctccttgg ccagctcatc agctatccag ctgtctgcgc cttccttgaa    5160
ggcaacatgc actaccegtc atgactcccc ggacgctgac ctcatcgagg ccaacctcct    5220
gtggcggcag gagatgggcg ggaacatcac ccgcgtggag tcagaaaata aggtagtaat    5280
tttggactct ttcgagccgc tccaagcgga ggaggatgag agggaagtat ccgttccggc    5340
ggagatcctg cggaggtcca ggaaattccc tcgagcgatg cccatatggg cacgcccgga    5400
ttacaaccct ccactgttag agtcctggaa ggacccggac tacgtccctc cagtggtaca    5460
cgggtgtcca ttgccgcctg ccaaggcccc tccgatacca cctccacgga ggaagaggac    5520
ggttgtcctg tcagaatcta ccgtgtcttc tgccttggcg gagctcgcca caagaccttt    5580
cggcagctcc gaatcgtcgg ccgtcgacag cggcacggca acggcctctc ctgaccagcc    5640
ctccgacgac ggcgacgcgg gatccgacgt tgagtcgtac tcctccatgc cccccttga    5700 gggggagccg ggggatcccg atctcagcga cgggtcttgg tctaccgtaa gcgaggaggc    5760
tagtgaggac gtcgtctgct gctcgatgtc ctacacatgg acaggcgccc tgatcacgcc    5820
atgcgctgcg gaggaaacca agctgcccat caatgcactg agcaactctt tgctccgtca    5880
ccacaacttg gtctatgcta caacatctcg cagcgcaagc ctgcggcaga agaaggtcac    5940 cttgacaga ctgcaggtcc tggacgacca ctaccgggac gtgctcaagg agatgaaggc      6000
gaaggcgtcc acagttaagg ctaaacttct atccgtggag gaagcctgta agctgacgcc    6060
cccacattcg gccagatcta aatttggcta tgggcaaag gacgtccgga acctatccag      6120
caaggccgtt aaccacatcc gctccgtgtg gaaggacttg ctggaagaca ctgagacacc    6180
aattgacacc accatcatgg caaaaaatga ggttttctgc gtccaaccag agaagggggg    6240
ccgcaagcca gctcgcctta tcgtattccc agatttgggg gttcgtgtgt gcgagaaaat    6300
ggccctttac gatgtggtct ccaccctccc tcaggccgtg atgggctctt catacggatt    6360
ccaatactct cctggacagc gggtcgagtt cctggtgaat gcctggaaag cgaagaaatg    6420
ccctatgggc ttcgcatatg acacccgctg ttttgactca acggtcactg agaatgacat    6480
ccgtgttgag gagtcaatct accaatgttg tgacttggcc cccgaagcca gacaggccat    6540
aaggtcgctc acagagcggc tttacatcgg ggggccccctg actaattcta aagggcagaa    6600
```

-continued

```
ctgcggctat cgccggtgcc gcgcgagcgg tgtactgacg accagctgcg gtaatacccT    6660
cacatgttac ttgaaggccg ctgcggcctg tcgagctgcg aagctccagg actgcacgat    6720
gctcgtatgc ggagacgacc ttgtcgttat ctgtgaaagc gcgggaccc aagaggacga     6780 ggcgagccta cgggccttca cggaggctat gactagatac tctgccccc ctggggaccc     6840 gcccaaacca gaatacgact tggagttgat aacatcatgc tcctccaatg tgtcagtcgc    6900
gcacgatgca tctggcaaaa gggtgtacta tctcacccgt gaccccacca ccccccttgc    6960
gcgggctgcg tgggagacag ctagacacac tccagtcaat tcctggctag caacatcat     7020 catgtatgcg cccaccttgt gggcaaggat gatcctgatg actcatttct tctccatcct    7080
tctagctcag gaacaacttg aaaaagccct agattgtcag atctacgggg cctgttactc    7140
cattgagcca cttgacctac ctcagatcat tcaacgactc catggcctta gcgcattttc    7200
actccatagt tactctccag gtgagatcaa tagggtggct tcatgcctca ggaaacttgg    7260
ggtaccgccc ttgcgagtct ggagacatcg ggccagaagt gtccgcgcta ggctactgtc    7320
ccaggggggg agggctgcca cttgtggcaa gtacctcttc aactgggcag taaggaccaa    7380
gctcaaactc actccaatcc cggctgcgtc ccagttggat ttatccagct ggttcgttgc    7440
tggttacagc gggggagaca tatatcacag cctgtctcgt gcccgacccc gctggttcat    7500
gtggtgccta ctcctacttt ctgtagggggt aggcatctat ctactcccca accgatgaac    7560
ggggacctaa acactccagg ccaataggcc atcctgtttt tttcccttttt tttttttctt    7620 tttttttttt tttttttttt tttttttttt ttctccttttt tttttcctct ttttttcctt    7680
ttctttcctt tggtggctcc atcttagccc tagtcacggc tagctgtgaa aggtccgtga    7740
gccgcttgac tgcagagagt gctgatactg gcctctctgc agatcaagt                7789
```

<210> SEQ ID NO 23
<211> LENGTH: 11062
<212> TYPE: DNA
<213> ORGANISM: Hepatitis C virus

<400> SEQUENCE: 23

```
gccagccccc gattgggggc gacactccac catagatcac tcccctgtga ggaactactg      60
tcttcacgca gaaagcgtct agccatggcg ttagtatgag tgtcgtgcag cctccaggac     120 ccccctccc gggagagcca tagtggtctg cggaaccggt gagtacaccg gaattgccag      180
gacgaccggg tcctttcttg gatcaacccg ctcaatgcct ggagatttgg gcgtgccccc    240
gcgagactgc tagccgagta tgttgggtc gcgaaaggcc ttgtggtact gcctgatagg      300
gtgcttgcga gtgccccggg aggtctcgta gaccgtgcac catgagcacg aatcctaaac     360
ctcaaagaaa aaccaagggg cgcgccatga ttgaacaaga tggattgcac gcaggttctc     420
cggccgcttg ggtggagagg ctattcggct atgactgggc acaacagaca atcggctgct    480
ctgatgccgc cgtgttccgg ctgtcagcgc aggggcgccc ggttcttttt gtcaagaccg    540
acctgtccgg tgccctgaat gaactgcagg acgaggcagc gcggctatcg tggctggcca    600
cgacgggcgt tccttgcgca gctgtgctcg acgttgtcac tgaagcggga agggactggc    660
tgctattggg cgaagtgccg gggcaggatc tcctgtcatc tcaccttgct cctgccgaga    720
aagtatccat catggctgat gcaatgcggc ggctgcatac gcttgatccg ctacctgcc    780 cattcgacca ccaagcgaaa catcgcatcg agcgagcacg tactcggatg aagccggtc    840 ttgtcgatca ggatgatctg gacgaagagc atcaggggct cgcgccagcc gaactgttcg    900
ccaggctcaa ggcgcgcatg cccgacggcg aggatctcgt cgtgacccat ggcgatgcct    960
```

```
gcttgccgaa tatcatggtg gaaaatggcc gcttttctgg attcatcgac tgtggccggc    1020
tgggtgtggc ggaccgctat caggacatag cgttggctac ccgtgatatt gctgaagagc    1080
ttggcggcga atgggctgac cgcttcctcg tgctttacgg tatcgccgct cccgattcgc    1140
agcgcatcgc cttctatcgc cttcttgacg agttcttctg agtttaaaca gaccacaacg    1200
gtttccctct agcgggatca attccgcccc tctccctccc cccccctaa cgttactggc    1260 cgaagccgct tggaataagg ccggtgtgcg tttgtctata tgttattttc caccatattg    1320
ccgtcttttg gcaatgtgag ggcccggaaa cctggccctg tcttcttgac gagcattcct    1380
aggggtcttt cccctctcgc caaggaatg caaggtctgt tgaatgtcgt gaaggaagca    1440
gttcctctgg aagcttcttg aagacaaaca acgtctgtag cgacccttg caggcagcgg    1500 aacccccac ctggcgacag gtgcctctgc ggccaaaagc cacgtgtata agatacacct    1560
gcaaaggcgg cacaacccca gtgccacgtt gtgagttgga tagttgtgga aagagtcaaa    1620
tggctctcct caagcgtatt caacaagggg ctgaaggatg cccagaaggt accccattgt    1680
atgggatctg atctgggcc tcggtgcaca tgctttacat gtgtttagtc gaggttaaaa    1740
aacgtctagg cccccgaac cacggggacg tggttttcct ttgaaaaaca cgataataat    1800
gagcacgaat cctaaacctc aaagaaaaac caaacgtaac accaaccgcc gcccacagga    1860
cgtcaagttc ccgggcggtg gtcagatcgt cggtggagtt tacctgttgc cgcgcagggg    1920
ccccaggttg ggtgtgcgcg cgactaggaa gacttccgag cggtcgcaac ctcgtggaag    1980
gcgacaacct atccccaagg ctcgccagcc cgagggtagg gcctgggctc agcccgggta    2040
cccctggccc ctctatggca atgagggctt ggggtgggca ggatggctcc tgtcaccccg    2100
tggctctcgg cctagttggg gccccacgga cccccggcgt aggtcgcgca atttgggtaa    2160
ggtcatcgat accctcacgt gcggcttcgc cgatctcatg gggtacattc cgctcgtcgg    2220
cgccccccta gggggcgctg ccaggcccct ggcgcatggc gtccgggttc tggaggacgg    2280
cgtgaactat gcaacaggga atctgcccgg ttgctccttt tctatcttcc ttttggcttt    2340
gctgtcctgt ttgaccatcc cagcttccgc ttatgaagtg cgcaacgtat ccggagtgta    2400
ccatgtcacg aacgactgct ccaacgcaag cattgtgtat gaggcagcgg acatgatcat    2460
gcataccccc gggtgcgtgc cctgcgttcg ggagaacaac tcctcccgct gctgggtagc    2520
gctcactccc acgctcgcgg ccaggaacgc tagcgtcccc actacgacga tacgacgcca    2580
tgtcgatttg ctcgttgggg cggctgctct ctgctccgct atgtacgtgg gagatctctg    2640
cggatctgtt ttcctcgtcg cccagctgtt caccttctcg cctcgccggc acgagacagt    2700
acaggactgc aattgctcaa tatatcccgg ccacgtgaca ggtcaccgta tggcttggga    2760
tatgatgatg aactggtcac ctacagcagc cctagtggta tcgcagttac tccggatccc    2820
acaagctgtc gtggatatgg tggcggggcc ccattgggga gtcctagcgg gccttgccta    2880
ctattccatg gtggggaact gggctaaggt tctgattgtg atgctactct tgccggcgt    2940 tgacggggga acctatgtga caggggggac gatggccaaa acaccctcg ggattacgtc    3000 cctcttttca cccgggtcat cccagaaaat ccagcttgta acaccaacg gcagctggca    3060 catcaacagg actgccctga actgcaatga ctccctcaac actgggttcc ttgctgcgct    3120
gttctacgtg cacaagttca actcatctgg atgcccagag cgcatggcca gctgcagccc    3180
catcgacgcg ttcgctcagg ggtgggggcc catcacttac aatgagtcac acagctcgga    3240
ccagaggcct tattgttggc actacgcacc ccggccgtgc ggtatcgtac ccgcggcgca    3300
```

```
ggtgtgtggt ccagtgtact gcttcacccc aagccctgtc gtggtgggga cgaccgaccg    3360
gttcggcgtc cctacgtaca gttggggga gaatgagacg gacgtgctgc ttcttaacaa     3420
cacgcggccg ccgcaaggca actggtttgg ctgtacatgg atgaatagca ctgggttcac    3480
caagacgtgc gggggccccc cgtgtaacat cggggggatc ggcaataaaa ccttgacctg    3540
ccccacggac tgcttccgga agcaccccga ggccacttac accaagtgtg gttcggggcc    3600
ttggttgaca cccagatgct tggtccacta cccatacagg ctttggcact acccctgcac    3660
tgtcaacttt accatcttca aggttaggat gtacgtgggg ggagtggagc acaggctcga    3720
agccgcatgc aattggactc gaggagagcg ttgtaacctg gaggacaggg acagatcaga    3780
gcttagcccg ctgctgctgt ctacaacgga gtggcaggta ttgccctgtt ccttcaccac    3840
cctaccggct ctgtccactg gtttgatcca tctccatcag aacgtcgtgg acgtacaata    3900
cctgtacggt atagggtcgg cggttgtctc ctttgcaatc aaatgggagt atgtcctgtt    3960
gctcttcctt cttctggcgg acgcgcgcgt ctgtgcctgc ttgtggatga tgctgctgat    4020
agctcaagct gaggccgccc tagagaacct ggtggtcctc aacgcggcat ccgtggccgg    4080
ggcgcatggc attctctcct tcctcgtgtt cttctgtgct gcctggtaca tcaagggcag    4140
gctggtccct ggggcggcat atgccctcta cggcgtatgg ccgctactcc tgctcctgct    4200
ggcgttacca ccacgagcat acgccatgga ccgggagatg gcagcatcgt gcggaggcgc    4260
ggttttcgta ggtctgatac tcttgacctt gtcaccgcac tataagctgt tcctcgctag    4320
gctcatatgg tggttacaat attttatcac cagggccgag gcacacttgc aagtgtggat    4380
cccccccctc aacgttcggg ggggccgcga tgccgtcatc ctcctcacgt gcgcgatcca    4440
cccagagcta atctttacca tcaccaaaat cttgctcgcc atactcggtc cactcatggt    4500
gctccaggct ggtataacca aagtgccgta cttcgtgcgc gcacacgggc tcattcgtgc    4560
atgcatgctg gtgcggaagg ttgctggggg tcattatgtc caaatggctc tcatgaagtt    4620
ggccgcactg acaggtacgt acgtttatga ccatctcacc ccactgcggg actgggccca    4680
cgcgggccta cgagaccttg cggtggcagt tgagcccgtc gtcttctctg atatggagac    4740
caaggttatc acctgggggg cagacaccgc ggcgtgtggg gacatcatct tgggcctgcc    4800
cgtctccgcc cgcaggggga gggagataca tctgggaccg gcagacagcc ttgaagggca    4860
ggggtggcga ctcctcgcgc ctattacggc ctactcccaa cagacgcgag gcctacttgg    4920
ctgcatcatc actagcctca caggccggga caggaaccag gtcgaggggg aggtccaagt    4980
ggtctccacc gcaacacaat cttttcctgg cgacctgcgtc aatggcgtgt gttggactgt    5040
ctatcatggt gccggctcaa agaccccttgc cggcccaaag ggcccaatca cccaaatgta    5100
caccaatgtg gaccaggacc tcgtcggctg gcaagcgccc ccggggcgc gttccttgac     5160
accatgcacc tgcggcagct cggacccttta cttggtcacg aggcatgccg atgtcattcc    5220
ggtgcgccgc cggggcgaca gcaggggggag cctactctcc cccaggcccg tctcctactt    5280
gaagggctct cgggcggtc cactgctctg cccctcgggg cacgctgtgg gcatctttcg    5340
ggctgccgtg tgcacccgag gggttgcgaa ggcggtggac tttgtacccg tcgagtctat    5400
ggaaaccact atgcggtccc cggtcttcac ggacaactcg tcccctccgg ccgtaccgca    5460
gacattccag gtgcccatc tacacgcccc tactggtagc ggcaagagca ctaaggtgcc    5520
ggctgcgtat gcagcccaag ggtataaggt gcttgtcctg aacccgtccg tcgccgccac    5580
cctaggtttc ggggcgtata tgtctaaggc acatggtatc gacccctaaca tcagaaccgg    5640
ggtaaggacc atcaccacgg gtgccccat cacgtactcc acctatggca agttccttgc    5700
```

```
cgacggtggt tgctctgggg gcgcctatga catcataata tgtgatgagt gccactcaac    5760
tgactcgacc actatcctgg gcatcggcac agtcctggac caagcggaga cggctggagc    5820
gcgactcgtc gtgctcgcca ccgctacgcc tccgggatcg gtcaccgtgc cacatccaaa    5880
catcgaggag gtggctctgt ccagcactgg agaaatcccc ttttatggca aagccatccc    5940
catcgagacc atcaagggg ggaggcacct cattttctgc cattccaaga gaaatgtga     6000 tgagctcgcc gcgaagctgt ccggcctcgg actcaatgct gtagcatatt accggggcct    6060
tgatgtatcc gtcataccaa ctagcggaga cgtcattgtc gtagcaacgg acgtctaat    6120 gacgggcttt accggcgatt tcgactcagt gatcgactgc aatacatgtg tcacccagac    6180
agtcgacttc agcctggacc cgaccttcac cattgagacg acgaccgtgc acaagacgc    6240 ggtgtcacgc tcgcagcggc gaggcaggac tggtaggggc aggatgggca tttacaggtt    6300
tgtgactcca ggagaacggc cctcgggcat gttcgattcc tcggttctgt gcgagtgcta    6360
tgacgcgggc tgtgcttggt acgagctcac gcccgccgag acctcagtta ggttgcgggc    6420
ttacctaaac acaccagggt tgcccgtctg ccaggaccat ctggagttct gggagagcgt    6480
ctttacaggc ctcacccaca tagacgccca tttcttgtcc cagactaagc aggcaggaga    6540
caacttcccc tacctggtag cataccaggc tacggtgtgc gccagggctc aggctccacc    6600
tccatcgtgg gaccaaatgt ggaagtgtct catacggcta aagcctacgc tgcacgggcc    6660 aacgccctg ctgtataggc tgggagccgt tcaaaacgag gttactacca cacaccccat     6720
aaccaaatac atcatggcat gcatgtcggc tgacctggag gtcgtcacga gcacctgggt    6780
gctggtaggc ggagtcctag cagctctggc cgcgtattgc ctgacaacag gcagcgtggt    6840
cattgtgggc aggatcatct tgtccggaaa gccggccatc attcccgaca gggaagtcct    6900
ttaccgggag ttcgatgaga tggaagagtg cgcctcacac ctcccttaca tcgaacaggg    6960
aatgcagctc gccgaacaat tcaaacagaa ggcaatcggg ttgctgcaaa cagccaccaa    7020
gcaagcggag gctgctgctc ccgtggtgga atccaagtgg cggacccctg aagccttctg    7080
ggcgaagcat atgtggaatt tcatcagcgg gatacaatat ttagcaggct tgtccactct    7140
gcctggcaac cccgcgatag catcactgat ggcattcaca gcctctatca ccagcccgct    7200 caccaccccaa cataccctcc tgtttaacat cctgggggga tgggtggccg cccaacttgc    7260
tcctcccagc gctgcttctg ctttcgtagg cgccggcatc gctggagcgg ctgttggcag    7320
cataggcctt gggaaggtgc ttgtggatat tttggcaggt tatggagcag gggtggcagg    7380
cgcgctcgtg gcctttaagg tcatgagcgg cgagatgccc tccaccgagg acctggttaa    7440
cctactccct gctatcctct cccctggcgc cctagtcgtc ggggtcgtgt gcgcagcgat    7500
actgcgtcgg cacgtgggcc caggggaggg ggctgtgcag tggatgaacc ggctgatagc    7560
gttcgcttcg cggggtaacc acgtctcccc cacgcactat gtgcctgaga gcgacgctgc    7620
agcacgtgtc actcagatcc tctctagtct taccatcact cagctgctga agaggcttca    7680
ccagtggatc aacgaggact gctccacgcc atgctccggc tcgtggctaa gagatgtttg    7740
ggattggata tgcacggtgt tgactgattt caagacctgg ctccagtcca agctcctgcc    7800
gcgattgccg ggagtcccct tcttctcatg tcaacgtggg tacaagggag tctggcgggg    7860
cgacggcatc atgcaaacca cctgcccatg tggagcacag atcaccggac atgtgaaaaa    7920
cggttccatg aggatcgtgg ggcctaggac ctgtagtaac acgtggcatg gaacattccc    7980
cattaacgcg tacaccacgg gcccctgcac gcccctcccg cgccaaatt attctagggc    8040
```

```
gctgtggcgg gtggctgctg aggagtacgt ggaggttacg cgggtggggg atttccacta   8100
cgtgacgggc atgaccactg acaacgtaaa gtgcccgtgt caggttccgg cccccgaatt   8160
cttcacagaa gtggatgggg tgcggttgca caggtacgct ccagcgtgca aaccectect   8220
acgggaggag gtcacattcc tggtcgggct caatcaatac ctggttgggt cacagctccc   8280
atgcgagccc gaaccggacg tagcagtgct cacttccatg ctcaccgacc cctcccacat   8340
tacgcggag acggctaagc gtaggctggc caggggatct ccccctcct tggccagctc   8400
atcagctatc cagctgtctg cgccttcctt gaaggcaaca tgcactaccc gtcatgactc   8460
cccggacgct gacctcatcg aggccaacct cctgtggcgg caggagatgg gcgggaacat   8520
cacccgcgtg gagtcagaaa ataaggtagt aattttggac tctttcgagc cgctccaagc   8580
ggaggaggat gagagggaag tatccgttcc ggcggagatc ctgcggaggt ccaggaaatt   8640
ccctcgagcg atgcccatat gggcacgccc ggattacaac cctccactgt tagagtcctg   8700
gaaggacccg gactacgtcc ctccagtggt acacgggtgt ccattgccgc ctgccaaggc   8760
ccctccgata ccacctccac ggaggaagag gacggttgtc ctgtcagaat ctaccgtgtc   8820
ttctgccttg gcggagctcg ccacaaagac cttcggcagc tccgaatcgt cggccgtcga   8880
cagcggcacg gcaacggcct ctcctgacca gccctccgac gacggcgacg cgggatccga   8940
cgttgagtcg tactcctcca tgccccccct tgaggggag ccggggatc ccgatctcag   9000
cgacgggtct tggtctaccg taagcgagga ggctagtgag gacgtcgtct gctgctcgat   9060
gtcctacaca tggacaggcg ccctgatcac gccatgcgct gcggaggaaa ccaagctgcc   9120
catcaatgca ctgagcaact cttgctccg tcaccacaac ttggtctatg ctacaacatc   9180
tcgcagcgca agcctgcggc agaagaaggt caccttgac agactgcagg tcctggacga   9240
ccactaccgg gacgtgctca aggagatgaa ggcgaaggcg tccacagtta aggctaaact   9300
tctatccgtg gaggaagcct gtaagctgac gcccccacat tcggccagat ctaaatttgg   9360
ctatggggca aaggacgtcc ggaacctatc cagcaaggcc gttaaccaca tccgctccgt   9420
gtggaaggac ttgctggaag acactgagac accaattgac accaccatca tggcaaaaaa   9480
tgaggttttc tgcgtccaac cagagaaggg gggccgcaag ccagctcgcc ttatcgtatt   9540
cccagatttg ggggttcgtg tgtgcgagaa aatggcccctt tacgatgtgg ctccacccct   9600
ccctcaggcc gtgatgggct cttcatacgg attccaatac tctcctggac agcgggtcga   9660
gttcctggtg aatgcctgga aagcgaagaa atgccctatg gcttcgcat atgacacccg   9720
ctgttttgac tcaacggtca ctgagaatga catccgtgtt gaggagtcaa tctaccaatg   9780
ttgtgacttg gccccccgaag ccagacaggc cataaggtcg ctcacagagc ggctttacat   9840
cgggggcccc ctgactaatt ctaaagggca gaactgcggc tatcgccggt gccgcgcgag   9900
cggtgtactg acgaccagct gcggtaatac cctcacatgt tacttgaagg ccgctgcggc   9960
ctgtcgagct gcgaagctcc aggactgcac gatgctcgta tgcggagacg accttgtcgt  10020
tatctgtgaa agcgcgggga cccaagagga cgaggcgagc ctacgggcct tcacggaggc  10080
tatgactaga tactctgccc cccctgggga cccgcccaaa ccagaatacg acttggagtt  10140
gataacatca tgctcctcca atgtgtcagt cgcgcacgat gcatctggca aagggtgta  10200
ctatctcacc cgtgaccca ccacccccct tgcgcgggct gcgtgggaga cagctagaca  10260
cactccagtc aattcctggc taggcaacat catcatgtat gcgcccacct tgtgggcaag  10320
gatgatcctg atgactcatt tcttctccat ccttctagct caggaacaac ttgaaaaagc  10380
cctagattgt cagatctacg gggcctgtta ctccattgag ccacttgacc tacctcagat  10440
```

-continued

| | |
|---|---|
| cattcaacga ctccatggcc ttagcgcatt ttcactccat agttactctc caggtgagat | 10500 |
| caatagggtg gcttcatgcc tcaggaaact tggggtaccg cccttgcgag tctggagaca | 10560 |
| tcgggccaga agtgtccgcg ctaggctact gtcccagggg gggagggctg ccacttgtgg | 10620 |
| caagtacctc ttcaactggg cagtaaggac caagctcaaa ctcactccaa tcccggctgc | 10680 |
| gtcccagttg gatttatcca gctggttcgt tgctggttac agcggggag acatatatca | 10740 |
| cagcctgtct cgtgcccgac cccgctggtt catgtggtgc ctactcctac tttctgtagg | 10800 |
| ggtaggcatc tatctactcc ccaaccgatg aacggggacc taaacactcc aggccaatag | 10860 |
| gccatcctgt tttttttcct tttttttttt ctttttttt ttttttttt tttttttttt | 10920 |
| ttttctcct ttttttttcc tcttttttttc cttttctttc ctttggtggc tccatcttag | 10980 |
| ccctagtcac ggctagctgt gaaaggtccg tgagccgctt gactgcagag agtgctgata | 11040 |
| ctggcctctc tgcagatcaa gt | 11062 |

<210> SEQ ID NO 24
<211> LENGTH: 9605
<212> TYPE: DNA
<213> ORGANISM: Hepatitis C virus

<400> SEQUENCE: 24

| | |
|---|---|
| gccagccccc gattgggggc gacactccac catagatcac tccctgtga ggaactactg | 60 |
| tcttcacgca gaaagcgtct agccatggcg ttagtatgag tgtcgtgcag cctccaggac | 120 |
| cccccctccc gggagagcca tagtggtctg cggaaccggt gagtacaccg gaattgccag | 180 |
| gacgaccggg tccttcttg gatcaacccg ctcaatgcct ggagatttgg gcgtgccccc | 240 |
| gcgagactgc tagccgagta gtgttgggtc gcgaaaggcc ttgtggtact gcctgatagg | 300 |
| gtgcttgcga gtgccccggg aggtctcgta gaccgtgcac catgagcacg aatcctaaac | 360 |
| ctcaaagaaa aaccaaacgt aacaccaacc gccgcccaca ggacgtcaag ttcccgggcg | 420 |
| gtggtcagat cgtcggtgga gtttacctgt tgccgcgcag gggccccagg ttgggtgtgc | 480 |
| gcgcgactag gaagacttcc gagcggtcgc aacctcgtgg aaggcgacaa cctatcccca | 540 |
| aggctcgcca gcccgagggt agggcctggg ctcagcccgg gtaccctgg cccctctatg | 600 |
| gcaatgaggg cttggggtgg gcaggatggc tcctgtcacc ccgtggctct cggcctagtt | 660 |
| ggggccccac ggacccccgg cgtaggtcgc gcaatttggg taaggtcatc gataccctca | 720 |
| cgtgcggctt cgccgatctc atggggtaca ttccgctcgt cggcgccccc ctaggggcg | 780 |
| ctgccagggc cctggcgcat ggcgtccggg ttctggagga cggcgtgaac tatgcaacag | 840 |
| ggaatctgcc cggttgctcc ttttctatct tccttttggc tttgctgtcc tgtttgacca | 900 |
| tcccagcttc cgcttatgaa gtgcgcaacg tatccggagt gtaccatgtc acgaacgact | 960 |
| gctccaacgc aagcattgtg tatgaggcag cggacatgat catgcatacc cccgggtgcg | 1020 |
| tgccctgcgt tcgggagaac aactcctccc gctgctgggt agcgctcact cccacgctcg | 1080 |
| cggccaggaa cgctagcgtc cccactacga cgatacgacg ccatgtcgat tgctcgttg | 1140 |
| gggcggctgc tctctgctcc gctatgtacg tgggagatct ctgcggatct gttttcctcg | 1200 |
| tcgcccagct gttcaccttc tcgcctcgcc ggcacgagac agtacaggac tgcaattgct | 1260 |
| caatatatcc cggccacgtg acaggtcacc gtatggcttg gatatgatg atgaactggt | 1320 |
| cacctacagc agccctagtg gtatcgcagt tactccggat cccacaagct gtcgtggata | 1380 |
| tggtggcggg ggcccattgg ggagtcctag cgggccttgc ctactattcc atggtgggga | 1440 |

```
actgggctaa ggttctgatt gtgatgctac tctttgccgg cgttgacggg ggaacctatg    1500
tgacaggggg gacgatggcc aaaaacaccc tcgggattac gtccctcttt tcacccgggt    1560
catcccagaa aatccagctt gtaaacacca acggcagctg gcacatcaac aggactgccc    1620
tgaactgcaa tgactccctc aacactgggt tccttgctgc gctgttctac gtgcacaagt    1680
tcaactcatc tggatgccca gagcgcatgg ccagctgcag ccccatcgac gcgttcgctc    1740
aggggtgggg gcccatcact tacaatgagt cacacagctc ggaccagagg ccttattgtt    1800
ggcactacgc accccggccg tgcggtatcg tacccgcggc gcaggtgtgt ggtccagtgt    1860
actgcttcac cccaagccct gtcgtggtgg ggacgaccga ccggttcggc gtccctacgt    1920
acagttgggg ggagaatgag acggacgtgc tgcttcttaa caacacgcgg ccgccgcaag    1980
gcaactggtt tggctgtaca tggatgaata gcactgggtt caccaagacg tgcgggggcc    2040
ccccgtgtaa catcgggggg atcggcaata aaaccttgac ctgccccacg gactgcttcc    2100
ggaagcaccc cgaggccact tacaccaagt gtggttcggg gccttggttg acacccagat    2160
gcttggtcca ctacccatac aggctttggc actaccoctg cactgtcaac tttaccatct    2220
tcaaggttag gatgtacgtg gggggagtgg agcacaggct cgaagccgca tgcaattgga    2280
ctcgaggaga gcgttgtaac ctggaggaca gggacagatc agagcttagc ccgctgctgc    2340
tgtctacaac ggagtggcag gtattgccct gttccttcac cacccctaccg gctctgtcca    2400 ctggtttgat ccatctccat cagaacgtcg tggacgtaca atacctgtac ggtatagggt    2460
cggcggttgt ctccttttgca atcaaatggg agtatgtcct gttgctcttc cttcttctgg    2520
cggacgcgcg cgtctgtgcc tgcttgtgga tgatgctgct gatagctcaa gctgaggccg    2580
ccctagagaa cctggtggtc ctcaacgcgg catccgtggc cggggcgcat ggcattctct    2640
ccttcctcgt gttcttctgt gctgcctggt acatcaaggg caggctggtc cctggggcgg    2700
catatgccct ctacggcgta tggccgctac tcctgctcct gctggcgtta ccaccacgag    2760
catacgccat ggaccgggag atggcagcat cgtgcggagg cgcggttttc gtaggtctga    2820
tactcttgac cttgtcaccg cactataagc tgttcctcgc taggctcata tggtggttac    2880 aatatttat caccagggcc gaggcacact tgcaagtgtg gatccccccc ctcaacgttc    2940 ggggggggccg cgatgccgtc atcctcctca cgtgcgcgat ccaccagag ctaatcttta    3000 ccatcaccaa aatcttgctc gccatactcg gtccactcat ggtgctccag gctggtataa    3060
ccaaagtgcc gtacttcgtg cgcgcacacg ggctcattcg tgcatgcatg ctggtgcgga    3120
aggttgctgg gggtcattat gtccaaatgg ctctcatgaa gttggccgca ctgacaggta    3180
cgtacgttta tgaccatctc accccactgc gggactgggc ccacgcgggc ctacgagacc    3240
ttgcggtggc agttgagccc gtcgtcttct ctgatatgga gaccaaggtt atcacctggg    3300
gggcagacac cgcggcgtgt ggggacatca tcttgggcct gccgtctcc gcccgcaggg    3360 ggagggagat acatctggga ccggcagaca gccttgaagg gcaggggtgg cgactcctcg    3420
cgcctattac ggcctactcc caacagacgc gaggcctact tggctgcatc atcactagcc    3480
tcacaggccg ggacaggaac caggtcgagg gggaggtcca agtggtctcc accgcaacac    3540
aatctttcct ggcgacctgc gtcaatggcg tgtgttggac tgtctatcat ggtgccggct    3600 caaagacoct tgccggccca aagggcccaa tcacccaaat gtacaccaat gtggaccagg    3660
acctcgtcgg ctggcaagcg ccccccgggg cgcgttcctt gacaccatgc acctgcggca    3720
gctcggacct ttacttggtc acgaggcatg ccgatgtcat tccggtgcgc cggcggggcc    3780
acagcagggg gagcctactc tcccccaggc ccgtctccta cttgaagggc tcttcgggcg    3840
```

```
gtccactgct ctgcccctcg gggcacgctg tgggcatctt tcgggctgcc gtgtgcaccc      3900
gaggggttgc gaaggcggtg gactttgtac ccgtcgagtc tatggaaacc actatgcggt      3960
ccccggtctt cacggacaac tcgtcccctc cggccgtacc gcagacattc caggtggccc      4020
atctacacgc ccctactggt agcggcaaga gcactaaggt gccggctgcg tatgcagccc      4080
aagggtataa ggtgcttgtc ctgaacccgt ccgtcgccgc caccctaggt ttcggggcgt      4140
atatgtctaa ggcacatggt atcgacccta acatcagaac cggggtaagg accatcacca      4200
cgggtgcccc catcacgtac tccacctatg caagtttct tgccgacggt ggttgctctg      4260
ggggcgccta tgacatcata atatgtgatg agtgccactc aactgactcg accactatcc      4320
tgggcatcgg cacagtcctg gaccaagcgg agacggctgg agcgcgactc gtcgtgctcg      4380
ccaccgctac gcctccggga tcggtcaccg tgccacatcc aaacatcgag gaggtggctc      4440
tgtccagcac tggagaaatc ccctttatg gcaaagccat ccccatcgag accatcaagg      4500
gggggaggca cctcattttc tgccattcca agaagaaatg tgatgagctc gccgcgaagc      4560
tgtccggcct cggactcaat gctgtagcat attaccgggg ccttgatgta tccgtcatac      4620
caactagcgg agacgtcatt gtcgtagcaa cggacgctct aatgacgggc tttaccggcg      4680
atttcgactc agtgatcgac tgcaatacat gtgtcaccca gacagtcgac ttcagcctgg      4740
acccgacctt caccattgag acgacgaccg tgccacaaga cgcggtgtca cgctcgcagc      4800
ggcgaggcag gactggtagg ggcaggatgg gcatttacag gtttgtgact ccaggagaac      4860
ggccctcggg catgttcgat tcctcggttc tgtgcgagtg ctatgacgcg ggctgtgctt      4920
ggtacgagct cacgcccgcc gagacctcag ttaggttgcg ggcttaccta aacacaccag      4980
ggttgcccgt ctgccaggac catctggagt tctgggagag cgtctttaca ggcctcaccc      5040
acatagacgc ccatttcttg tcccagacta agcaggcagg agacaacttc ccctacctgg      5100
tagcatacca ggctacggtg tgcgccaggg ctcaggctcc acctccatcg tgggaccaaa      5160
tgtggaagtg tctcatacgg ctaaagccta cgctgcacgg gccaacgccc tgctgtata      5220 ggctgggagc cgttcaaaac gaggttacta ccacacaccc cataaccaaa tacatcatgg      5280
catgcatgtc ggctgacctg gaggtcgtca cgagcacctg ggtgctggta ggcggagtcc      5340
tagcagctct ggccgcgtat tgcctgacaa caggcagcgt ggtcattgtg gcaggatca      5400 tcttgtccgg aaagccggcc atcattcccg acagggaagt cctttaccgg gagttcgatg      5460
agatggaaga gtgcgcctca cacctccctt acatcgaaca gggaatgcag ctcgccgaac      5520
aattcaaaca gaaggcaatc gggttgctgc aaacagccac caagcaagcg gaggctgctg      5580
ctcccgtggt ggaatccaag tggcggaccc tcgaagcctt ctgggcgaag catatgtgga      5640
atttcatcag cgggatacaa tatttagcag gcttgtccac tctgcctggc aaccccgcga      5700
tagcatcact gatggcattc acagcctcta tcaccagccc gctcaccacc caacatacec      5760 tcctgttta catcctgggg ggatgggtgg ccgcccaact tgctcctccc agcgctgctt      5820
ctgctttcgt aggcgccggc atcgctggag cggctgttgg cagcataggc cttgggaagg      5880
tgcttgtgga tattttggca ggttatggag caggggtggc aggcgcgctc gtggcctta      5940 aggtcatgag cggcgagatg ccctccaccg aggacctggt taacctactc cctgctatcc      6000
tctcccctgg cgccctagtc gtcggggtcg tgtgcgcagc gatactgcgt cggcacgtgg      6060
gcccagggga gggggctgtg cagtggatga accggctgat agcgttcgct tcgcggggta      6120
accacgtctc ccccacgcac tatgtgcctg agagcgacgc tgcagcacgt gtcactcaga      6180
```

```
tcctctctag tcttaccatc actcagctgc tgaagaggct tcaccagtgg atcaacgagg    6240
actgctccac gccatgctcc ggctcgtggc taagagatgt ttgggattgg atatgcacgg    6300
tgttgactga tttcaagacc tggctccagt ccaagctcct gccgcgattg ccgggagtcc    6360
ccttcttctc atgtcaacgt gggtacaagg gagtctggcg gggcgacggc atcatgcaaa    6420
ccacctgccc atgtggagca cagatcaccg gacatgtgaa aaacggttcc atgaggatcg    6480
tggggcctag gacctgtagt aacacgtggc atggaacatt ccccattaac gcgtacacca    6540
cgggcccctg cacgccctcc ccggcgccaa attattctag ggcgctgtgg cgggtggctg    6600
ctgaggagta cgtggaggtt acgcgggtgg gggatttcca ctacgtgacg ggcatgacca    6660
ctgacaacgt aaagtgcccg tgtcaggttc cggcccccga attcttcaca gaagtggatg    6720
gggtgcggtt gcacaggtac gctccagcgt gcaaacccct cctacgggag gaggtcacat    6780
tcctggtcgg gctcaatcaa tacctggttg ggtcacagct cccatgcgag cccgaaccgg    6840
acgtagcagt gctcacttcc atgctcaccg acccctccca cattacggcg gagacggcta    6900
agcgtaggct ggccagggga tctcccccct ccttggccag ctcatcagct atccagctgt    6960
ctgcgccttc cttgaaggca acatgcacta cccgtcatga ctccccggac gctgacctca    7020
tcgaggccaa cctcctgtgg cggcaggaga tgggcgggaa catcacccgc gtggagtcag    7080
aaaataaggt agtaatttg gactctttcg agccgctcca agcggaggag gatgagaggg    7140
aagtatccgt tccggcggag atcctgcgga ggtccaggaa attccctcga gcgatgccca    7200
tatgggcacg cccggattac aaccctccac tgttagagtc ctggaaggac ccggactacg    7260
tccctccagt ggtacacggg tgtccattgc cgcctgccaa ggcccctccg ataccacctc    7320
cacggaggaa gaggacggtt gtcctgtcag aatctaccgt gtcttctgcc ttggcggagc    7380
tcgccacaaa gaccttcggc agctccgaat cgtcggccgt cgacagcggc acggcaacgg    7440
cctctcctga ccagccctcc gacgacggcg acgcgggatc cgacgttgag tcgtactcct    7500
ccatgccccc ccttgagggg gagccggggg atcccgatct cagcgacggg tcttggtcta    7560
ccgtaagcga ggaggctagt gaggacgtcg tctgctgctc gatgtcctac acatggacag    7620
gcgccctgat cacgccatgc gctgcggagg aaaccaagct gcccatcaat gcactgagca    7680
actctttgct ccgtcaccac aacttggtct atgctacaac atctcgcagc gcaagcctgc    7740
ggcagaagaa ggtcacccttt gacagactgc aggtcctgga cgaccactac cgggacgtgc    7800
tcaaggagat gaaggcgaag gcgtccacag ttaaggctaa acttctatcc gtggaggaag    7860
cctgtaagct gacgccccca cattcggcca gatctaaatt tggctatggg gcaaaggacg    7920
tccggaacct atccagcaag gccgttaacc acatccgctc cgtgtggaag acttgctggg    7980
aagacactga gacaccaatt gacaccacca tcatggcaaa aaatgaggtt ttctgcgtcc    8040
aaccagagaa gggggggccgc aagccagctc gccttatcgt attcccagat ttgggggttc    8100
gtgtgtgcga gaaaatggcc ctttacgatg tggtctccac cctccctcag gccgtgatgg    8160
gctcttcata cggattccaa tactctcctg acagcgggt cgagttcctg gtgaatgcct    8220
ggaaagcgaa gaaatgccct atgggcttcg catatgacac ccgctgtttt gactcaacgg    8280
tcactgagaa tgacatccgt gttgaggagt caatctacca atgttgtgac ttggccccccg    8340 aagccagaca ggccataagg tcgctcacag agcggctta catcggggc cccctgacta    8400 attctaaagg gcagaactgc ggctatcgcc ggtgccgcgc gagcggtgta ctgacgacca    8460
gctgcggtaa tacctcaca tgttacttga aggccgctgc ggcctgtcga gctgcgaagc    8520
tccaggactg cacgatgctc gtatgcggag acgaccttgt cgttatctgt gaaagcgcgg    8580
```

```
                                                    -continued ggacccaaga ggacgaggcg agcctacggg ccttcacgga ggctatgact agatactctg    8640
ccccccctgg ggacccgccc aaaccagaat acgacttgga gttgataaca tcatgctcct    8700
ccaatgtgtc agtcgcgcac gatgcatctg gcaaaagggt gtactatctc acccgtgacc    8760
ccaccacccc ccttgcgcgg gctgcgtggg agacagctag acacactcca gtcaattcct    8820
ggctaggcaa catcatcatg tatgcgccca ccttgtgggc aaggatgatc ctgatgactc    8880
atttcttctc catccttcta gctcaggaac aacttgaaaa agccctagat tgtcagatct    8940
acggggcctg ttactccatt gagccacttg acctacctca gatcattcaa cgactccatg    9000
gccttagcgc attttcactc catagttact ctccaggtga gatcaatagg gtggcttcat    9060
gcctcaggaa acttggggta ccgcccttgc gagtctggag acatcgggcc agaagtgtcc    9120
gcgctaggct actgtcccag gggggagggg ctgccacttg tggcaagtac ctcttcaact    9180
gggcagtaag gaccaagctc aaactcactc caatcccggc tgcgtcccag ttggatttat    9240
ccagctggtt cgttgctggt tacagcgggg gagacatata tcacagcctg tctcgtgccc    9300 gacccgctg gttcatgtgg tgcctactcc tactttctgt aggggtaggc atctatctac     9360
tccccaaccg atgaacgggg acctaaacac tccaggccaa taggccatcc tgttttttc     9420 cctttttttt tttctttttt ttttttttt tttttttttt tttttttct cctttttttt      9480 tcctcttttt ttccttttct ttcctttggt ggctccatct tagccctagt cacggctagc    9540
tgtgaaaggt ccgtgagccg cttgactgca gagagtgctg atactggcct ctctgcagat    9600
caagt                                                                9605
```